US011279705B2

(12) United States Patent
Murray et al.

(10) Patent No.: US 11,279,705 B2
(45) Date of Patent: Mar. 22, 2022

(54) CRYSTALLINE FORMS OF 3-(IMIDAZO[1,2-B]PYRIDAZIN-3-YLETHYNYL)-4-METHYL-N-{4-[(4-METHYLPIPERAZIN-1-YL)METHYL]-3-(TRIFLUOROMETHYL)PHENYL} BENZAMIDE AND ITS MONO HYDROCHLORIDE SALT

(71) Applicant: ARIAD Pharmaceuticals, Inc., Cambridge, MA (US)

(72) Inventors: Christopher K. Murray, Lexington, MA (US); Leonard W. Rozamus, Andover, MA (US); John J. Chaber, Westford, MA (US); Pradeep K. Sharma, Westford, MA (US)

(73) Assignee: ARIAD PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/881,790

(22) Filed: May 22, 2020

(65) Prior Publication Data

US 2021/0024527 A1     Jan. 28, 2021

Related U.S. Application Data

(60) Continuation of application No. 16/146,143, filed on Sep. 28, 2018, now Pat. No. 10,662,197, which is a division of application No. 15/341,898, filed on Nov. 2, 2016, now Pat. No. 10,125,136, which is a division of application No. 14/651,577, filed as application No. PCT/US2013/074571 on Dec. 12, 2013, now Pat. No. 9,493,470.

(60) Provisional application No. 61/736,543, filed on Dec. 12, 2012, provisional application No. 61/737,007, filed on Dec. 13, 2012, provisional application No. 61/788,208, filed on Mar. 15, 2013.

(51) Int. Cl.
C07D 487/04     (2006.01)

(52) U.S. Cl.
CPC ........ *C07D 487/04* (2013.01); *C07B 2200/13* (2013.01); *H05K 999/99* (2013.01)

(58) Field of Classification Search
CPC .................................................... C07D 487/04
See application file for complete search history.

(56) References Cited

U.S. PATENT DOCUMENTS

| | | |
|---|---|---|
| 5,099,067 A | 3/1992 | Barrett et al. |
| 6,635,641 B2 | 10/2003 | Bender et al. |
| 8,071,609 B2 | 12/2011 | Wang et al. |
| 8,114,874 B2 | 2/2012 | Zou et al. |
| 8,278,307 B2 | 10/2012 | Shakespeare et al. |
| 8,461,167 B2 | 6/2013 | Wang et al. |
| 8,470,851 B2 | 6/2013 | Zou et al. |
| 8,586,566 B2 | 11/2013 | Wang et al. |
| 8,778,942 B2 | 7/2014 | Zou et al. |
| 9,029,533 B2 | 5/2015 | Zou et al. |
| 9,090,561 B2 | 7/2015 | Wang et al. |
| 9,278,971 B2 | 3/2016 | Zou et al. |
| 9,493,470 B2 | 11/2016 | Murray et al. |
| 2003/0207885 A1 | 11/2003 | Hutchison et al. |
| 2004/0092747 A1 | 5/2004 | Bender et al. |
| 2006/0217380 A1 | 9/2006 | Chaffee et al. |
| 2007/0191376 A1 | 8/2007 | Zou et al. |
| 2009/0131651 A1 | 5/2009 | Brown et al. |
| 2009/0149471 A1 | 6/2009 | Shakespeare et al. |
| 2009/0176781 A1 | 7/2009 | Wang et al. |
| 2010/0273772 A1 | 10/2010 | O'Neil et al. |
| 2011/0028511 A1 | 2/2011 | Hildbrand et al. |
| 2011/0112110 A1 | 5/2011 | Gambacorti-Passerini et al. |
| 2012/0135986 A1 | 5/2012 | Zou et al. |
| 2013/0005738 A1 | 1/2013 | Shakespeare et al. |
| 2013/0018046 A1 | 1/2013 | Wang et al. |
| 2013/0196979 A1 | 8/2013 | Zou et al. |
| 2013/0231337 A1 | 9/2013 | Zou et al. |
| 2014/0288082 A1 | 9/2014 | Zou et al. |
| 2015/0315194 A1 | 11/2015 | Murray et al. |
| 2016/0368917 A1 | 12/2016 | Zou et al. |

FOREIGN PATENT DOCUMENTS

| | | |
|---|---|---|
| CN | 101389338 A | 3/2009 |
| CN | 102770129 A | 11/2012 |
| EP | 1973545 B1 | 1/2013 |
| WO | WO 2001/034587 A2 | 5/2001 |
| WO | WO 2001/081311 A1 | 11/2001 |
| WO | WO 2003/006471 A1 | 1/2003 |
| WO | WO 2004/043379 A2 | 5/2004 |
| WO | WO 2004/058776 A1 | 7/2004 |
| WO | WO 2005/051366 A2 | 6/2005 |
| WO | WO 2005/060969 A1 | 7/2005 |
| WO | WO 2005/060970 A1 | 7/2005 |
| WO | WO 2005/097773 A1 | 10/2005 |
| WO | WO 2006/019831 A1 | 2/2006 |
| WO | WO 2006/082404 A1 | 8/2006 |

(Continued)

OTHER PUBLICATIONS

Acevedo et al., "Inducible FGFR-1 Activation Leads to Irreversible Prostate Adenocarcinoma and an Epithelial-to-Mesenchymal Transition," Cancer Cell, 2007, pp. 559-571, vol. 12.

(Continued)

*Primary Examiner* — Paul V Ward

(74) *Attorney, Agent, or Firm* — Finnegan, Henderson, Farabow, Garrett & Dunner, LLP

(57) ABSTRACT

Novel crystalline forms of 3-(imidazo[1,2-b]pyridazin-3-ylethynyl)-4-methyl-N-{4-[(4-methylpiperazin-1-yl)methyl]-3-(trifluoromethyl)phenyl}benzamide free base and 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride, pharmaceutical compositions thereof and methods of their preparation and use are disclosed herein.

3 Claims, 91 Drawing Sheets

(56) References Cited

FOREIGN PATENT DOCUMENTS

| | | |
|---|---|---|
| WO | WO 2006/103449 A2 | 10/2006 |
| WO | WO 2007/013673 A1 | 2/2007 |
| WO | WO 2007/021937 A2 | 2/2007 |
| WO | WO 2007/075869 A2 | 7/2007 |
| WO | WO 2011/053938 A8 | 5/2011 |
| WO | WO 2012/139027 A1 | 10/2012 |
| WO | WO 2013/101281 A1 | 7/2013 |
| WO | WO 2013/162727 A1 | 10/2013 |
| WO | WO 2014/093579 A2 | 6/2014 |
| WO | WO 2014/093583 A2 | 6/2014 |

OTHER PUBLICATIONS

Armarego et al., "Purification of Laboratory Chemicals," 2009, pp. 71-72, Butterworth-Heinemann, Sixth Edition (Retrieved from Internet on May 12, 2014 at URL http://www.pyrobin.com/files/purification%20of%20laboratory%20chemicals%206e%20).

Bauer, "Polymorphism—A Critical Consideration in Pharmaceutical Development, Manufacturing, and Stability," Journal of Validation of Technology, 2008, pp. 15-23, vol. 14.5 Autumn.

Bernstein, "Polymorphism in Molecular Crystals," Oxford University Press, 2002, pp. 1-28, 240-256, Oxford University Press.

Byrn, et al., "Solid-State Chemistry of Drugs-Second Edition," SSCI Inc., Ch. 11, Hydrates and Solvates, 1999, pp. 233-247, West Layfayette, IN.

Cee, Victor J. et al., "Alkynylpyrimidine Amide Derivatives as Potent, Selective, and Orally Active Inhibitors of Tie-2 Kinase," J. Med. Chem. 2007, pp. 627-640, vol. 50:4.

"Chaper 4—Methods for Crystallization of Drugs: Handbook for Preparation of Organic Compound Crystals—Principles and Know-how," published on Jul. 25, 2008, pp. 57-59.

CN Search Report dated Apr. 10, 2014 for CN Application No. 201210427822.9, 2 pages.

Cortes et al., "A Phase 1 Trial of Oral Ponatinib (AP24534) in Patients with Refractory Chronic Myelogenous Leukemia (CML) and Other Hematologic Malignancies: Emerging Safety and Clinical Response Findings," American Society of Hematology (ASH), 2010, Abstract No. 210.

Definition of Isomer, Merriam-Webster Online Directory, http://www.merriam-webster.com/dictionary/isomer. Accessed Dec. 4, 2008.

Deng et al., "Broad Spectrum Alkynyl Inhibitors of T315I Bcr-Abl," Bioorganic & Medicinal Chem. Ltrs., 2010, pp. 4196-4200, vol. 20.

Dictionary of Cancer Terms, Nat'l Cancer Inst, at the Nat'l Institutes of Health for BCR-ABL fusion gene at http://www.cancer.gov/dictionary?CdrID=561237. Accessed Aug. 1, 2011.

Dorwald, "Side Reactions in Organic Synthesis: A Guide to Successful Synthesis Design," 2005, Weinhein: Wiley-Veh Verlag GmbH Co. KGaA; Preface.

English translation of Chinese Search Report issued in Chinese Patent Application No. 201380072027.5 dated Sep. 27, 2016, 2 pages.

English translation of First Office Action issued in Chinese Patent Application No. 201380072027.5 dated Oct. 10, 2016, 7 pages.

English translation of Notification of Reason for Rejection issued in Japanese Patent Application No. 2015-547524 dated Oct. 24, 2017, 4 pages.

English translation of Second Office Action issued in Chinese Patent Application No. 20138007207.5 dated Aug. 29, 2017, 3 pages.

EP Extended Search Report dated Feb. 10, 2010 for EP Application No. 06845939.5, 7 pages.

EP Extended Search Report dated Jul. 31, 2012 for EP Application No. 12169710.6, 10 pages.

Finn, "Targeting Src in Breast Cancer," Annals of Oconology, 2008, pp. 1379-1386, vol. 19(8).

Gozgit et al., "Ponatinib (AP24534), a Potent Pan-FGFR Inhibitor with Activity in Multiple FGFR-Driven Cancer Models with Distinct Mechnisims of Activation," American Assoc. for Cancer Research (AACR), 2011, Poster Abstract No. 3560.

Gozgit et al., "Potent Activity of Ponatinib (AP24534) in Models of FLT3-Driven Acute Myeloid Leukemia and Other Hematologic Malignancies," Molecular Cancer Therapeutics, 2011, pp. 1028-1035, vol. 10(6).

Gozgit et al., The Orally Active Kinase Inhibitor AP24534 has Potent Activity Against the FGF Receptor Family in Multiple Cancer Models American Assoc. for Cancer Research (AACR), 2009, Poster Abstract No. 1739.

Guillory, "Polymorphism in Pharmaceutical Solids," Ch. 5, Generation of Polymorphs, Hydrates, Solvates, and Amorphous Solids, 1999, vol. 95, pp. 183-226, Marcel Dekker Inc., New York.

Hiscox et al., "Src as a Therapeutic Target in Anti-Hormone/Anti Growth Factor-Resistant Breast Cancer," Endocrine-Related Cancer, 2006, pages S54-S59, vol. 13.

Huang et al., "Discovery of 3-[2-(lmidazo[1,2-b]pyridazin-3-yl)ethynl]-4-methyl-N-{4-[(4-methylpiperazin-1-yl)-methyl]-3-(trifluoromethyl)phenyl}benzamide (AP24534), a Potent, Orally Active Pan-Inhibitor of Breakpoint Cluster Region-Abelson (BCR-ABL) Kinase Including the T315I Gatekeeper Mutant," Journal of Medicinal Chemistry, 2010, pp. 4701-4719, vol. 53.

Huron et al., "A Novel Pyridopyrimidine Inhibitor of Abl Kinase is a Picomolar Inhibitor of Bcr-abl-driven K562 Cells and Is Effective Against STI571-Resistant Bcr-abl Mutants," 2003, Clinical Cancer Research, pp. 1267-1273, vol. 9.

International Search Report and Written Opinion dated May 23, 2014 for PCT/US2013/074571 filed Dec. 12, 2013, 15 pages.

International Search Report and Written Opinion dated May 27, 2014 for PCT/US2013/074585 filed Dec. 12, 2013, 16 pages.

International Search Report and Written Opinion dated Sep. 28, 2007 for PCT/US2006/048758 filed Dec. 22, 2006, 8 pages.

Jordan, "Tamoxifen: A Most Unlikely Pioneering Medicine," Nature Reviews: Drug Discovery, 2003, pp. 205-213, vol. 2.

Kendall et al., "Vascular Endothelial Growth Factor Receptor . . . Loop Tyrosine Residues," Journal of Biological Chemistry, 1999, pp. 6453-6460, vol. 274, No. 10.

Koziczak et al., "Blocking of FGFR Signaling Inhibits Breast Cancer Cell Proliferation through Downregulation of D-type Cyclins," Oncogene, 2004, pp. 3501-3508, vol. 23.

Maddox, "Crystals From First Principles," Nature, 1988, vol. 335, p. 201.

McMahon, "VEGF Receptor Signaling in Tumor Angiogenesis," The Oncologist 2000, pp. 3-10, vol. 5 (suppl 1).

Office Action issued in Mexican Patent Application No. MX/a/2015/007578 dated Aug. 3, 2017, 4 pages.

Office Action issued in Mexican Patent Application No. MX/a/2015/007578 dated May 8, 2017, 4 pages.

O'Hare et al., "AP24534, a Pan-BCR-ABL Inhibitor for Chronic Myeloid Leukemia, Potentially Inhibits the T315I Mutant and Overcomes Mutation-Based Resistance," Cancer Cell, 2009, pp. 401-412 and supplemental data, vol. 16.

O'Hare et al., "In Vitro Activity of BCR-ABL Inhibitors AMN107 and BMS-354825 Against Clinically Relevant Imatinib-Resistant ABL Kinase Domain Mutuants," Cancer Res, 2005, pp. 4500-4505, vol. 65(11).

Okamoto et al., "Identification of c-Src as a Potential Therapeutic Target for Gastric Cancer and of MET Activation as a Cause of Resistance to c-Src Inhibition," Molecular Cancer Therapeutics, 2010, pp. 1188-1197, vol. 9(5).

Pinedo et al., "Translational Research: The Role of VEGF in Tumor Angiogenesis," The Oncologist, 2000, pp. 1-2, vol. 5 (suppl 1).

Rivera et al., "Pharmacodynamics (PD) and Pharmacokinetics (PK) of Ponatinib (AP24534) in a Phase 1 Trial in Patients with Refractory Chronic Myeloid Leukemia (CML) and Hematologic Malignancies," European School of Hematology (ESH), 2010, Poster Abstract No. 42.

Talpaz et al., "Phase 1 Trial of AP24534 in Patients with Refractory Chronic Myeloid Leukemia (CML) and Hematologic Malignancies," American Society of Clinical Oncology (ASCO), 2010, Poster Abstract No. 6511.

Talpaz et al., "Ponatinib in Patients with Acute Myeloid Leukemia (AML): Preliminary Findings from a Phase 1 Study in Hematologic Malignancies," American Society of Clinical Oncology (ASCO), 2011, Poster Abstract No. 6518.

(56) References Cited

OTHER PUBLICATIONS

Vippagunta et al., "Crystalline Solids," Advanced Drug Delivery Reviews, 2001, pp. 3-26, vol. 48.
Wuts et al., "Greene's Protective Group in Organic Syntheses," 2007, pp. 927-929, J. Wiley & Sons, Fourth Edition (Retrieved from Internet on May 12, 2014 at URL http://users.ugent.be/~pespeel/Greene.pdf).
Zhou et al., "Structural Mechanism of the Pan-BCR-ABL Inhibitor Ponatinib (AP24534): Lessons for Overcoming Kinase Inhibitor Resistance," Chem Biol Drug Des, 2011, pp. 1-11, vol. 77.
Zhou et al., "Tumor Angiogenesis Correlated with bFGF and FGFR-1 in Lung Cancer," Chinese-German Journal of Clinical Oncology, 2005, pp. 93-98, vol. 4(2).
Zhu et al., "Structural Analysis of the Inhibitory Mechanism of AP24534, a Pan-BCR-ABL Inhibitor Overriding the T315I Gatekeeper Mutation," American Assoc. for Cancer Research (AACR), 2010, Poster Abstract No. 2671.

| Designation | Nature or Origin | Notes |
|---|---|---|
| Form A (HCl-1) | Anhydrate | Preferred form; single crystal X-ray structure |
| Form B (HCl2) | From water | Converts to HCl2b |
| Form C (HCl2b) | Trihydrate (from water/anti-solvent) | Single crystal X-ray structure |
| Form D (HCl3-class) | Solvate e.g., 0.5 eq. toluene; 0.5 eq. p-xylene | Single crystal X-ray structure |
| Form E (HCl4) | Only as mixture with HCl-1 | Converts to HCl-1 |
| Form F (HCl5-class) | Solvate e.g., 1.0 butyl acetate | — |
| Form G (HCl5 desolvate) | From desolvation of HCl5 | — |
| Form H (HCl6-class) | Solvate e.g., 1.0 eq. methanol;0.5 eq. methanol | — |
| Form I (HCl6 desolvate) | From desolvation of HCl6 | — |
| Form J (HCl7) | Pentahydrate (from water/antisolvent) | Single crystal X-ray structure |
| Form K (HCl8) | Solvate/hydrate 1.0 eq. trifluoroethanol, 0.75 eq. water | Single crystal X-ray structure |

Fig. 1

| Starting form[a] | Obtained form (Occurrence)[b] | Crystallization mode | Solvent (S), anti-solvent (AS) |
|---|---|---|---|
| Pure form | | | |
| HCl or Am[c] | Form A: HCl1 (128, 50.4%), wet (1, 0.4%) | cooling-evaporative, grinding, slurry, vapor diffusion onto solid, solubility assessment, crash crystallization with anti-solvent addition | Various solvents |
| HCl or Am | Form B: HCl2 (4, 1.5%) | cooling-evaporative, grinding, slurry, crash crystallization with anti-solvent addition | Water (S) Methanol, (AS) Water |
| HCl or Am | Form C: HCl2b (3, 1.2%), low yield (1, 0.4%), plus peaks (2, 0.8%) | grinding, slurry, solubility assessment, vapor diffusion onto solid, crash crystallization with anti-solvent addition | Water (S) DMSO, (AS) Water |
| HCl or Am | Form D: HCl3-Class (9, 3.5%) | cooling-evaporative, grinding, vapor diffusion onto solid | Toluene, chlorobenzene, methanol/acetonitrile 50:50, Toluene, o-xylene, Thiophene, Chlorobenzene |
| Am | Form E: HCl5 (1, 0.4%) | vapor diffusion onto solid | Butyl acetate |
| Am | Form F: HCl5b (1, 0.4%) | vapor diffusion onto solid | Butyl acetate (after drying) |
| Am | Form G: HCl6-Class (3, 1.2%), low yield (2, 0.8) | vapor diffusion onto solid, vapor diffusion into solution | Methanol (S) Methanol, (AS) Water, etc |
| HCl or Am | Am (19, 7.5%), Low crystalline | Freeze-drying, cooling-evaporative, vapor diffusion onto solid, crash crystallization with anti-solvent addition | TFE/water, methanol Cyclohexane, methanol/chloroform 50:50, heptane/cyclohexane 50:50, (S) Methanol, (AS) THF |
| Mixtures | | | |
| Am | HCl1+Am (3, 1.2%) | cooling-evaporative | Hexane, heptane, methylcyclohexane |
| Am | HCl3+Am (1, 0.4%) | vapor diffusion onto solid | 1,2-Dimethylcyclohexane |
| HCl or Am | HCl1+HCl3-Class (8, 3.1%) | cooling-evaporative grinding, vapor diffusion onto solid | 1,4-Dioxane, Trifluorotoluene, xylene, DCM, toluene, ethylene glycol dimethyl ether |
| HCl1 | Form H: HCl1+HCl4 (1, 0.4%) | grinding | Hexafluorobenzene |
| HCl1 | HCl1+HCl6-class (2, 0.8%) | crash crystallization with anti-solvent addition | (S) Methanol, (AS) 2-Methyltetrahydrofuran |

Fig. 2

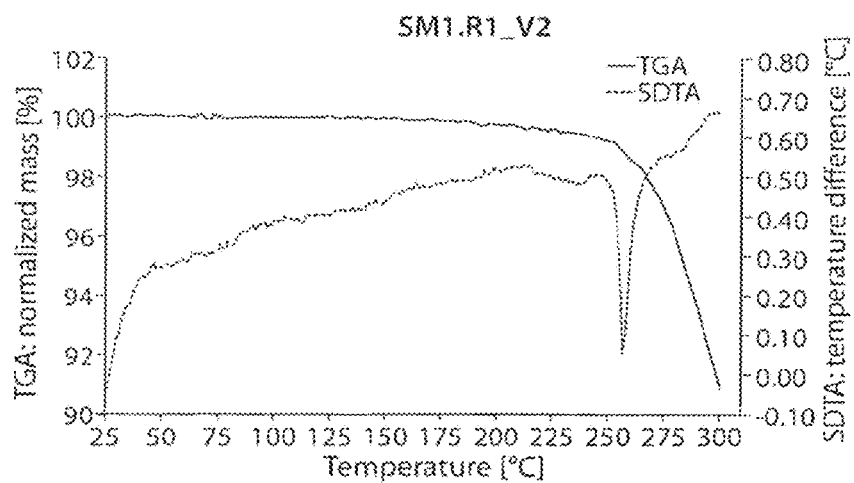
Fig. 6A
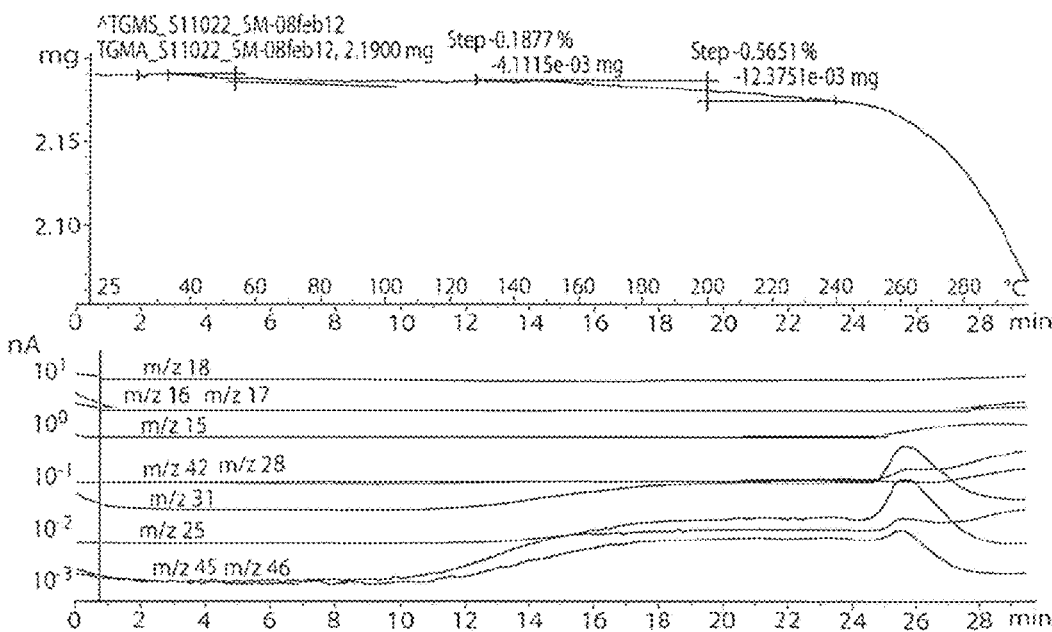
Fig. 6B
Fig. 6C

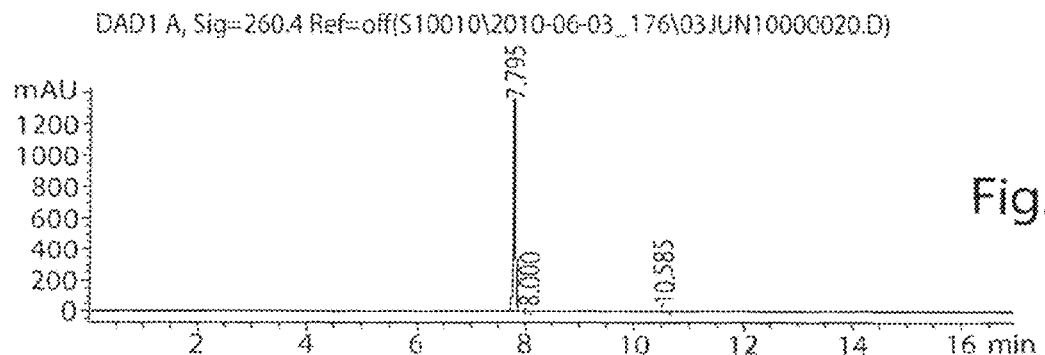
Fig. 14A
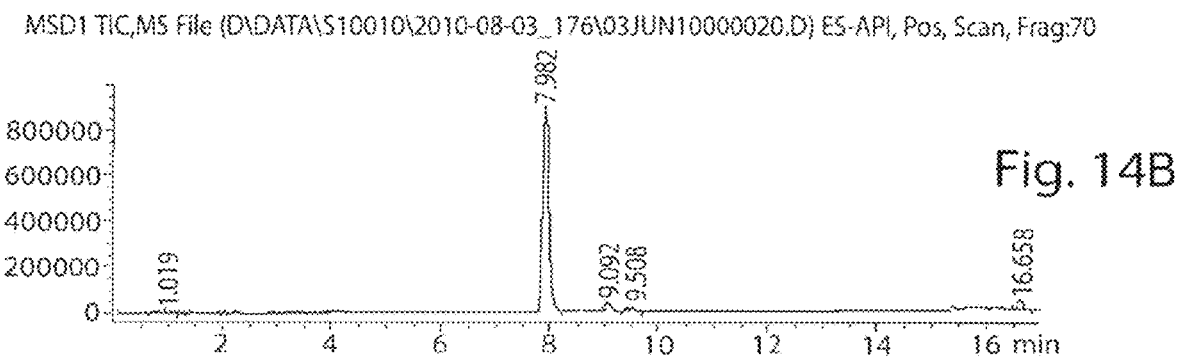
Fig. 14B
Area Percent Report
Sorted By         : Signal
Multiplier        : 1.0000
Dilution          : 1.0000
Use Multiplier & Dilution Factor with ISTDs
Fig. 14C
Signal 1: DAD1 A, Sig=260,4 Ref=off
| Peak # | Ret. Time [min] | Type | Width [min] | Area [mAU*s] | Height [mAU] | Area % |
|---|---|---|---|---|---|---|
| 1 | 7.795 | BV | 0.0380 | 3398.07788 | 1368.11536 | 99.8160 |
| 2 | 8.000 | VB | 0.0567 | 3.87636 | 9.69407e-1 | 0.1139 |
| 3 | 10.585 | BB | 0.0415 | 2.38806 | 8.84484e-1 | 0.0701 |
Totals :                          3404.34230  1369.96925

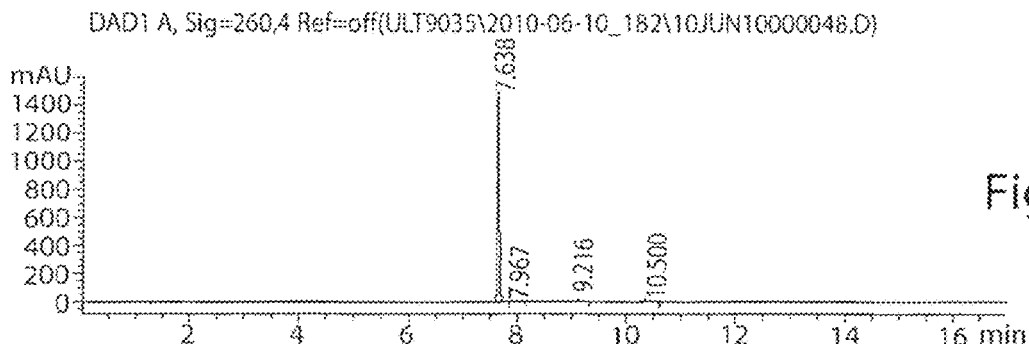
Fig. 16A
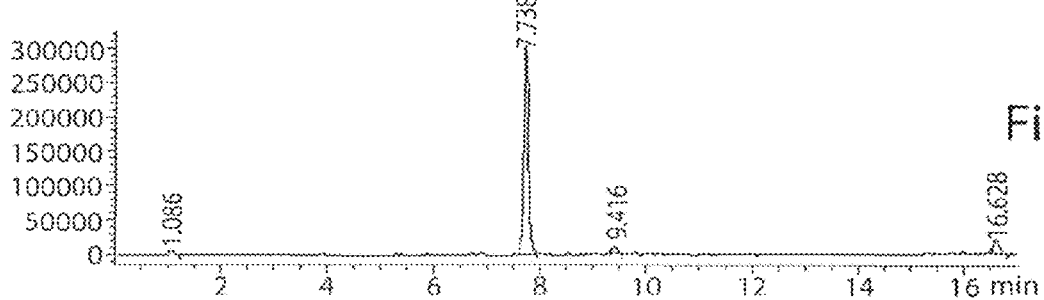
Fig. 16B
Area Percent Report
Sorted By       : Signal
Multiplier      : 1.0000
Dilution        : 1.0000
Use Multiplier & Dilution Factor with ISTDs
Signal 1: DAD1 A, Sig=260,4 Ref=off
Fig. 16C
| Peak # | Ret. Time [min] | Type | Width [min] | Area [mAU*s] | Height [mAU] | Area % |
|---|---|---|---|---|---|---|
| 1 | 7.638 | BB | 0.0385 | 3886.57593 | 1539.14441 | 99.7535 |
| 2 | 7.967 | BB | 0.0880 | 4.24789 | 6.27617e-1 | 0.1090 |
| 3 | 9.216 | BB | 0.0459 | 2.00765 | 6.52805e-1 | 0.0515 |
| 4 | 10.500 | BB | 0.0531 | 3.34889 | 9.50049e-1 | 0.0860 |
Totals: 3896.18036 1541.37488

DSC thermogram of QSA21.1 with endothermic events at $T_{peak} = 122.9°C$, $T_{peak} = 158.2°C$ and $T_{peak} = 256.2°C$.

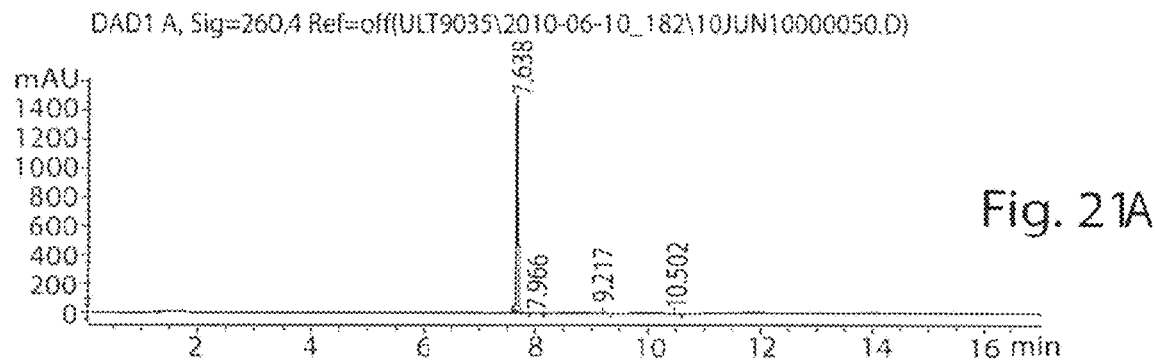
Fig. 21A
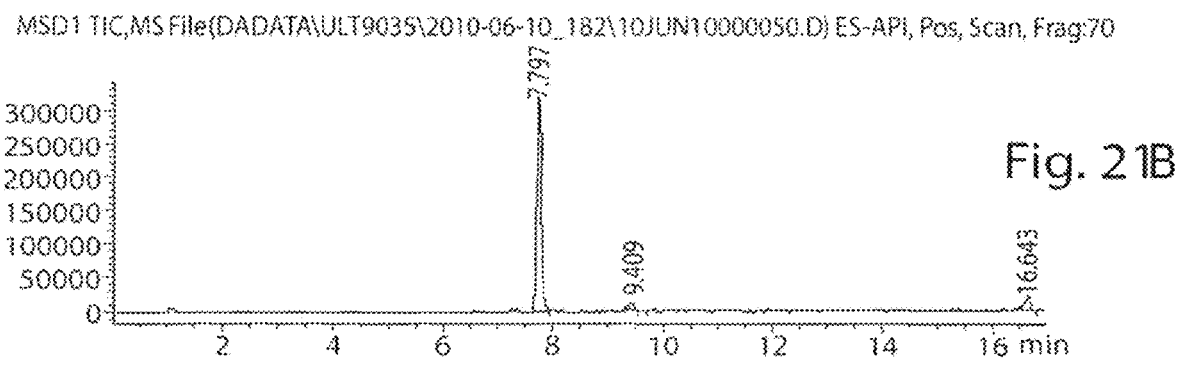
Fig. 21B
Area Percent Report
Sorted By        :  Signal
Multiplier       :  1.0000
Dilution         :  1.0000
Use Multiplier & Dilution Factor with ISTDs
Fig. 21C
Signal 1: DAD1 A, Sig=260,4 Ref=off
| Peak # | Ret. Time [min] | Type | Width [min] | Area [mAU*s] | Height [mAU] | Area % |
|---|---|---|---|---|---|---|
| 1 | 7.638 | BB | 0.0385 | 3838.75879 | 1519.24438 | 99.7850 |
| 2 | 7.966 | BB | 0.0841 | 4.21857 | 6.55231e-1 | 0.1097 |
| 3 | 9.217 | BB | 0.0400 | 1.58020 | 6.15402e-1 | 0.0411 |
| 4 | 10.502 | BB | 0.0423 | 2.47093 | 8.93274e-1 | 0.0642 |
Totals :                3847.02849   1521.40829

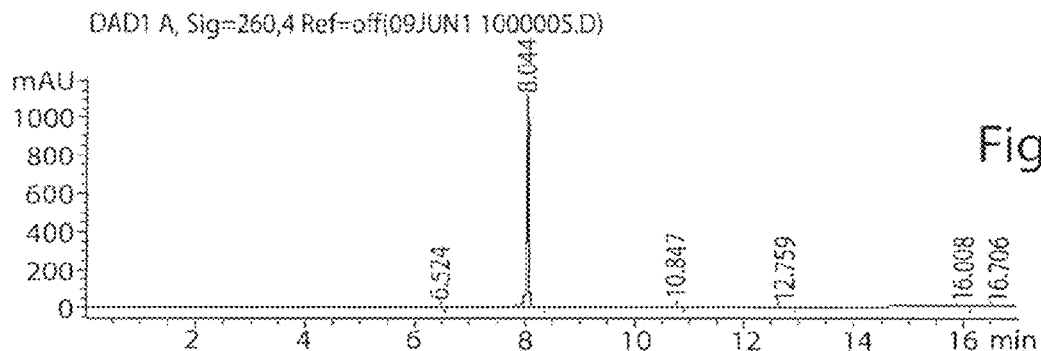
Fig. 26A
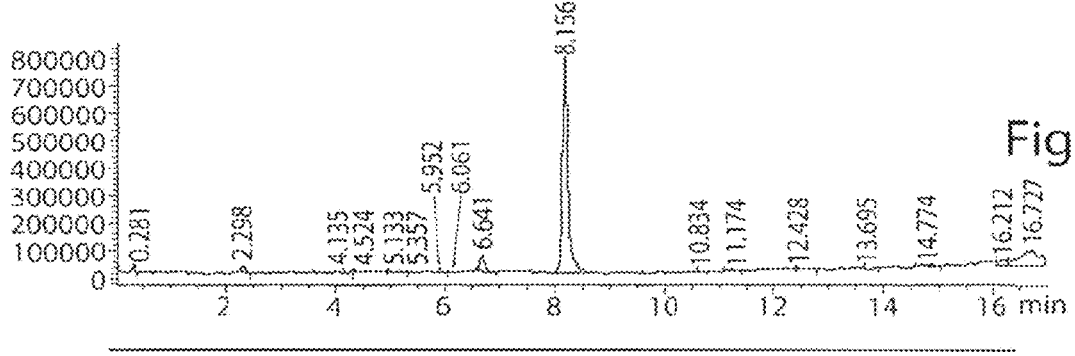
Fig. 26B
Area Percent Report
Sorted By          :  Signal
Multiplier         :  1.0000
Dilution           :  1.0000
Use Multiplier & Dilution Factor with ISTDs
Signal 1: DAD1 A, Sig=260,4 Ref=off
Fig. 26C
| Peak # | Ret. Time [min] | Type | Width [min] | Area [mAU*s] | Height [mAU] | Area % |
|---|---|---|---|---|---|---|
| 1 | 6.524 | BV | 0.0395 | 2.01668 | 7.97950e-1 | 0.0640 |
| 2 | 8.044 | BB | 0.0403 | 3069.08374 | 1145.24390 | 97.3664 |
| 3 | 10.847 | BB | 0.0444 | 2.10735 | 7.15527e-1 | 0.0669 |
| 4 | 12.759 | BB | 0.0972 | 10.23136 | 1.62982 | 0.3246 |
| 5 | 16.008 | BB | 0.1324 | 10.24474 | 1.04493 | 0.3250 |
| 6 | 16.706 | BBA | 0.2486 | 58.41394 | 2.96862 | 1.8532 |
Totals :                            3152.09780   1152.40074

VDS3.1R2

VDS4.2R6_V1

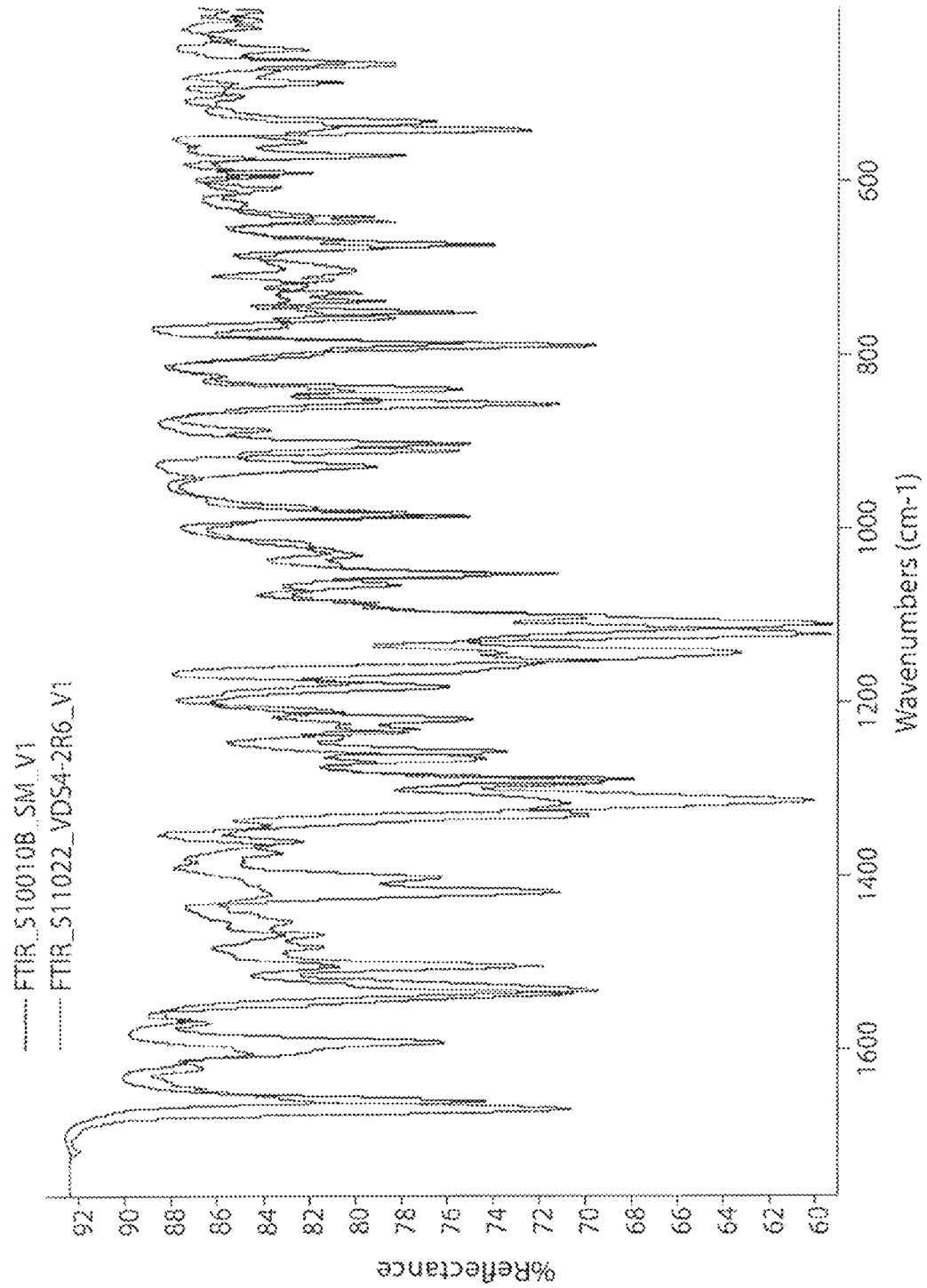

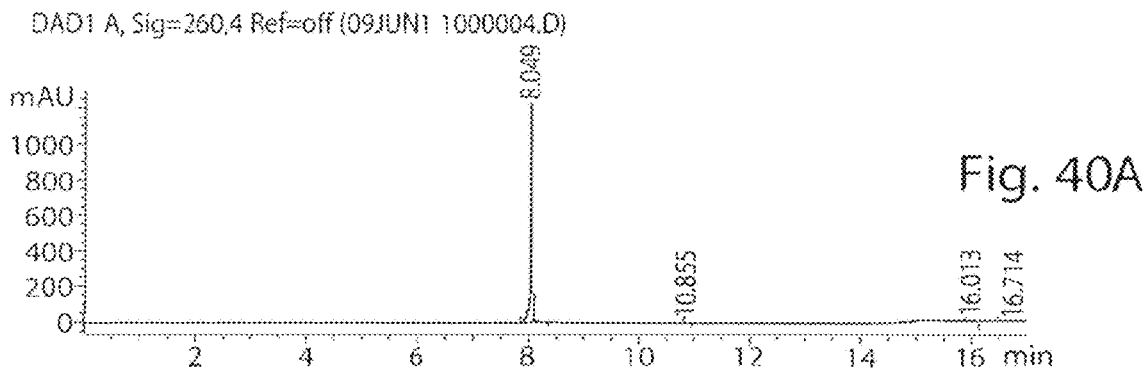
Fig. 40A
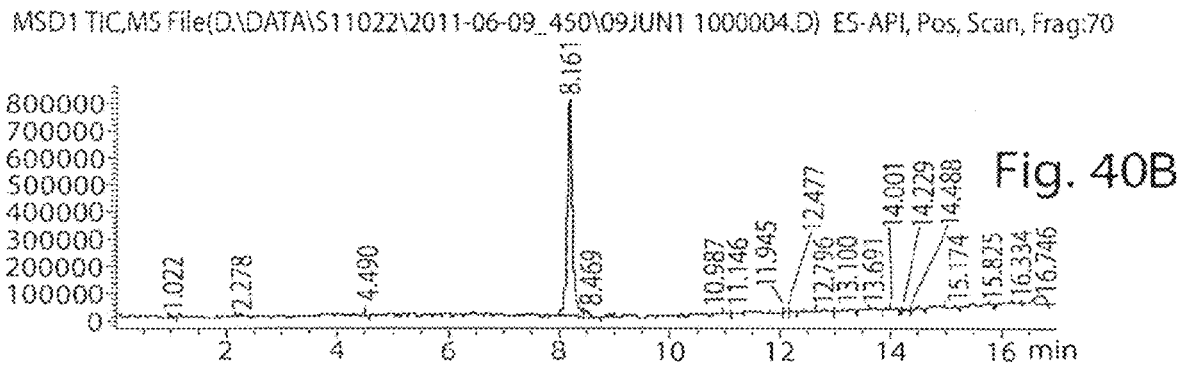
Fig. 40B
Area Percent Report
Sorted By         : Signal
Multiplier        : 1.0000
Dilution          : 1.0000
Use Multiplier & Dilution Factor with ISTDs
Fig. 40C
Signal 1: DAD1 A, Sig=260,4 Ref=off
| Peak # | Ret. Time [min] | Type | Width [min] | Area [mAU*s] | Height [mAU] | Area % |
|---|---|---|---|---|---|---|
| 1 | 8.049 | BB | 0.0414 | 3317.56738 | 1233.95715 | 97.9794 |
| 2 | 10.855 | BB | 0.0433 | 2.28550 | 7.99987e-1 | 0.0675 |
| 3 | 16.013 | BB | 0.1223 | 9.62147 | 1.00871 | 0.2842 |
| 4 | 16.714 | BBA | 0.2424 | 56.51128 | 2.88619 | 1.6690 |
Totals: 3385.98564  1238.65205

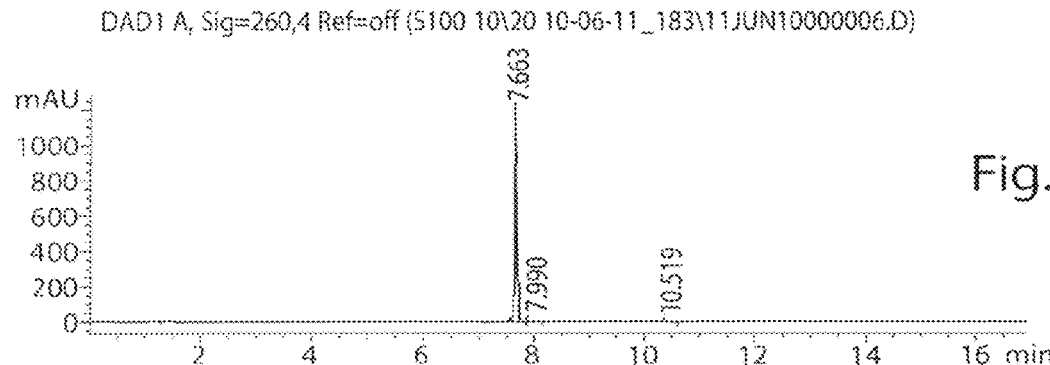
Fig. 47A
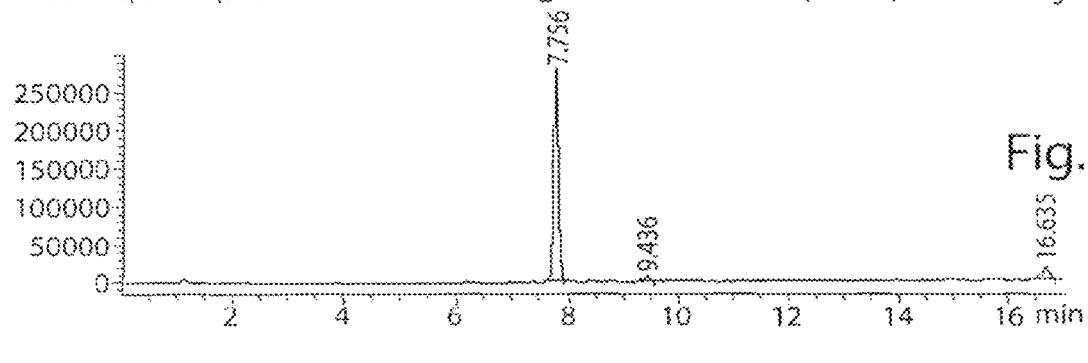
Fig. 47B
Area Percent Report
Sorted By       : Signal
Multiplier      : 1.0000
Dilution        : 1.0000
Use Multiplier & Dilution Factor with ISTDs
Fig. 47C
Signal 1: DAD1 A, Sig=260,4 Ref=off
| Peak # | Ret. Time [min] | Type | Width [min] | Area [mAU*s] | Height [mAU] | Area % |
|---|---|---|---|---|---|---|
| 1 | 7.663 | BB | 0.0394 | 3142.24609 | 1247.80469 | 99.7877 |
| 2 | 7.990 | BB | 0.0822 | 3.60784 | 5.91085e-1 | 0.1146 |
| 3 | 10.519 | BB | 0.0556 | 3.07647 | 7.86388e-1 | 0.0977 |
Totals :  3148.93041  1249.18216

| Starting form[e] | Obtained form[a] (Occ)[c] | Cryst. Mode[b] | Solvent (S), anti-solvent (AS) |
|---|---|---|---|
| Pure forms | | | |
| A or LC | Form A (136, 53.7%), low yield (6, 2.4%), wet (6, 2.4%), PO[d] (8, 3.2%) | PSM, AS, GRP, SLP, QSA, VDL, VDS | Various solvents |
| A or LC | B-Class of forms (28, 11.1%), low yield (2, 0.8%), PO (3, 1.2%), wet (5, 2.0%) | PSM<br>AS<br>GRP<br>SLP, VDS<br>QSA<br>VDL | 1,4-Dioxane, 1,4-dioxane/cyclohexane 50:50<br>(S) THF, 1,4-dioxane, etc, (AS) cyclohexane, chloroform, etc<br>1,4-Dioxane, toluene, cyclohexanone<br>1,4-dioxane<br>Cyclohexanone, 2-methylTHF<br>(S) 1,4-Dioxane, THF, 2-methylTHF, propionitrile, (AS) Fluorobenzene, etc |
| A | C Low crystalline | QSA | Methanol |
| A | Form D (5, 2.0%), low yield (3, 1.2%) | AS<br><br>QSA<br>VDL | (S) Butylacetate, diethyleneglycol dimethylether, etc, (AS) Water, cumene, etc<br>DMA<br>(S) Butyronitrile, (AS) Chlorobenzene |
| A or LC | E-Class of forms (5, 2.0%) | SLP, VDS<br>QSA | THF, Chloroform<br>THF, DCM |
| A | Form F (10, 3.9%), low yield (1, 0.4%), wet (2, 0.8%), plus peak (1, 0.4%) | AS<br>GRP<br>SLP<br>VDL | (S) Acetone, methanol, 4-hydroxy-4-methyl-2-pentanone, etc, (AS) Water<br>Hexafluorobenzene, cyclohexane, diethoxyethane<br>1,2-Dimethoxyethane<br>(S) Methanol, (AS) Water |
| A | Form G (1, 0.4%) | AS | (S) 3-Methyl-1-butanol, (AS) Cyclohexane |
| A | Form H (1, 0.4%) | VDL | (S) 2-Methoxyethanol, (AS) Water |
| A | Form I Low crystalline (1, 0.4%) | FD | DCM |
| LC | Form J Low crystalline (2, 0.8%) | VDS | Thiophene |
| LC | Am Form (1, 0.4%) | VDS | 2,2,2-Trifluoroethanol |
| Mixtures | | | |
| A or LC | A+B-Class (11, 4.3%) | AS<br>SLP<br>VDL<br>VDS | (S) 1,4-dioxane, THF, etc, (AS) chloroform, toluene, etc<br>Toluene<br>(S) Ethylformate, THF, (AS) Chloroform, Cyclohexane<br>Chlorobenzene |
| A | A+C low crystalline (1, 0.4%) | SLP | Methanol |
| A | A+D (1, 0.4%) | AS | (S) Ethylformate, (AS) Chloroform |
| A | A+E-class (1, 0.4%) | VDS | 1,2-Dichloroethane |
| A or LC | A+F (6, 2.4%) | PSM<br>AS<br>SLP, VDS | Water,<br>(S) 2-Methoxyethanol, (AS) water<br>Water |
| A | B-Class+D (2, 0.8%) | AS | (S) Cyclohexanone, (AS) Water, diethylcarbonate |

Fig. 48

| Polymorphic form | Occurrence[a] | Crystallization solvent/mode[b] | Form nature[c] | Endotherms (°C)[d] | Purity (%)[e] |
|---|---|---|---|---|---|
| Form A[f] | 156, 66.4% | Various/All | Anhydrate | 199.6 | 99.5 |
| B[f]-Class of forms (isomorphic solvate) | 38, 16.2% | 1,4-Dioxane/AS, GRP, SLP | Cyclohexanone solvate (1:1) | 110.0, 198.6 | 99.7 |
| | | | 2-MethylTHF solvate (1:0.4) | 87.1, 197.5 | 99.6 |
| C Low crystalline | 1 | Methanol/SLP | Contains methanol (1:0.2) | 95.9, 198.1 | 99.5 |
| Form D | 8, 3.2% | DMA/AS | DMA solvate (1:1) | 103.3, 125.6, 198.4 | 99.5 |
| Form E-Class of forms | 5, 2.0% | THF/SLP | THF solvate (1:1) | 95.9, 198.1 | 99.5 |
| Form F | 14, 6.0% | 1,2-Dimethoxyethane/SLP | Hydrate (1:1) | 100, 130 (exo), 189[h] | Nd |
| Form G | 1, 0.6% | 3-Methyl-1-butanol/AS | Nd[g] | Nd | Nd |
| Form H | 1, 0.6% | 2-Methoxyethanol/VDL | Nd | Nd | Nd |
| Form I Low crystalline | 1, 0.6% | DCM / freeze-drying | Contains DCM (1:0.03) | 196.7 | 99.6 |
| Form J Low crystalline | 2, 1.2% | Thiophene/VDS | Nd | Nd | Nd |

[a] Occ: the total occurrence included 192 experiments carried out in Phase 4 for which 61 samples were analyzed additionally wet or the mother liquor was evaporated and analyzed giving a total of 253 materials characterized. For example, "(2, 1.2%)" correspond to 2 occurrences of the form out of 253 measurements, giving a percentage of 1.2%. For 4 out of the 253 measurements (1.6%), the product yield or the scattering intensity of some products was too low to identify the solid form, or the materials were wet.
[b] Crystallization modes: cooling-evaporative (PSM), crash crystallization with anti-solvent addition (AS), grinding (GRP), slurry (SLP), vapour diffusion onto solid (VDS) and vapour diffusion into solution (VDL).
[c] Solvation state assessed from the TGMS results
[d] Melting point assessed from the DSC results
[e] Chemical purity assessed from HPLC results
[f] Structure determined by single crystal analysis
[g] Not determined
[h] Assessed from TGMS/SDTA data

Fig. 49

| Solid form[a] | Crystallization mode | Form nature[b] | Form after 10 months |
|---|---|---|---|
| A | - | Anhydrate | A |
| B-class | cooling/evaporation<br>anti-solvent<br>grinding<br>slurry, vapor onto solid<br>evaporation<br>vapor into liquid | Isomorphic solvates | A |
| C "low crystalline" | evaporation | Residual solvent | Not conclusive (low yield) |
| D | anti-solvent[c]<br>qsas[c]<br>vapor into liquid[c] | Isomorphic solvates, DMA solvate (1:1) confirmed | D |
| E-class | slurry, vapor onto solid<br>evaporation<br>anti-solvent | THF solvates (1:1) | A |
| F | grinding<br>slurry<br>vapor into liquid | Hydrate (1:1) | F |
| G | anti-solvent | Nd | A |
| H | vapor into liquid | Nd | A |
| I-"low crystalline" | freeze drying | Residual solvent | A |
| J-"low crystalline" | vapor onto solid | Nd | A |

[a] As classified by XRPD after completion of the crystallization experiments in S10010A.
[b] Solvation state assessed from the TGMS results. Nd = not determined
[c] Solvents involved: DMA, N,N-Dimethylformamide, tert-amylalcohol, butyronitrile, diethyleneglycol-dimethylether, chlorobenzene, water, p-xylene, cumene.

Fig. 89

| Targeted Form | Crystallization method | Solvent (AS) | Anti-solvent | Form obtained |
|---|---|---|---|---|
| G | Anti-solvent addition | 1-Methyl 3-Butanol | Cyclohexane | A |
| | | 1-Methyl 3-Butanol | Cyclohexane | A |
| | | 1-Methyl 3-Butanol | Cyclohexane | A |
| | | 1-Methyl 3-Butanol | Cyclohexane | A |
| H | Vapor diffusion into liquids | 2-Methoxyethanol | Water | H |
| | | 2-Methoxyethanol | Water | H |
| J-"low crystalline" | Vapor diffusion onto solids | Thiophene | | J-"low crystalline" |
| | | Thiophene | | J-"low crystalline" |
| | | Thiophene | | J-"low crystalline" |
| | | Thiophene | | J-"low crystalline" |

Fig. 90

| Exp ID | Form[1] | Form nature[6] | Endotherm[1] (°C) -Mass loss %[5] (°C) | Purity[2] (%) | FTIR (cm⁻¹)[7] | Physical stability[4] 1 w/ stress[2] | Physical stability[4] 10 m/ ambient[3] | DVS results[9] | Form[1] obtained after DVS |
|---|---|---|---|---|---|---|---|---|---|
| Starting material | A | Anhydrate | 189.6 -residual solvents 0.9 (25-210) | 99.5 | 1496, 1416, 1329, 1292, 1280, 1265, 1250, 1168, 1152, 1142, 1108, 1052, 1013, 896, 852, 790, 737 | - | A | - | - |
| VDL1 | H | 2-Methoxyethanol solvate (1:0.93) | 96.1, 198.8 -2-Methoxyethanol 11.7 (60-120) | 98.0 | 1678, 1508, 1319, 1301, 1281, 1169, 1117, 1104, 1055, 915, 798 | A | A | 3.6% | H |
| VDS2 | J | Thiophene solvate (1:0.32) | 83.7, 197.3 -Thiophene 11.4 (40-130) | 96.5 | 1672, 1541, 1322, 1281, 1162, 1152, 1110, 1054, 794, 726 | A | A | 1.1% | A |

[1] Forms as assessed by XRPD
[2] Stability study: the samples obtained in this study were exposed at 40°C, 75% RH for one week before to be re-analyzed by XRPD.
[3] Stability study: a selection of samples obtained in project S1010A were re-analyzed by XRPD after being stored at ambient conditions for 10 months.
[4] Endotherms assessed by DSC analysis.
[5] Mass loss determined by TGMS analysis (temperature range).
[6] Solvation state assessed from the TGMS results (API/solvent ratio).
[7] FTIR differences observed compared to the starting material free base.
[8] Chemical purity (area percentage) assessed by HPLC.
[9] Water uptake at maximum relative humidity (95% RH). The reversibility of the mass uptake, sample appearance and physical stability of the solid form is indicated following the DVS cycling.

Fig. 91

CRYSTALLINE FORMS OF 3-(IMIDAZO[1,2-B]PYRIDAZIN-3-YLETHYNYL)-4-METHYL-N-{4-[(4-METHYLPIPERAZIN-1-YL)METHYL]-3-(TRIFLUOROMETHYL)PHENYL} BENZAMIDE AND ITS MONO HYDROCHLORIDE SALT

CROSS-REFERENCE TO RELATED APPLICATIONS

This application is a continuation of U.S. application Ser. No. 16/146,143, filed Sep. 28, 2018, and issued as U.S. Pat. No. 10,066,197, which is a division of U.S. patent application Ser. No. 15/341,898, filed Nov. 2, 2016, and issued as U.S. Pat. No. 10,125,136, which is a division of U.S. patent application Ser. No. 14/651,577, filed Jun. 11, 2015, and issued as U.S. Pat. No. 9,493,470, which is a § 371 national stage entry of International Application No. PCT/US2013/074571, filed Dec. 12, 2013, which claims priority to U.S. Provisional Patent Application No. 61/736,543, filed Dec. 12, 2012; U.S. Provisional Patent Application No. 61/737,007, filed Dec. 13, 2012; and U.S. Provisional Patent Application No. 61/788,208, filed Mar. 15, 2013, which are incorporated herein by reference in their entireties.

BACKGROUND

The instant application is directed to novel crystalline forms of 3-(imidazo[1,2-b]pyridazin-3-ylethynyl)-4-methyl-N-{4-[(4-methylpiperazin-1-yl)methyl]-3-(trifluoromethyl)phenyl}benzamide and 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride, compositions comprising such crystalline forms, and to methods of their preparation and use.

3-(Imidazo[1,2-b]pyridazin-3-ylethynyl)-4-methyl-N-{4-[(4-methylpiperazin-1-yl)methyl]-3-(trifluoromethyl)phenyl}benzamide has the chemical formula $C_{29}H_{27}F_3N_6O$ which corresponds to a formula weight of 532.56 g/mol. Its chemical structure is shown below:

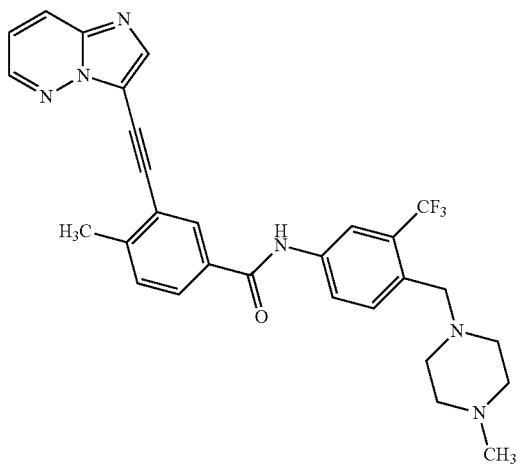 [SMILES: Cc1ccc(C(=O)Nc2ccc(CN3CCN(C)CC3)c(C(F)(F)F)c2)cc1C#Cc1cnc2cccnn12]

The CAS Registry number for 3-(imidazo[1,2-b]pyridazin-3-ylethynyl)-4-methyl-N-{4-[(4-methylpiperazin-1-yl)methyl]-3-(trifluoromethyl)phenyl}benzamide is 943319-70-8. 3-(Imidazo[1,2-b]pyridazin-3-ylethynyl)-4-methyl-N-{4-[(4-methylpiperazin-1-yl)methyl]-3-(trifluoromethyl)phenyl}benzamide mono hydrochloride has the chemical formula $C_{29}H_{28}ClF_3N_6O$ which corresponds to a formula weight of 569.02 g/mol. Its chemical structure is shown below:

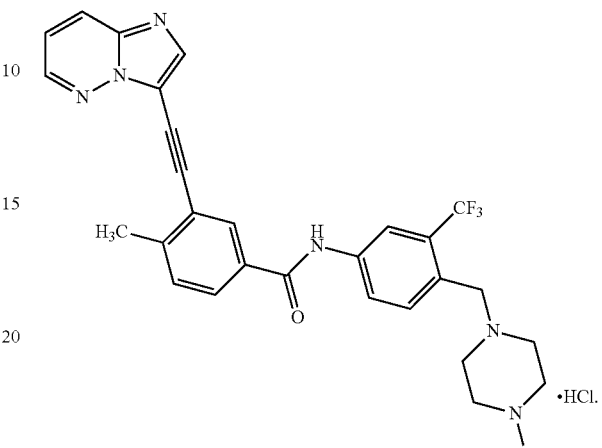

The CAS Registry number for 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride is 1114544-31-8.

The United States Adopted Name (USAN) and International Nonproprietary Name (INN) of 3-(imidazo[1,2-b]pyridazin-3-ylethynyl)-4-methyl-N-{4-[(4-methylpiperazin-1-yl)methyl]-3-(trifluoromethyl)phenyl}benzamide is ponatinib. Alternative chemical names for ponatinib include benzamide, 3-(2-imidazo[1,2-b]pyridazin-3-ylethynyl)-4-methyl-N-[4-[(4-methyl-1-piperazinyl)methyl]-3-(trifluoromethyl)phenyl] and 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide.

The United States Adopted Name (USAN) and International Nonproprietary Name (INN) of 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride is ponatinib hydrochloride. Alternative chemical names for ponatinib hydrochloride include benzamide, 3-(2-imidazo[1,2-b]pyridazin-3-ylethynyl)-4-methyl-N-[4-[(4-methyl-1-piperazinyl)methyl]-3-(trifluoromethyl)phenyl]-, hydrochloride (1:1) and 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide monohydrochloride.

Ponatinib is a multi-targeted tyrosine-kinase inhibitor useful for the treatment of chronic myeloid leukemia (CML) and other diseases. Ponatinib hydrochloride is a small molecule pan-BCR-ABL inhibitor in clinical development for the treatment of adult patients with chronic phase, accelerated phase, or blast phase CML or Philadelphia chromosome positive acute lymphoblastic leukemia (Ph+ALL) resistant or intolerant to prior tyrosine-kinase inhibitor therapy. Other tyrosine-kinase inhibitors relevant to such CML or Ph+ALL therapy include GLEEVEC® (imatinib mesylate) and TASIGNA® (nilotinib) (both from Novartis AG), SPRYCEL® (dasatinib) (from Bristol Myers Squibb Company) and BOSULIF® (bosutinib) (from Pfizer Inc). A New Drug Application (NDA) for ponatinib hydrochloride was filed with the United States FDA on Jul. 30, 2012. The US FDA approved the NDA on Dec. 14, 2012, and ponatinib hydrochloride is marketed under the brand name ICLUSIG® (ponatinib).

In addition, ponatinib hydrochloride is potentially clinically useful for the treatment of other disorders or conditions implicated by the inhibition of other protein kinases. Such kinases and their associated disorders or conditions are mentioned in O'Hare, T., et al., Cancer Cell, Volume 16, Issue 5, 401-412 (2009) and WO 2011/053938, both of which are hereby incorporated herein by reference for all purposes.

Having an understanding of the potential polymorphic forms for active pharmaceutical ingredients (API) such as ponatinib and ponatinib hydrochloride is useful in the development of drugs. This is because not knowing the specific polymorphic form present or desired in the API may result in inconsistent manufacturing of the API and as a result, results with the drug may vary between various lots of the API. In addition, it is important to discover the potential polymorphic forms of an API so that one can systematically determine the stability of that form over a prolonged period of time for similar reasons. Once a specific polymorphic form is selected for pharmaceutical development, it is important to be able to reproducibly prepare that polymorphic form. It is also desirable for there to be a process for making APIs such as ponatinib and ponatinib hydrochloride in high purity due to the potential for impurities to affect the performance of the drug.

The earliest patent publication known by Applicant to disclose the chemical structure of ponatinib hydrochloride is WO 2007/075869, which is also owned by Applicant (ARIAD Pharmaceuticals, Inc.) and is hereby incorporated herein by reference for all purposes. Example 16 of WO 2007/075869 states that the product was obtained as a solid: 533 m/z (M+H). This mass corresponds to the free base of ponatinib. Example 16 also discusses the preparation of a mono hydrochloride salt of ponatinib. Example 16 neither specifically mentions that the ponatinib hydrochloride obtained was crystalline, nor specifies any particular crystalline forms of ponatinib hydrochloride.

U.S. Ser. No. 11/644,849, which published as US 2007/0191376, is a counterpart application to WO 2007/075869 and granted on Feb. 14, 2012 as U.S. Pat. No. 8,114,874, which is hereby incorporated herein by reference for all purposes. U.S. Ser. No. 13/357,745 is a continuing application of U.S. Ser. No. 11/644,849, which also is hereby incorporated herein by reference for all purposes.

Additional patent applications owned by Applicant that cover ponatinib hydrochloride and published as of the filing date of this application include WO 2011/053938 and WO 2012/139027, both of which are hereby incorporated herein by reference for all purposes. Like WO 2007/075869, neither of WO 2011/053938 or WO 2012/139027 specifies any particular crystalline forms of ponatinib hydrochloride.

SUMMARY

It has now been discovered that both ponatinib and ponatinib hydrochloride can exist in certain crystalline and other polymorphic forms, certain of which are suitable for pharmaceutical formulation development.

In one aspect, the present disclosure is directed to polymorphs of ponatinib. The polymorphs of ponatinib are herein designated as Form A, Form B, Form C, Form D, Form E, Form F, Form G, Form H, Form I, Form J, and Form K.

In another aspect, the present disclosure is directed to pharmaceutical compositions comprising a therapeutically effective amount of a polymorph of ponatinib disclosed herein and at least one pharmaceutically acceptable carrier, vehicle or excipient.

In another aspect, the present disclosure is directed to substantially pure crystalline forms of ponatinib hydrochloride. The substantially pure crystalline forms of ponatinib hydrochloride are herein designated as Form A, Form B, Form C, Form D, Form E, Form F, Form G, Form H, Form I, Form J, and Form K.

In another aspect, the present disclosure is directed to pharmaceutical compositions comprising a therapeutically effective amount of a substantially pure crystalline form of ponatinib hydrochloride disclosed herein and at least one pharmaceutically acceptable carrier, vehicle or excipient.

In another aspect, the present disclosure provides a process for preparing a substantially pure crystalline form of ponatinib hydrochloride by contacting ponatinib with hydrochloric acid.

In another aspect, the present disclosure is directed to a method of treating a disorder or condition in a human that responds to the inhibition of a protein kinase by administering to the human a therapeutically effective amount of a polymorph of ponatinib disclosed herein. In certain embodiments, the disorder or condition is chronic myeloid leukemia (CML).

In another aspect, the present disclosure is directed to a method of treating a disorder or condition in a human that responds to the inhibition of a protein kinase by administering to the human a therapeutically effective amount of a substantially pure crystalline form of ponatinib hydrochloride disclosed herein. In certain embodiments, the disorder or condition is chronic myeloid leukemia (CML) or Philadelphia chromosome-positive acute lymphoblastic leukemia (Ph+ALL) when the protein kinase is Bcr-Abl or a mutant form thereof.

BRIEF DESCRIPTION OF THE DRAWINGS

The following drawings form part of the present specification and are included to further demonstrate certain aspects of the present inventions. The inventions may be better understood by reference to one or more of these drawings in combination with the detailed description of specific embodiments presented herein.

FIG. 1 is a summary of the eleven solid forms of ponatinib hydrochloride that include HCl polymorphs and pseudopolymorphs that are identified as Forms A through K and that were discovered and are disclosed herein.

FIG. 2 is a summary of certain of the solid forms of ponatinib hydrochloride identified in FIG. 1 that were discovered and are disclosed herein. The legend for FIG. 2 is as follows:

[a] Starting material: Form HCl1 or amorphous material (Am) obtained by freeze-drying.

[b] OCC: the total occurrence included 216 experiments carried out in Phase 2 (described in Example 1 herein) for which 39 samples were analyzed additionally wet or the mother liquor was evaporated and analyzed giving a total of 254 materials characterized. For example, "(3, 1.2%)" correspond to 3 occurrences of the form out of 254 measurements, giving a percentage of 1.2%. For 62 out of the 254 measurements (9%), the product yield was too low to identify the solid form, or the materials were wet.

[d] Am: amorphous form.

Figure 3:
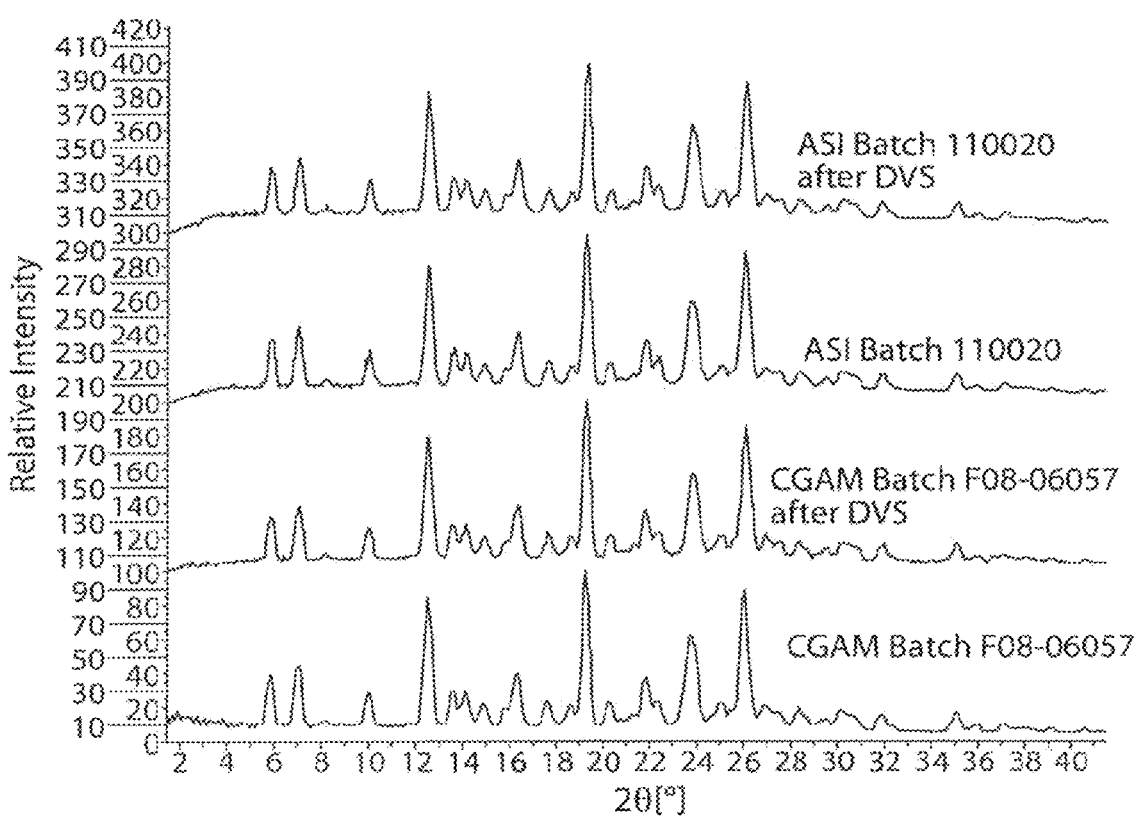

FIG. 3 is a characteristic X-ray powder diffraction (XRPD) pattern of two batches of Form A of ponatinib hydrochloride in which the data for each batch was acquired prior to and after DVS humidity cycling. Relative Intensity (in counts) is shown on the vertical axis and the degrees (2θ) is shown on the horizontal axis.

Figure 4:
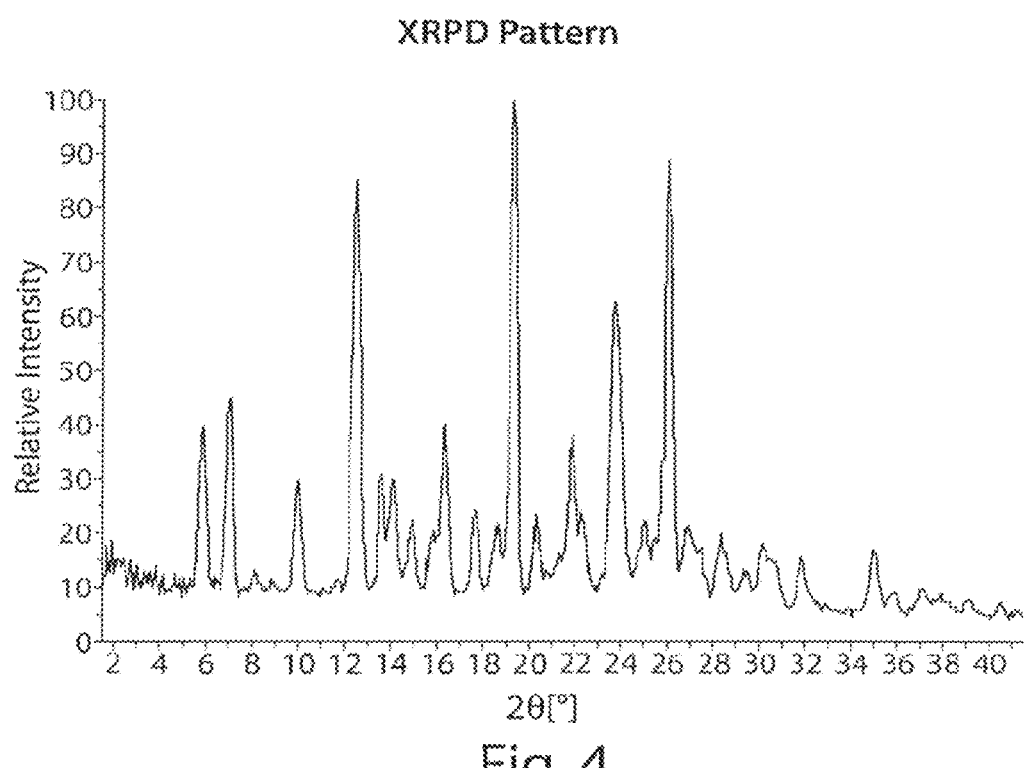

FIG. 4 is a characteristic X-Ray Powder Diffraction (XRPD) pattern obtained from Form A of ponatinib hydrochloride. Relative Intensity (in counts) is shown on the vertical axis and the degrees (2θ) is shown on the horizontal axis.

Figure 5:
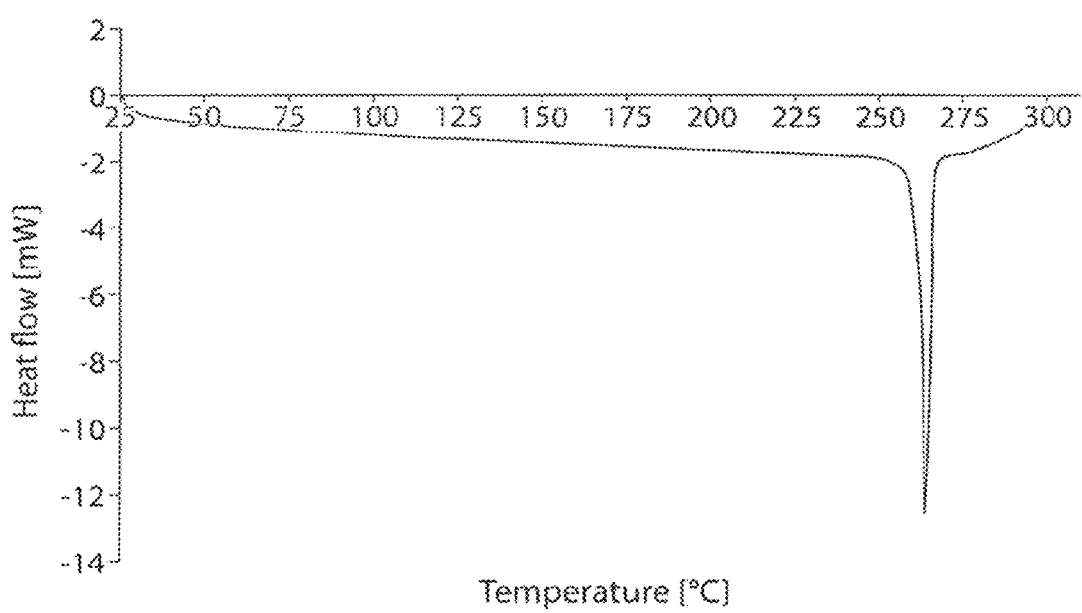

FIG. 5 is a characteristic differential scanning calorimetry (DSC) scan obtained from Form A of ponatinib hydrochloride. Heat flow [mW] is shown on the vertical axis and temperature (° C.) is shown on the horizontal axis.

FIG. 6A is a characteristic thermogravimetric analysis (TGA) and FIG. 6B and FIG. 6C are a thermogravimetric analysis with mass spectroscopic analysis of volatiles (TGMS) scan obtained from Form A of ponatinib hydrochloride.

Figure 7:
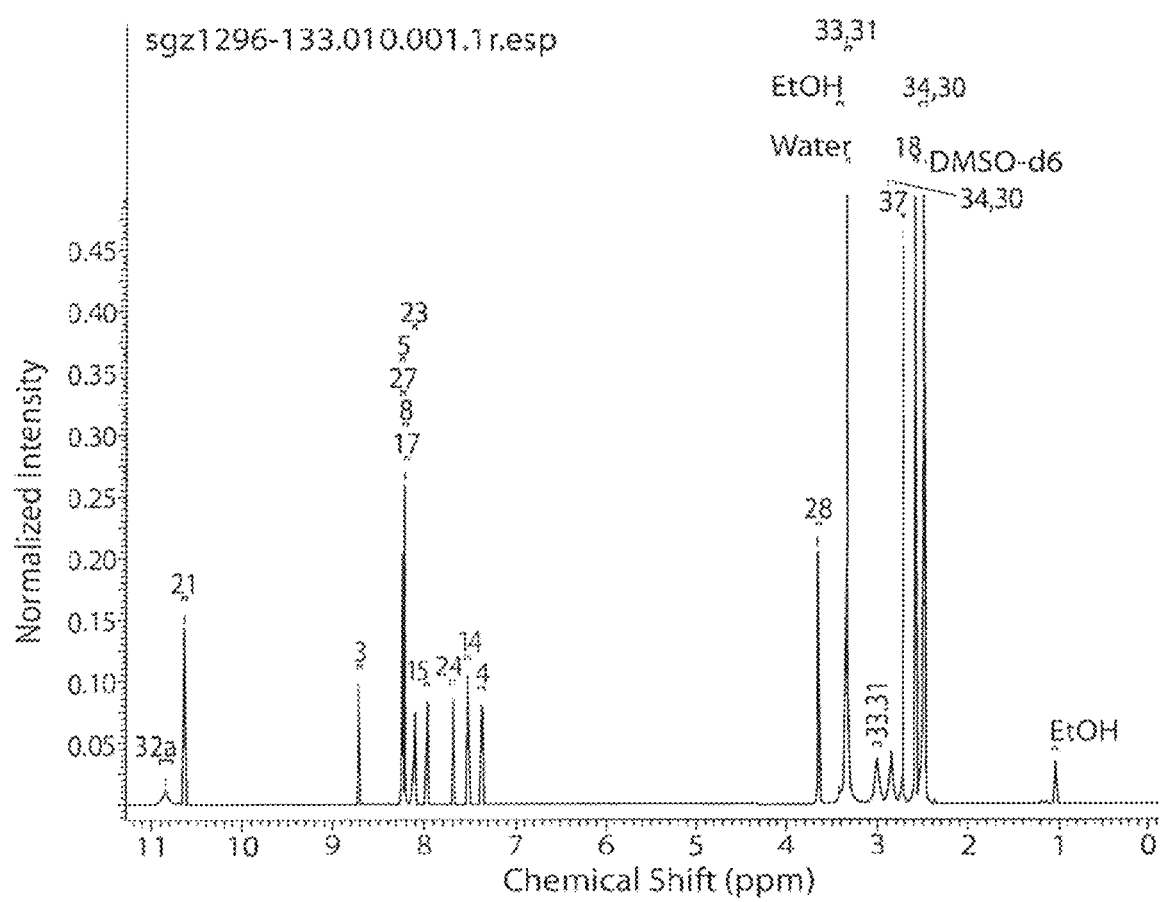

FIG. 7 is a characteristic $^1$H-NMR Spectrum (600 MHz) of ponatinib hydrochloride in solution obtained from Form A of ponatinib hydrochloride in DMSO-ds at 300 K. Normalized Intensity is shown on the vertical axis and chemical shift (ppm) is shown on the horizontal axis.

Figure 8:
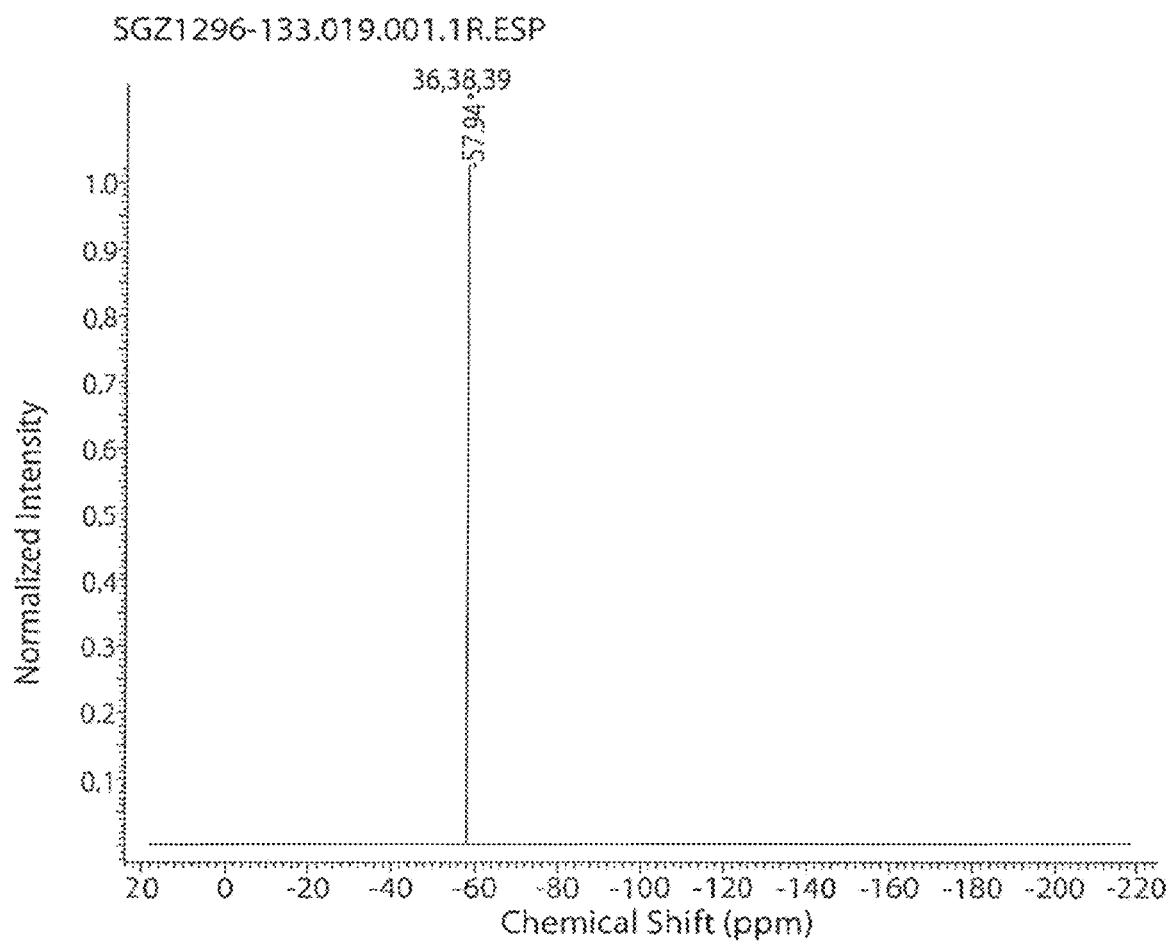

FIG. 8 is a characteristic $^{19}$F-NMR Spectrum (564 MHz) of ponatinib hydrochloride in solution obtained from Form A of ponatinib hydrochloride in DMSO-ds at 300 K. Normalized Intensity is shown on the vertical axis and chemical shift (ppm) is shown on the horizontal axis.

Figure 9:
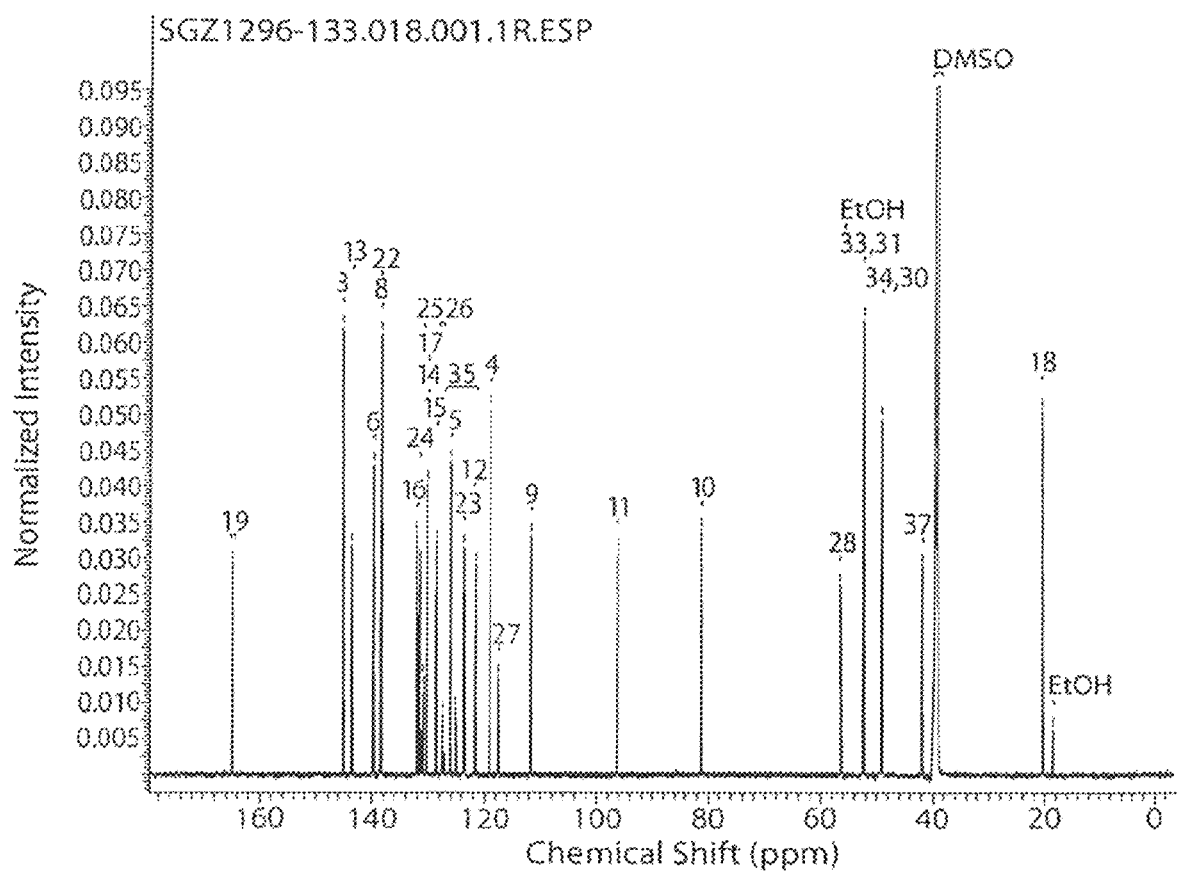

FIG. 9 is a characteristic $^{13}$C-NMR Spectrum (151 MHz) of ponatinib hydrochloride in solution obtained from Form A of ponatinib hydrochloride in DMSO-ds at 300 K. Normalized Intensity is shown on the vertical axis and chemical shift (ppm) is shown on the horizontal axis.

Figure 10A:
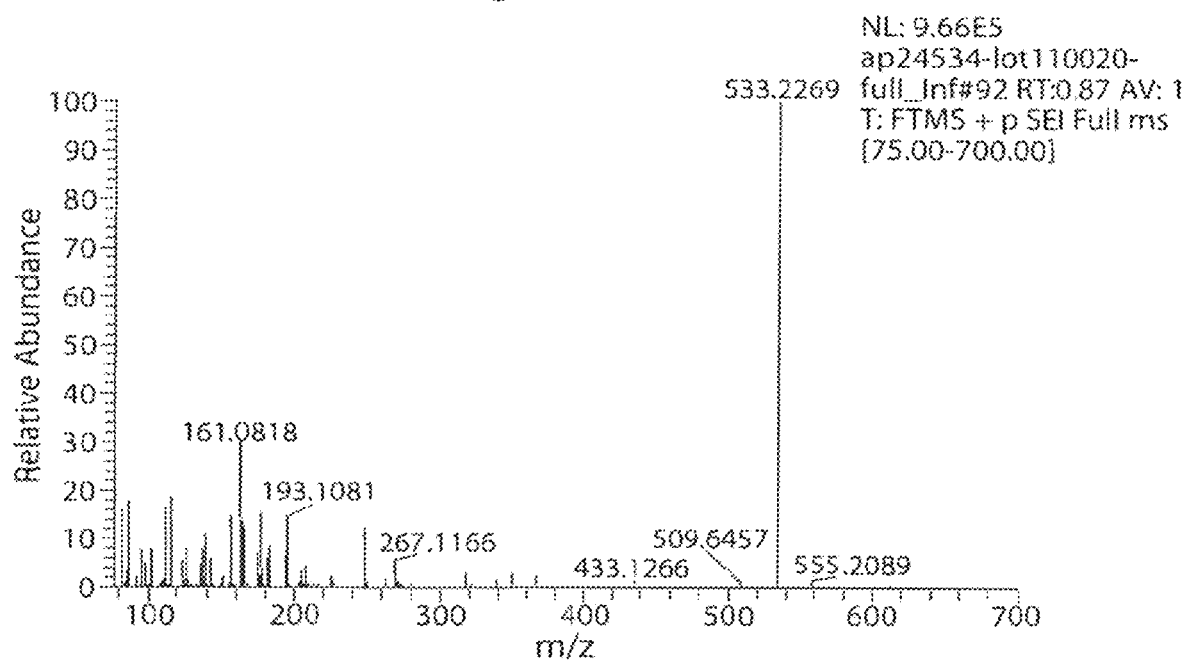
Figure 10B:
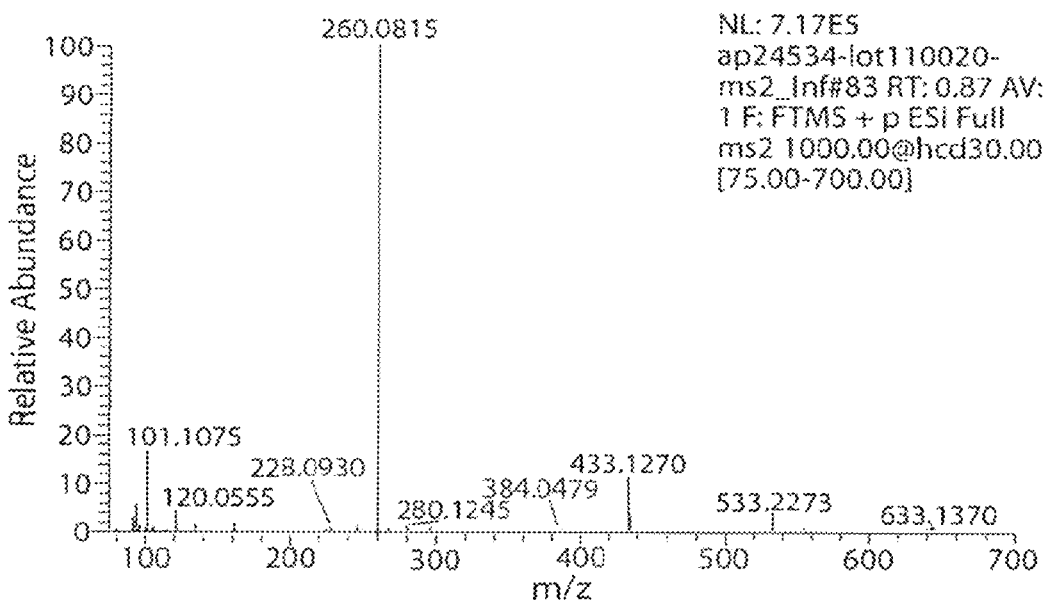
Figure 11A:
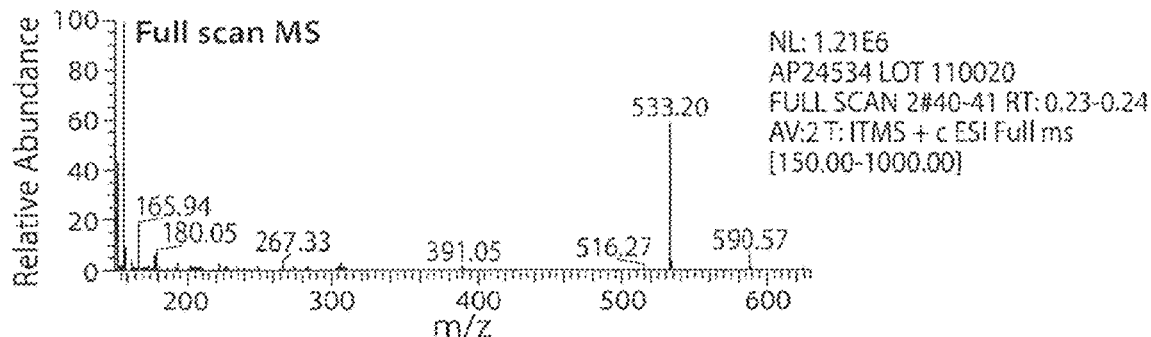
Figure 11B:
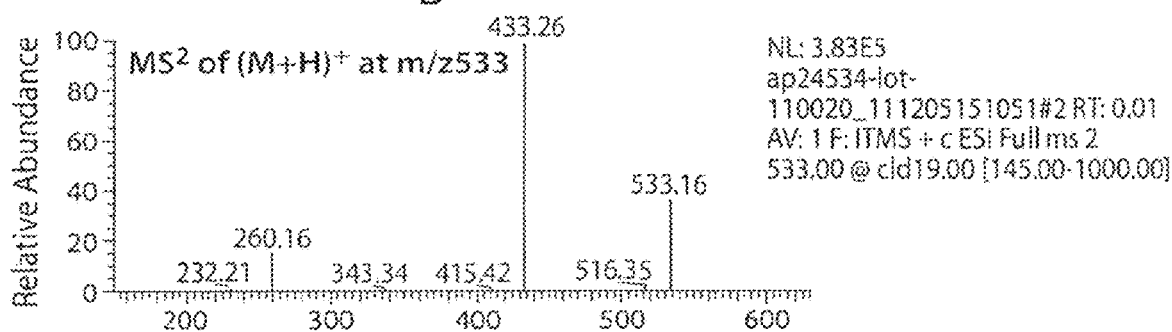
Figure 11C:
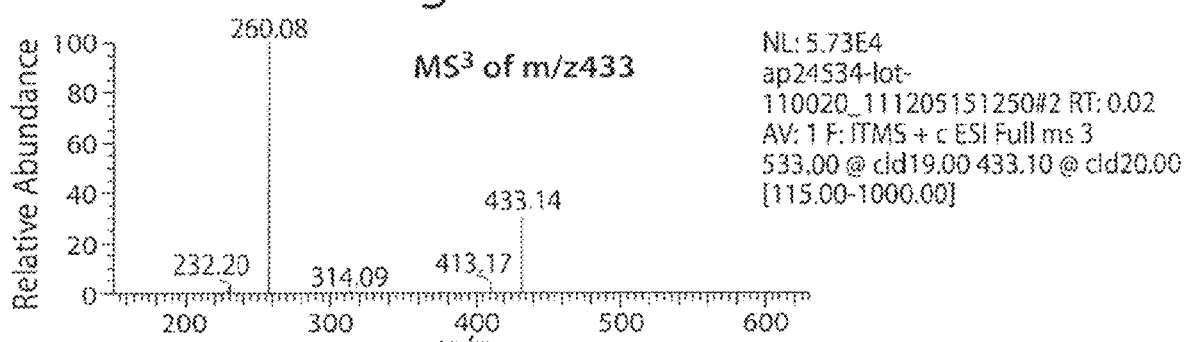
Figure 11D:
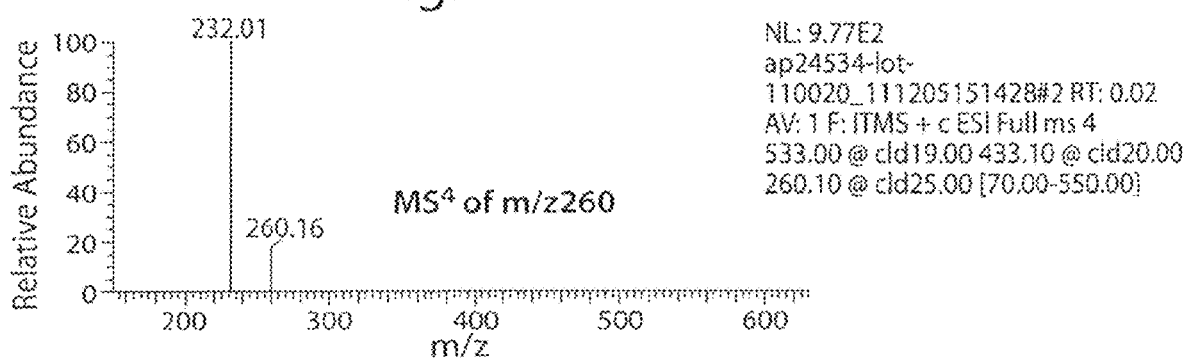

FIG. 10A is a characteristic mass spectral pattern obtained from Form A of ponatinib hydrochloride showing the observed mass of Form A and FIG. 10B is a daughter ion spectrum of the parent shown in FIG. 10A of Form A. Relative abundance is shown on the vertical axis and atomic weight (m/z) is shown on the horizontal axis.

FIG. 11A, FIG. 11B, FIG. 11C, and FIG. 11D depict characteristic mass spectral fragmentation patterns of Form A of ponatinib hydrochloride. Relative abundance is shown on the vertical axis and atomic weight (m/z) is shown on the horizontal axis.

Figure 12:
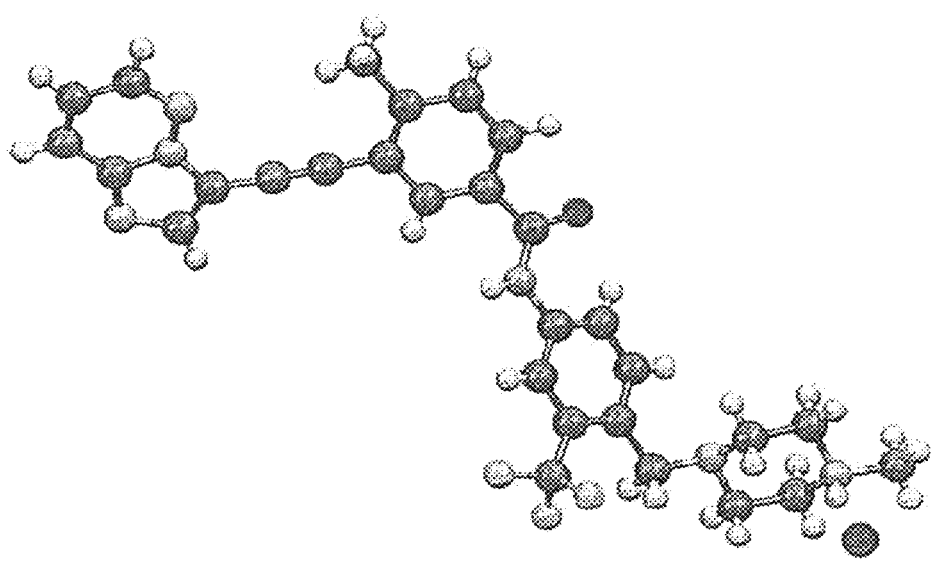

FIG. 12 shows the structure of Form A of ponatinib hydrochloride in accordance with the data presented in the table herein designated as "Crystal Data and Structure Refinement for Ponatinib Hydrochloride Form A." Atoms in FIG. 12 are color coded according to atom type: carbon, grey; nitrogen, blue; oxygen, red; hydrogen, white; fluorine, yellow; chlorine, green.

Figure 13:
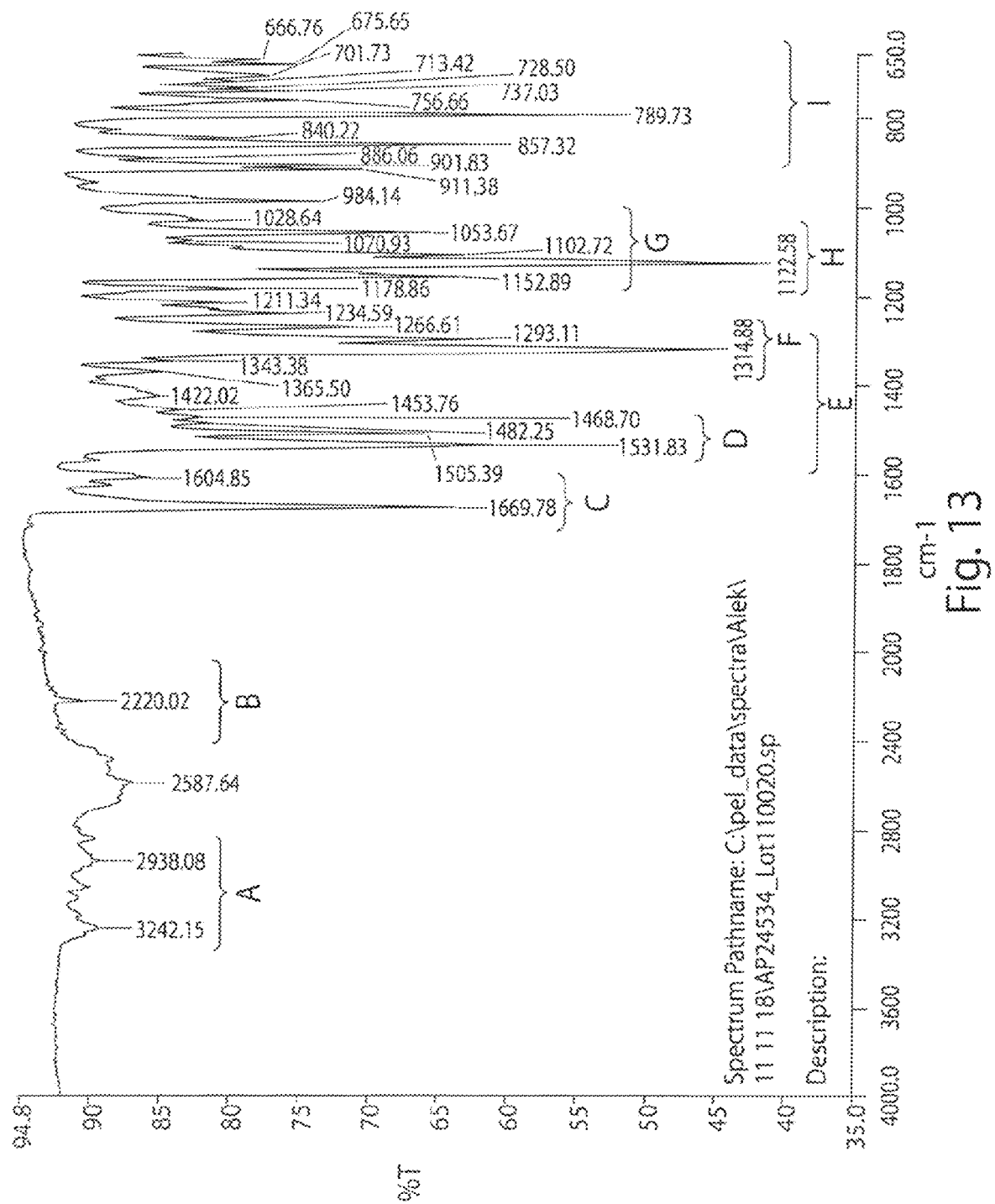

FIG. 13 is a characteristic FT-IR spectrum obtained from Form A of ponatinib hydrochloride. Percent transmittance (%) is shown on the vertical axis and wavenumber (cm$^{-1}$) is shown on the horizontal axis.

FIG. 14A is a characteristic HPLC spectrum obtained from Form A of ponatinib hydrochloride. Absorbance units are shown on the vertical axis (mAU) and time (minutes) is shown on the horizontal axis. FIG. 14B is a characteristic mass spectrum obtained from Form A of ponatinib hydrochloride. FIG. 14C is a tabulated form of the data presented in FIG. 14A.

Figure 15:
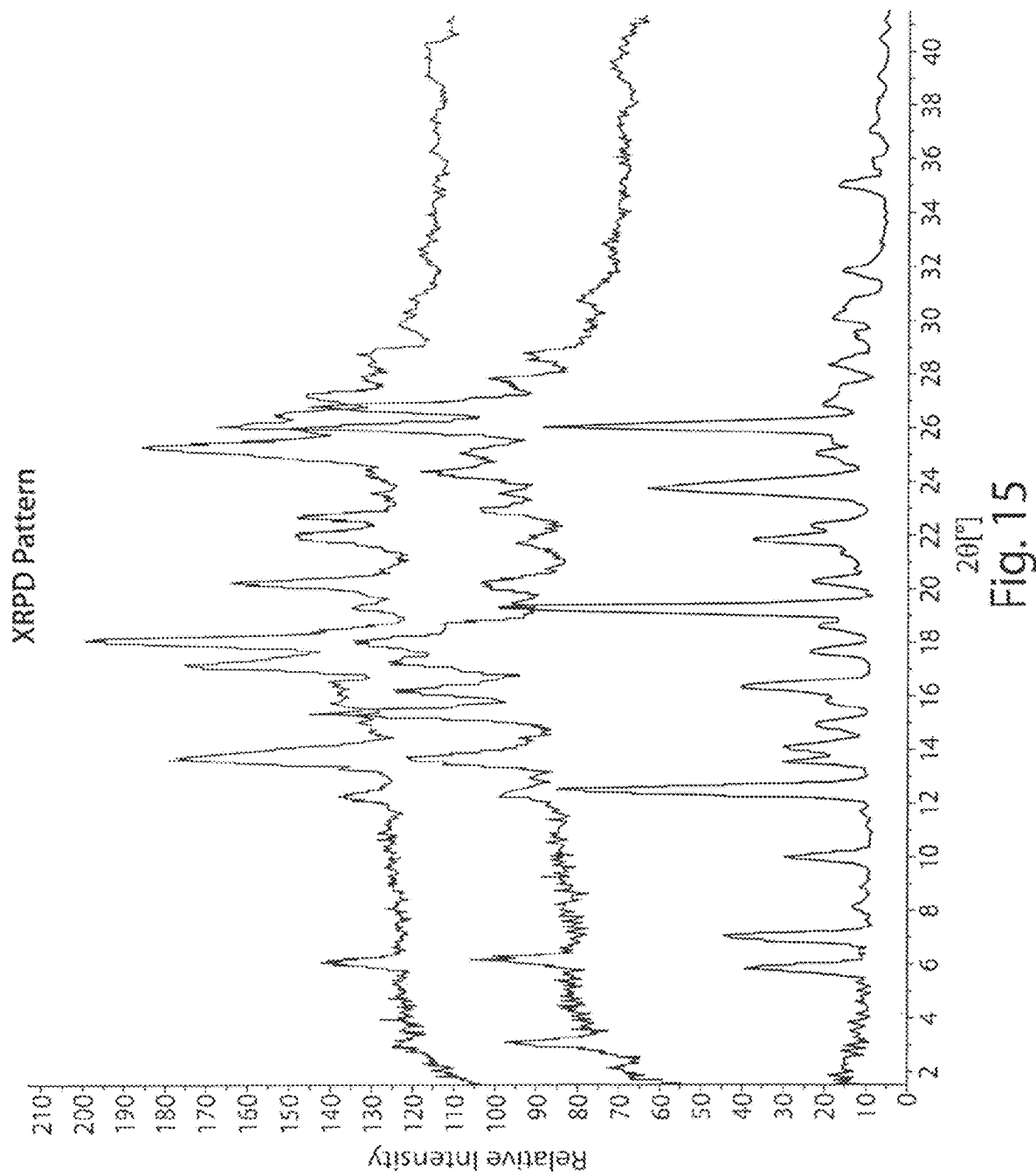

FIG. 15 is a characteristic X-Ray Powder Diffraction (XRPD) pattern obtained from Form A of ponatinib hydrochloride (bottom) as compared against a XRPD pattern of Form B (middle) and Form C (top). Relative Intensity (in counts) is shown on the vertical axis and the degrees (2θ) is shown on the horizontal axis.

FIG. 16A is a characteristic HPLC spectrum obtained from Form B of ponatinib hydrochloride. Absorbance units are shown on the vertical axis (mAU) and time (minutes) is shown on the horizontal axis. FIG. 16B is a characteristic mass spectrum obtained from Form B of ponatinib hydrochloride. FIG. 16C is a tabulated form of the data presented in FIG. 16A.

Figure 17:
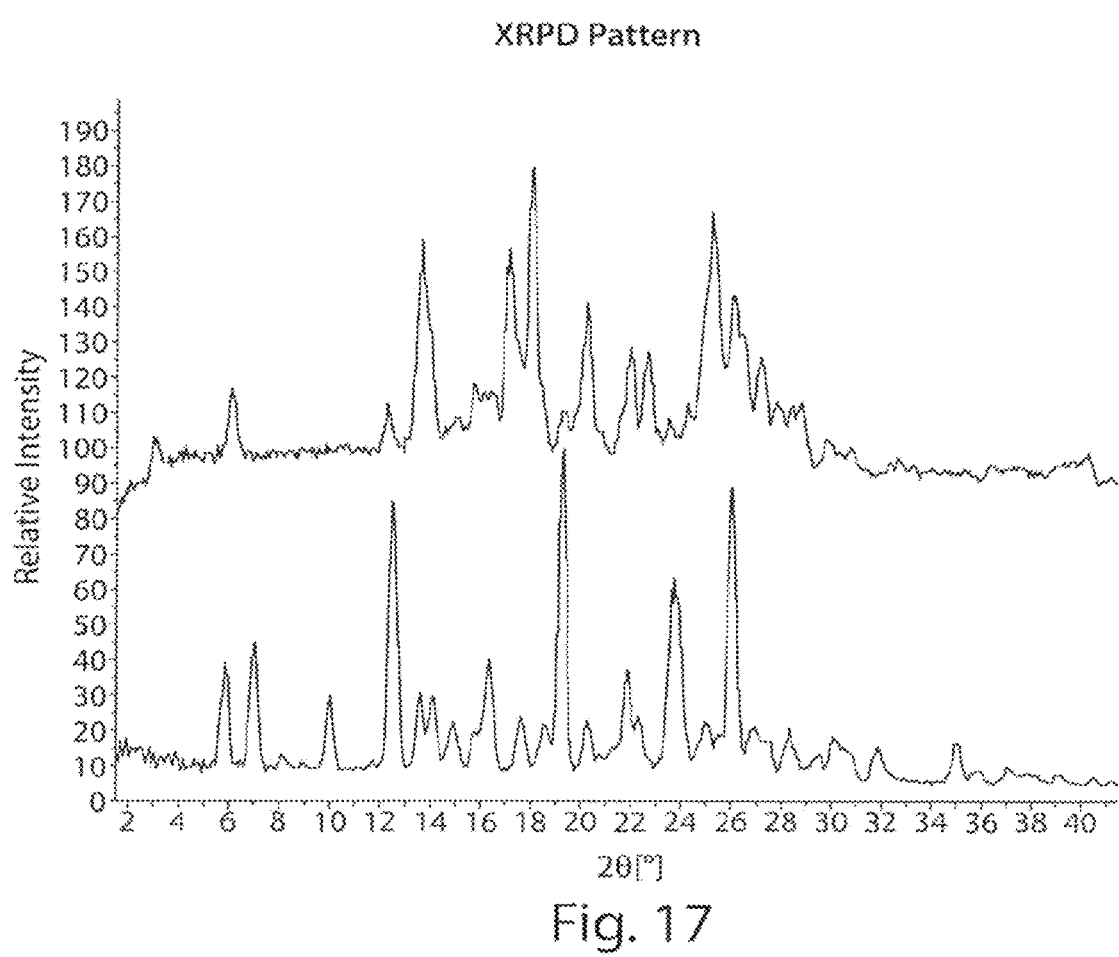

FIG. 17 is a characteristic X-Ray Powder Diffraction (XRPD) pattern obtained from Form C of ponatinib hydrochloride (top) as compared against a XRPD pattern of Form A (bottom).

Relative Intensity (in counts) is shown on the vertical axis and the degrees (2θ) is shown on the horizontal axis.

Figure 18:
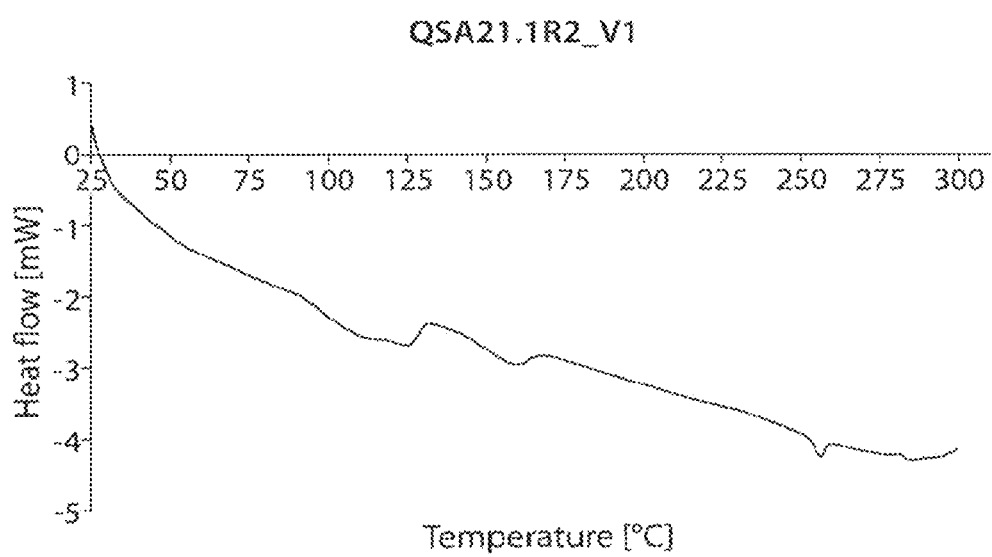

FIG. 18 is a characteristic differential scanning calorimetry (DSC) scan obtained from Form C of ponatinib hydrochloride. Heat flow [mW] is shown on the vertical axis and temperature (° C.) is shown on the horizontal axis.

Figure 19:
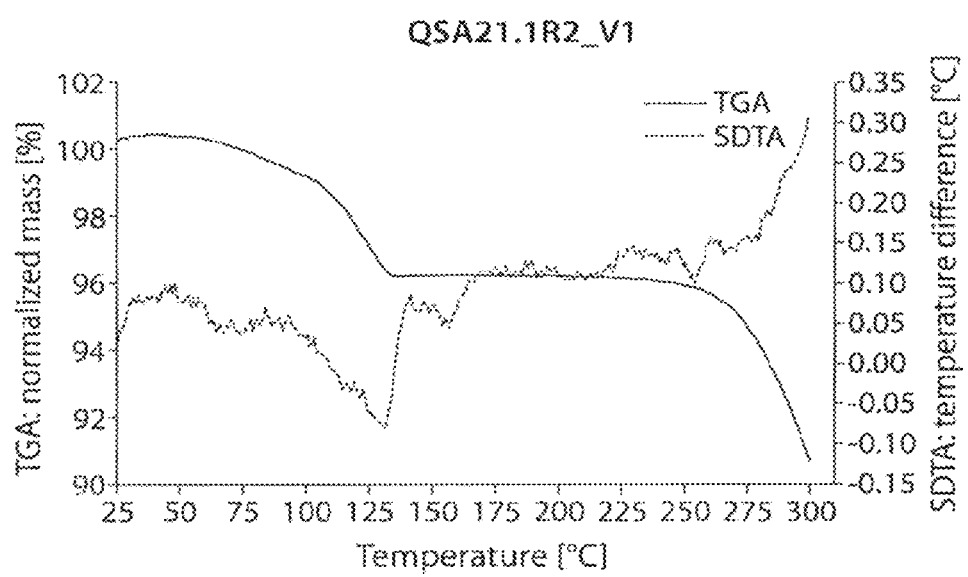

FIG. 19 is a characteristic thermogravimetric analysis (TGA) scan obtained from Form C of ponatinib hydrochloride.

Figure 20A:
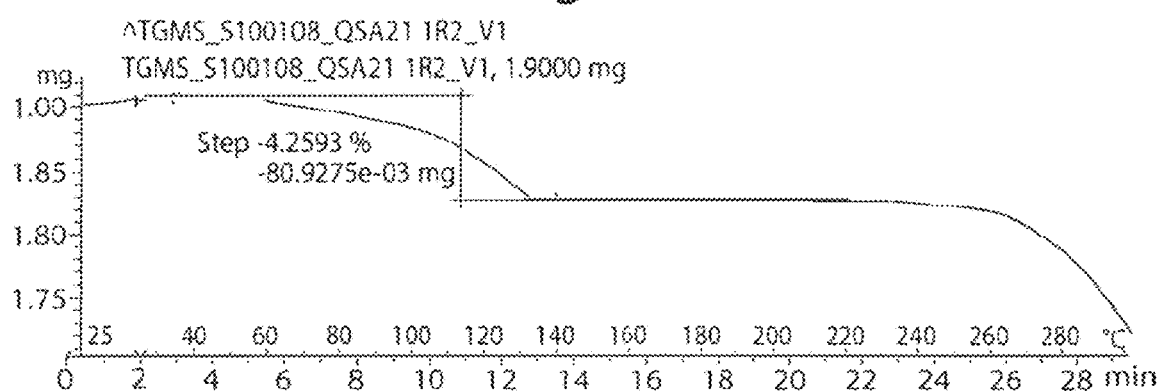
Figure 20B:
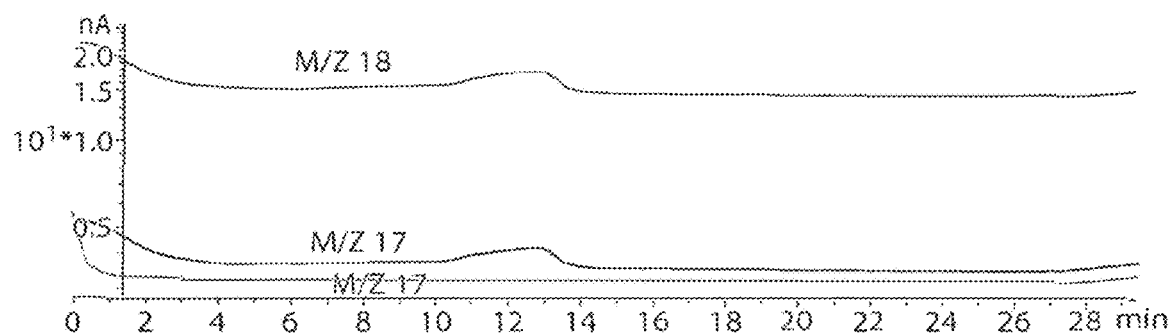

FIG. 20A and FIG. 20B are a characteristic TGMS thermogram obtained from Form C of ponatinib hydrochloride.

FIG. 21A is a characteristic HPLC spectrum obtained from Form C of ponatinib hydrochloride. Absorbance units are shown on the vertical axis (mAU) and time (minutes) is shown on the horizontal axis. FIG. 21B is a characteristic mass spectrum obtained from Form C of ponatinib hydrochloride. FIG. 21C is a tabulated form of the data presented in FIG. 21A.

Figure 22:
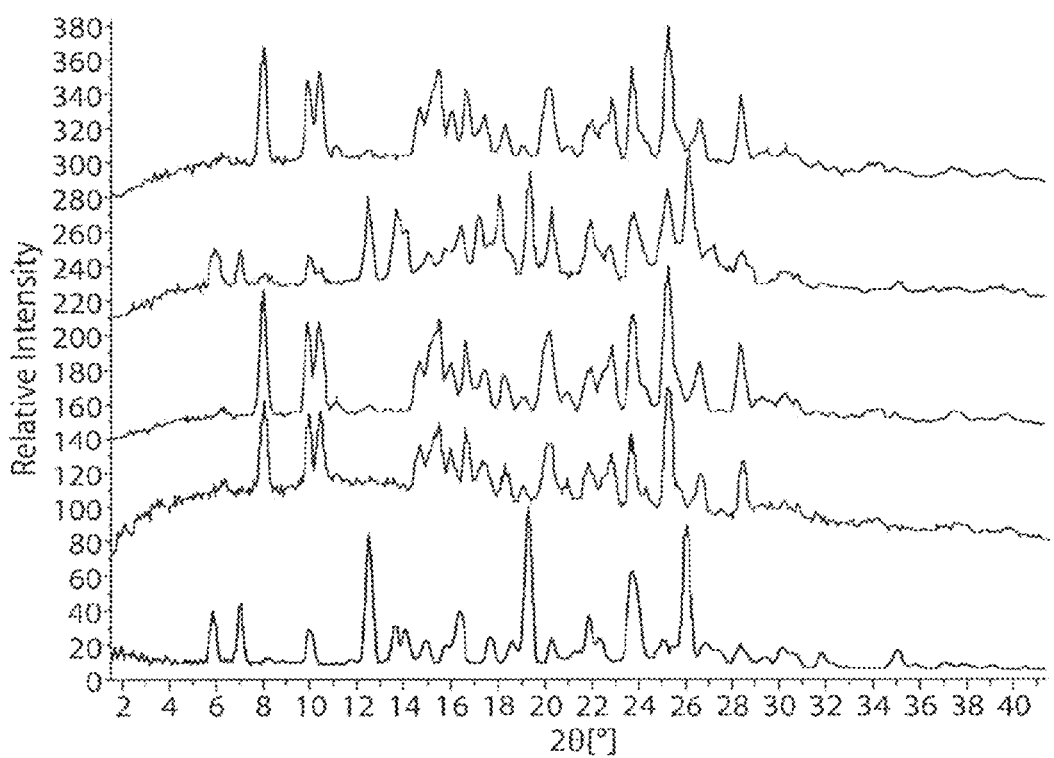

FIG. 22 is a characteristic X-Ray Powder Diffraction (XRPD) pattern obtained from Form D of ponatinib hydrochloride as compared against a XRPD pattern of Form A and certain other crystalline forms within the class of HCl3. Relative Intensity (in counts) is shown on the vertical axis and the degrees (2θ) is shown on the horizontal axis.

Figure 23:
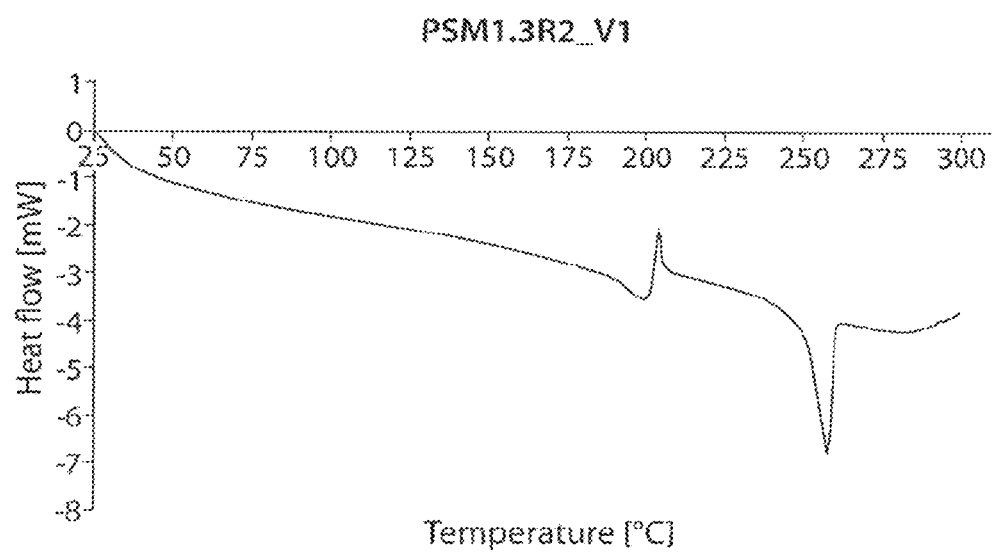

FIG. 23 is a characteristic differential scanning calorimetry (DSC) scan obtained from Form D of ponatinib hydrochloride. Heat flow [mW] is shown on the vertical axis and temperature (° C.) is shown on the horizontal axis.

Figure 24:
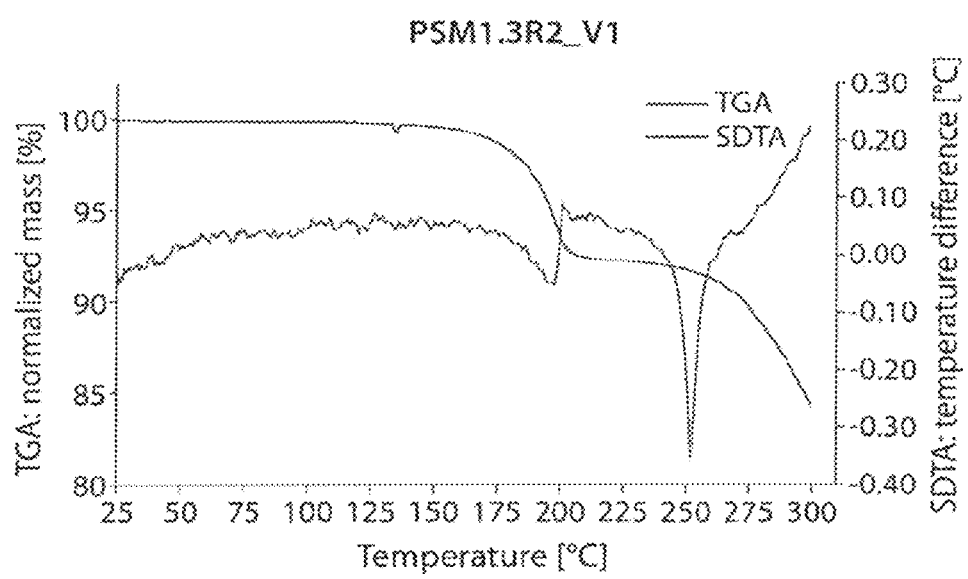

FIG. 24 is a characteristic thermogravimetric analysis (TGA) scan obtained from Form D of ponatinib hydrochloride.

Figure 25:
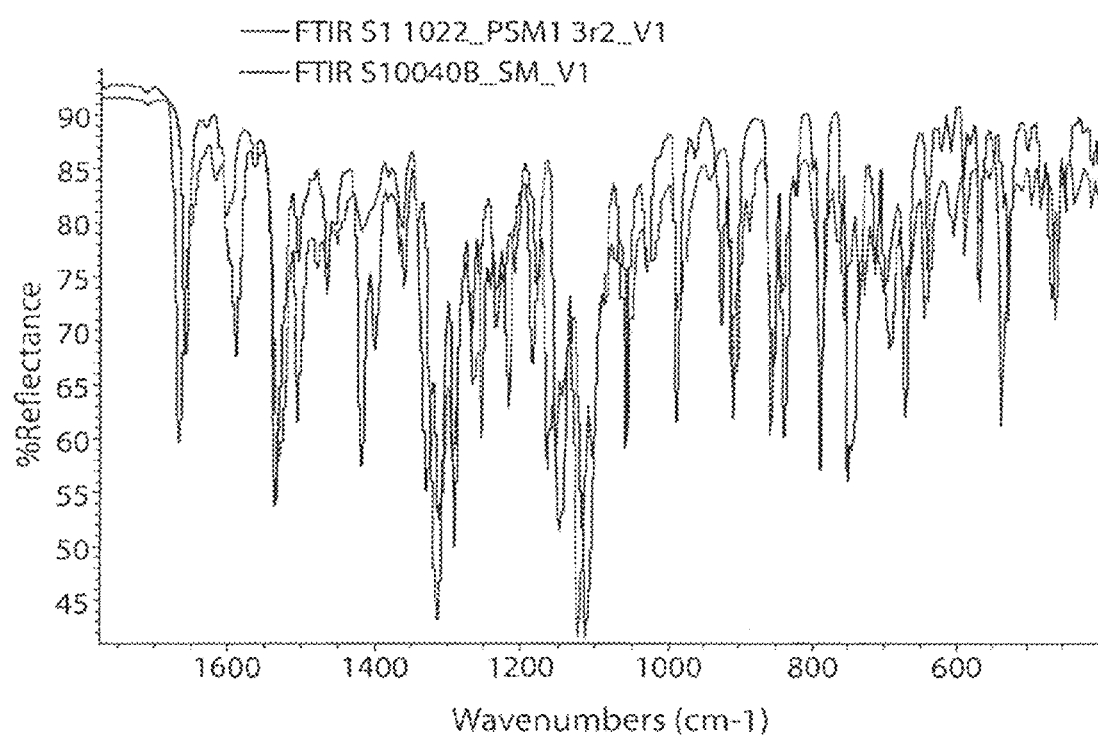

FIG. 25 is a characteristic FT-IR spectrum obtained from Form D of ponatinib hydrochloride. Percent transmittance (%) is shown on the vertical axis and wavenumber (cm$^{-1}$) is shown on the horizontal axis. The Form A starting material is shown in red and Form D (PSM1) is shown in blue.

FIG. 26A is a characteristic HPLC spectrum obtained from Form D of ponatinib hydrochloride. Absorbance units are shown on the vertical axis (mAU) and time (minutes) is shown on the horizontal axis. FIG. 26B is a characteristic mass spectrum obtained from Form D of ponatinib hydrochloride. FIG. 26C is a tabulated form of the data presented in FIG. 26A.

Figure 27:
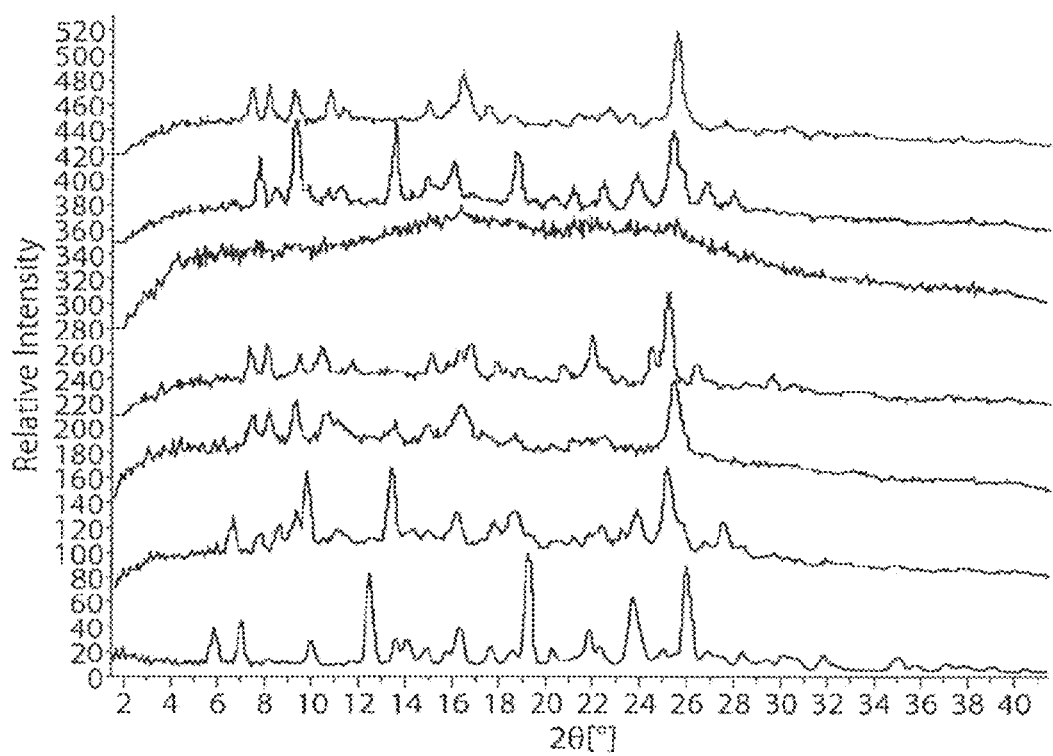

FIG. 27 is a characteristic X-Ray Powder Diffraction (XRPD) pattern obtained from Form F of ponatinib hydrochloride as compared against a XRPD pattern of Form A and certain other crystalline forms within the class of HCl5. Relative Intensity (in counts) is shown on the vertical axis and the degrees (2θ) is shown on the horizontal axis.

Figure 28A:
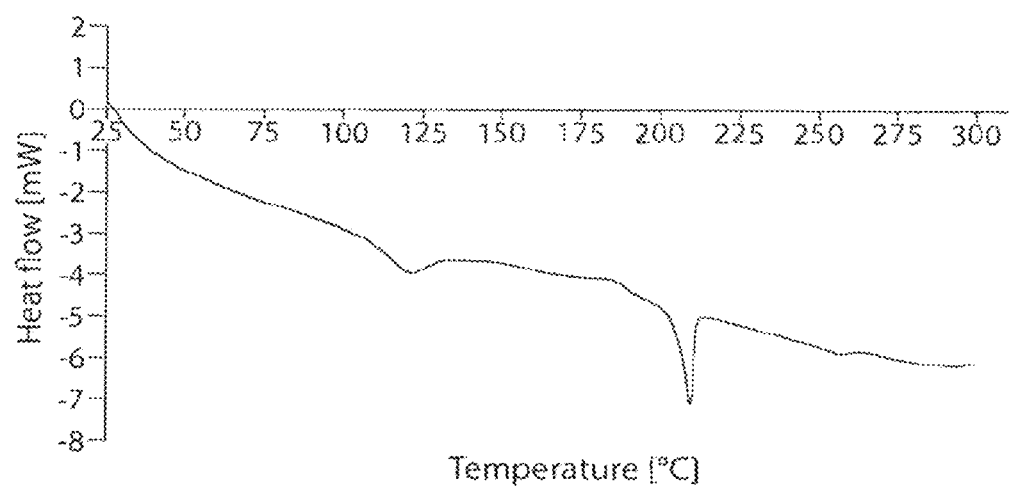
Figure 28B:
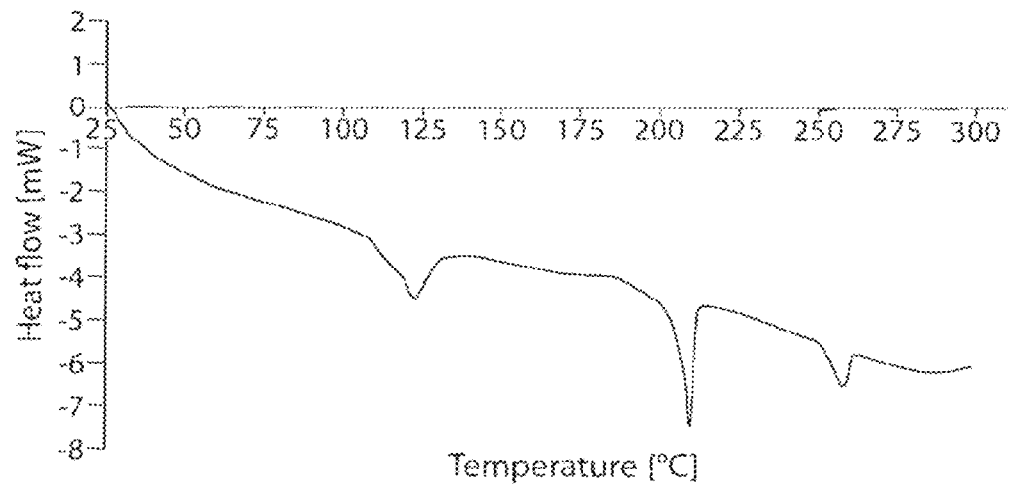

FIG. 28A and FIG. 28B show two characteristic differential scanning calorimetry (DSC) scans obtained from Form F of ponatinib hydrochloride. FIG. 28A is the DSC curve of VDS1.

FIG. 28B is the DSC curve of VDS2. Heat flow [mW] is shown on the vertical axis and temperature (° C.) is shown on the horizontal axis.

Figure 29A:
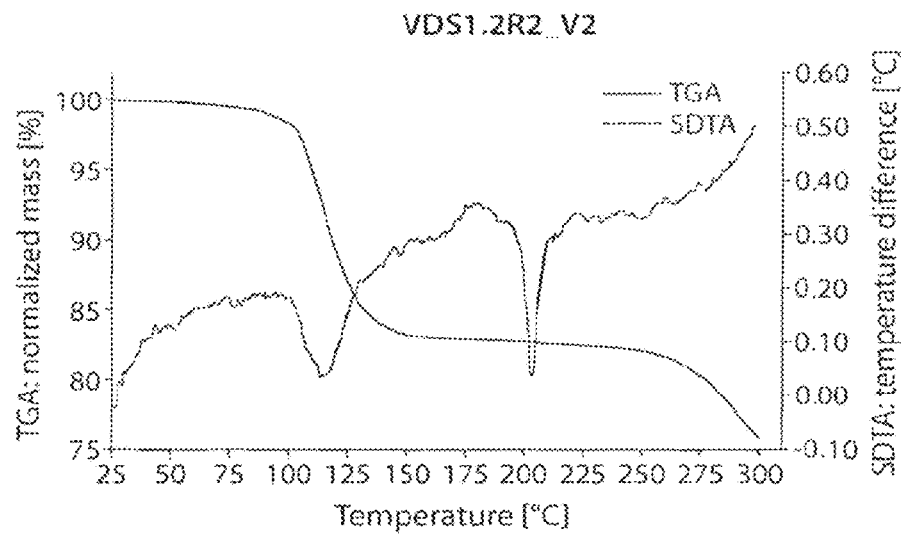
Figure 29B:
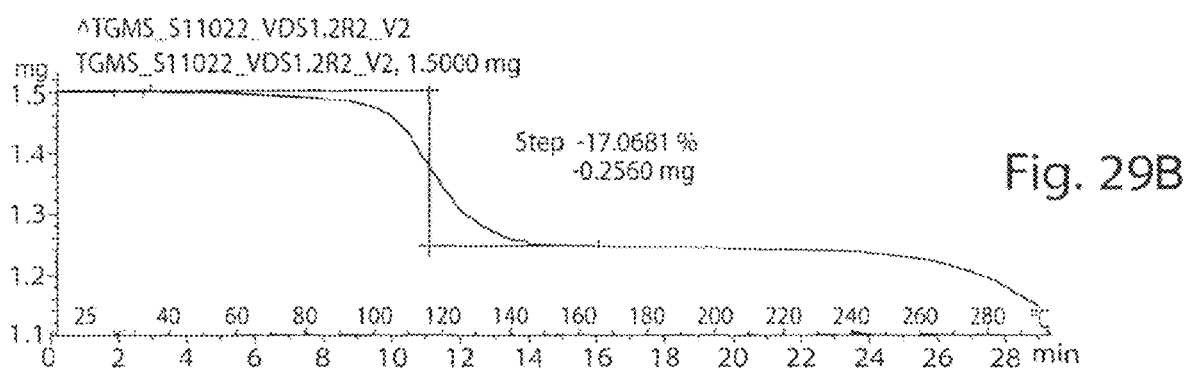
Figure 29C:
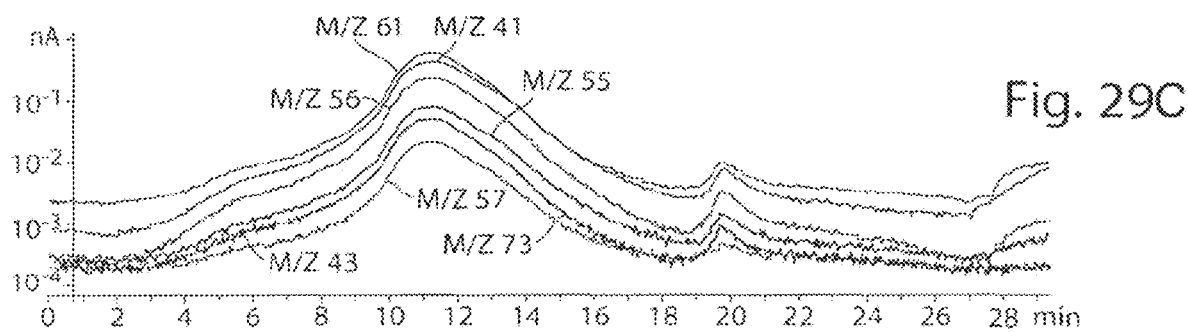

FIG. 29A is a characteristic overlay of thermogravimetric analysis and SDTA and FIG. 29B and FIG. 29C are a TGMS scan obtained from Form F of ponatinib hydrochloride (VDS1).

Figure 30A:
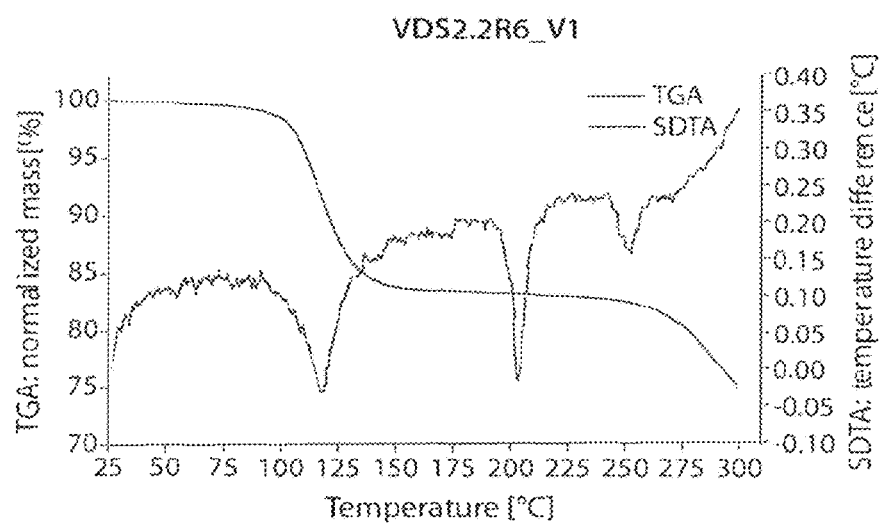
Figure 30B:
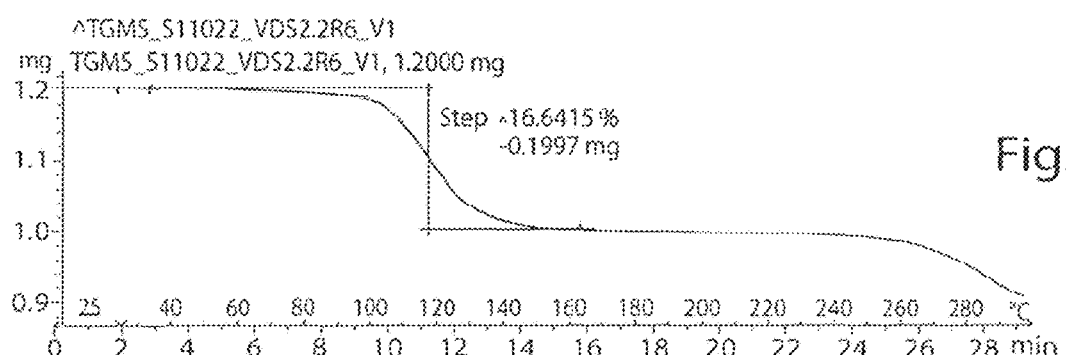
Figure 30C:
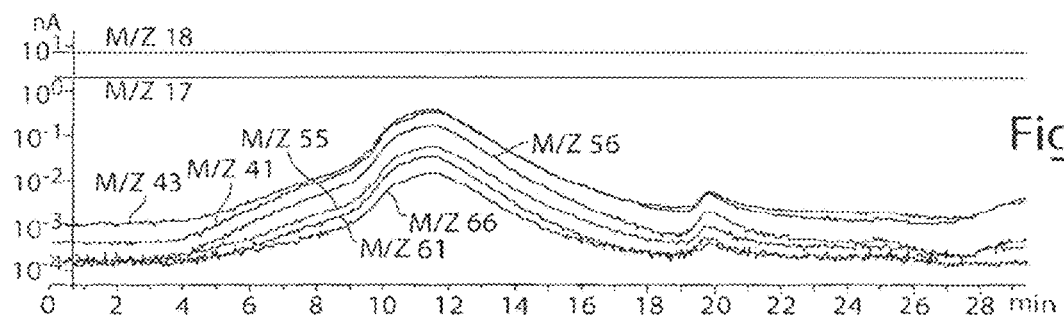

FIG. 30A is a characteristic overlay of thermogravimetric analysis and FIG. 30B and FIG. 30C are a TGMS scan obtained from Form F of ponatinib hydrochloride (VDS2).

Figure 31:
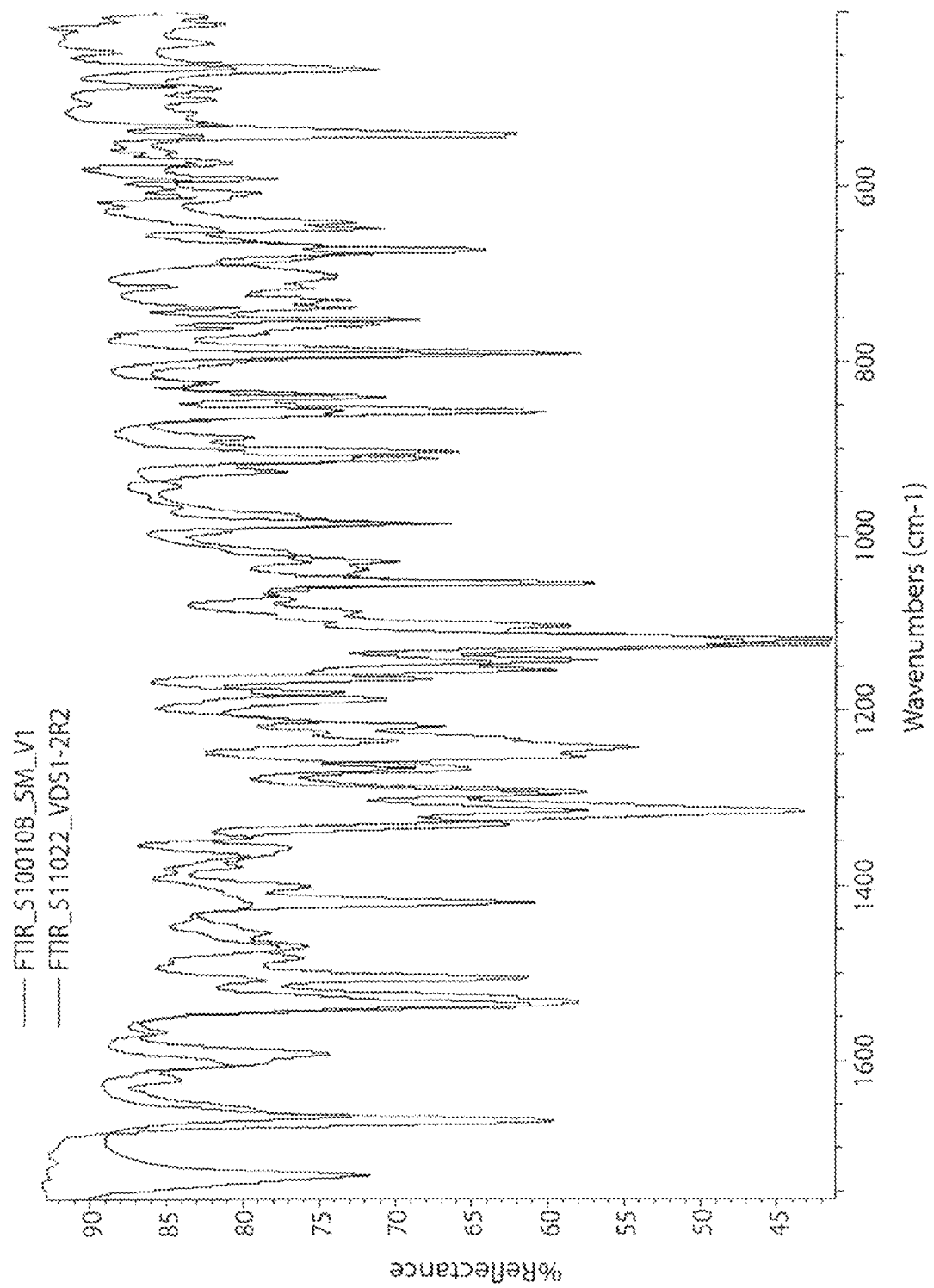

FIG. 31 is a characteristic FT-IR spectrum obtained from Form F of ponatinib hydrochloride. Percent transmittance (%) is shown on the vertical axis and wavenumber (cm$^{-1}$) is shown on the horizontal axis. The Form A starting material is shown in red and Form F (VDS1) is shown in green.

Figure 32:
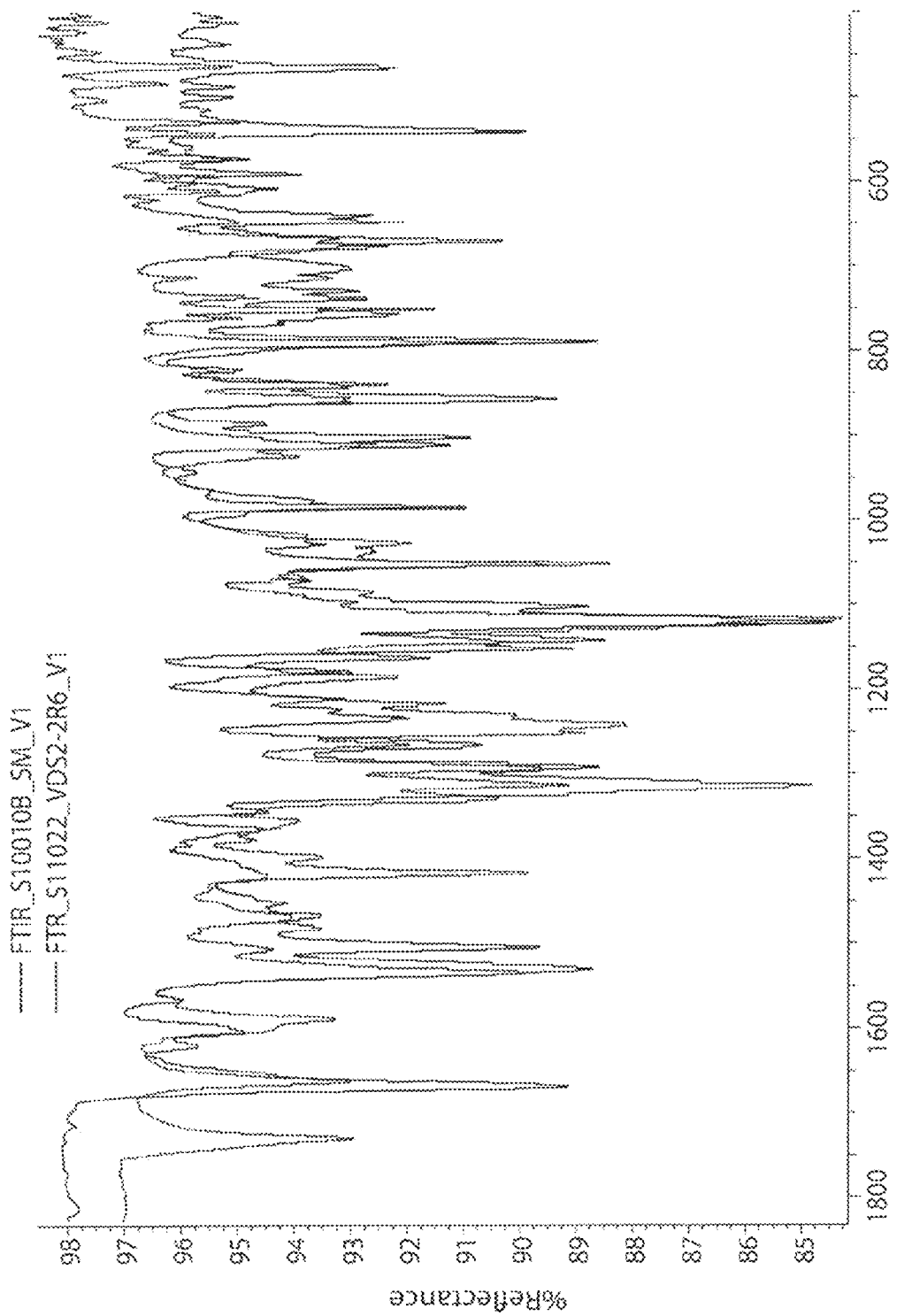

FIG. 32 is a characteristic FT-IR spectrum obtained from Form F of ponatinib hydrochloride. Percent transmittance (%) is shown on the vertical axis and wavenumber (cm$^{-1}$) is shown on the horizontal axis. The Form A starting material is shown in purple and Form F (VDS2) is shown in red.

Figure 33:
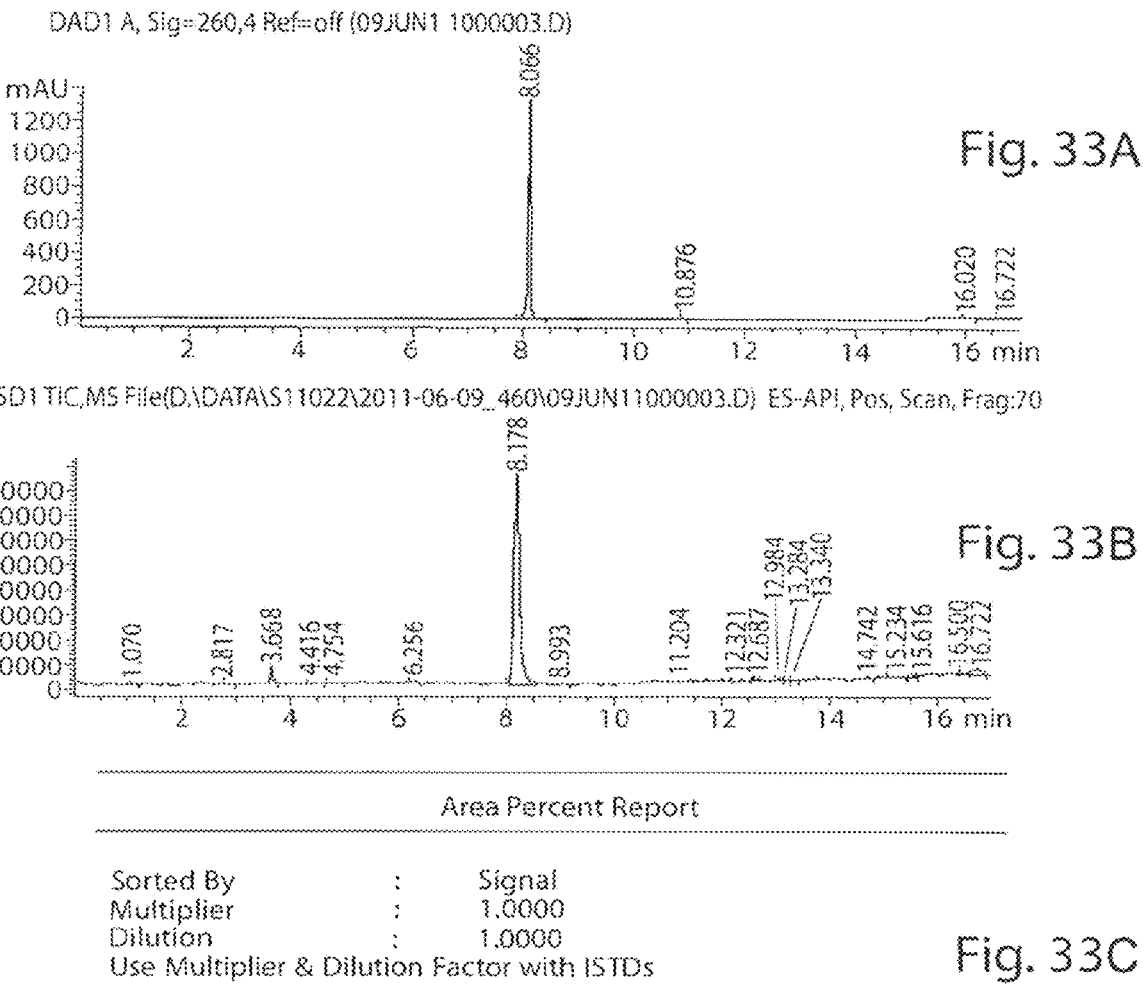

FIG. 33A is a characteristic HPLC spectrum obtained from Form F of ponatinib hydrochloride (VDS2). Absorbance units are shown on the vertical axis (mAU) and time (minutes) is shown on the horizontal axis. FIG. 33B is a characteristic mass spectrum obtained from Form F of ponatinib hydrochloride. FIG. 33C is a tabulated form of the data presented in FIG. 33A.

Figure 34:
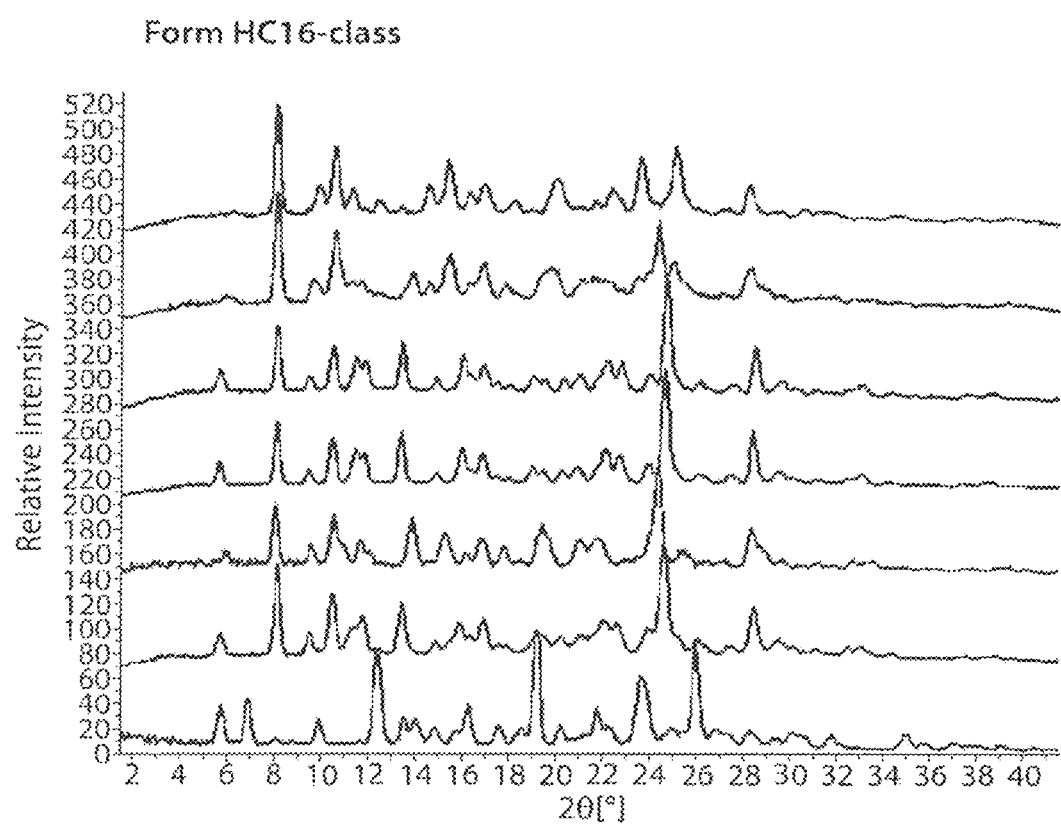

FIG. 34 is a characteristic X-Ray Powder Diffraction (XRPD) pattern obtained from Form H of ponatinib hydrochloride as compared against a XRPD pattern of Form A (bottom) and certain other crystalline forms within the class of HCl6. Relative Intensity (in counts) is shown on the vertical axis and the degrees (2θ) is shown on the horizontal axis.

Figure 35A:
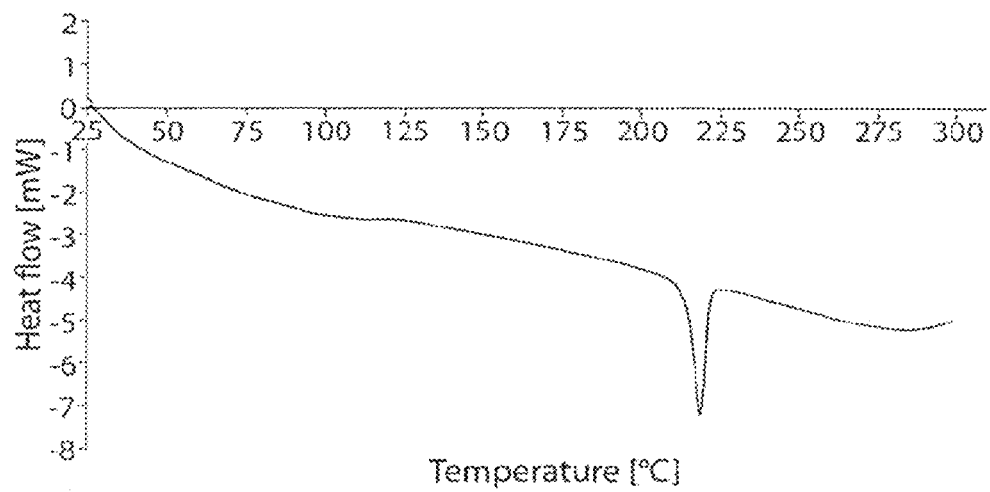
Figure 35B:
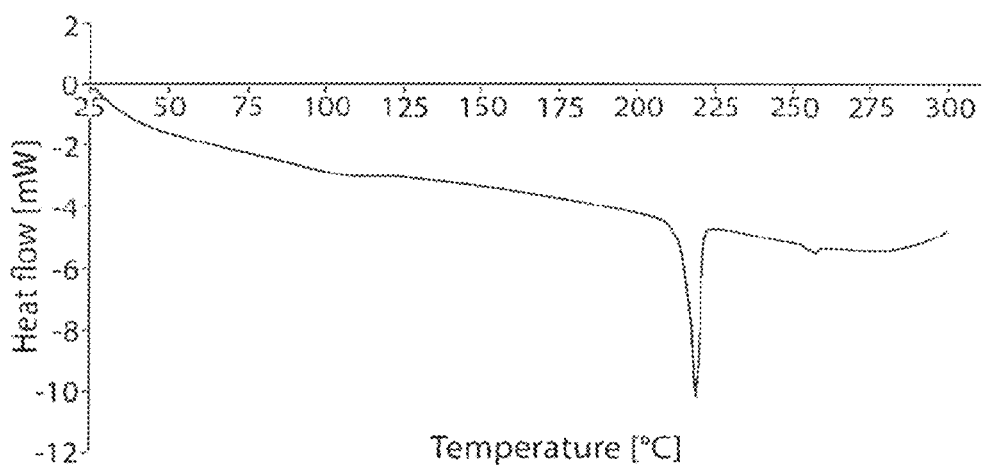

FIG. 35A and FIG. 35B show two characteristic differential scanning calorimetry (DSC) scans obtained from Form H of ponatinib hydrochloride. FIG. 35A is the DSC curve of VDS3. FIG. 35B is the DSC curve of VDS4. Heat flow [mW] is shown on the vertical axis and temperature (° C.) is shown on the horizontal axis.

Figure 36A:
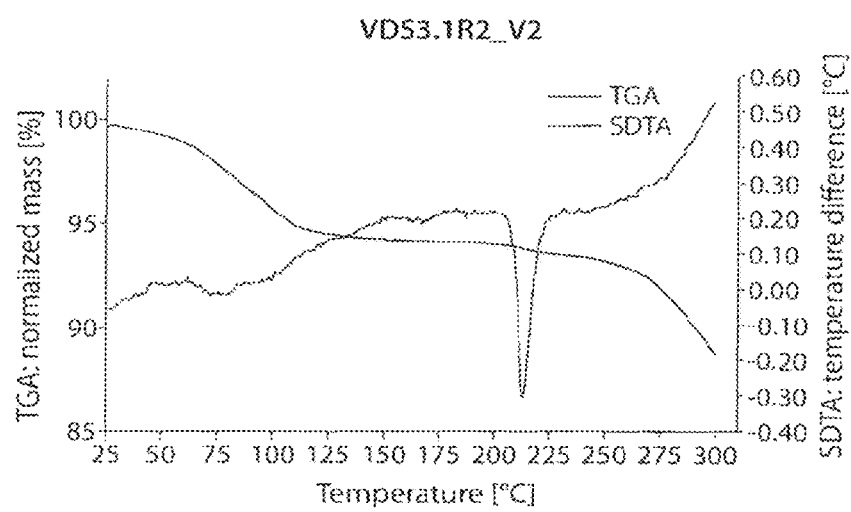
Figure 36B:
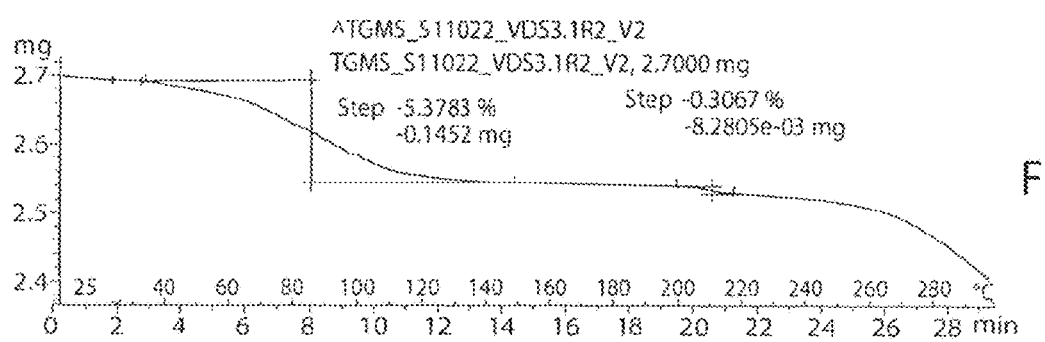
Figure 36C:
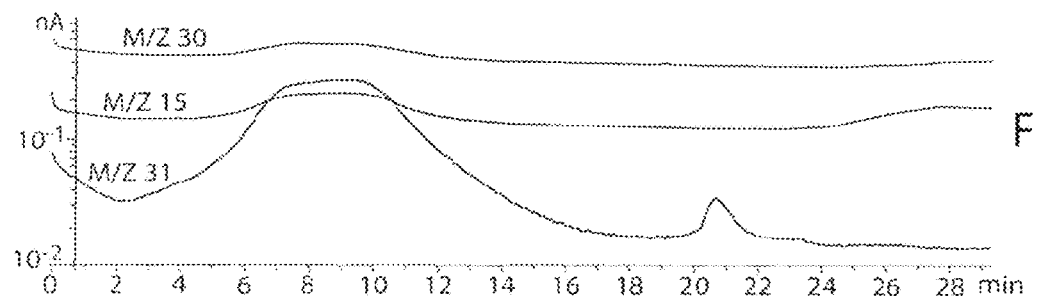

FIG. 36A is a characteristic overlay of thermogravimetric analysis and FIG. 36B and FIG. 36C are a TGMS scan obtained from Form H of ponatinib hydrochloride (VDS3).

Figure 37A:
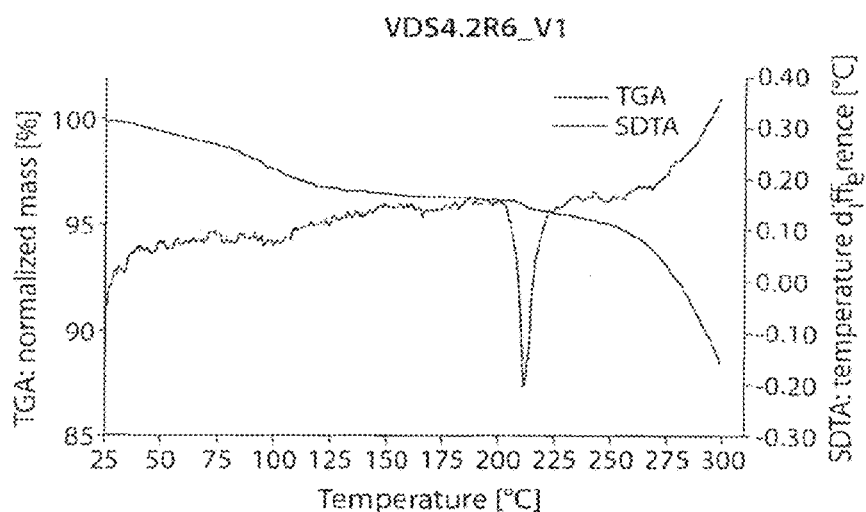
Figure 37B:
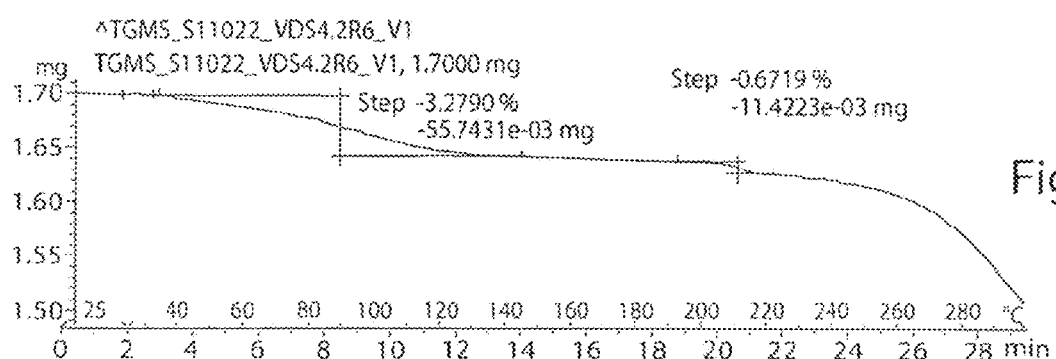
Figure 37C:
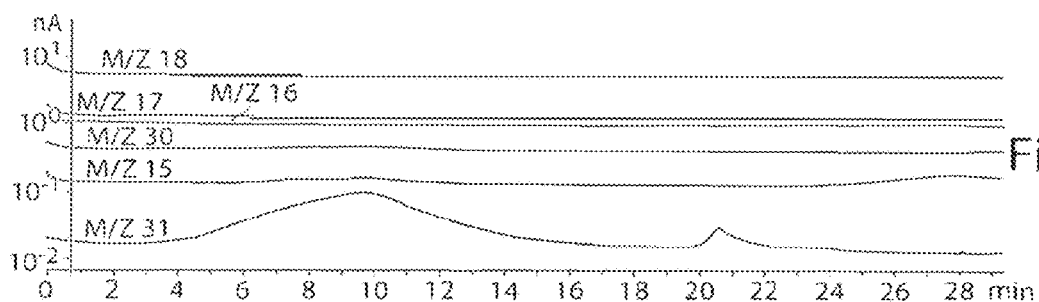

FIG. 37A is a characteristic overlay of thermogravimetric analysis and FIG. 37B and FIG. 37C are a TGMS scan obtained from Form H of ponatinib hydrochloride (VDS4).

Figure 38:
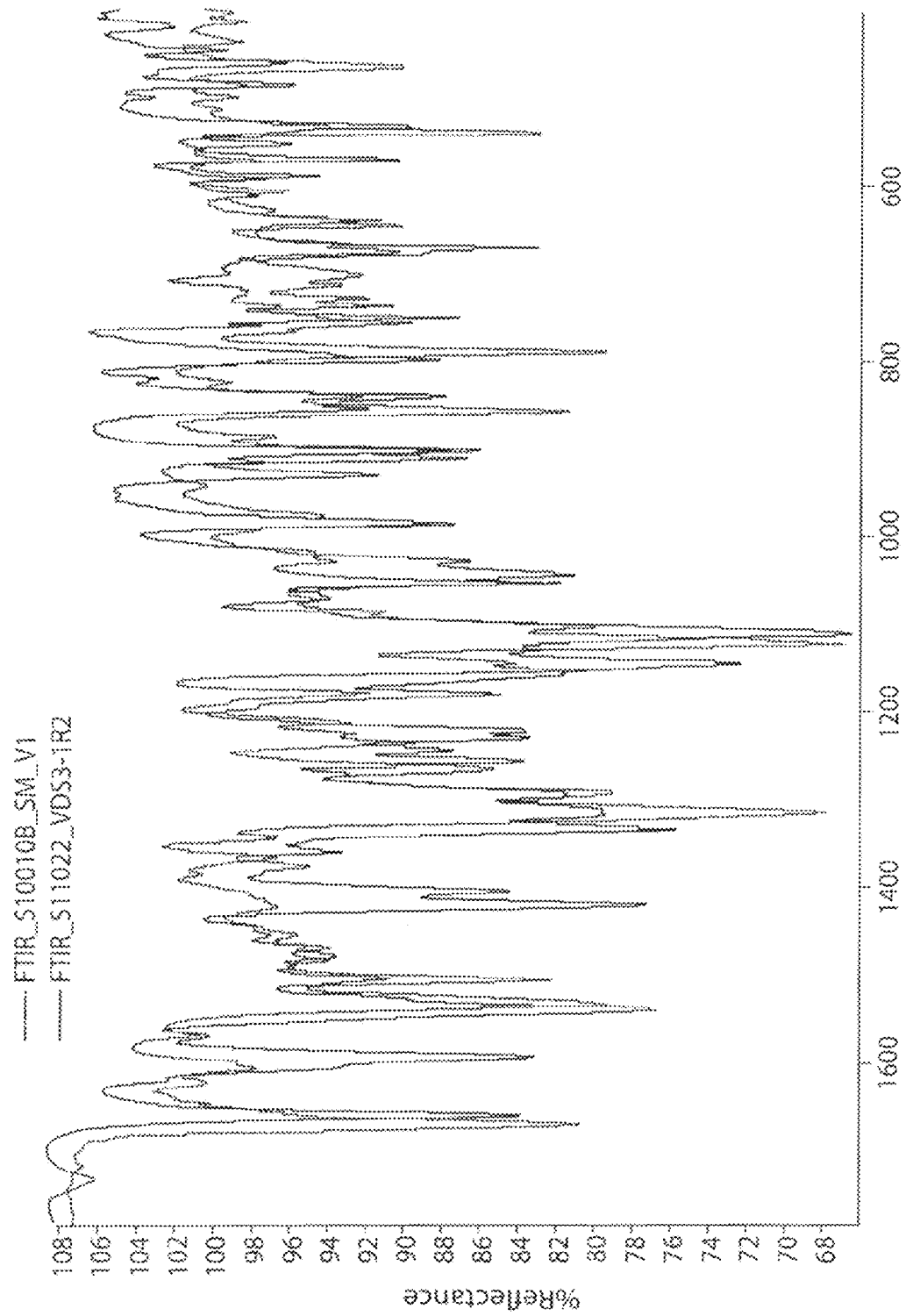

FIG. 38 is a characteristic FT-IR spectrum obtained from Form H of ponatinib hydrochloride. Percent transmittance (%) is shown on the vertical axis and wavenumber (cm$^{-1}$) is shown on the horizontal axis. The Form A starting material is shown in purple and Form H (VDS3) is shown in red.

FIG. 39 is a characteristic FT-IR spectrum obtained from Form H of ponatinib hydrochloride. Percent transmittance (%) is shown on the vertical axis and wavenumber (cm$^{-1}$) is shown on the horizontal axis. The Form A starting material is shown in purple and Form H (VDS4) is shown in red.

FIG. 40A is a characteristic HPLC spectrum obtained from Form H of ponatinib hydrochloride (VDS4). Absorbance units are shown on the vertical axis (mAU) and time (minutes) is shown on the horizontal axis. FIG. 40B is a characteristic mass spectrum obtained from Form H of ponatinib hydrochloride. FIG. 40C is a tabulated form of the data presented in FIG. 40A.

Figure 41:
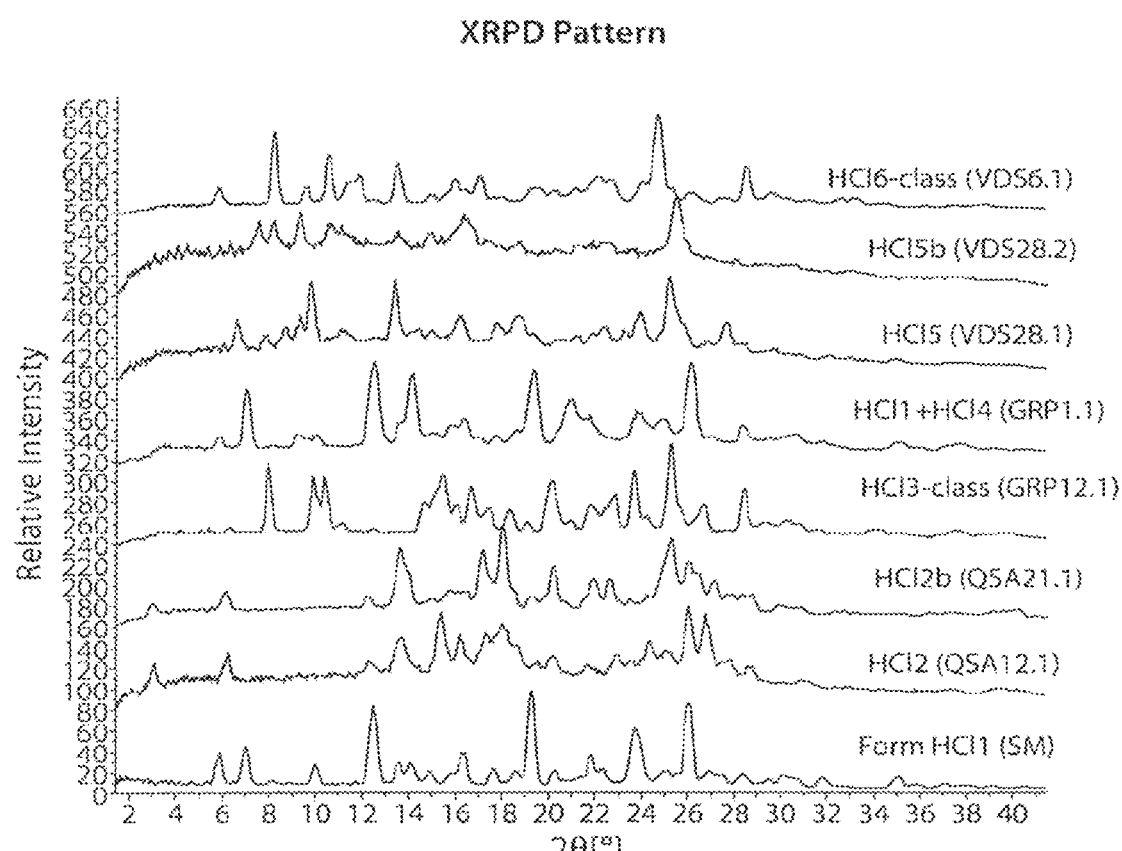

FIG. 41 is an overlay of characteristic X-Ray Powder Diffraction (XRPD) patterns for each of the solid forms identified in FIG. 1 where the vertical axis denotes relative intensity (counts) and the horizontal axis denotes Two Theta (Degrees). From the bottom to the top of this figure the following solid forms and solvents are as follows: the starting material ponatinib HCl (HCl1) (Form A), Form HCl2 (QSA12.1, solvent: water) (Form B), Form HCl2b (QSA21.1, solvent: water) (Form C), Form HCl3-class (GRP12.1, solvent: toluene) (Form D), mixture HCl1+HCl4 (GRP1.1, solvent: hexafluorobenzene) (Form E), Form HCl5 (VDS28.1, solvent: butylacetate) (Form F), Form HCl5b (VDS28.2 after drying, solvent: butylacetate) (Form G) and HCl6-class (VDS6.1, solvent: methanol) (Form H).

Figure 42:
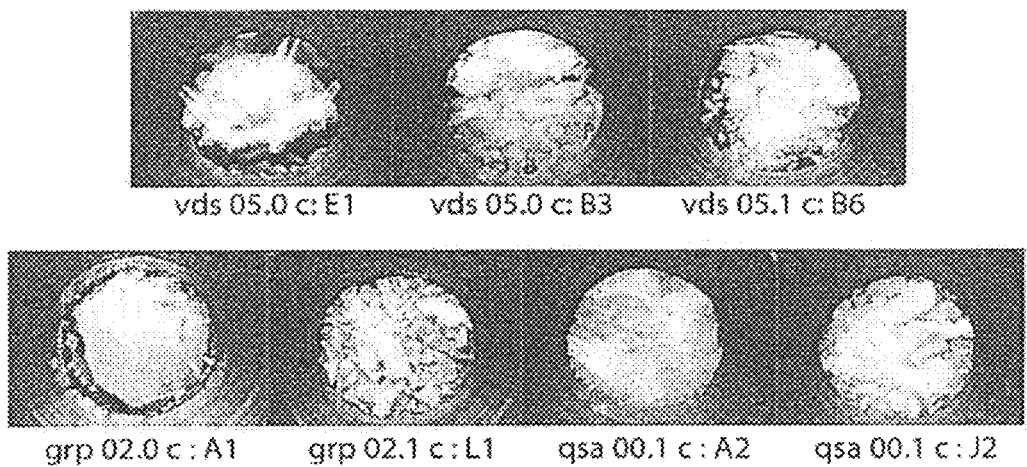

FIG. 42 shows representative digital images of (from top to bottom, left to right): HCl6-class (VDS6.1, vds050.0c:E1), Form HCl5 (VDS28.1, vds05.0c:B3), Form HCl5b (VDS28.2, vds05.1c:B6), mixture HCl1+HCl4 (GRP1.1, grp02.0c:A1), Form HCl3-class (GRP12.1, grp02.1c:L1), Form HCl2 (QSA12.1, qsa00.1c:A2) and Form HCl2b (QSA21.1, qsa00.1c:J2).

Figure 43:
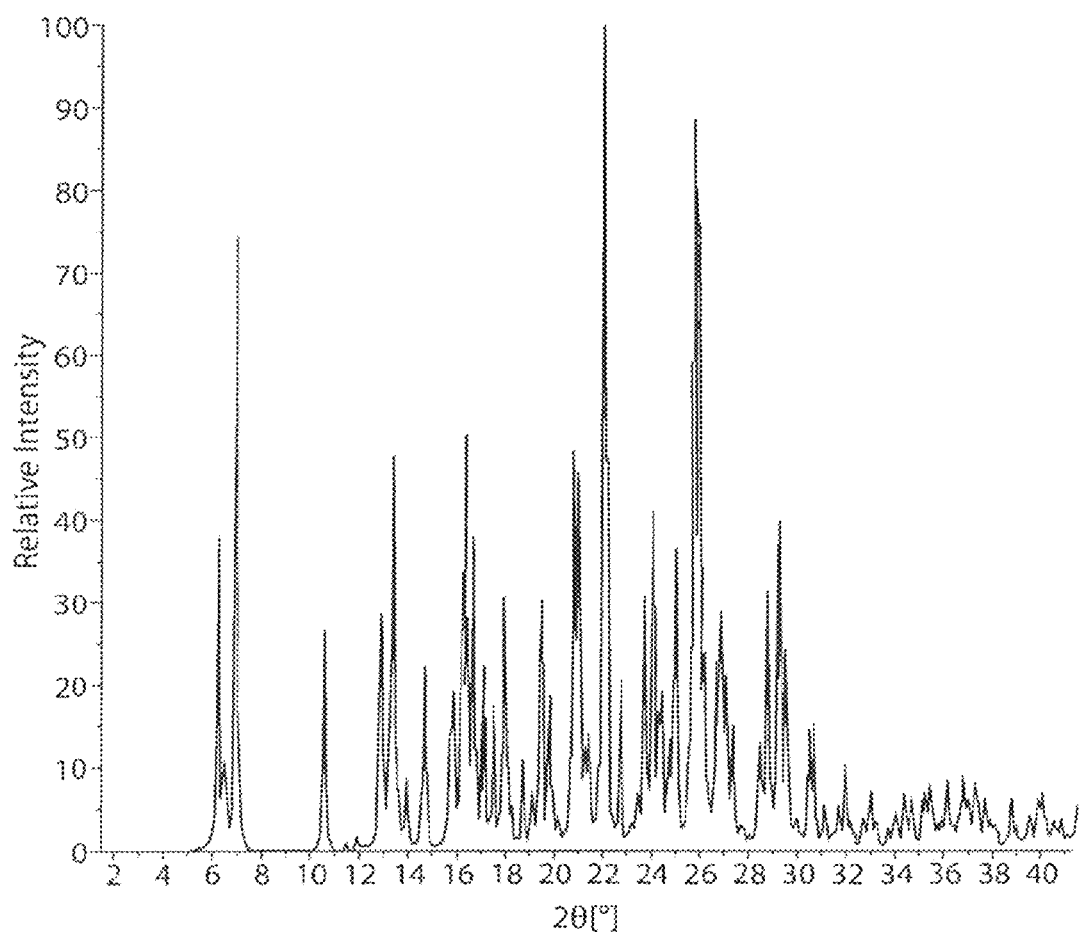

FIG. 43 is a characteristic X-Ray Powder Diffraction (XRPD) pattern obtained from Form J of ponatinib hydrochloride. Relative Intensity (in counts) is shown on the vertical axis and degrees (2θ) shown on the horizontal axis.

Figure 44:
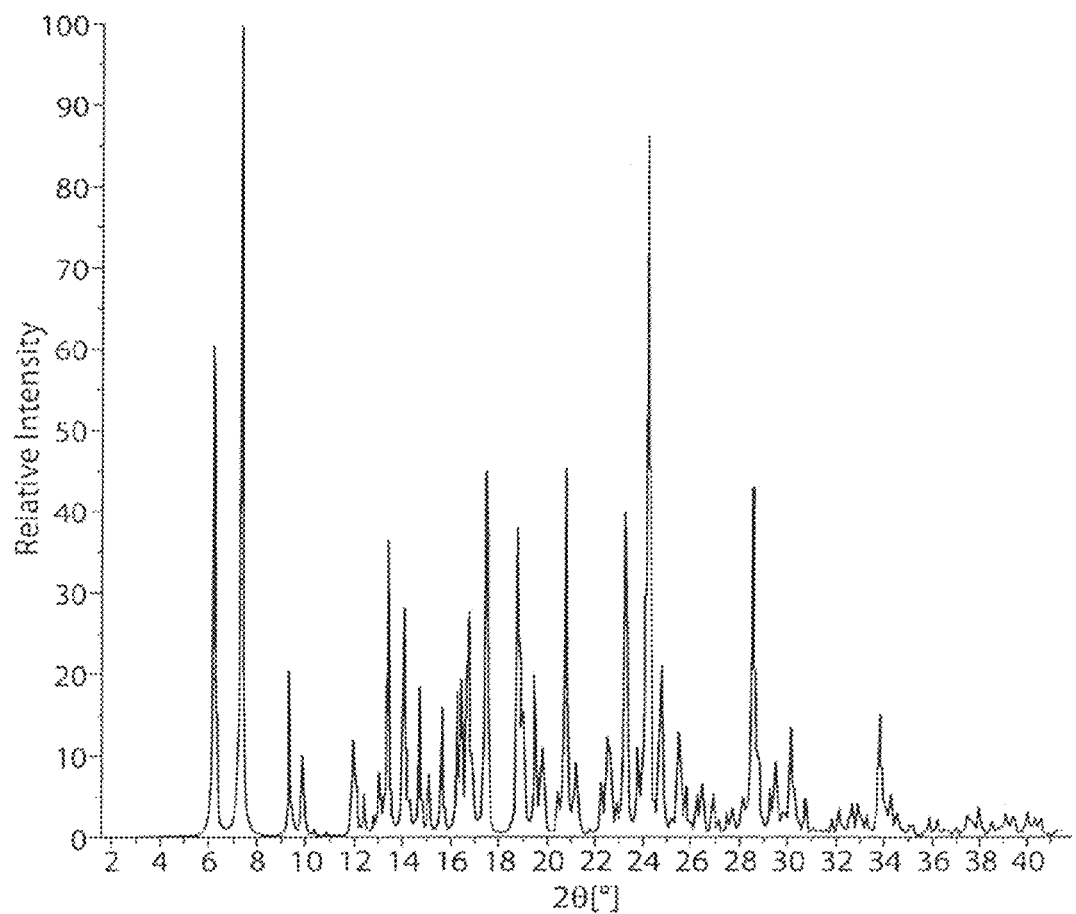

FIG. 44 is a characteristic X-Ray Powder Diffraction (XRPD) pattern obtained from Form K of ponatinib hydrochloride. Relative Intensity (in counts) is shown on the vertical axis and degrees (2θ) shown on the horizontal axis.

Figure 45:
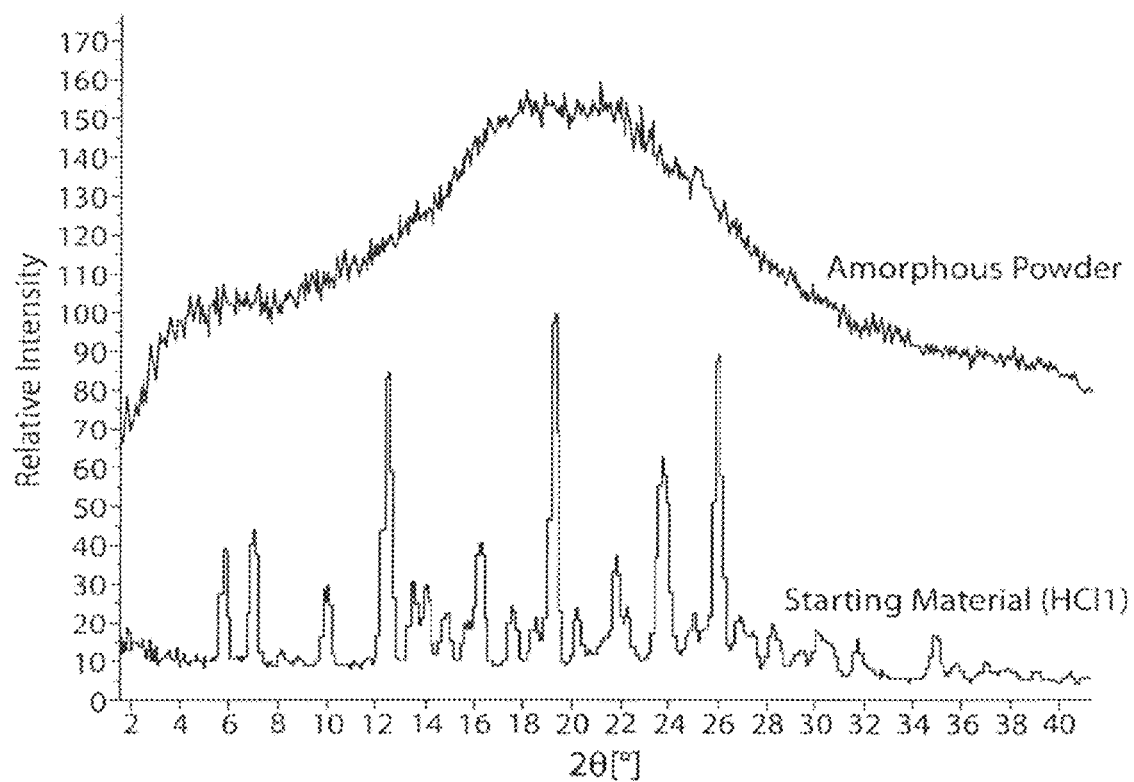

FIG. 45 shows characteristic XRPD patterns of Form A of ponatinib hydrochloride (bottom pattern) and amorphous ponatinib hydrochloride (top pattern) (solvent:2,2,2-trifluoroethanol) where the vertical axis denotes relative intensity (counts) and the horizontal axis denotes Two Theta (Degrees).

Figure 46:
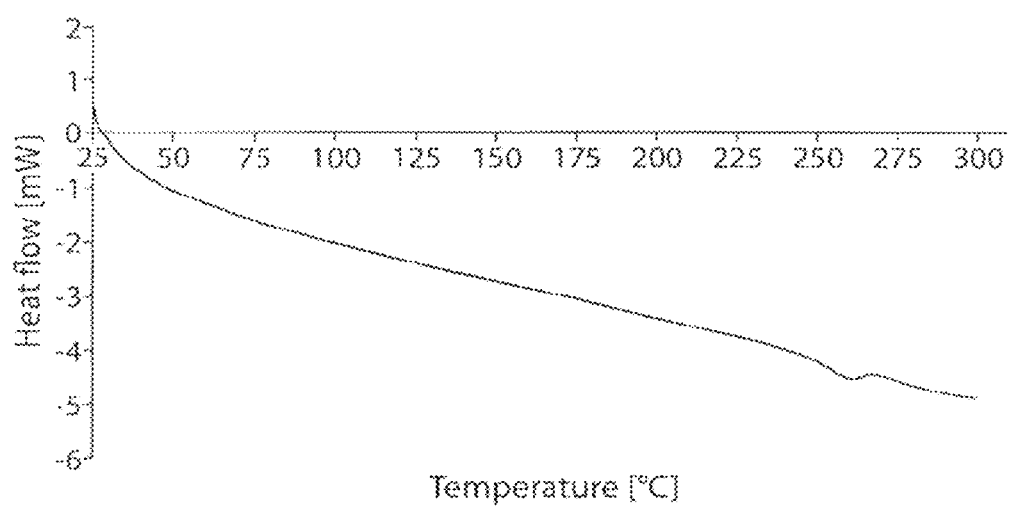

FIG. 46 is a characteristic Differential Scanning Calorimetry (DSC) thermogram of amorphous 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride. An intense endothermic event with a peak of 259.4° C. was observed, corresponding to the melting point of the amorphous form. The vertical axis denotes Heat Flow [mW] and the horizontal axis denotes Temperature (° C.).

FIG. 47A is a characteristic HPLC spectrum obtained from Form H of ponatinib hydrochloride (VDS4). Absorbance units are shown on the vertical axis (mAU) and time (minutes) is shown on the horizontal axis. Absorbance units are shown on the vertical axis (mAU) and time (minutes) is shown on the horizontal axis. FIG. 47B is a characteristic mass spectrum obtained from Form H of ponatinib hydrochloride. FIG. 47C is a tabulated form of the data presented in FIG. 47A.

FIG. 48 is a tabular summary of solid forms of ponatinib that include polymorphs and pseudo-polymorphs identified as Forms A through J.

FIG. 49 is a tabular summary of occurrences, crystallization methods, physical forms, endotherms and purities of ponatinib polymorphs and pseudo-polymorphs identified as Forms A through J.

Figure 50:
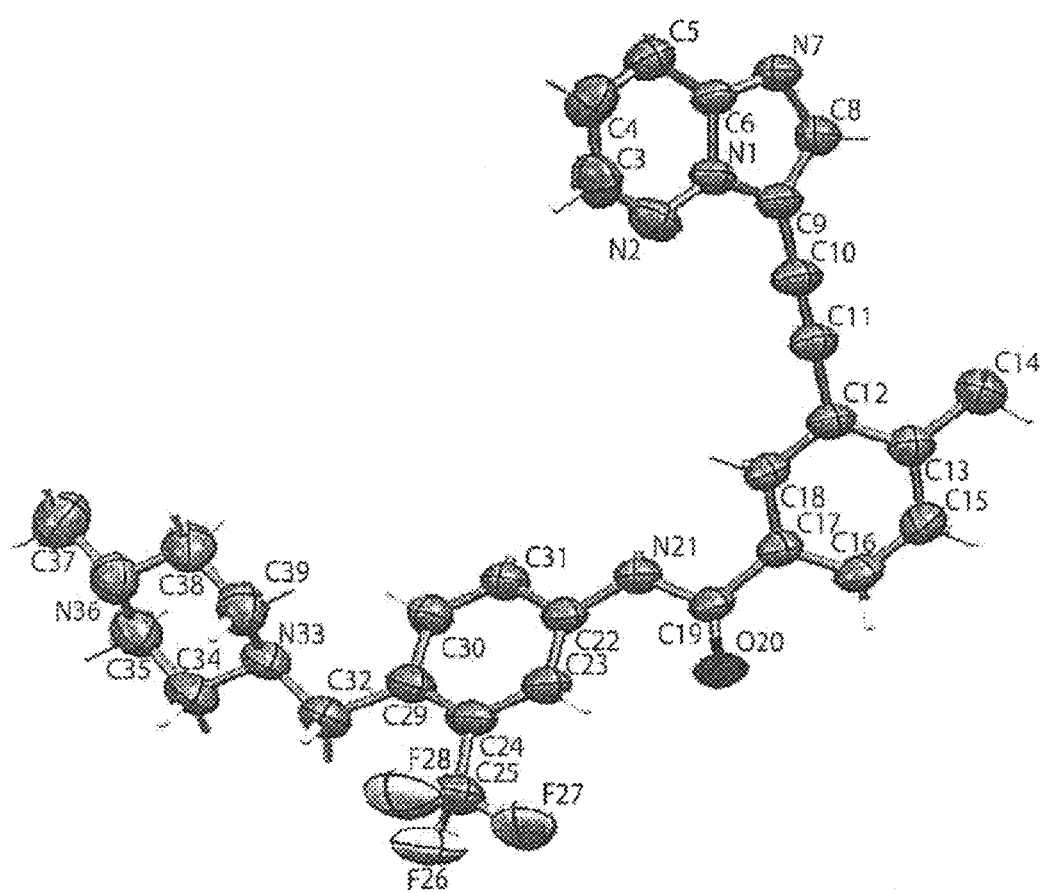

FIG. 50 shows the molecular structure and numbering scheme of ponatinib free base crystalline Form A (anhydrate) determined by single-crystal X-ray analysis.

Figure 51:
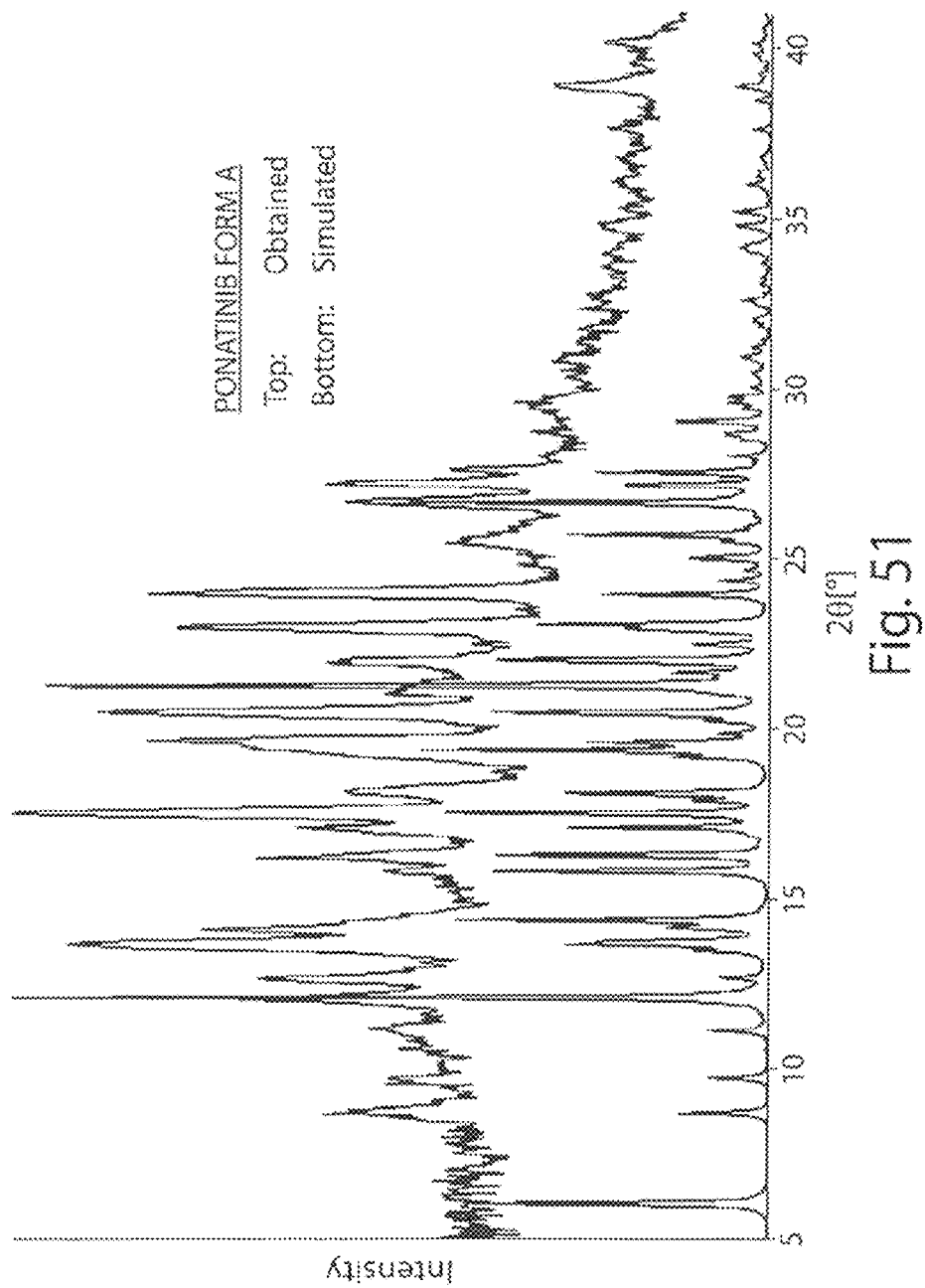

FIG. 51 shows XRPD patterns for ponatinib free base crystalline Form A (anhydrate) simulated and experimentally obtained.

Figure 52:
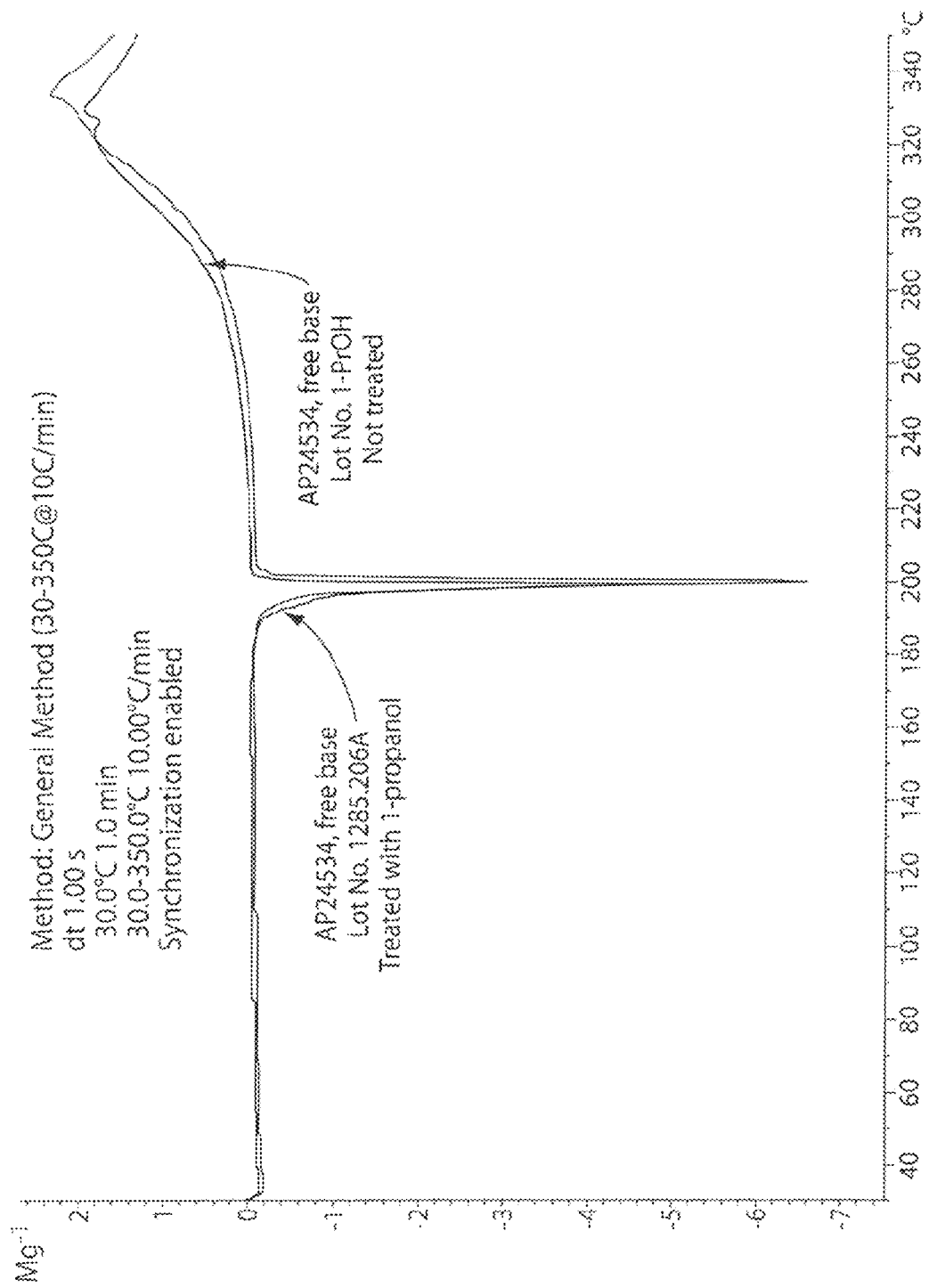

FIG. 52 is a characteristic differential scanning calorimetry (DSC) scan obtained from crystalline Form A of ponatinib free base (anhydrate). Heat flow [mW] is shown on the vertical axis and temperature (° C.) is shown on the horizontal axis.

Figure 53:
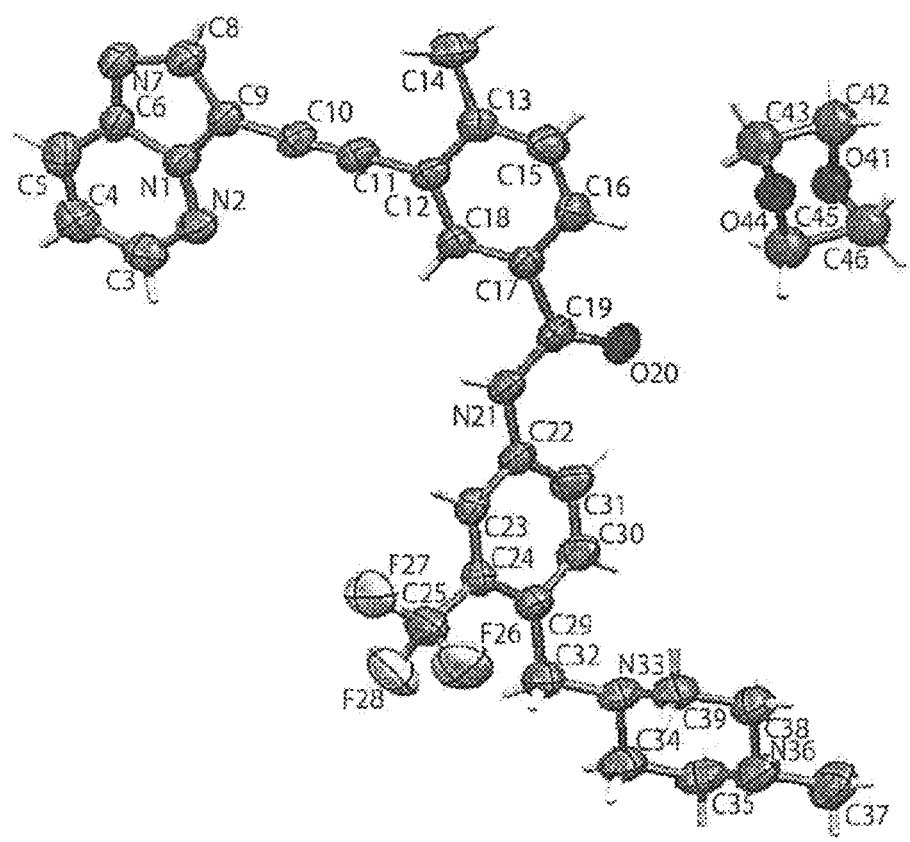

FIG. 53 shows the molecular structure and numbering scheme of B-Class ponatinib/1,4-dioxane (1:1) solvate (Form B) determined by single-crystal X-ray analysis.

Figure 54:
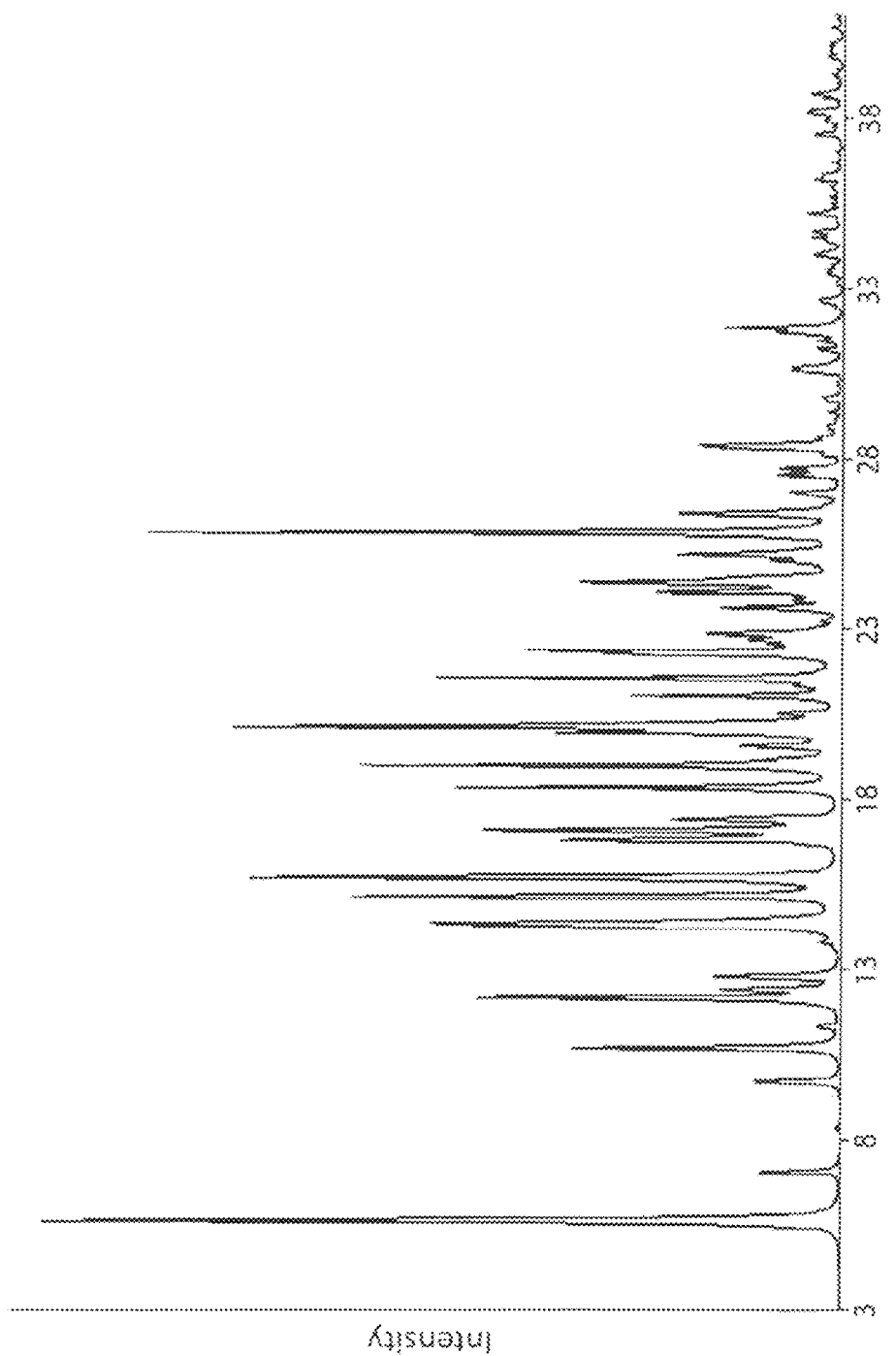

FIG. 54 is a simulated XRPD pattern for B-Class ponatinib/1,4-dioxane (1:1) solvate (Form B).

Figure 55:
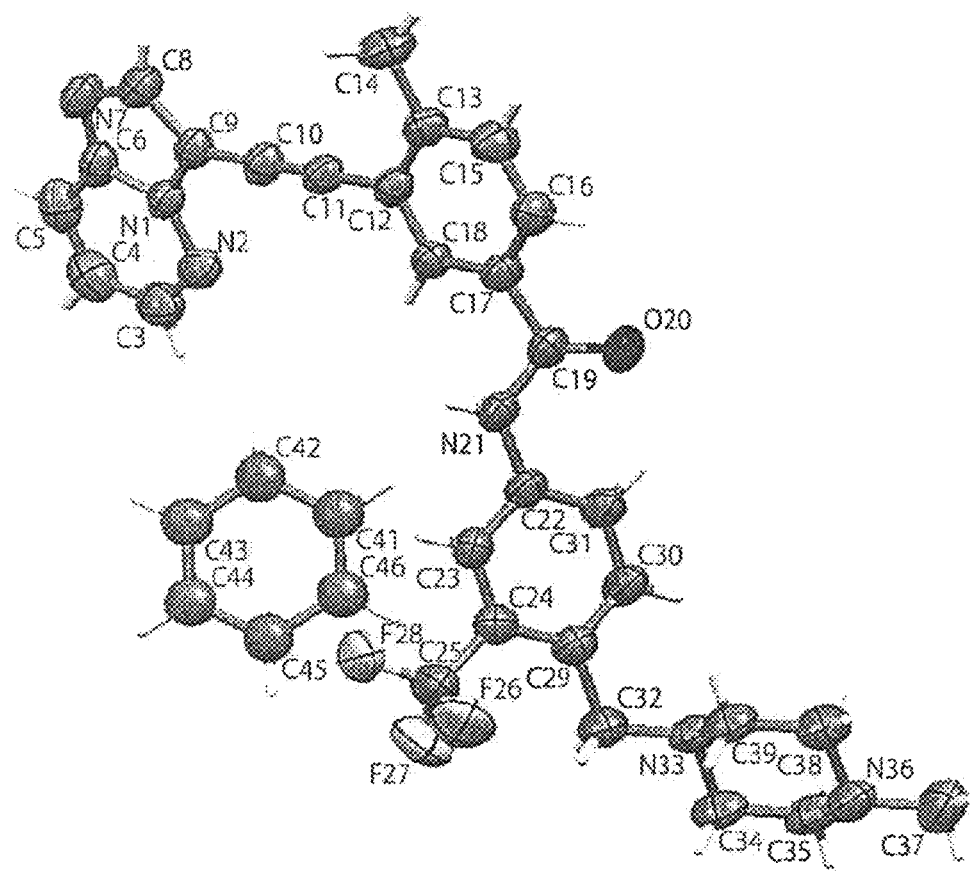

FIG. 55 shows the molecular structure and numbering scheme of B-Class ponatinib/perfluorobenzene (1:1) solvate (Form B) determined by single-crystal X-ray analysis.

Figure 56:
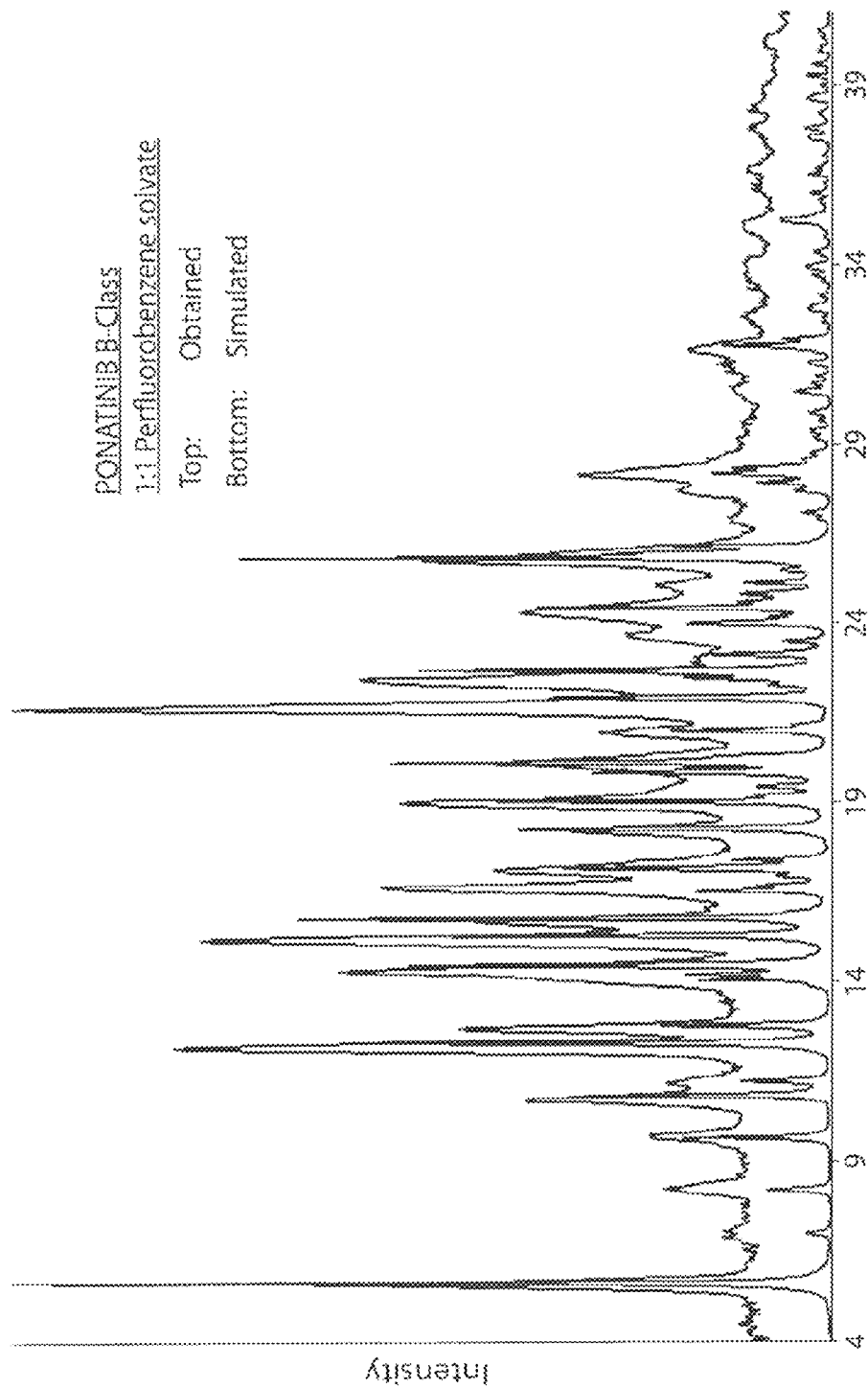

FIG. 56 is the XRPD patterns for B-Class ponatinib/perfluorobenzene (1:1) solvate (Form B) simulated and experimentally obtained.

Figure 57:
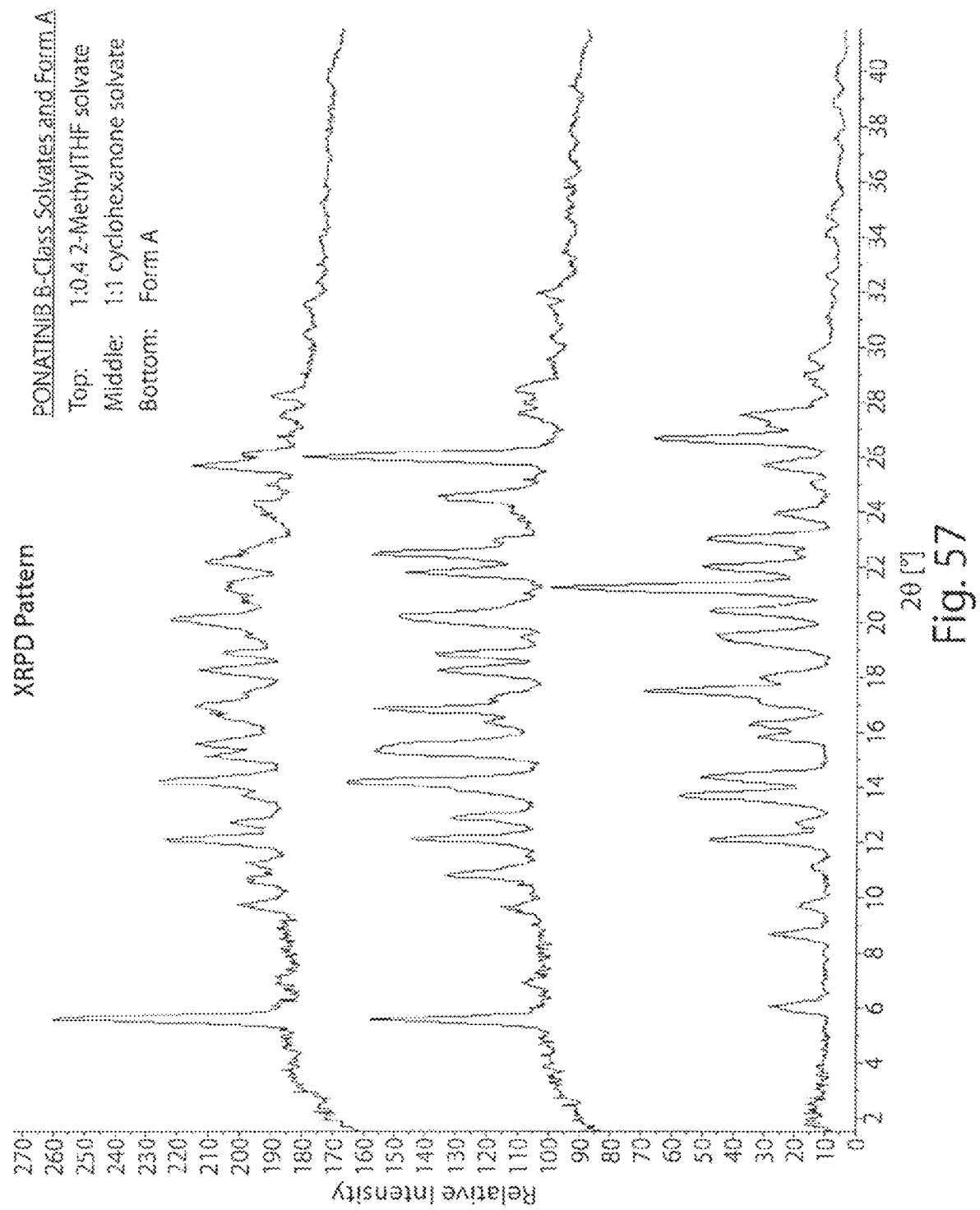

FIG. 57 shows XRPD patterns for Form B ponatinib/2-methylTHF (1:0.4) solvate (upper pattern); Form B ponatinib/cyclohexanone (1:1) solvate (middle pattern); and Form A (bottom pattern).

Figure 58:
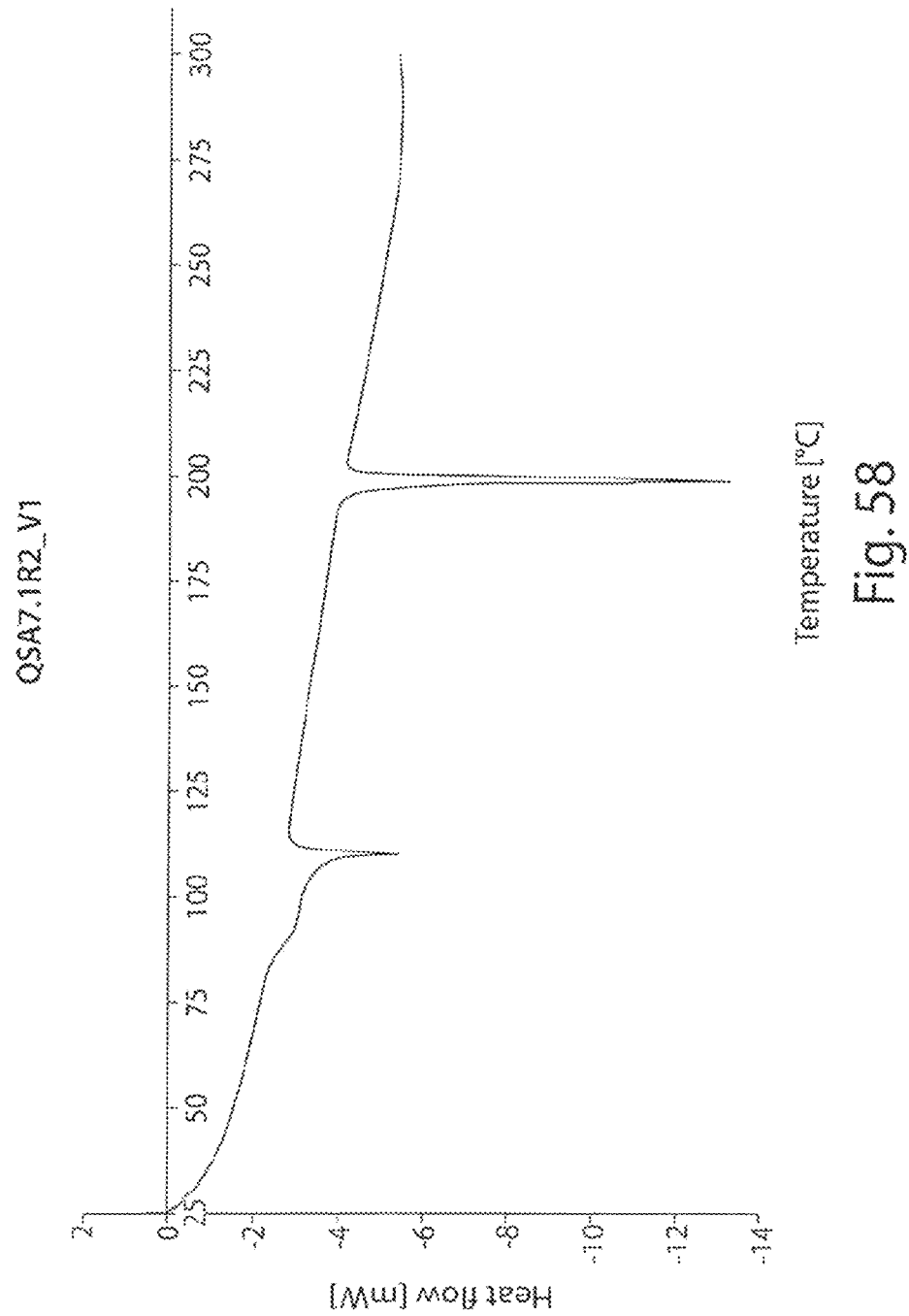

FIG. 58 is a characteristic differential scanning calorimetry (DSC) scan obtained from B-Class 1:1 ponatinib/cyclohexanone solvate (QSA7.1). Heat flow [mW] is shown on the vertical axis and temperature (° C.) is shown on the horizontal axis.

Figure 59:
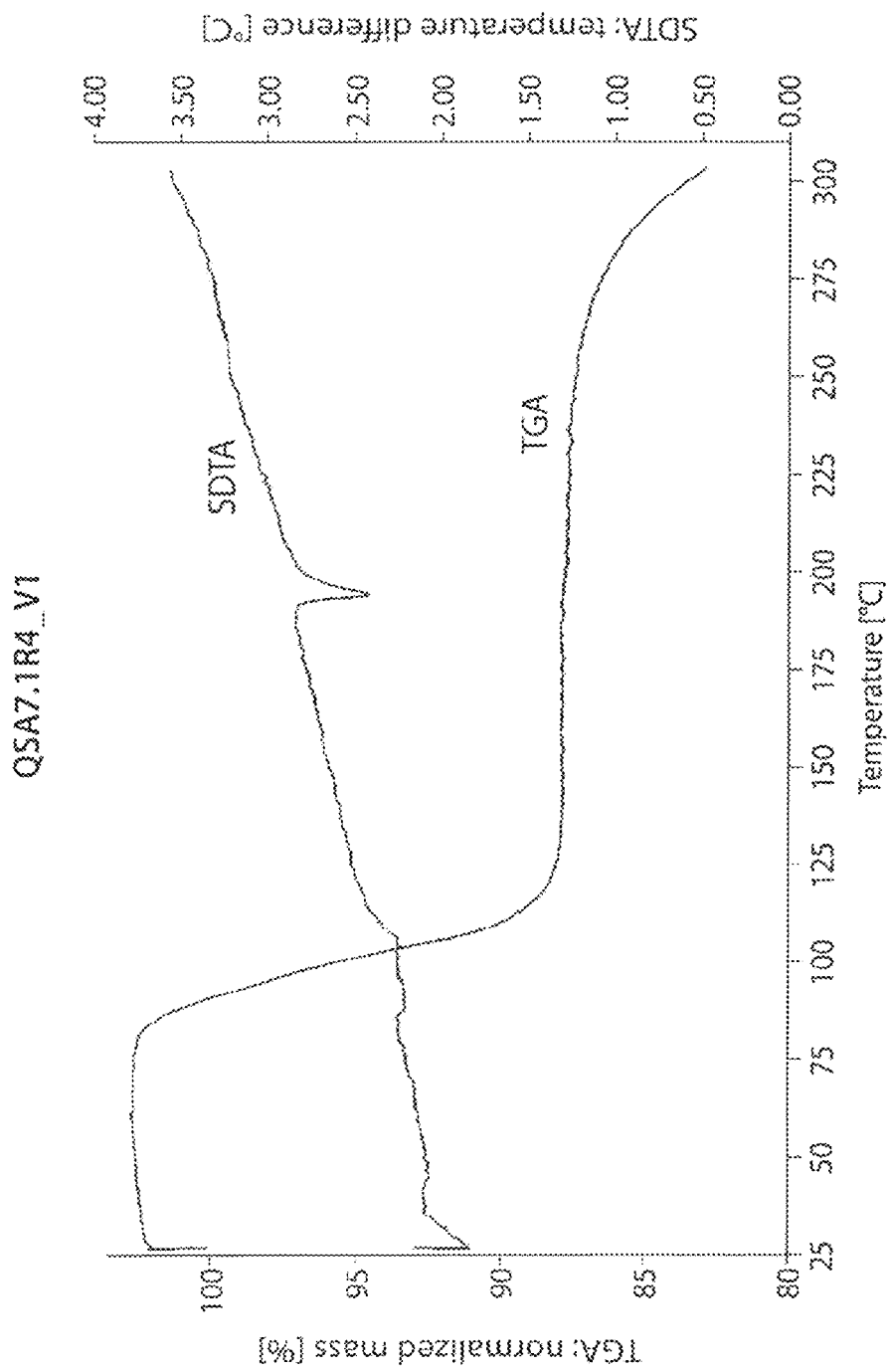

FIG. 59 is a characteristic overlay of TGA and SDTA thermograms of B-Class 1:1 ponatinib/cyclohexanone solvate (QSA7.1).

Figure 60:
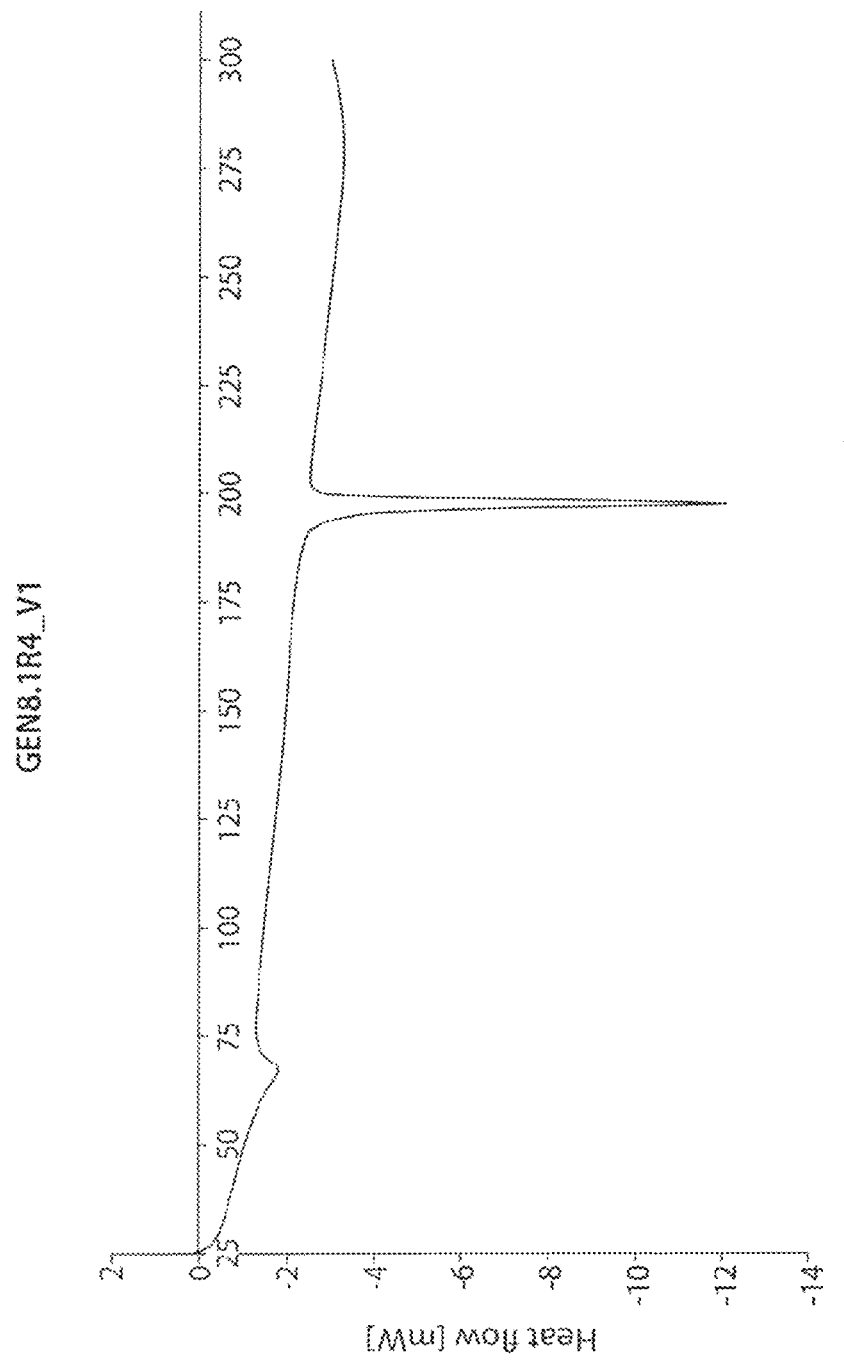

FIG. 60 is a characteristic differential scanning calorimetry (DSC) scan obtained from B-Class 1:0.4 ponatinib/2-methylTHF solvate (GEN8.1). Heat flow [mW] is shown on the vertical axis and temperature (° C.) is shown on the horizontal axis.

Figure 61:
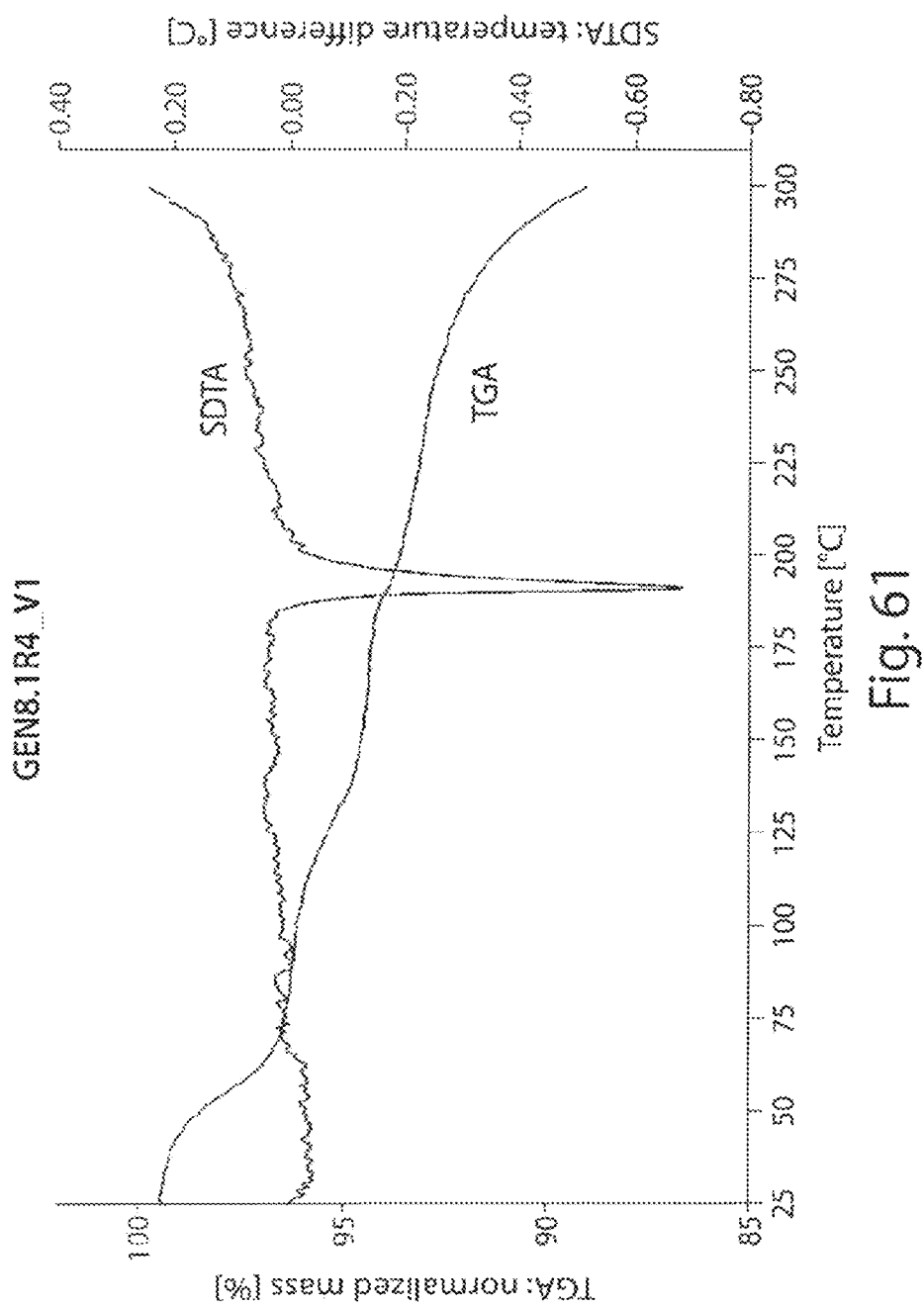

FIG. 61 is a characteristic overlay of TGA and SDTA thermograms of B-Class 1:0.4 ponatinib/2-methylTHF solvate (GEN8.1).

Figure 62:
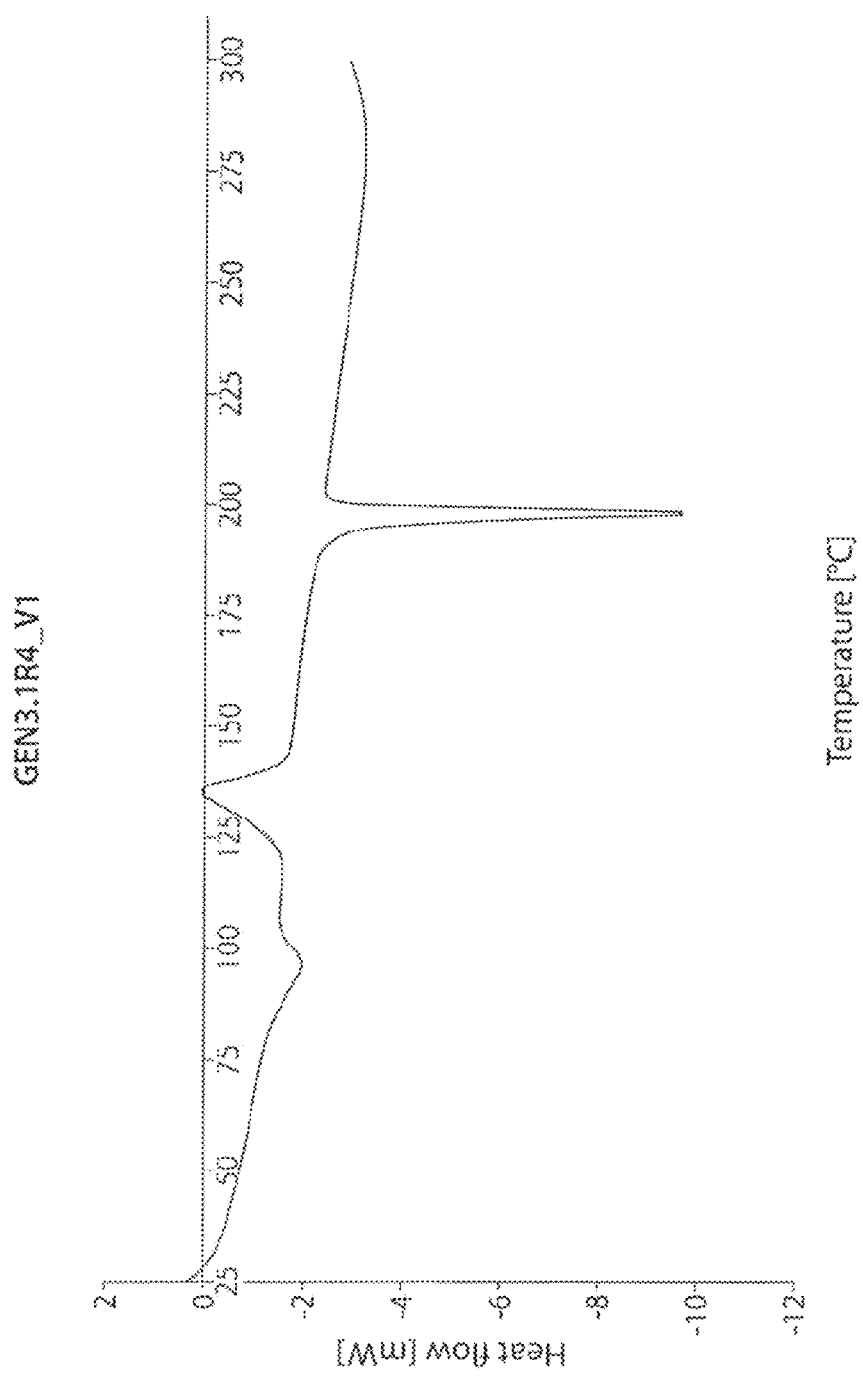

FIG. 62 is a characteristic differential scanning calorimetry (DSC) scan obtained from ponatinib low crystalline Form C (GEN3.1). Heat flow [mW] is shown on the vertical axis and temperature (° C.) is shown on the horizontal axis.

Figure 63:
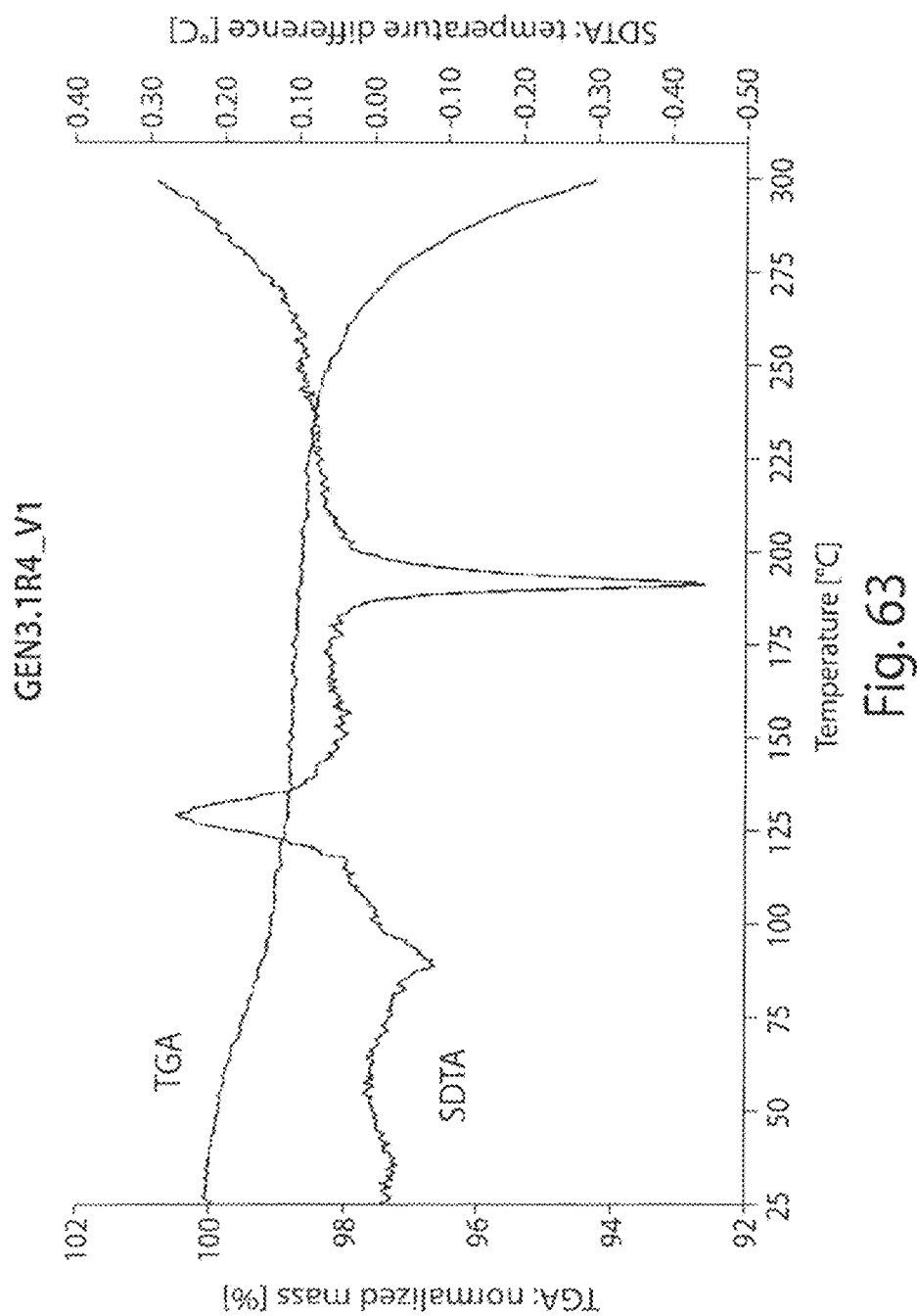

FIG. 63 is a characteristic overlay of TGA and SDTA thermograms of ponatinib low crystalline Form C (GEN3.1).

Figure 64:
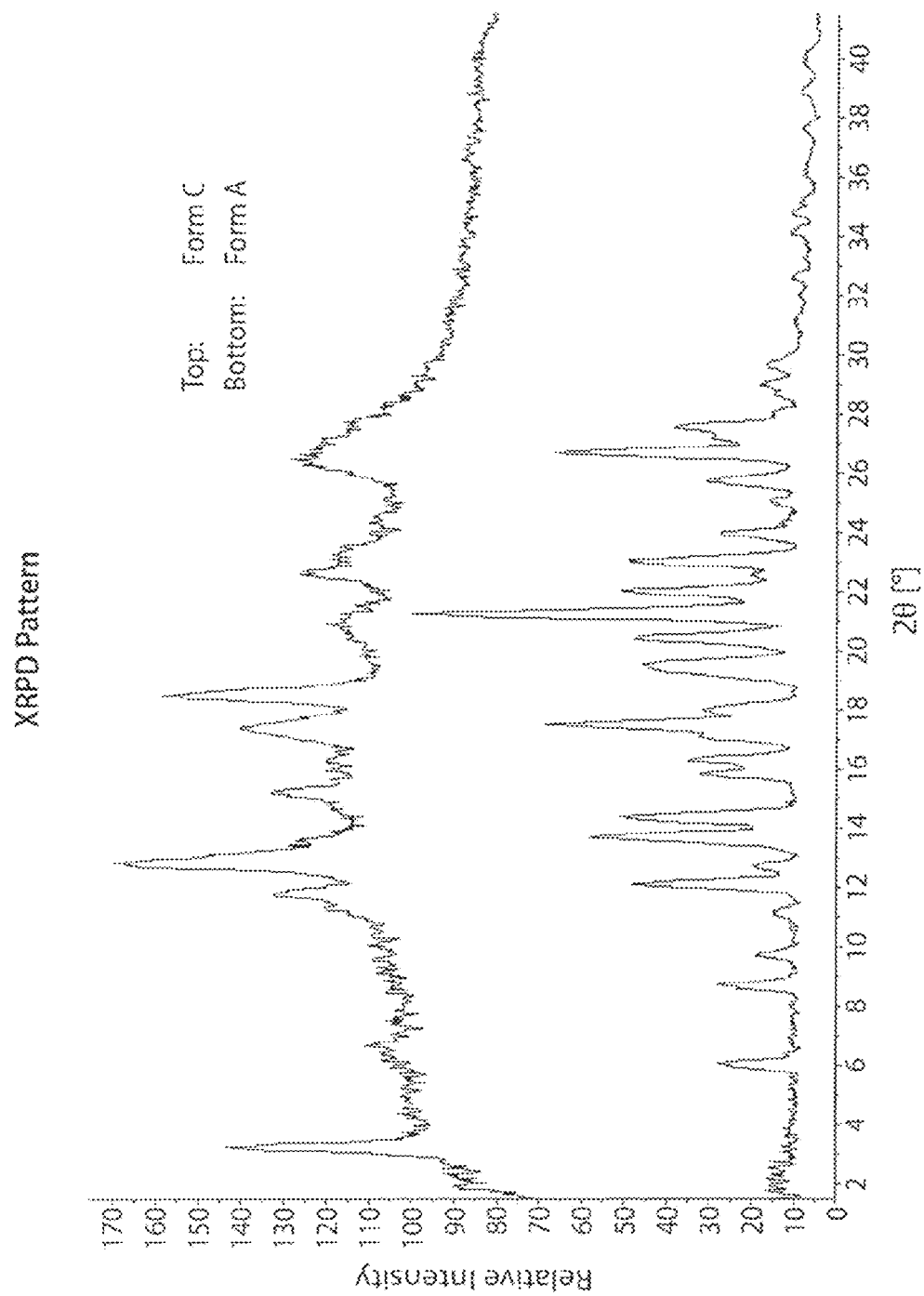

FIG. 64 shows XRPD patterns for ponatinib low crystalline Form C (GEN3.1) (top pattern) and Form A (bottom pattern).

Figure 65:
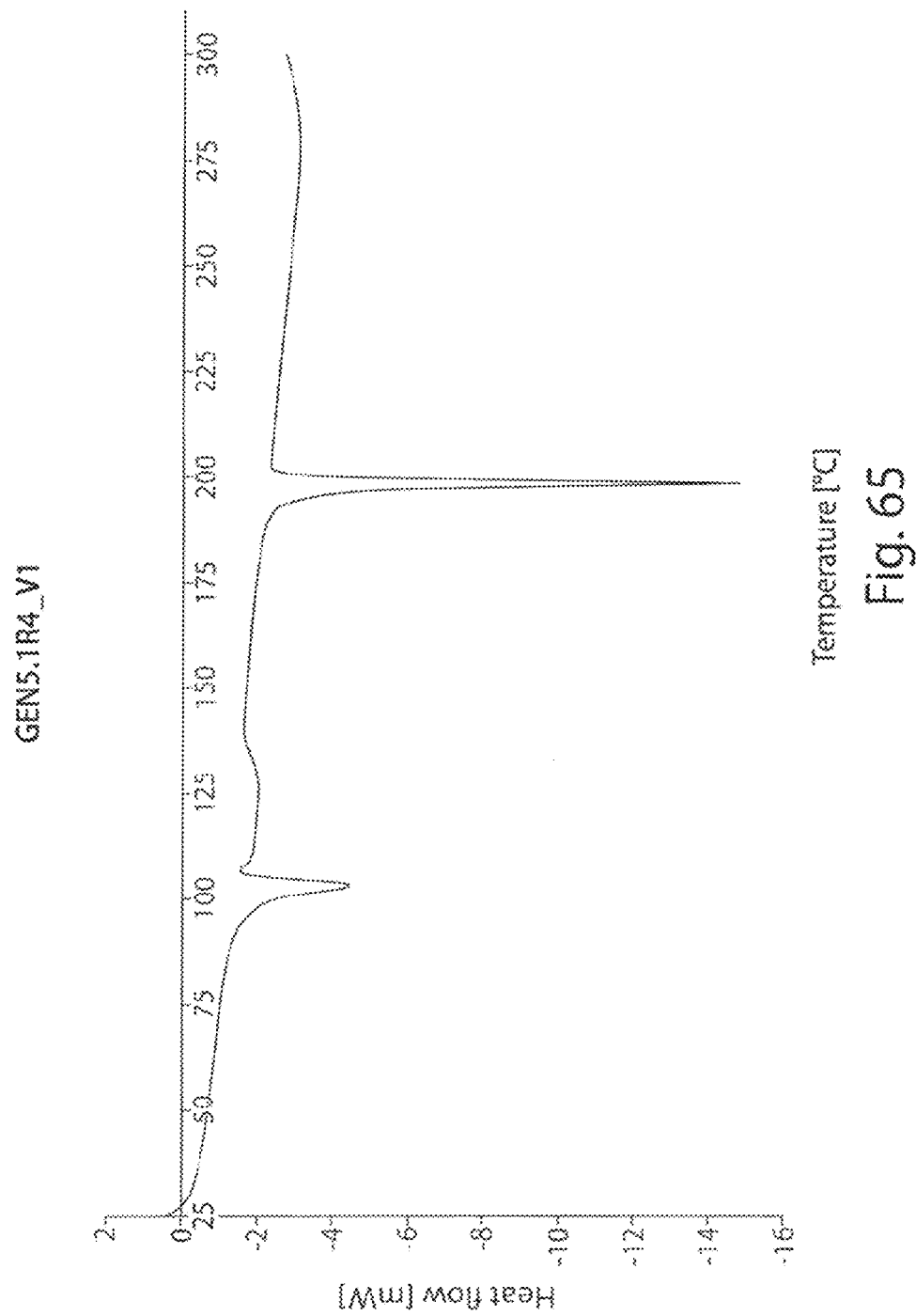

FIG. 65 is a characteristic differential scanning calorimetry (DSC) scan obtained from Form D (GEN5.1R1) of ponatinib. Heat flow [mW] is shown on the vertical axis and temperature (° C.) is shown on the horizontal axis.

Figure 66:
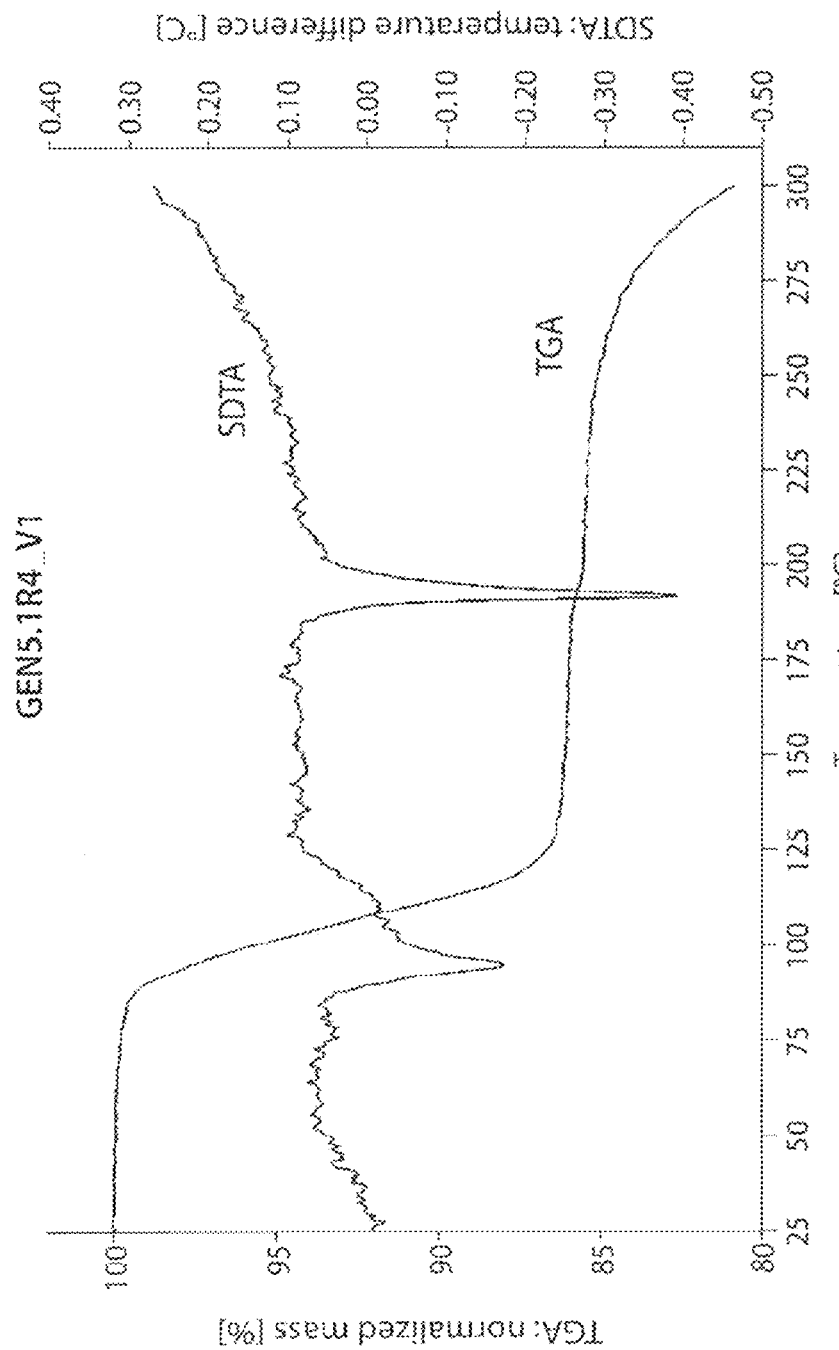

FIG. 66 is a characteristic overlay of TGA and SDTA thermograms of Form D (GEN5.1R1) of ponatinib.

Figure 67:
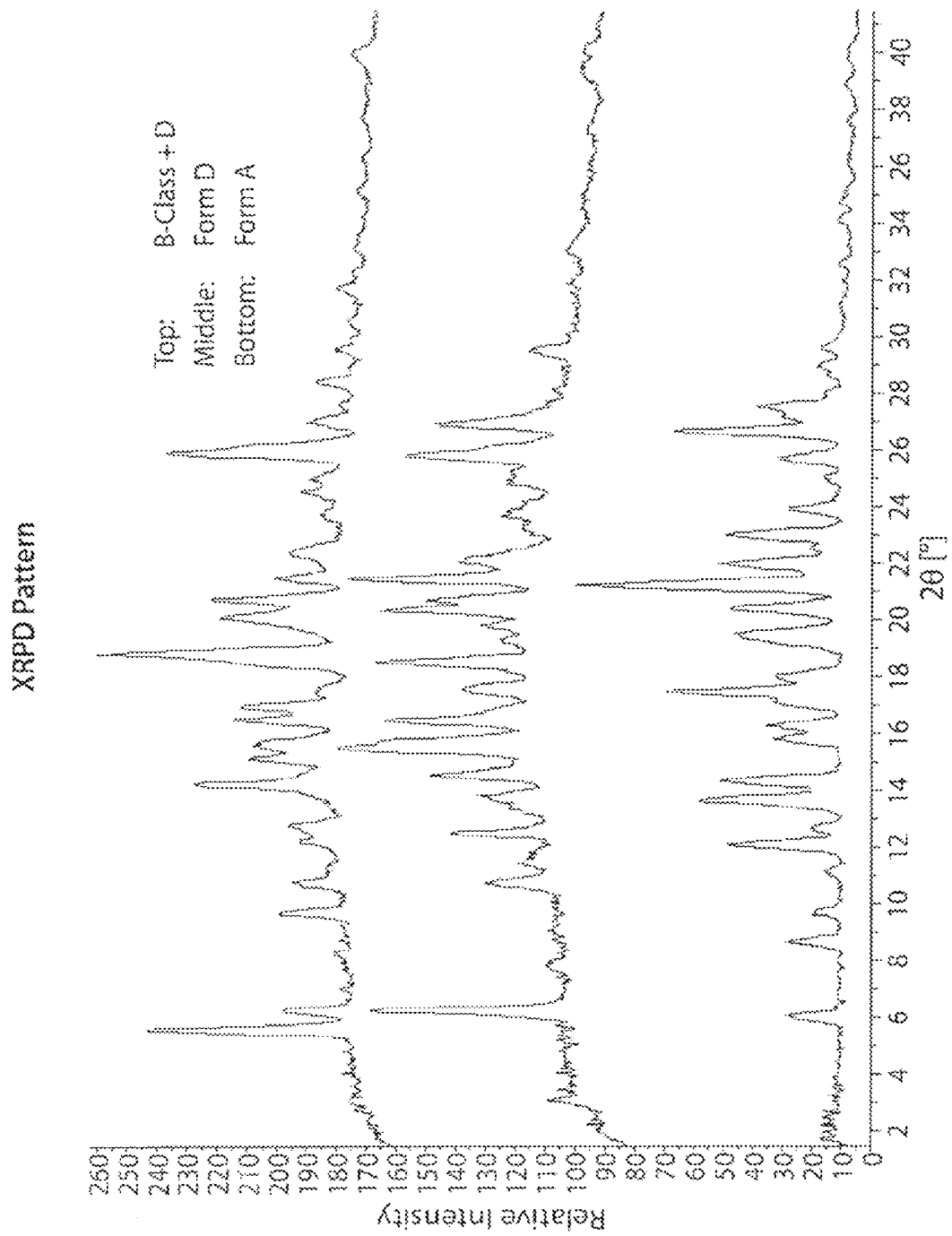

FIG. 67 shows XRPD patterns for Form D of ponatinib (middle pattern) and Form A (bottom pattern). Also shown is the XRPD pattern for a mixture of B-Class solvates and Form D of ponatinib (upper pattern).

Figure 68:
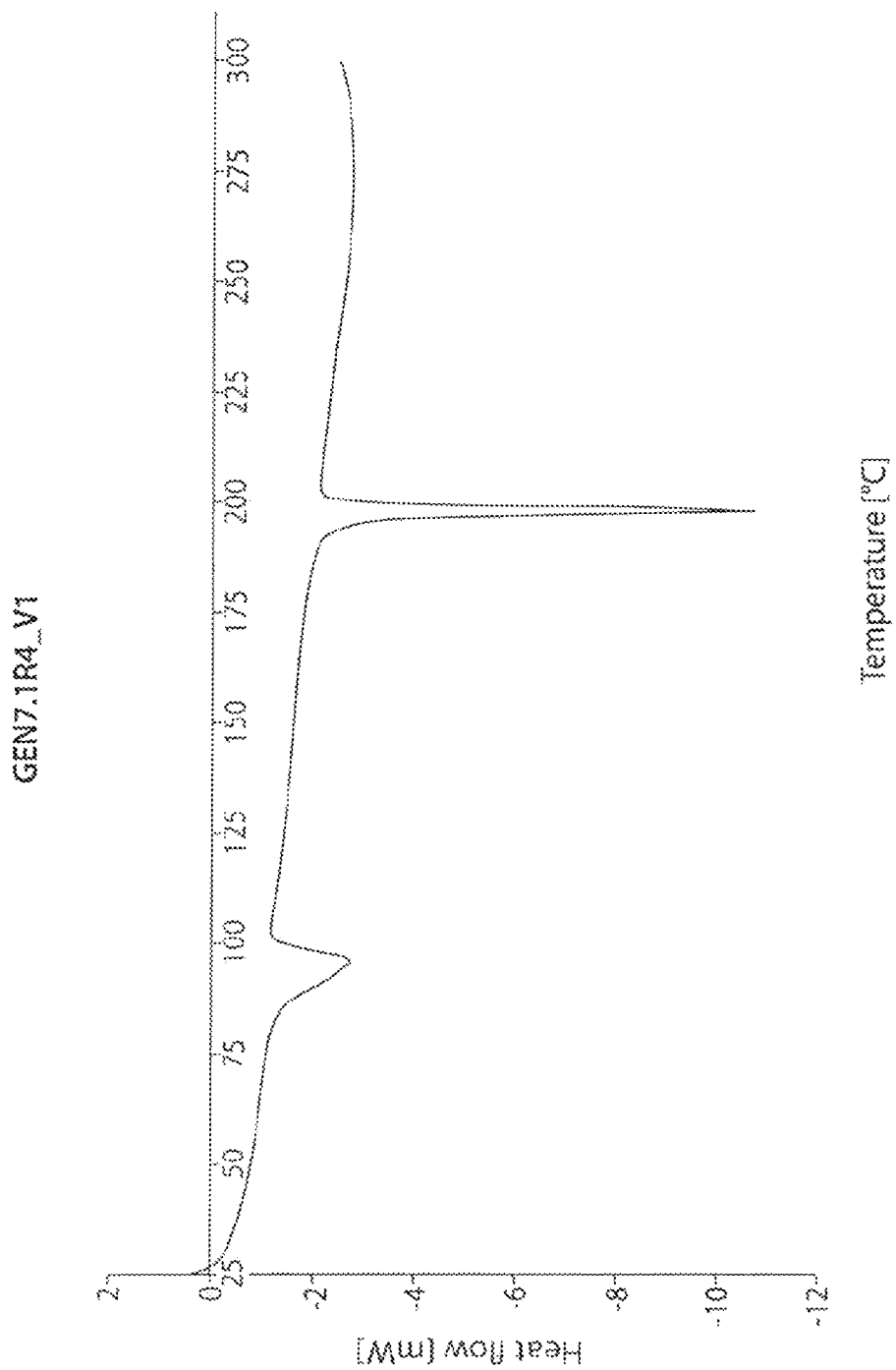

FIG. 68 is a characteristic differential scanning calorimetry (DSC) scan obtained from E-Class ponatinib/THF 1:1 solvate (GEN7.1). Heat flow [mW] is shown on the vertical axis and temperature (° C.) is shown on the horizontal axis.

Figure 69:
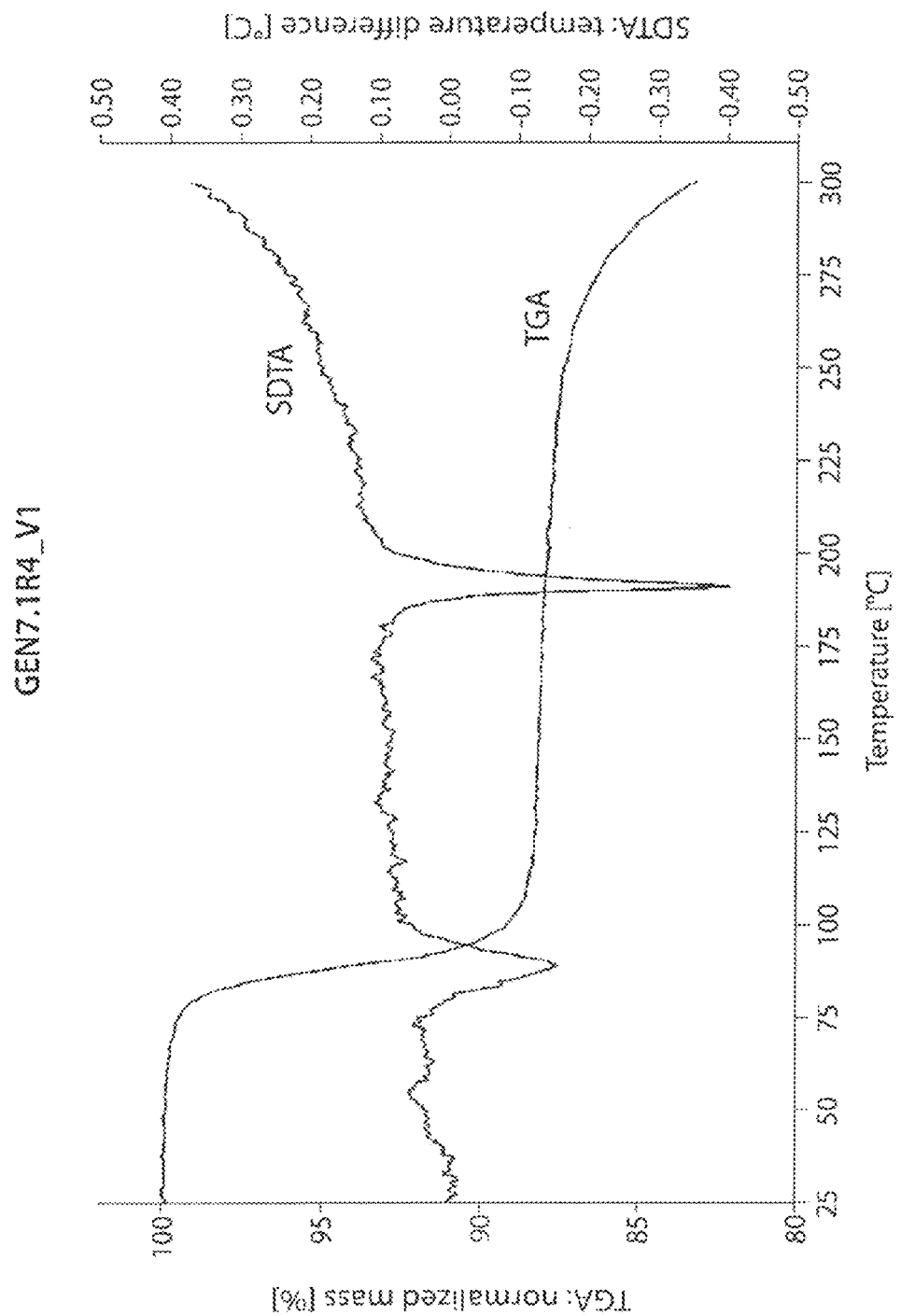

FIG. 69 is a characteristic overlay of TGA and SDTA thermograms of E-Class ponatinib/THF 1:1 solvate (GEN7.1).

Figure 70:
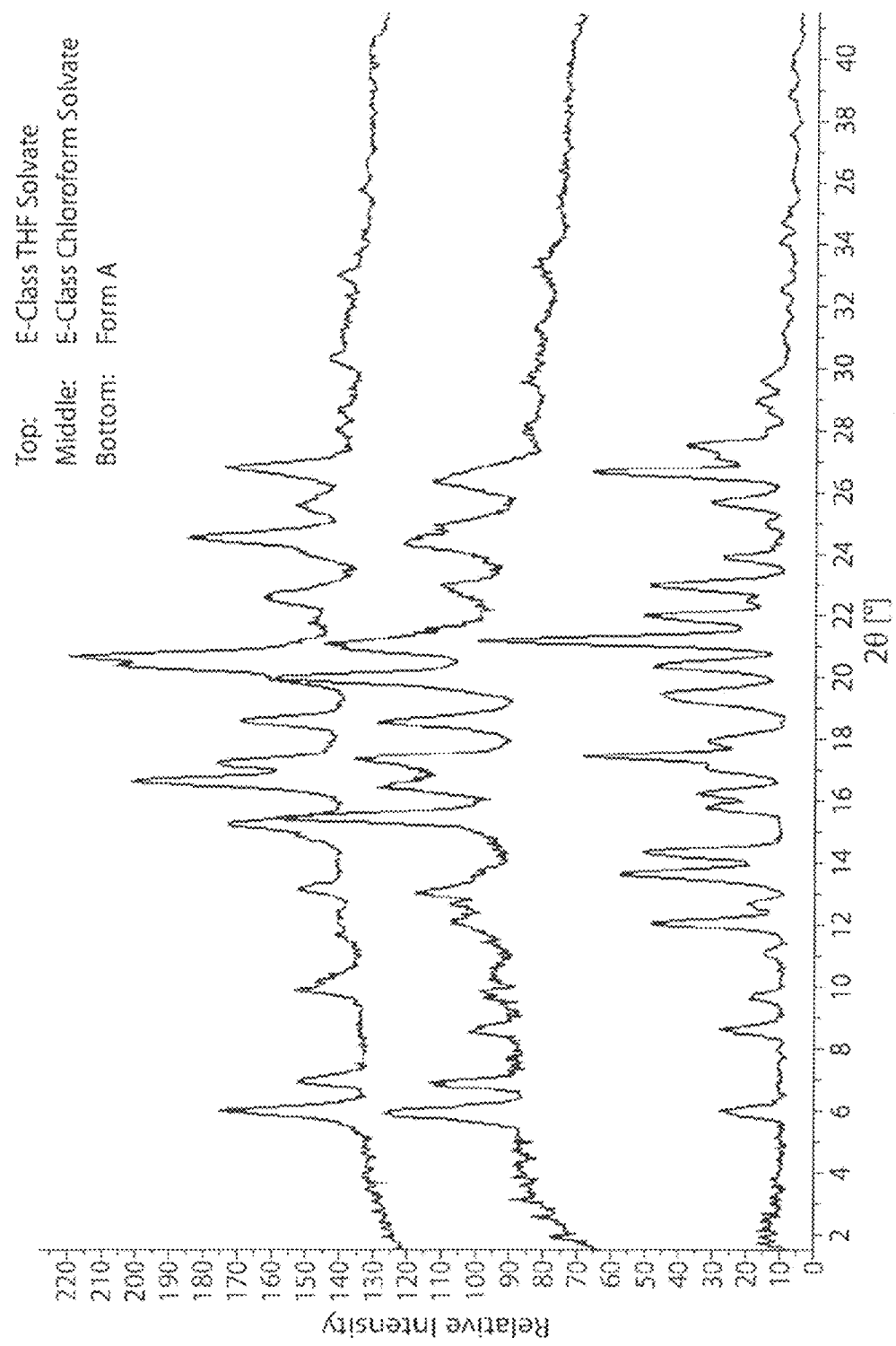

FIG. 70 shows XRPD patterns for E-Class ponatinib/THF 1:1 solvate (GEN7.1) (upper pattern); E-Class ponatinib/chloroform solvate (SLP3.1) (middle pattern); and Form A (bottom pattern).

Figure 71:
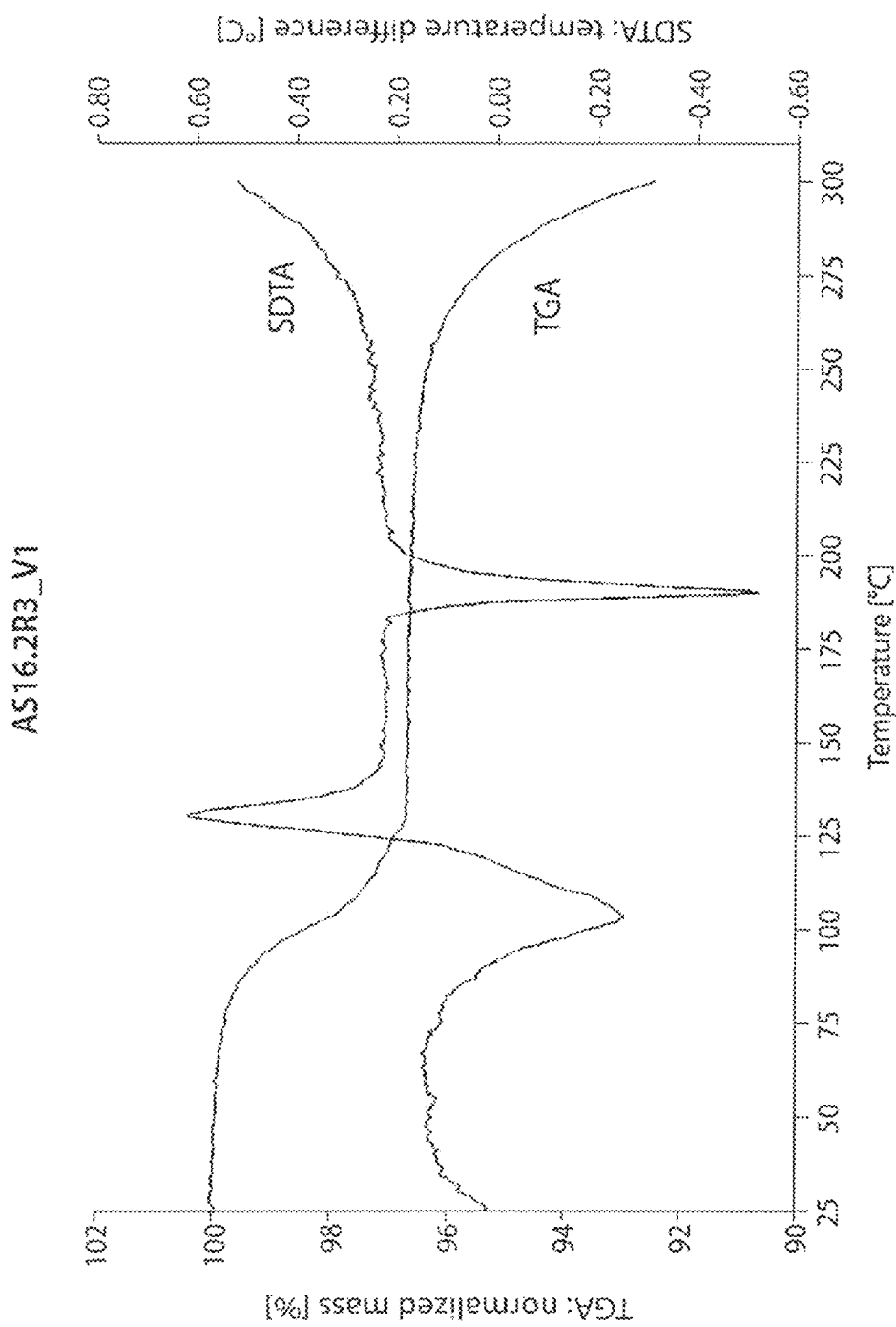

FIG. 71 is a characteristic overlay of TGA and SDTA thermograms of ponatinib Form F (AS16.2).

Figure 72:
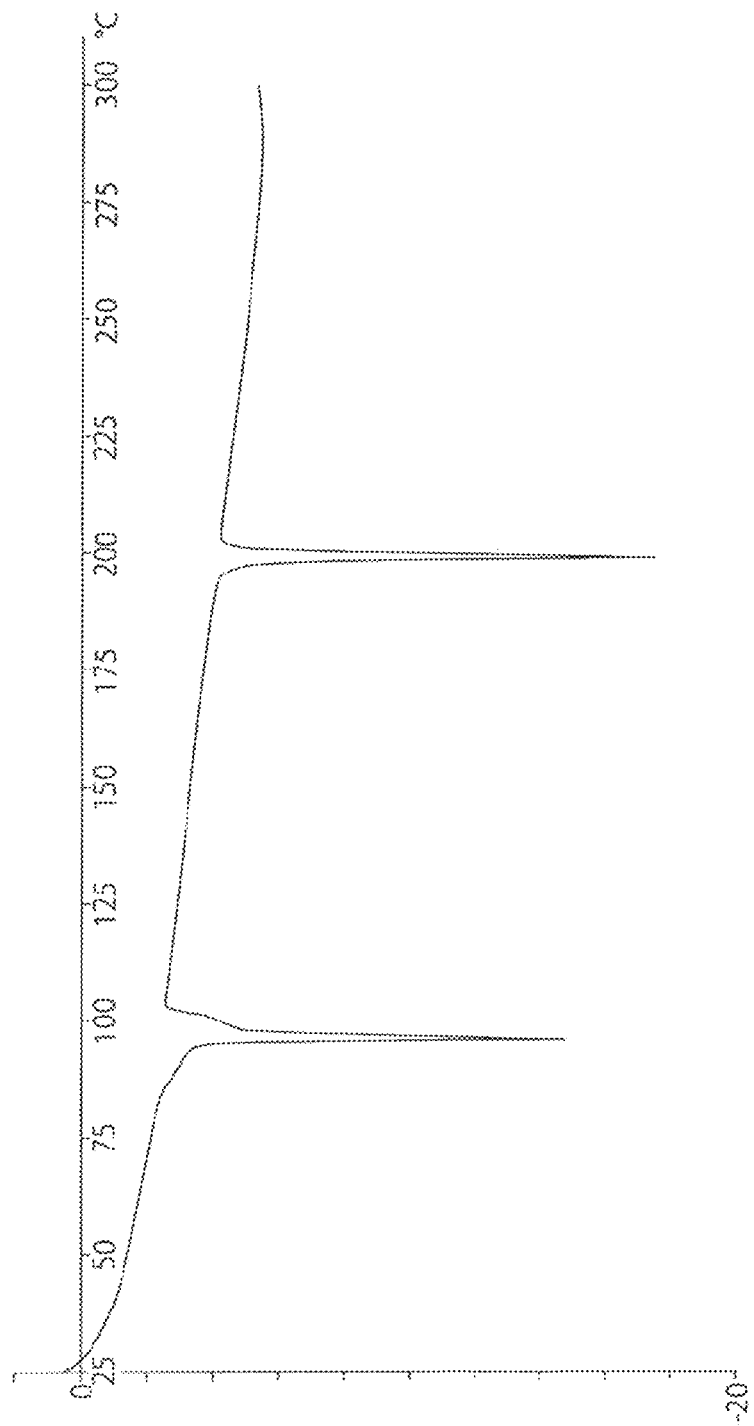

FIG. 72 a characteristic differential scanning calorimetry (DSC) scan obtained from Form H (VLD1, dried solid from stock). Heat flow [mW] is shown on the vertical axis and temperature (° C.) is shown on the horizontal axis.

Figure 73:
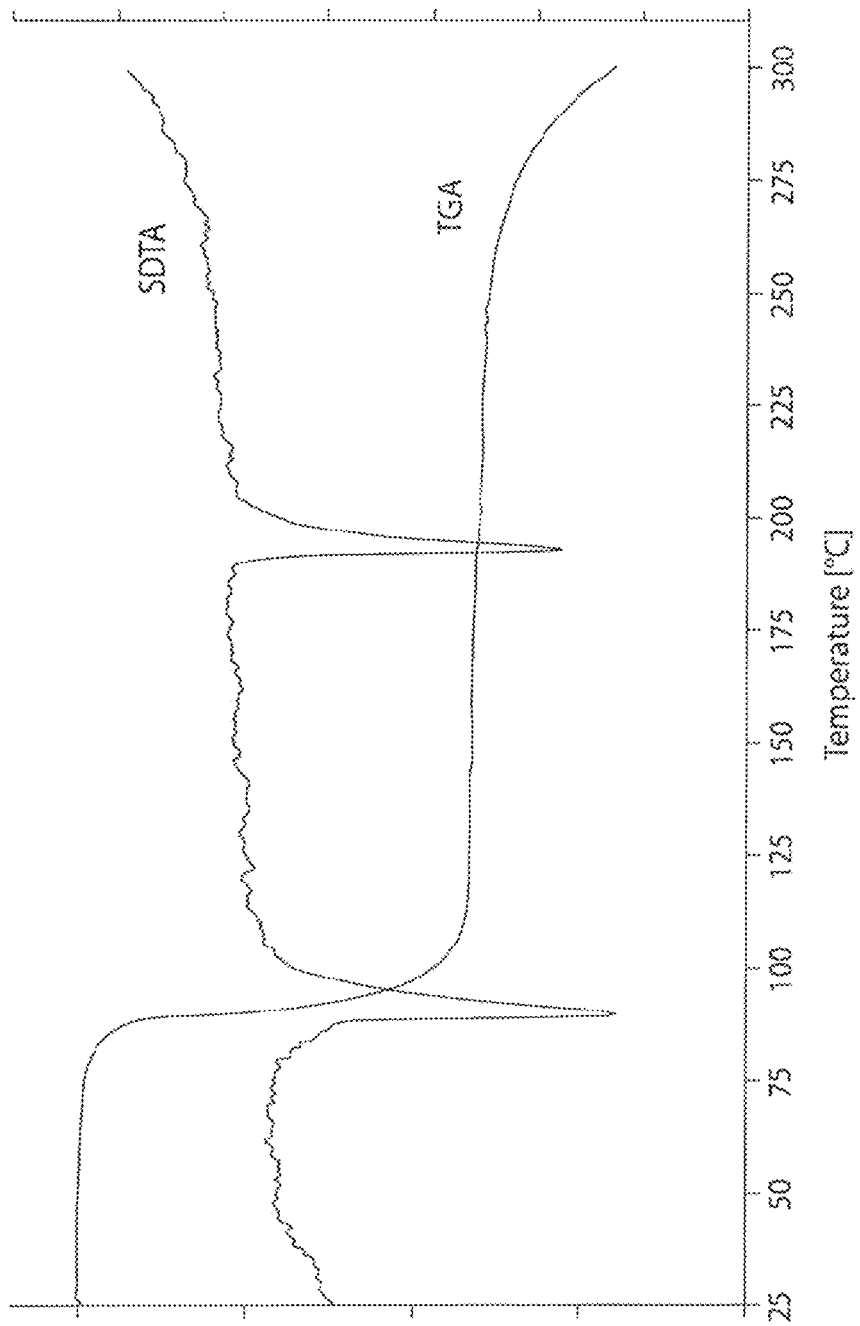

FIG. 73 is a characteristic overlay of TGA and SDTA thermograms of Form H (VLD1, dried solid from stock).

Figure 74:
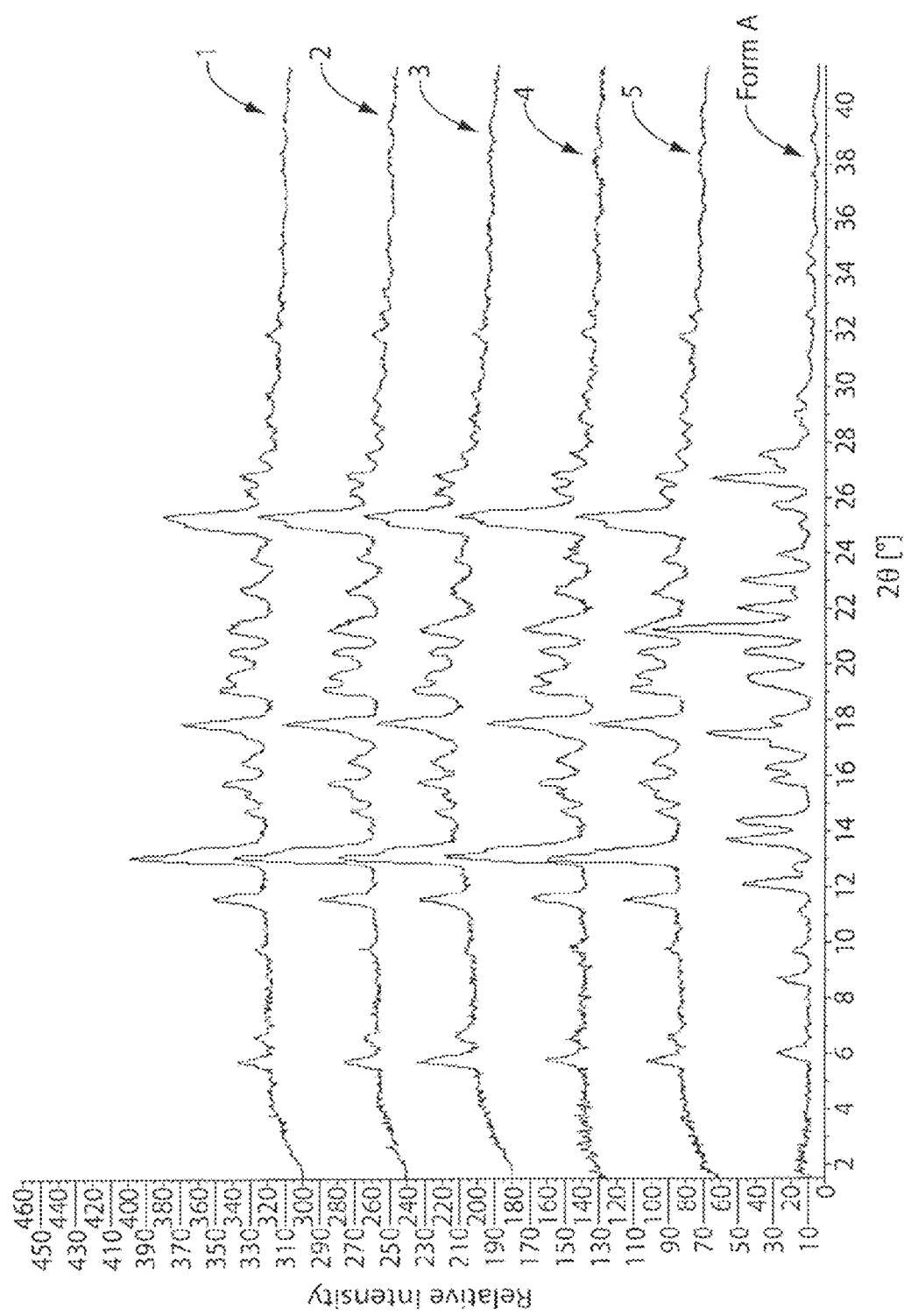

FIG. 74 shows a series of XRPD patterns as follows: Plot 1 is Form H (VLD2 experiment, after 2-weeks and drying); Plot 2 is Form H (VLD1 experiment, after 2-weeks and drying); Plot 3 is Form H (VLD1 experiment, dried solid from stock after DVS); Plot 4 is Form H (VLD1, dried solid from stock); Plot 5 is Form H (VLD19); and the bottom plot is the XRPD for Form A.

Figure 75:
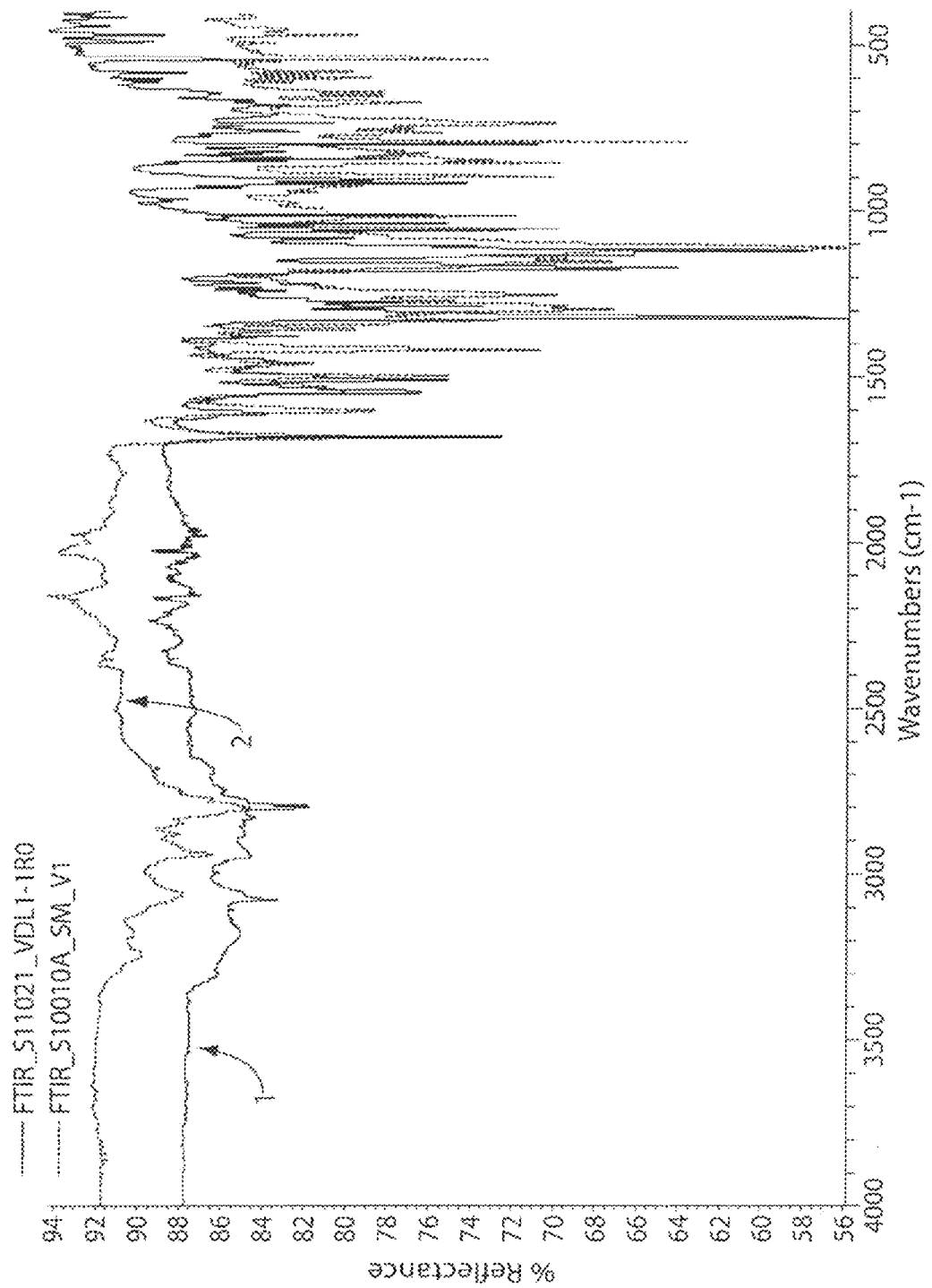

FIG. 75 is a characteristic FT-IR spectrum obtained from Form H of ponatinib overlaid with the FT-IR spectrum obtained for Form A. Percent transmittance (%) is shown on the vertical axis and wavenumber (cm$^{-1}$) is shown on the horizontal axis.

Figure 76:
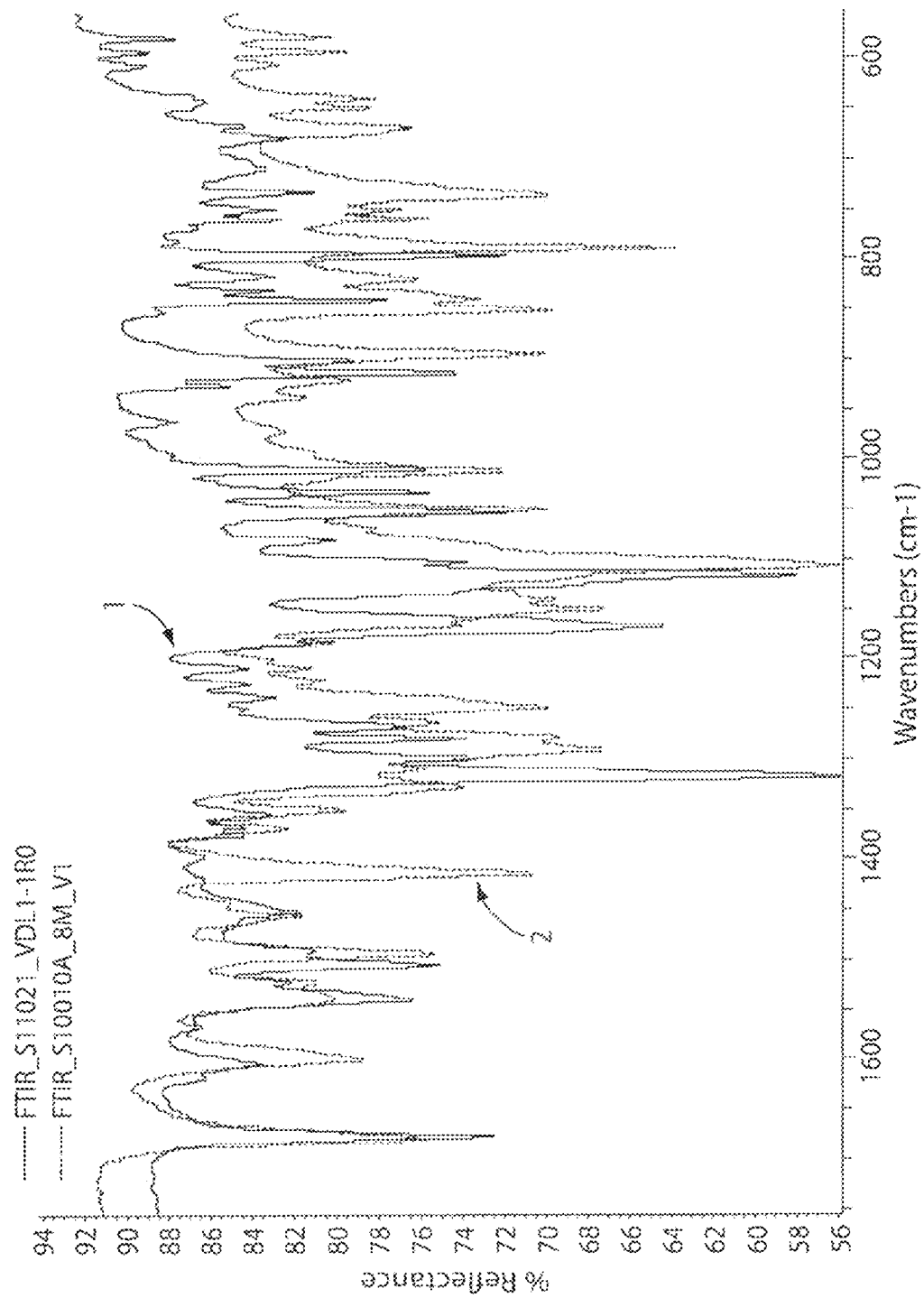

FIG. 76 is a characteristic FT-IR spectrum obtained from Form H of ponatinib overlaid with the FT-IR spectrum obtained for Form A, for the region of wavelength 1750-600 nm. Percent transmittance (%) is shown on the vertical axis and wavenumber (cm$^{-1}$) is shown on the horizontal axis.

Figure 77:
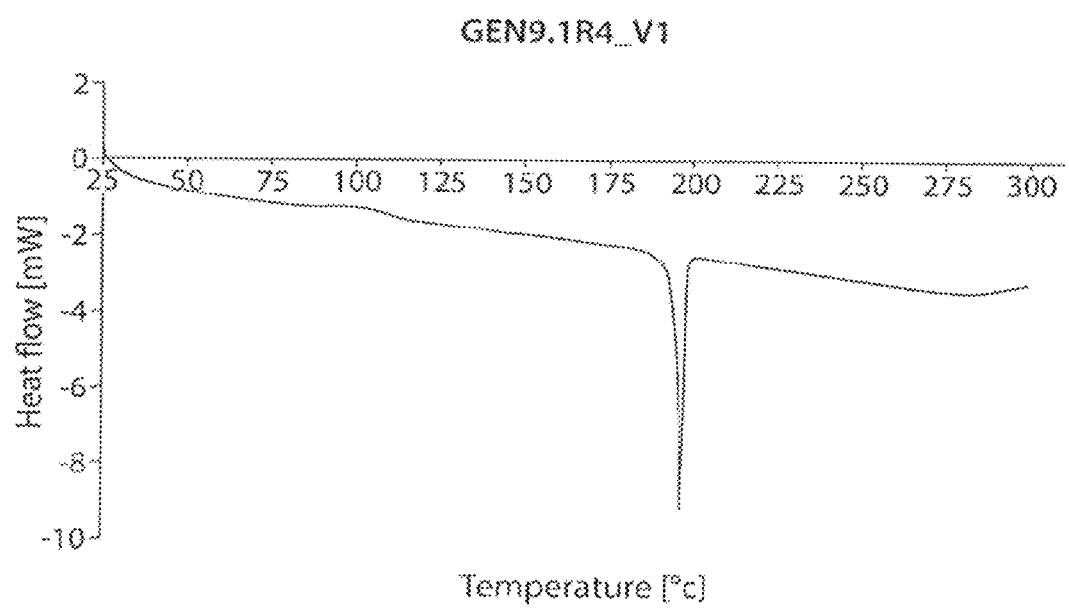

FIG. 77 is a characteristic differential scanning calorimetry (DSC) scan obtained for Form I (GEN9.1). Heat flow [mW] is shown on the vertical axis and temperature (° C.) is shown on the horizontal axis.

Figure 78:
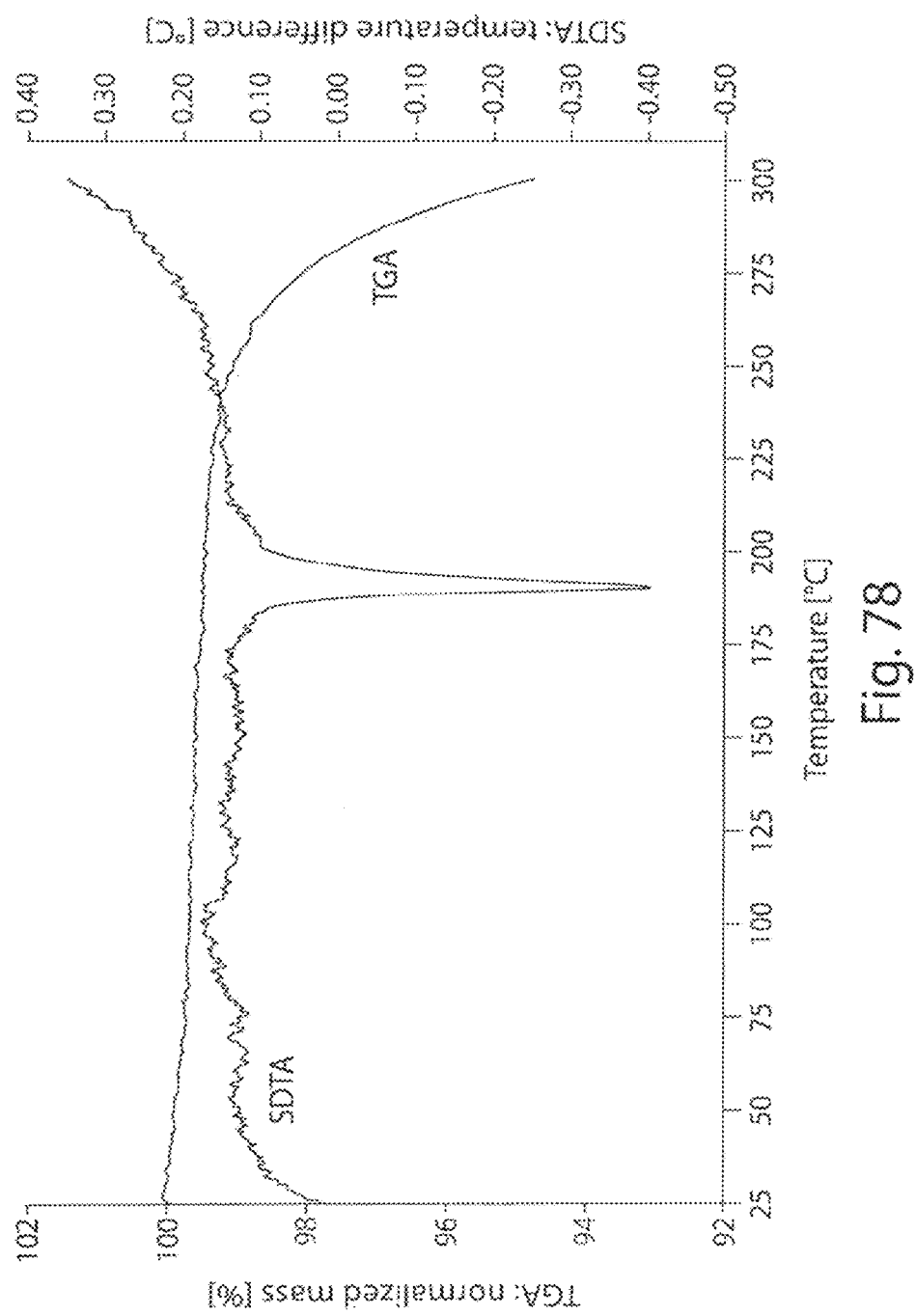

FIG. 78 is a characteristic overlay of TGA and SDTA thermograms of Form I (GEN9.1).

Figure 79:
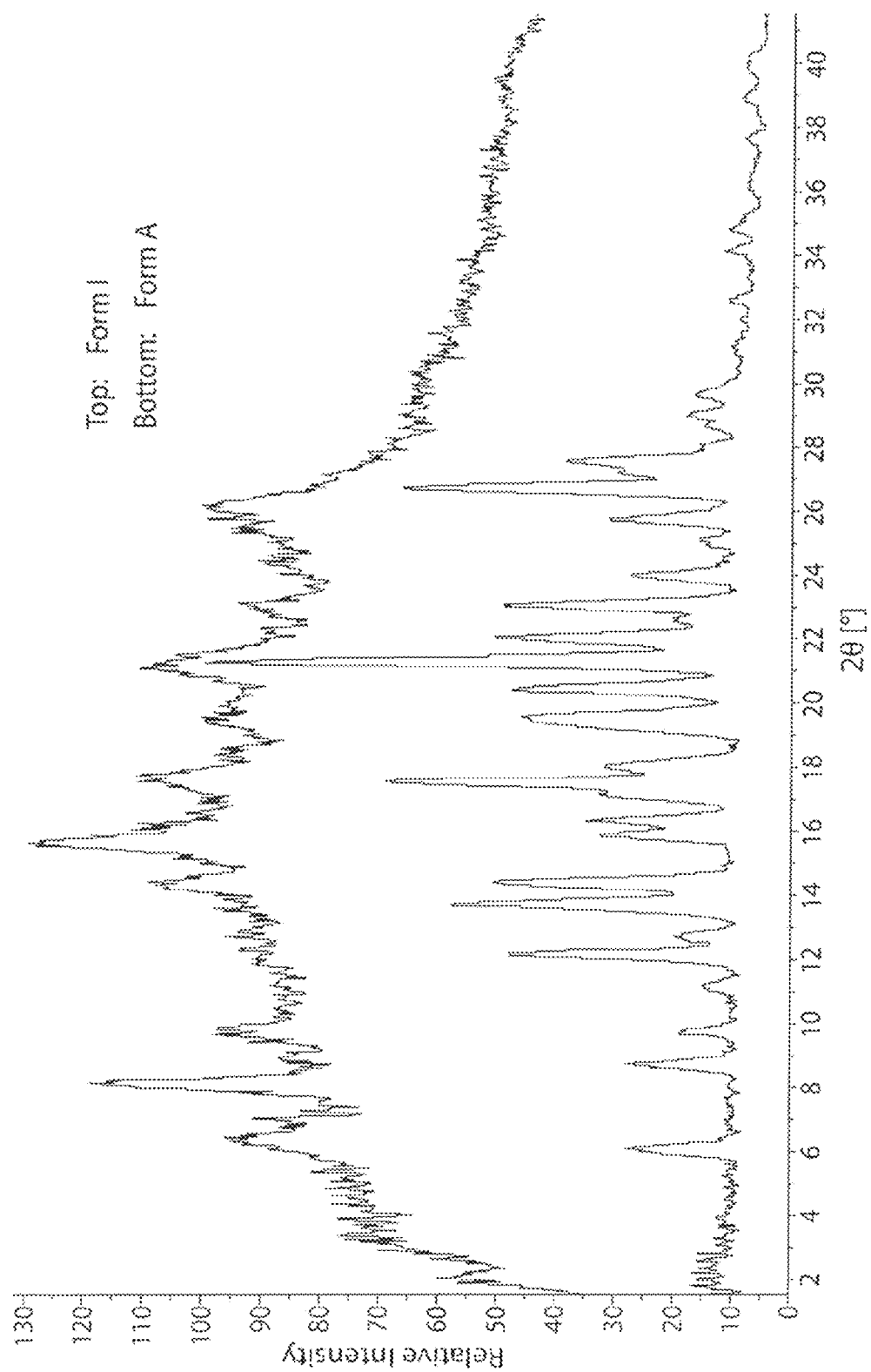

FIG. 79 shows XRPD patterns for ponatinib Form I (upper pattern) and Form A (bottom pattern) in overlay.

Figure 80:
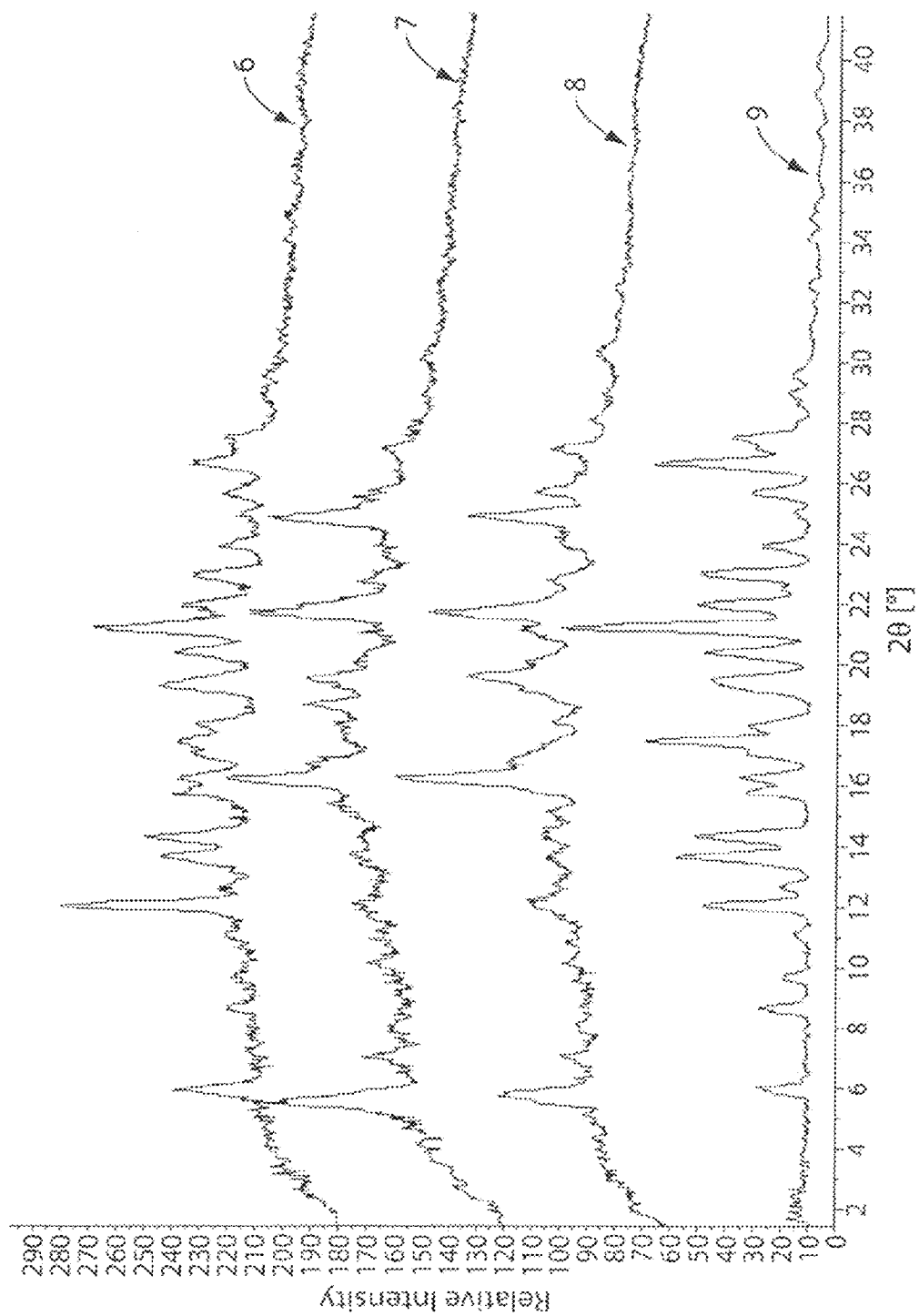

FIG. 80 shows an overlay of XRPD patterns as follows: Plot 6 is the XRPD pattern for Form A (VDS2, after stability study); Plot 7 is the XRPD pattern for Form J (VDS2); Plot 8 is the XRPD pattern for Form J (VDS10 of screen S10010A); and Plot 9 is another XRPD pattern of ponatinib Form A.

Figure 81:
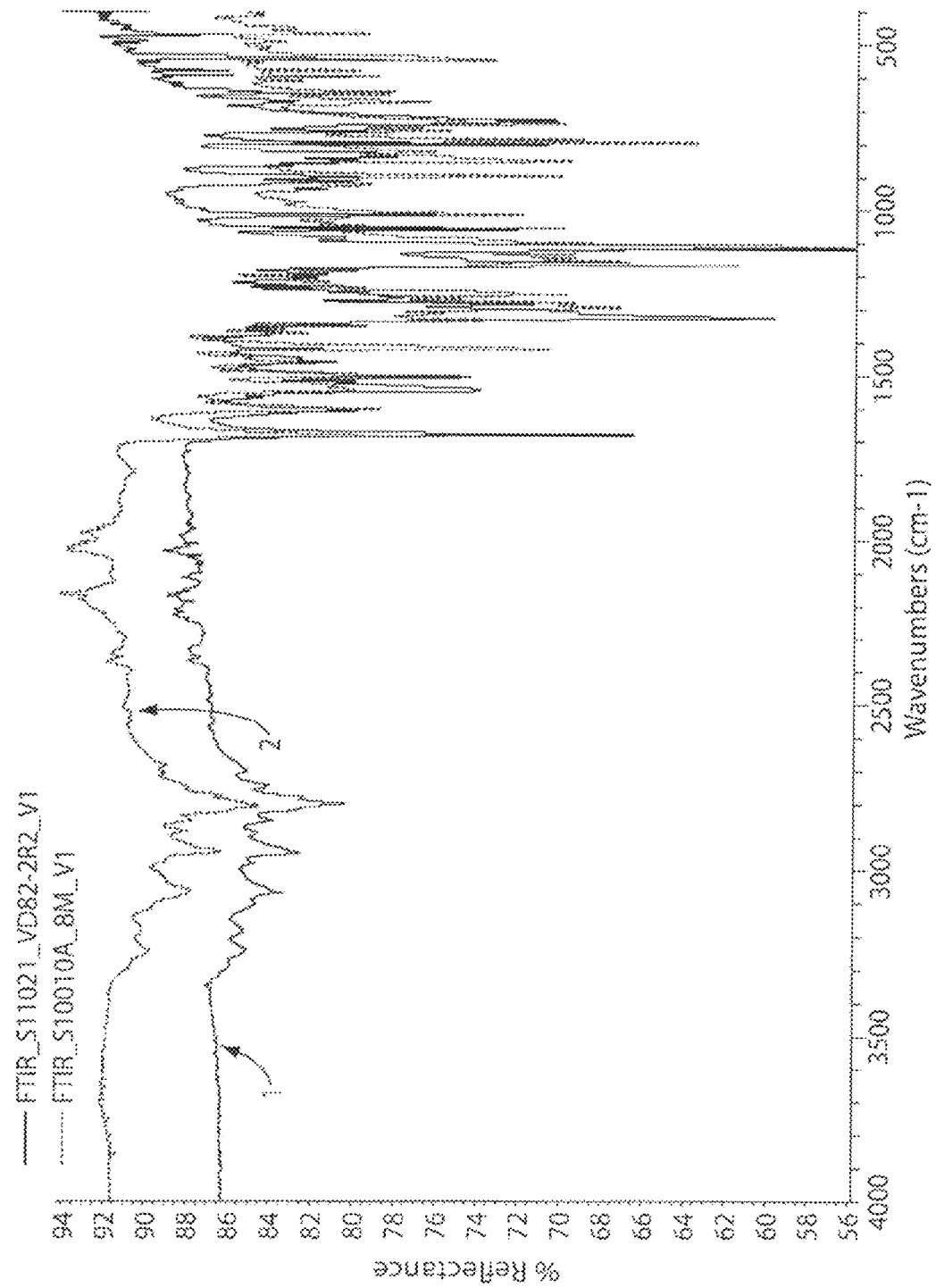

FIG. 81 shows a characteristic FT-IR spectrum obtained from Form J in overlay with the FT-IR spectrum obtained for Form A. Percent transmittance (%) is shown on the vertical axis and wavenumber (cm$^{-1}$) is shown on the horizontal axis.

Figure 82:
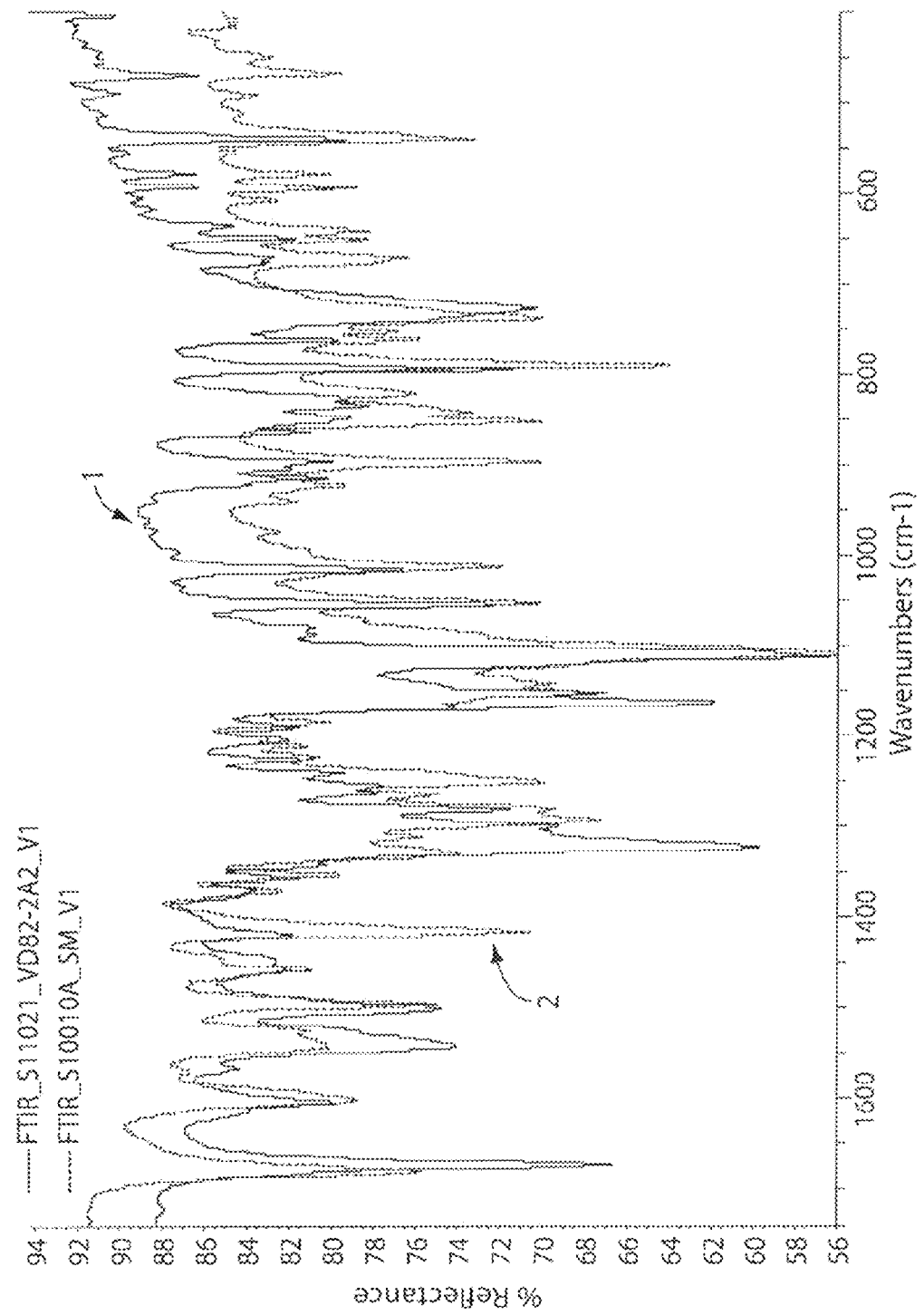

FIG. 82 shows a characteristic FT-IR spectrum obtained from Form J in overlay with the FT-IR spectrum obtained for Form A, for the region of wavelength 1750-600 nm. Percent transmittance (%) is shown on the vertical axis and wavenumber (cm$^{-1}$) is shown on the horizontal axis.

Figure 83:
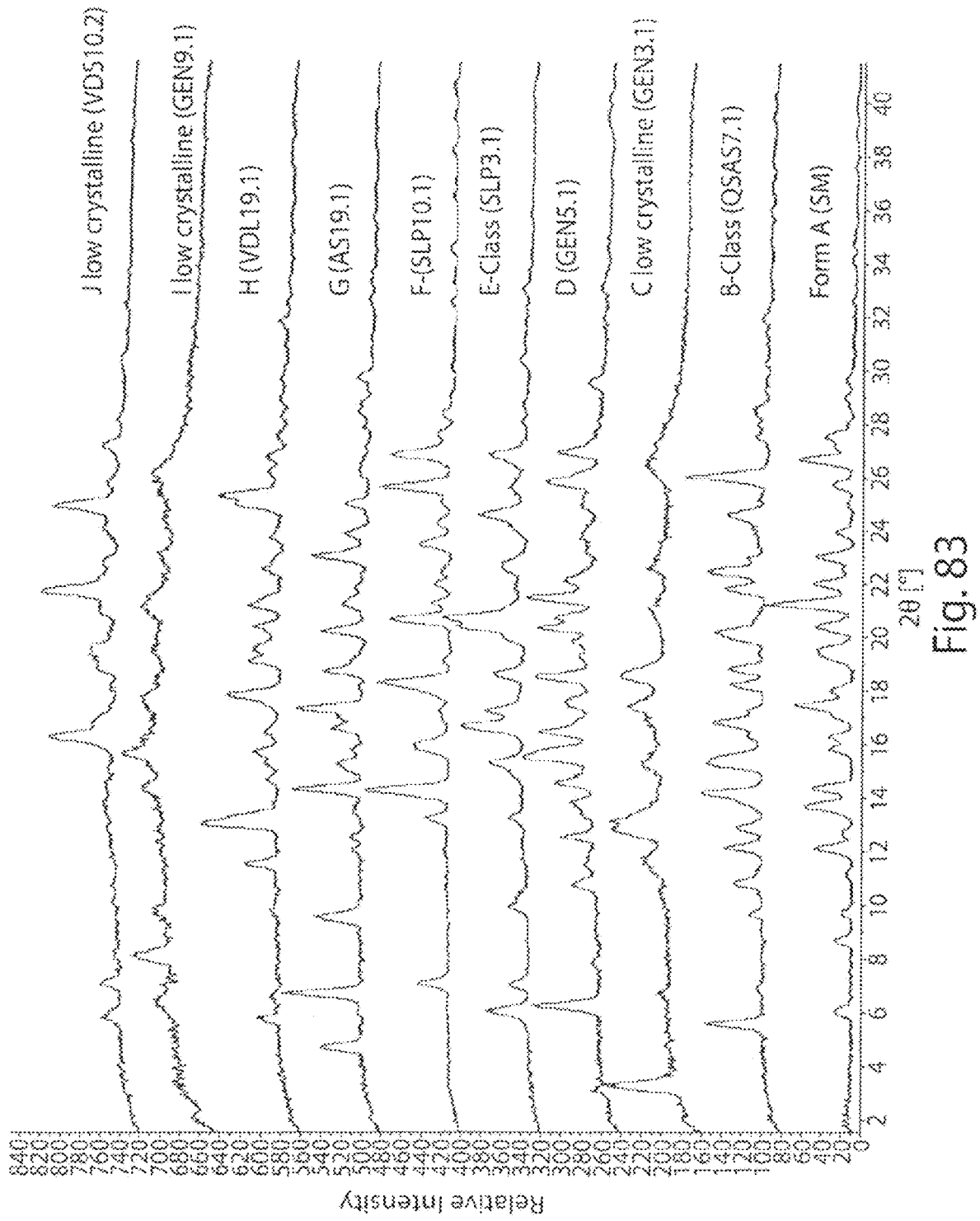

FIG. 83 shows an overlay of the XRPD results obtained for selected ponatinib free base polymorphs (from bottom to top): Form A (SM); B-Class (QSAS7.1); Form C, low crystalline (GEN3.1); Form D (GEN5.1); E-Class (SLP3.1); Form F (SLP10.1); Form G (AS19.1); Form H (VDL19.1); Form I, low crystalline (GEN9.1); and Form J, low crystalline (VDS10.1).

Figure 84:
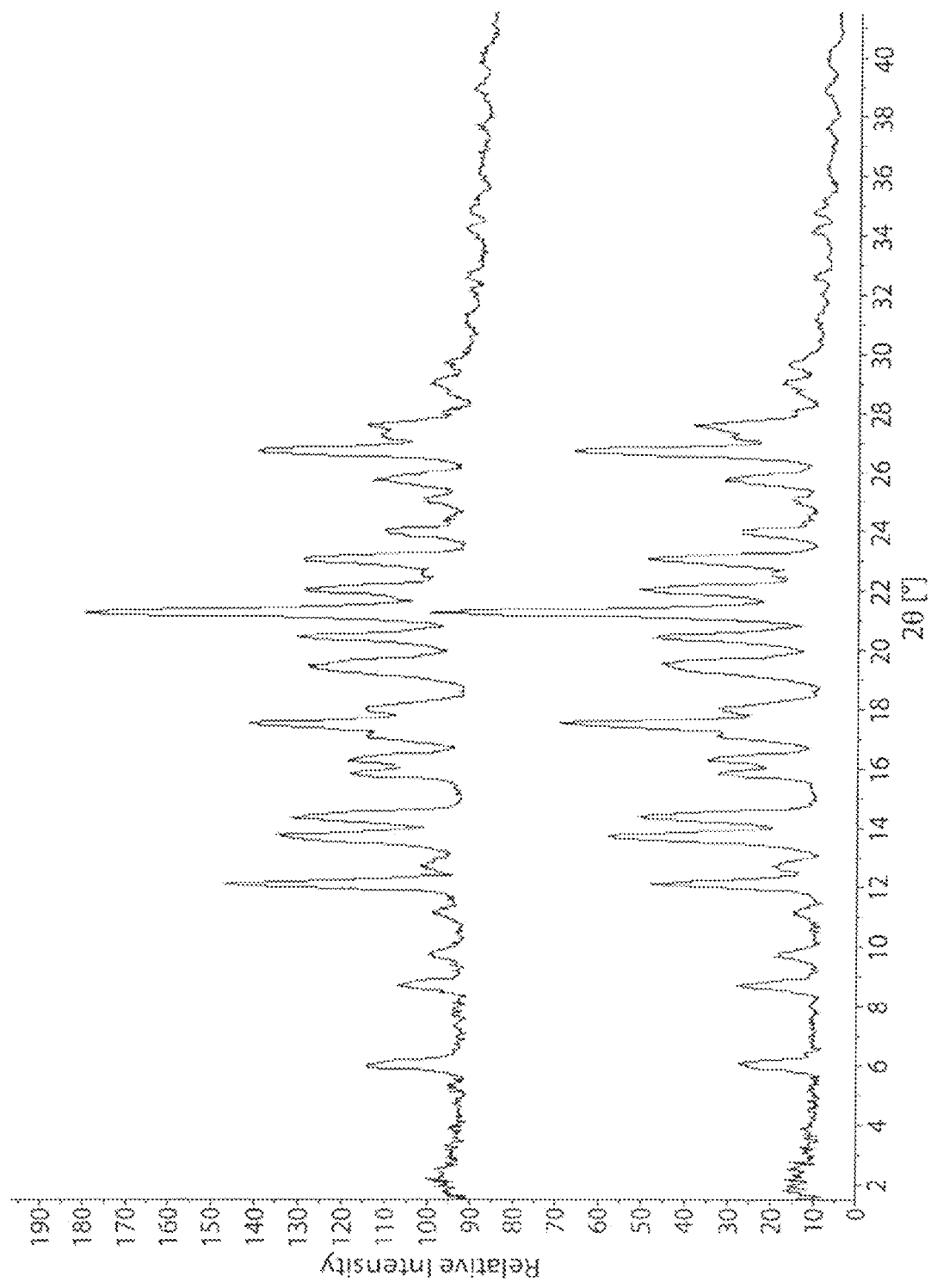

FIG. 84 shows an overlay of the XRPD patterns of the free base starting material, with the two patterns representing the two batches (F09-05575: lower pattern; and F09-05576: upper pattern).

Figure 85:
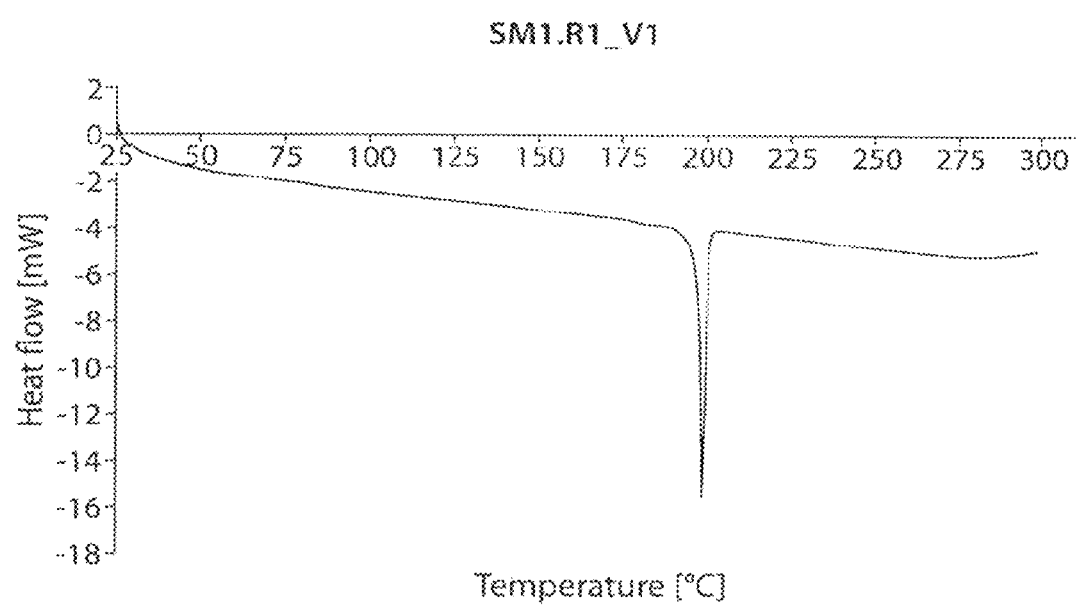

FIG. 85 is a characteristic differential scanning calorimetry (DSC) scan obtained for ponatinib free base starting material batch F09-05575. Heat flow [mW] is shown on the vertical axis and temperature (° C.) is shown on the horizontal axis.

Figure 86:
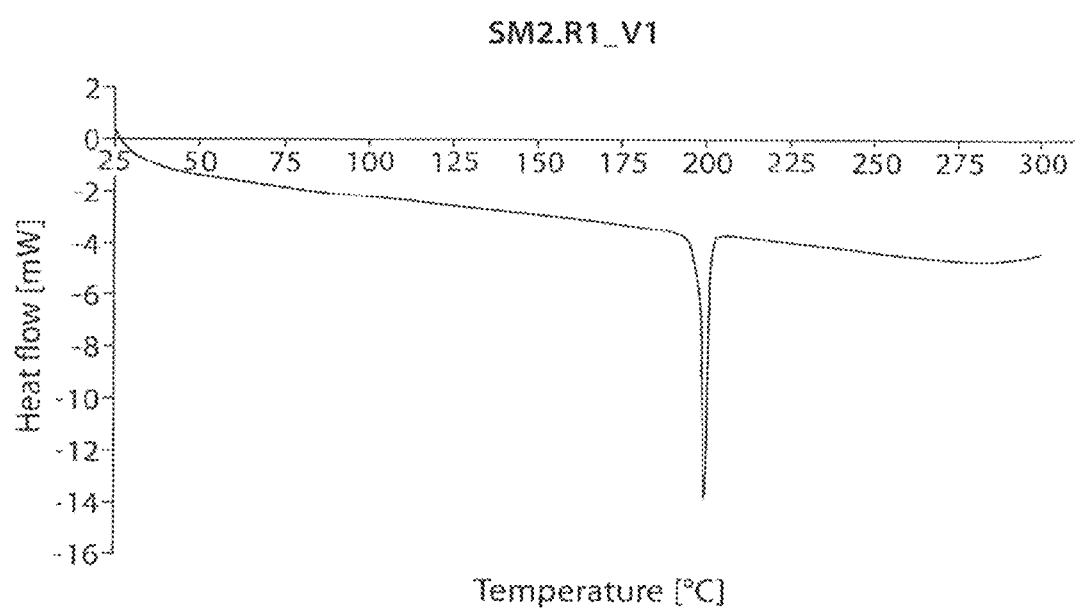

FIG. 86 is a characteristic differential scanning calorimetry (DSC) scan obtained for ponatinib free base starting material batch F09-05576. Heat flow [mW] is shown on the vertical axis and temperature (° C.) is shown on the horizontal axis.

Figure 87:
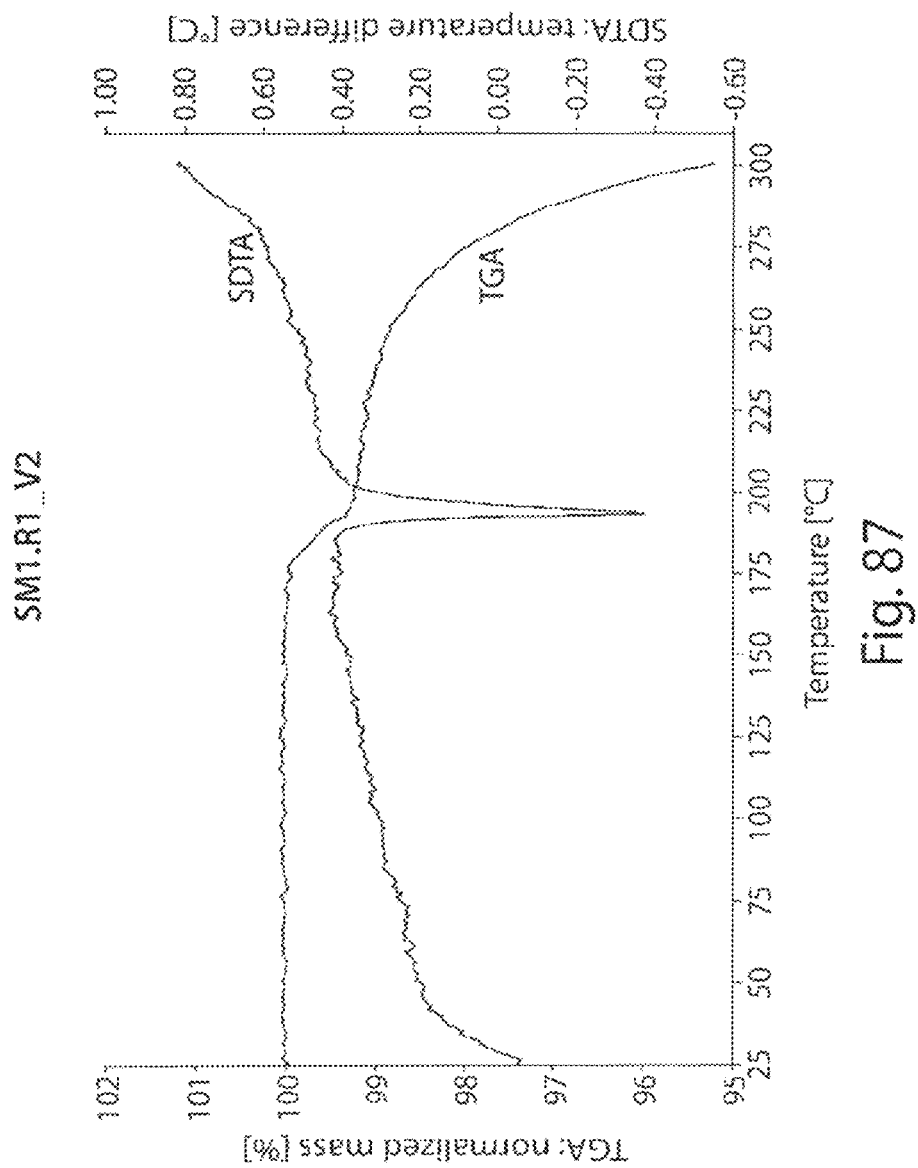

FIG. 87 is a characteristic overlay of TGA and SDTA thermograms of ponatinib free base starting material batch F09-05575.

Figure 88:
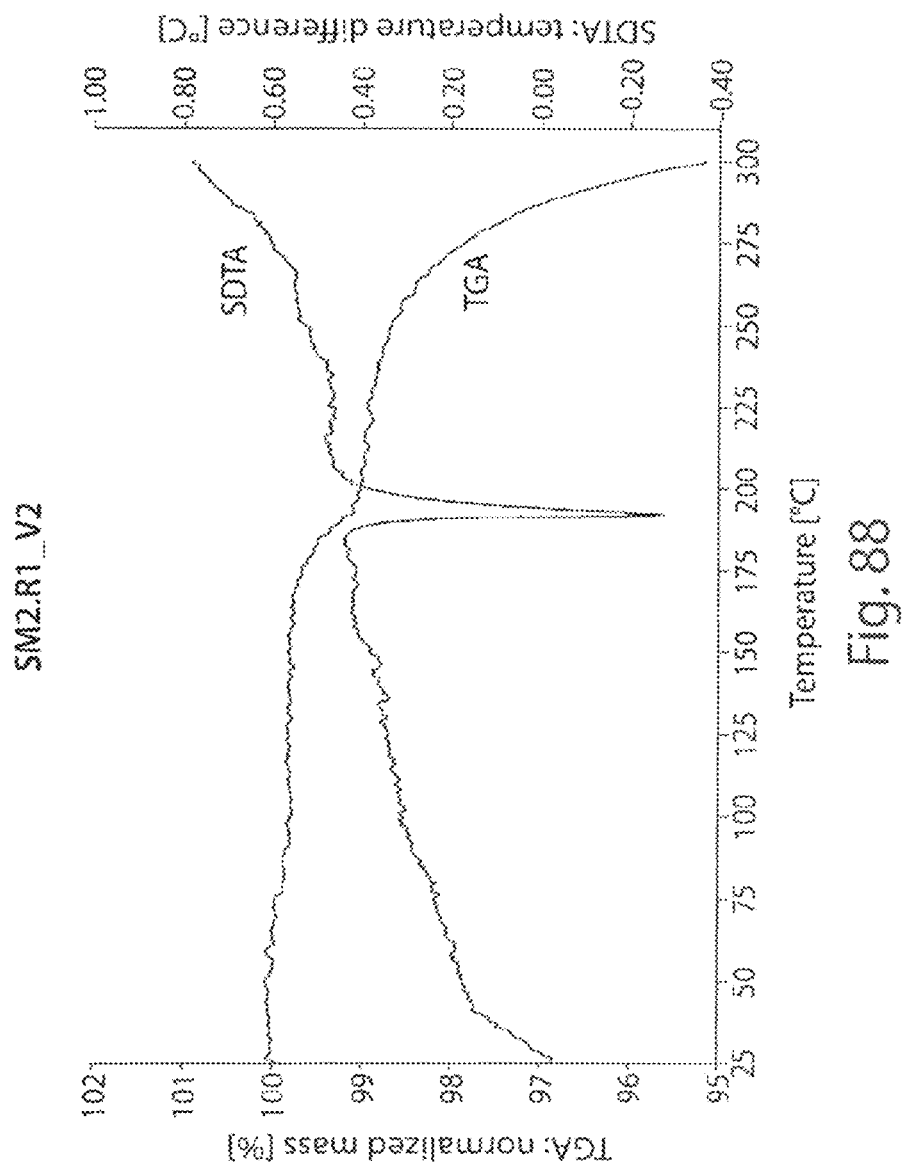

FIG. 88 is a characteristic overlay of TGA and SDTA thermograms of ponatinib free base starting material batch F09-05576.

FIG. 89 is a tabular summary of the physical stability of several of the ponatinib solid forms.

FIG. 90 is a tabular summary of the results from the scale-up experiments for selected free base forms.

FIG. 91 is a tabular summary of various characterizations of ponatinib free base forms reproduced at the 120 mg scale.

DETAILED DESCRIPTION OF THE INVENTION

It was discovered that both 3-(imidazo[1,2-b]pyridazin-3-ylethynyl)-4-methyl-N-{4-[(4-methylpiperazin-1-yl)methyl]-3-(trifluoromethyl)phenyl}benzamide and 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride can be obtained in various solid state crystalline forms.

The terms "crystalline form" or "polymorphic form" or "polymorph" may be used interchangeably herein, and refer to a crystalline form of ponatinib or ponatinib hydrochloride that is distinct from the amorphous form of ponatinib or ponatinib hydrochloride or other form(s) of ponatinib or ponatinib hydrochloride as determined by certain physical properties such thermodynamic stability, physical parameters, x-ray structure, DSC and preparation processes.

While polymorphism classically refers to the ability of a compound to crystallize into more than one distinct crystal species (having identical chemical structure but quite different physicochemical properties), the term "pseudopolymorphism" is typically applied to solvate and hydrate crystalline forms. For purposes of this disclosure, however, both true polymorphs as well as pseudopolymorphs, (i.e., hydrate and solvate forms), are included in the scope of the term "crystalline forms" and "polymorphic forms." In addition, "amorphous" refers to a disordered solid state.

It should be noted that different samples of a particular crystalline form may share the same major XRPD peaks, but that there can be variation in XRPD patterns with regard to the minor peaks. In regards to XRPD, the term "about," when used in relation to XRPD maxima values (in degrees two theta), generally means within 0.3 degrees two theta of the given value. Alternatively, the term "about" can mean (in this and all contexts) a value falls within an accepted standard of error of the mean when considered by one of ordinary skill in the art. As used herein, the terms "isolated" and "substantially pure" mean that more than about 50% of crystalline ponatinib or ponatinib hydrochloride is present (as can be determined by a method in accordance with the art) in the identified crystalline form relative to the sum of other solid form(s) present in the selected material.

Definitions and Abbreviations

Solvent abbreviation:
  DCM Dichloromethane
  DMA N,N-Dimethylacetamide
  DMF N,N-Dimethylformamide
  DMSO Dimethylsulfoxide
  TFE 2,2,2-Trifluoroethanol
  THF Tetrahydrofuran
  2-methylTHF 2-Methyltetrahydrofuran
  EtOH Ethanol
  MeOH Methanol
Other Abbreviations (Alphabetical Order):
  Am Amorphous
  API Active Pharmaceutical Ingredient
  AS Anti-solvent
  CI Counter-ion
  DSC Differential Scanning Calorimetry
  DVS Dynamic Vapor Sorption
  GRP ID for Grinding experiment
  HPLC High-Performance Liquid Chromatography
  HT-XRPD High Throughput X-Ray Powder Diffraction
  HR-XRPD High Resolution X-Ray Powder Diffraction
  LC Low Crystalline material
  MS Mass Spectroscopy
  PSM ID for Cooling/evaporative crystallization experiment
  SAS Solubility assessment
  SDTA Single Differential Thermal Analysis
  S Solvent
  SM Starting material
  TGA Thermogravimetric Analysis
  TGMS Thermogravimetric Analysis coupled with Mass Spectroscopy
  VDL ID for Vapor diffusion into liquids experiments
  VDS ID for Vapor diffusion onto solids experiments
  XRPD X-Ray Powder Diffraction Analytical Methods X-Ray Powder Diffraction XRPD patterns were obtained using an Avantium T2 high-throughput XRPD set-up. The plates were mounted on a Bruker GADDS diffractometer equipped with a Hi-Star area detector.

The XRPD platform was calibrated using Silver Behenate for the long d-spacings and Corundum for the short d-spacings.

Data collection was carried out at room temperature using monochromatic $CuK_\alpha$ radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 seconds for each frame. No background subtraction or curve smoothing was applied to the XRPD patterns. The carrier material used during XRPD analysis was transparent to X-rays and contributed only slightly to the background.

Thermal Analysis

Melting properties were obtained from DSC thermograms, recorded with a heat flux DSC822e instrument (Mettler-Toledo GmbH, Switzerland). The DSC822e was calibrated for temperature and enthalpy with a small piece of indium (m.p.=156.6° C.; ΔHf=28.45 J·g$^{-1}$). Samples were sealed in standard 40 μl aluminum pans, pin-holed and heated in the DSC from 25° C. to 300° C., at a heating rate of 10° C. min$^{-1}$. Dry N$_2$ gas, at a flow rate of 50 ml min$^{-1}$ was used to purge the DSC equipment during measurement.

Mass loss due to solvent or water loss from the various crystal samples was determined by TGA/SDTA. Monitoring the sample weight, during heating in a TGA/SDTA851e instrument (Mettler-Toledo GmbH, Switzerland), resulted in a weight vs. temperature curve. The TGA/SDTA851e was calibrated for temperature with indium and aluminum. Samples were weighed into 100 μl aluminum crucibles and sealed. The seals were pin-holed and the crucibles heated in the TGA from 25 to 300° C. at a heating rate of 10° C. min$^{-1}$. Dry N$_2$ gas was used for purging.

The gases evolved from the TGA samples were analyzed by a mass spectrometer Omnistar GSD 301 T2 (Pfeiffer Vacuum GmbH, Germany). The latter is a quadrupole mass spectrometer which analyses masses in the range of 0-200 amu.

Digital Imaging

Digital images were automatically collected for all the wells of each well-plate, employing a Philips PCVC 840K CCD camera controlled by Avantium Photoslider software.

Press

For the compression tests, an Atlas Power Press T25 (Specac) was used. The Atlas Power T25 is a power assisted hydraulic press operating up to 25 Tons.

HPLC Analytical Method

HPLC analysis was performed using an Agilent 1200SL HPLC system equipped with UV and MS detectors following the conditions presented below:

| HPLC Equipment: | LC-MS |
|---|---|
| Manufacturer: | Agilent |
| HPLC: | HP1200sl |
| UV-detector: | HP DAD |
| MS-detector: | HP1100 API-ES MSD VL-type |
| Column: | Waters Sunfire C18 (100 × 4.6 mm; 3.5 μm). |
| Column temp: | 35° C. |
| Mobile phase: | Gradient mode |
| Mobile phase A: | 1000/1; H$_2$O/TFA (v/v) |
| Mobile phase B: | 1000/1; ACN/TFA (v/v) |
| Flow: | 1.0 ml/min |
| Gradient program: | Time [min]:    % A:    % B: |
|  | 0    90    10 |
|  | 15    20    80 |
|  | 16    90    10 |
|  | 18    90    10 |
| Posttime: | 1 |
| UV-Detector: | DAD |
| Range: | 200-400 nm |
| Wavelength: | 260 nm |
| Slit Width: | 4 nm |
| Time: | 0-17 min |
| MS-Detector: | MSD |
| Scan: | positive |
| Mass Range: | 70-1000 amu |
| Fragmentator: | 70 |
| Time: | 0-17 min |
| Autosampler: | |
| Temperature: | Not controlled |
| Injection mode: | loop |
| Injection volume: | 5 μl |
| Needle wash: | 2/3; ACN/H$_2$O (v/v) |
| Dilution solvent: | 2,2,2-Trifluoroethanol |

The compound integrity is expressed as a peak-area percentage, calculated from the area of each peak in the chromatogram, except the 'injection peak', and the total peak-area, as follows:

$$\text{peak} - \text{area } \% = \frac{\text{peak} - \text{area}}{\text{total} - \text{area}} * 100\%$$

The peak-area percentage of the compound of interest is employed as an indication of the purity of the component in the sample.

I. Polymorphic Forms of Ponatinib Mono Hydrochloride

Through XRPD analysis, a total of eleven polymorphic forms of ponatinib hydrochloride were discovered. Each of the eleven new polymorphic forms are referred to herein as: HCl1 (also referred to herein as "Form A"), HCl2 (also referred to herein as "Form B"), HCl2b (also referred to herein as "Form C"), HCl3-class (also referred to herein as "Form D"), a mixture HCl1+HCl4 (also referred to herein as "Form E"), HCl5-class or simply HCl5 (also referred to herein as "Form F"), HCl5b or HCl5 desolvate (also referred to herein as "Form G"), HCl6-class (also referred to herein as "Form H"), HCl6 desolvate (also referred to herein as "Form I"), HCl7 (also referred to herein as "Form J"), and HCl8 (also referred to herein as "Form K"). The nature or origin of these eleven polymorphic forms is indicated in FIG. 1. In addition, certain characteristics of the referenced polymorphic forms are provided as well in FIG. 2. For instance, Form A is indicated as being an anhydrate of ponatinib hydrochloride and additionally was obtained as a single crystal.

In general, crystalline forms of ponatinib hydrochloride have physical properties (such as high stability, etc.) that are advantageous for the commercial preparation of solid dosage forms as compared to amorphous ponatinib hydrochloride. The distinction between crystalline ponatinib hydrochloride and amorphous ponatinib hydrochloride can be readily seen with the same type of physical chemical data (e.g., DSC, XRPD, thermal analysis) that is used to distinguish the individual crystalline forms of ponatinib hydrochloride disclosed herein.

With reference to the foregoing methodologies, attention is now drawn to each of the discovered polymorphs of 3-(imidazo[1,2-b]pyridazin-3-ylethynyl)-4-methyl-N-{4-[(4-methylpiperazin-1-yl)methyl]-3-(trifluoromethyl) phenyl}benzamide mono hydrochloride.

Characteristics of Form a (HCl1):

The anhydrate HCl (same crystalline form as the starting material) was the predominant crystalline form discovered.

The chemical structure of ponatinib hydrochloride has been unambiguously established by a combination of nuclear magnetic resonance spectroscopy (NMR), mass spectrometry (MS), and single crystal X-ray crystallography with confirmatory data from elemental and chloride analysis, Fourier transform infra-red (FT-IR) spectroscopy, and ultraviolet (UV) spectroscopy. The preferred solid form of ponatinib hydrochloride is the anhydrous crystalline HCl-1 solid form or Form A.

With reference to FIG. 3, samples of Ponatinib HCl, ASI Batch 110020 and CGAM Batch F08-06057 were analyzed by X-ray powder diffraction (XRPD). In each case, the material was analyzed prior to and after DVS humidity cycling. XRPD patterns were obtained using a high-throughput XRPD diffractometer. Data collection was carried out at room temperature using monochromatic CuK$_\alpha$ radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 seconds for each frame. No background subtraction or curve smoothing was applied to the XRPD patterns. FIG. 3 shows the X-ray powder diffraction pattern of these materials, each in the HCl-1 solid form. This powder pattern is consistent with the powder pattern simulated from single crystal X-ray diffraction experiments on the HCl-1 form. XRPD data acquired prior to, and after DVS humidity cycling experiments, indicates that the HCl-1 solid form is maintained after humidity cycling. In the XRPD pattern of Form A shown in FIG. 3, at least one or all of the following peaks in degrees two theta (2θ) is shown: 5.9; 7.1; 10.0; 12.5; 16.4; 19.3; 21.8; 23.8; and 26.1. In certain embodiments, the XRPD pattern of Form A shows two peaks, three peaks, four peaks or five peaks. The term "about" applies to each listed peak for this and all other forms mentioned in this disclosure.

FIG. 4 shows a characteristic X-Ray Powder Diffraction (XRPD) pattern for Form A of ponatinib hydrochloride in which greater detail relative to the XRPD is seen. The XRPD pattern of Form A shown in FIG. 4 shows at least one or more of the following peaks in degrees two theta (2θ): 5.9; 7.1; 10.0; 12.5; 13.6; 14.1; 15.0; 16.4; 17.7; 18.6; 19.3; 20.4; 21.8; 22.3; 23.8; 24.9; 26.1; 27.0; 28.4; 30.3; 31.7; and 35.1. In certain embodiments, Form A is characterized by a XRPD pattern comprising one or more of the following peaks two theta (2θ): 12.5; 19.3; 23.8; and 26.1. In certain embodiments, the XRPD pattern of Form A shows two peaks, three peaks, four peaks or five peaks.

In differential vapor sorption (DVS) experiment with HCl-1, the relative humidity was cycled from 45% to 95% (sorption), to 0% (desorption) and back to 45% (sorption) at a constant temperature of 25° C., with a hold time of 60 minutes per step. The results of this DVS experiment on ponatinib HCl CGAM Batch F08-060507 exhibited a 1.1% water uptake at 95% humidity, and ponatinib HCl ASI Batch 110020 exhibited a 1.4% water uptake at a relative humidity of 95%. This water uptake was reversible on cycling to lower humidity. These results demonstrate that HCl-1 is not a hygroscopic compound. The effect of the humidity cycling on HCl-1 was also assessed by X-ray powder diffraction (XRPD) analysis before and after the DVS experiment. The XRPD data revealed that humidity cycling had no effect on the solid form of the material, which remained in the HCl-1 solid form.

With reference to FIG. 5, the melting point of ponatinib HCl in the HCl-1 solid form, was determined by differential scanning calorimetry (DSC). The sample of ponatinib HCl, ASI Batch 110020, was analyzed in a pin-holed crucible in the temperature range of 25° C. to 300° C. at a heating rate of 10° C. per minute using dry N$_2$ gas purge. An intense endothermic event with a peak of 264.1° C. was observed, corresponding to the melting point of Form A.

With reference to FIGS. 6A-6C, Thermogravimetric analysis (TGA) and thermogravimetric analysis with mass spectroscopic analysis of volatiles (TGMS) was performed on ponatinib HCl, ASI Batch 110020. The sample, contained in a pin-holed crucible, was heated in the TGA instrument from 25° C. to 300° C. at a heating rate of 10° C. min-1, with dry N$_2$ gas used for purging. Gases evolved from the TGA were analyzed using a quadrupole mass spectrometer. Ponatinib HCl, ASI Batch 110020, in the HCl-1 solid form, contained 0.31% water by weight and 0.85% ethanol by weight at the time of release. The TGA/TGMS experiment indicated that mass losses of 0.2% (water) and 0.6% (ethanol, from the crystallization solvent) are observed between the temperature range of 25-130° C. and 130-240° C., respectively. These losses are consistent with the water and ethanol content at the time of release. Ethanol is released from the material at a higher temperature than water, although not associated with ponatinib HCl in the HCl-1 solid form as a solvate.

Extensive solution phase NMR studies using a combination of multiple 1D and 2D NMR methods were performed on Form A of ponatinib HCl to obtain a complete assignment of H, $^{19}$F, and $^{13}$C resonances, and hence to confirm the chemical structure of ponatinib HCl. Analyses were performed at ARIAD Pharmaceuticals, Inc., Cambridge, Mass., on a sample of ponatinib HCl (ASI Batch 110020) dissolved in deuterated DMSO (DMSO-ds) solvent. NMR spectra were acquired at a temperature of 300 K on a Bruker Avance 111-600 MHz NMR spectrometer equipped with a 5 mm BBFO z-gradient probe. All $^1$H chemical shifts were referenced to the DMSO peak at 2.5 ppm. With reference to FIG. 7, the 1D $^1$H-NMR spectra of Form A of ponatinib HCl in DMSO-ds is shown. $^1$H resonance 32a arises from the protonated piperazine moiety in ponatinib HCl. The EtOH resonances appearing in both $^1$H (FIG. 7) and $^{13}$C spectra (FIG. 9) arise from residual EtOH present in ponatinib HCl. FIG. 8 shows the 1D $^{19}$F-NMR spectra of Form A of ponatinib HCl in DMSO-ds with a characteristic chemical shift at 57.94 ppm. FIG. 9 shows the 1D $^{13}$C-NMR spectra of Form A of ponatinib HCl in DMSO-d$_6$.

Table 1 summarizes the relevant chemical shift data of ponatinib monohydrochloride Form obtained from the $^1$Hand $^{13}$C-NMR experiments. The number of signals and the irrelative intensity (integrals) confirm the number of protons and carbons in the structure of Form A of ponatinib HCl. These chemical shift data are reported in according to the atom numbering scheme shown immediately below:

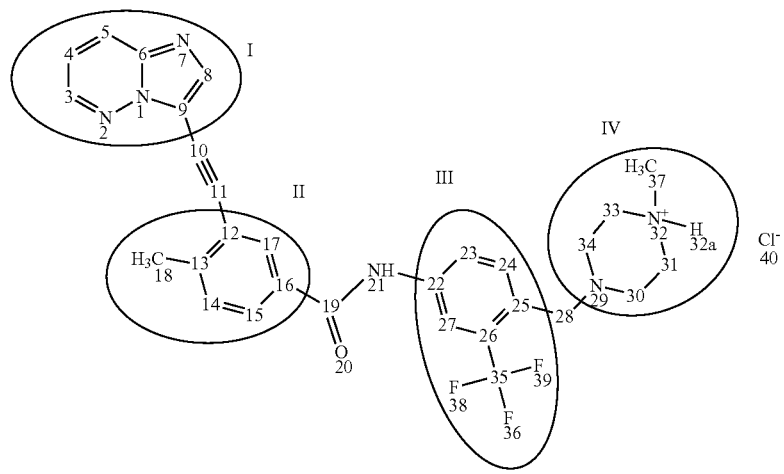

TABLE 1

$^1$H and $^{13}$C Chemical Shift Data (in ppm) of Form A of ponatinib HCl, in DMSO-$d_6$ at 300 K.

| Atom Number | Group | $^1$H, ppm | $^{13}$C, ppm | Integral | $^1$H Multiplicity, Hz | $^{13}$C Multiplicity, Hz |
|---|---|---|---|---|---|---|
| 3 | CH | 8.72 | 145.03 | 0.98 | m[1] | |
| 4 | CH | 7.39 | 119.05 | 1.02 | dd[2] (J = 9.2, 4.4) | |
| 5 | CH | 8.25 | 126.06 | ND[7] | m | |
| 6 | C | — | 139.63 | — | — | |
| 8 | CH | 8.22 | 138.2 | ND | m | |
| 9 | C | — | 111.69 | — | — | |
| 10 | C | — | 81.11 | — | — | |
| 11 | C | — | 96.38 | — | — | |
| 12 | C | — | 121.76 | — | — | |
| 13 | C | — | 143.52 | — | — | |
| 14 | CH | 7.54 | 130.03 | 1.01 | d[3] (J = 8.1) | |
| 15 | CH | 7.98 | 128.49 | 1.02 | dd (J = 8, 1.4) | |
| 16 | C | — | 132.12 | — | — | |
| 17 | CH | 8.22 | 130.19 | ND | m | |
| 18 | CH$_3$ | 2.6 | 20.36 | 3.09 | s[4] | |
| 19 | C | — | 164.63 | — | — | |
| 21 | NH | 10.65 | — | 1.03 | s | |
| 22 | C | — | 138.53 | — | — | |
| 23 | CH | 8.13 | 123.54 | 1.02 | d (J = 8.4) | |
| 24 | CH | 7.71 | 131.42 | 1.01 | d (J = 8.4) | |
| 25 | C | — | 130.95 | — | — | |
| 26 | C | — | 127.53 | — | — | q[6] (J = 29.7) |
| 27 | CH | 8.25 | 117.42 | ND | m | q (J = 6.2) |
| 28 | CH$_2$ | 3.66 | 56.56 | 2.01 | s | — |
| 35 | C | — | 124.25 | — | — | q (J = 272.9) |
| 37 | CH$_3$ | 2.74 | 41.96 | 3.07 | s | |
| 30, 34[8] | CH$_2$ | 2.87 | 49.16 | 1.76 | m | |
| 30', 34'[8] | CH$_2$ | 2.52 | 49.16 | ND | m | |
| 31, 33[8] | CH$_2$ | 3.02 | 52.53 | 1.78 | m | |
| 31', 33'[8] | CH$_2$ | 3.35 | 52.53 | — | — | |
| 32a | NH | 10.85 | — | 0.74 | br. s.[5] | |
| 36, 38, 39 | CF$_3$ | $^{19}$F: −57.9 | — | — | — | | m: multiplet
dd: doublet of doublets
d: doublet
s: singlet
br. s: broad singlet
q: quartet
ND: not determined due to spectral overlap in the H NMR spectrum.
Due to symmetry, the resonance pair 30 and 34 as well as the resonance pair 31 and 33 have degenerate chemical shifts.
In addition the methylene protons of these resonances appear as diastereotopic pairs.

With reference to FIGS. 1A-10B, mass spectral experiments and collisionally activated MS2 fragmentation of Form A of ponatinib HCl were carried out using Thermo Finnegan Exactive accurate mass and LTQ XL ion trap mass spectrometers, each operating in positive ion electrospray mode. Samples of Form A of ponatinib HCl (ASI Batch 110020), dissolved in acetonitrile, were introduced into the mass spectrometers via infusion by a syringe pump. The accurate mass for ponatinib HCl was obtained on the Exactive mass spectrometer using full scan mode. The mass observed in this infusion experiment is m/z 533.2269 (MH+) with the calculated exact mass being 533.2271 (M H+) yielding a mass difference of 0.2 mmu (Δ ppm of −0.38) (FIG. 10A). The fragmentation spectrum of ponatinib HCl on the Exactive mass spectrometer is shown in FIGS. 10A-10B, and contains the product ions from m/z of 533.2269 (the molecular ion of ponatinib HCl), as well as ions from any other co-eluted compounds.

FIG. 11 shows MS fragmentation data obtained on the LTQ XL ion trap mass spectrometer. FIG. 11(A) shows the full scan MS of m/z 533, (MH+) of the sample during infusion. FIG. 11(B) ($MS^2$ scan) shows the fragment spectrum of the selected mass m/z 533. FIG. 11(C) and FIG. 11(D) show the product ions from m/z 433 and 260 respectively; ions m/z 433, and 260 were themselves the initial productions from m/z 533 (the molecular ion).

Single-crystal X-Ray diffraction analysis was employed to determine the crystal structure of the Form A of ponatinib hydrochloride. Single crystals of ponatinib HCl, in the anhydrate HI-1 form were obtained using the vapor diffusion into liquid crystallization method using ponatinib HCl CGAM Batch F08-06057. A single crystal obtained using methanol as a solvent with ethyl acetate as anti-solvent was analyzed by single crystal X-ray diffraction. From prior experiments, it was known that crystals of this form diffracted well, leading to the solution of the structure of ponatinib HCl shown in FIG. 12, with crystallographic parameters summarized in Table 2. The terminal nitrogen of the piperazine is the site of protonation in ponatinib HCl, consistent with the previously described NMR analysis of ponatinib HCl. The chloride counter-ion occurs in the crystal structure immediately adjacent to the site of protonation. Based on this structure analysis, it was determined that Form A is an anhydrated form.

TABLE 2

Crystal Data and Structure Refinement for Ponatinib Hydrochloride Form A.

| Identification code | S11022 |
|---|---|
| Empirical formula | $C_{29}H_{28}F_3N_6O^+$ $Cl^-$ |
| Fw | 569.02 |
| T [K] | 296(2) |
| λ [Å] | 0.71073 |
| Crystal system | Monoclinic |
| Space group | C 2/c |
| Unit cell dimensions: | |
| a [Å] | 35.883(9) |
| b [Å] | 7.306(3) |
| c [Å] | 25.684(6) |
| β [°] | 122.923(9) |
| V [Å$^3$] | 5652(3) |
| Z | 8 |
| $D_c$ [g/cm$^3$] | 1.337 |
| μ [mm$^{-1}$] | 0.189 |
| F(000) | 2368 |
| Crystal size [mm$^3$] | 0.40 × 0.30 × 0.20 |
| θ range for data collection [°] | 3.2-32.5 |
| Reflections collected | 29574 |
| Independent reflections | 10117 [$R_{int}$ = 0.0395] |
| Completeness to θ = 32.5° [%] | 98.8 |
| Max. and min. transmission | 0.9632 and 0.9283 |
| Data/restraints/parameters | 10117/0/473 |
| Goodness-of-fit on F$^2$ | 1.070 |
| Final R indices [I > 2σ(I)] | R1 = 0.0644, wR2 = 0.1501 |
| R indices (all data) | R1 = 0.0957, wR2 = 0.1672 |

The attenuated total reflectance (ATR) FT-IR spectrum of Form A of ponatinib HCl, ASI Batch 110020, is shown in FIG. 13. Table 3 provides a summary of selected IR band assignment of ponatinib HCl based on the FT-IR shown in FIG. 13.

TABLE 3

Selected IR Band Assignment of Ponatinib HCl

| Absorption band | Frequency (cm$^{-1}$) | Region in FIG. 13 |
|---|---|---|
| C—H stretch (vCH3, vCH2) | 2938.1 (2870-2960) | A |
| N—H stretch | 3242.1 | A |
| C≡C stretch | 2220.0 | B |
| C═O stretch (Amide 1) | 1669.8 | C |
| N—H bending (Amide 2) | 1531.8 | D |
| C—N stretch | 1314.9 | F |
| C—F stretch | 1122.6 | H |
| aromatic C—H out-of-plane bending | 857.3, 789.7 | I |

In the FT-IR, the functional group region extends from 4000 to 1300 cm-1. In the region from 3300 to 2800 cm-1 (region A), there are multiple overlapping, absorption bands arising from stretching vibrations between hydrogen and some other atom, likely amide N—H stretching, aromatic C—H stretching (from the imidazo-pyridazine heterocycle and phenyl groups) and aliphatic C—H stretching (in methyl and methylene groups), all present in the structure of ponatinib HCl. A weak band in the 2100-2260 cm-1 (region B) is due to triple C—C bond stretching. A medium intensity band due to amide C═O stretching (Amide 1) can be expected in 1640-1690 cm-1 range, likely the band observed at 1669.8 cm-1 (region C). Secondary amide N—H bending gives absorption bands in the 1500-1560 cm-1 range (Amide 2), where two strong bands are observed (region D). Multiple weak to medium bands observed in the 1300-1600 cm-1 range are due to (hetero)aromatic resonance-stabilized double C—C and double C—N bonds (ring stretching vibrations), and C—H bending vibrations (from methyl and methylene groups) (region E). Aromatic and aliphatic amine C—N stretching bands can be expected in the 1250-1335 cm-1 range and in the 1250-1020 cm-1 range, respectively, where multiple bands are observed, including a particularly strong band at 1314.9 cm-1 (regions F, G). The fingerprint region, 1300 to 910 cm-1, is complex with a strong, broad band at 1122.6 cm-1 (region H), likely due to C—F stretching. The aromatic region, 910 to 650 cm-1, absorption bands are primarily due to the out-of-plane bending of heteroaromatic ring C—H bonds indicating the hetero-aromatic nature of the compound (region I). These data in the FT-IR spectrum support the proposed structure of Form A of ponatinib hydrochloride.

Experiments to determine the purity of Form A were carried out. With reference to FIGS. 14A-14C, it was determined that the purity of Form A of ponatinib hydrochloride is 99.8160% (area percent).

Characteristics of Form B (HCl2):

Form HCl2 was obtained from a solubility assessment in TFE/water and it was converted to form HCl2b one day after storage of the measuring plate at ambient conditions, as confirmed by the XRPD re-measurement of the specific sample. HCl2 was also obtained in the experiments performed in Phase 2 described herein from aqueous solvent systems (water and MeOH/water) and it also converted to form HCl2b upon storage at ambient conditions (see overview in FIG. 2).

Form B was analyzed by X-ray powder diffraction (XRPD). FIG. 15 shows XRPD patterns of (from bottom to top): starting material (Form A), Form HCl2 (Form B) (QSA12.1, solvent: water) and Form HCl2b (Form C) (QSA12.2, remeasurement after few days at ambient conditions). In the XRPD pattern of Form B shown in FIG. 15, at least one or all of the following peaks in degrees two theta (2θ) is shown: 3.1; 6.5; 12.4; 13.8; 15.4; 16.2; 17.4; 18.0; 20.4; 23.2; 24.4; 26.1; and 26.9. For reference, in the XRPD pattern of Form C shown in FIG. 15, at least one or all of the following peaks in degrees two theta (2θ) is shown: 6.5; 12.4; 13.8; 17.4; 18.0; 20.6; 22.0; 23.0; 25.5; 26.5; and 27.4. In certain embodiments, Form B is characterized by a XRPD pattern comprising one or more of the following peaks two theta (2θ): 13.8; 15.4; 17.4; 18.0; 26.1; and 26.9. In these embodiments, the XRPD pattern of Form B and C shows two peaks, three peaks, four peaks or five peaks.

Experiments to determine the purity of Form B were carried out. With reference to FIGS. 16A-16C, it was determined that the purity of Form B of ponatinib hydrochloride is 99.7535% (area percent).

Characteristics of Form C (HCl2b):

Form C is a hydrated form. Form HCl2b was initially obtained from the solubility assessment experiments, either by conversion of Form B, over a number of days under ambient conditions or directly from TFE/water solvent mixtures. Form C was also obtained in the Phase 2 experiments from aqueous solvent systems (water and water/DMSO) (see overview in FIG. 2).

Form C was analyzed by X-ray powder diffraction (XRPD). FIG. 17 shows XRPD patterns of (from bottom to top): starting material (HCl1) and Form HCl2b (QSA21.1, solvent: water). In the XRPD pattern of Form C shown in FIG. 17, at least one or all of the following peaks in degrees two theta (2θ) is shown: 3.1; 6.5; 12.4; 13.8; 17.4; 18.0; 20.6; 22.0; 23.0; 25.5; 26.5; 27.4; 28.4; and 29.0. In certain embodiments, Form C is characterized by a XRPD pattern comprising one or more of the following peaks two theta (2θ): 13.8; 17.4; 18.0; and 25.5. In certain embodiments, the XRPD pattern of Form C shows two peaks, three peaks, four peaks or five peaks.

With reference to FIG. 18, the melting point of Form C of ponatinib HCl was determined by differential scanning calorimetry (DSC). The sample of was analyzed in a pin-holed crucible in the temperature range of 25° C. to 300° C. at a heating rate of 10° C. per minute using dry $N_2$ gas purge. Intense endothermic events occurred at $T_{peak}$=122.9° C., $T_{peak}$=158.2° C. and $T_{peak}$=256.2° C.

FIG. 19 shows TGA and SDTGA thermograms of QSA21.1. FIGS. 20A and 20B show a TGMS thermogram of Form C from experiment QSA21.1. A mass loss of 4.3% (water) is observed in the temperature interval 40° C.-140° C. The API:water ratio was assessed as 1:1.4.

Experiments to determine the purity of Form C were carried out. With reference to FIGS. 21A-21C, it was determined that the purity of Form C of ponatinib hydrochloride is 99.7850% (area percent).

Characteristics of Form D (HCl3-Class):

HCl3-class was mostly obtained from aromatic solvents, as can be seen in the overview in FIG. 2, with the exception of the MeOH/acetonitrile mixture. Form D was successfully reproduced at the 120 mg scale using cooling-evaporative crystallization in toluene.

Based on the thermal analyses, the sample representative of the Form D was assigned as a toluene solvated form (API:toluene 1:0.5). The form desolvated at 199.5° C., recrystallized and a second melting was observed at 257.6° C. (most likely corresponding to the melting point of Form A). HCl3-class is mildly hygroscopic, with 2.5% water mass uptake at 95% RH. The process was reversible regarding to physical stability and sample appearance.

HCl3-class sample was found to be physically stable after 8 months storage under ambient conditions and following the DVS cycle. However, HCl3-class sample converted to HCl1 after 1 week in the humidity chamber (40° C./75% RH).

Form D was analyzed by X-ray powder diffraction (XRPD). FIG. 22 shows XRPD patterns of a XRPD overlay of (from bottom to top): HCl1 (AP24534 HCl salt starting material), HCl3-class (PSM17, solvent: toluene), HCl3 (PSM1, solvent: toluene), HCl1+HCl3 (PSM1 after one week at 40° C./75% RH) and HCl3 (PSM1 after DVS). In the XRPD pattern shown in FIG. 22, at least one or all of the following peaks in degrees two theta (2θ) is shown for HCl3: 8.2; 10.1; 10.9; 14.9; 16.0; 16.3; 16.8; 17.7; 18.7; 20.2; 22.9; 24.0; 25.6; 26.7; and 28.5. In certain embodiments, Form D is characterized by a XRPD pattern comprising one or more of the following peaks two theta (2θ): 8.2; 10.1; 14.9; and 25.6. In the XRPD pattern shown in FIG. 22, at least one or all of the following peaks in degrees two theta (2θ) is shown for HCl3+HCl1: 6.5; 7.4; 12.5; 13.6; 14.1; 16.7; 17.4 18.0; 19.3; 20.4 21.8; 24.0; 25.1; 26.3; and 28.0. In certain embodiments, HCl3+HCl1 is characterized by a XRPD pattern comprising one or more of the following peaks two theta (2θ): 12.5; 19.3; and 26.3. In certain embodiments, the XRPD pattern of Form D shows two peaks, three peaks, four peaks or five peaks.

With reference to FIG. 23, the melting point of Form D of ponatinib HCl (PSM1) was determined by differential scanning calorimetry (DSC). The sample of was analyzed in a pin-holed crucible in the temperature range of 25° C. to 300° C. at a heating rate of 10° C. per minute using dry $N_2$ gas purge. Intense endothermic events occurred at $T_{peak}$=199.5° C., $T_{peak}$=204.1° C. and $T_{peak}$=257.6° C.

With reference to FIG. 24, TGA and SDTGA thermograms of Form D (PSM1) are provided. A mass loss of 7.7% (toluene, ratio API:Solvent is 1:0.51) was observed in the temperature interval 120° C.-220° C.

With reference to FIG. 25, a FT-IR spectrum of the region of 1750-500 $cm^{-1}$ is shown. These data support the proposed structure of Form D of ponatinib hydrochloride. In addition, this spectrum show the unique identity of Form D relative to Form A.

Experiments to determine the purity of Form D (PSM1) were carried out. With reference to FIGS. 26A-26C, it was determined that the purity of Form D of ponatinib hydrochloride is 97.3664% (area percent).

Characteristics of Form E (Mixture of HCl4+HCl1):

HCl4 was only obtained as a mixture with Form A from a grinding experiment with hexafluorobenzene (see overview in FIG. 2).

Form E of ponatinib hydrochloride was found not to be physically stable upon storage at ambient conditions. The mixture HCl1+HCl4 was re-measured by XRPD after 8 months of storage and it had converted to Form A.

Characteristics of Form F (HCl5-Class):

Form HCl5 was obtained from one vapor diffusion onto solids experiment described here in butyl acetate (see overview in FIG. 2). HCl5-class was characterized by DSC, cycling-DSC, TGMS, FTIR, HPLC and DVS. The physical stability under short-term storage conditions (i.e. one week at 40° C. and 75% RH) was investigated. HCl5-class samples were physically stable, as assessed by XRPD, after 8 months storage under ambient conditions. After 1 week in the humidity chamber (40° C./75% RH), the material was still HCl5-class, however with a slightly different XRPD pattern.

A DVS experiment showed that HCl5-class is highly hygroscopic, with a 37% water mass adsorption. The material lost its crystallinity as indicated by the XRPD following the DVS experiment.

Form F was successfully scaled up at the 120 mg scale using the same conditions as those of the original experiment to identify the previously discovered polymorphs. Two scale-up experiments were performed and the corresponding XRPD patterns indicated forms isostructural to HCl5. These isostructural forms together with HCl5 and HCl5b were designated HCl5-class or Form F.

FIG. 27 shows XRPD patterns of a XRPD overlay of (from bottom to top): HCl (Form A starting material); HCl5 and HCl5b (VDS28 wet and dry, solvent: butyl acetate); HCl5-class (VDS1, solvent: butyl acetate), Low crystalline (VDS1 after DVS); HCl5-class (VDS2, solvent: butyl acetate); and HCl5-class (VDS2 after one week at 40°, 75% RH). In the XRPD pattern shown in FIG. 27, at least one or all of the following peaks in degrees two theta (2θ) is shown for HCl5: 6.8; 9.8; 12.4; 16.2; 17.9; 19.0; 24.0; and 25.1. In certain embodiments, HCl5 is characterized by a XRPD pattern comprising one or more of the following peaks two theta (2θ): 9.8; 12.4; and 25.1. In the XRPD pattern shown in FIG. 27, at least one or all of the following peaks in degrees two theta (2θ) is shown for HCl5-class (top pattern): 7.9; 8.7; 9.7; 11.4; 15.6; 16.5; and 25.8. In certain embodiments, HCl5-class is characterized by a XRPD pattern comprising one or more of the following peaks two theta (2θ): 15.6; 16.5; 25.8. In certain embodiments, the XRPD pattern of Form F shows two peaks, three peaks, four peaks or five peaks.

With reference to FIGS. 28A and 28B, the melting point of Form F of ponatinib HCl (PSM1) was determined by differential scanning calorimetry (DSC). Samples from two different experiments were analyzed in a pin-holed crucible in the temperature range of 25° C. to 300° C. at a heating rate of 10° C. per minute using dry $N_2$ gas purge. A sample from one experiment (VDS1, FIG. 28A) evidenced intense endothermic events occurred at $T_{peak}$=120.7° C., $T_{peak}$=184.3° C. and $T_{peak}$=209.4° C. A sample from another experiment (VDS2, FIG. 28B) evidenced intense endothermic events occurred at $T_{peak}$=122.1° C., $T_{peak}$=209.7° C. and $T_{peak}$=252.1° C.

A cycling DSC experiment showed that upon desolvation, HCl5-class converted to a form designated "HCl5-desolvate", which melted at circa 210° C.

With reference to FIGS. 29A-29C, a TGA/SDTA thermogram of Form F (VDS1, FIG. 29A) and TGMS (FIGS. 29B and 29C) thermogram are provided. A mass loss of 17.1% (Butyl acetate, ratio API:Solvent 1:1.01) was observed in the temperature interval 25° C.–160° C. TG-MS analyses showed that HCl5-class is a butyl acetate solvate with a ratio API:butyl acetate of 1:1 and it desolvates at around 120° C. FIGS. 30A-30C provide a corresponding TGA/SDTA (FIG. 30A) and TGMS (FIGS. 30B and 30C) thermogram of Form F for VDS2. A mass loss of 16.6% (Butyl acetate, ratio API:Solvent 1:0.98) was observed in the temperature interval 25° C.–160° C.

With reference to FIGS. 31 and 32, a FT-IR spectrum of the region of 1750-500 cm$^{-1}$ is shown. These data support the proposed structure of Form F of ponatinib hydrochloride. In addition, these spectra show the unique identity of Form F relative to Form A.

Experiments to determine the purity of Form F (VDS2) were carried out. With reference to FIGS. 33A-33C, it was determined that the purity of Form D of ponatinib hydrochloride is 98.2833% (area percent).

Characteristics of Form G (HCl5b):

Form G of ponatinib hydrochloride was obtained by conversion of HCl5, upon drying for 3 days under full vacuum. HCl5b form was found to be physically stable after 8 months storage under ambient conditions.

Characterization data for Form G is provided herein in the context of Form F.

Characteristics of Form H (HCl6-Class):

HCl6 was obtained from two experiments; vapor into solution and vapor onto solids, in MeOH/water and MeOH solvent systems, respectively (see overview in FIG. 2). Different time points of material sampling showed that the corresponding XRPD patterns were slightly different, without being bound by theory, indicating that HCl6 is a class of forms, likely isostructural. HCl6-class was successfully scaled up to 120 mg using the same conditions as those of the MeOH vapor onto solids experiment of the original screening experiment.

HCl6-class was characterized by DSC, cycling-DSC, TGMS, FTIR, HPLC and DVS. The physical stability under short-term storage conditions (i.e. one week at 40° C. and 75% RH) was investigated. Form H samples were physically stable, as assessed by XRPD, after 8 months storage under ambient conditions. After 1 week in the humidity chamber (40° C./75% RH), the material was still HCl6-class, however with a slightly different XRPD.

FIG. 34 shows XRPD patterns of a XRPD overlay of (from bottom to top): Form A (ponatinib hydrochloride starting material), HCl6-class (VDS6, solvent: methanol), HCl6-class (VDS3, solvent: methanol), HCl6 (VDS3 after DVS), HCl6-class (VDS3 after climate chamber), HCl6-class (VDS4, solvent: methanol) and HCl6-class (VDS4 after DVS). In the XRPD pattern shown in FIG. 34, at least one or all of the following peaks in degrees two theta (2θ) is shown for HCl6 (immediately above Form A pattern): 5.9; 8.1; 9.5; 10.7; 13.4; 16.0; 17.0; 22.0; 22.8; 24.7; and 28.3. In certain embodiments, HCl6 is characterized by a XRPD pattern comprising one or more of the following peaks two theta (2θ): 8.1; 10.7; 13.4; 24.7; and 28.3. In the XRPD pattern shown in FIG. 34, at least one or all of the following peaks in degrees two theta (2θ) is shown for HCl6-class (top pattern): 8.0; 10.2; 10.9; 11.8; 14.1; 15.4; 16.3; 19.9; 22.3; 23.7; 25.0; and 28.2. In certain embodiments, HCl6-class is characterized by a XRPD pattern comprising one or more of the following peaks two theta (2θ): 10.2; 15.4; 23.7; 25.0. In certain embodiments, the XRPD pattern of Form F shows two peaks, three peaks, four peaks or five peaks. Although XRPD analysis of both samples showed that similar patterns were observed after the DVS run, the TGMS analysis of VDS4 showed that methanol molecules were no longer present in the sample but they had been replaced by water molecules (forming presumably a hemi-hydrated form belonging to the HCl6-class.

With reference to FIGS. 35A and 35B, the melting point of Form H of ponatinib HCl was determined by differential scanning calorimetry (DSC). Samples from two different experiments were analyzed in a pin-holed crucible in the temperature range of 25° C. to 300° C. at a heating rate of 10° C. per minute using dry $N_2$ gas purge. A sample from one experiment (VDS3, FIG. 35A) evidenced an intense endothermic event at $T_{peak}$=219.4° C. A sample from another experiment (VDS4, FIG. 35B) evidenced intense endothermic events occurred at $T_{peak}$=219.4° C. and $T_{peak}$=256.8° C.

With reference to FIGS. 36A-36C, a TGA/SDTA thermogram of Form H (VDS3, FIG. 36A) and TGMS (VDS3, FIGS. 36B and 36C) thermogram are provided. A mass loss of 5.4% (Methanol, ratio API:Solvent 1:1.01) was observed in the temperature interval 30° C.-150° C. and a mass loss of 0.3% (Methanol ratio API:Solvent 1:0.05) was observed in the temperature interval 190° C.-220° C. A corresponding TGA/SDTA thermogram of Form H (FIG. 37A) and TGMS (FIGS. 37B and 37C) thermogram is shown for VDS4. A mass loss of 3.3% (Methanol, ratio API:Solvent 1:0.6) was observed in the temperature interval 30° C.-150° C. and a mass loss of 0.7% (Methanol, ratio API:Solvent 1:0.12) was observed in the temperature interval 190° C.-220° C.

With reference to FIGS. 38 and 39, a FT-IR spectrum of the region of 1750-500 cm$^{-1}$ is shown. These data support the proposed structure of Form H of ponatinib hydrochloride. In addition, these spectra show the unique identity of Form H relative to Form A.

Experiments to determine the purity of Form H (VDS4) were carried out. With reference to FIGS. 40A-40C, it was determined that the purity of Form H of ponatinib hydrochloride is 97.9794% (area percent).

Characteristics of Form I (HCl6 Desolvate):

A cycling DSC experiment conducted in connection with the experiments for Form H showed that upon desolvation, HCl6-class converted to a form designated "HCl6-desolvate", which melted at circa 220° C.

Characteristics of Form J (HCl7):

Form J is a pentahydrate of ponatinib HCl and was discovered in the context of a single crystal analysis. Form J is the most stable hydrated structure identified, as competitive slurries in water between the trihydrate and pentahydrate showed.

Single crystals of suitable size were obtained in the vapor diffusion experiment performed with the solvent mixture methanol/water 20:80 and n-butyl acetate as anti-solvent. One parallelepiped single crystal of approximate size 0.45× 0.25×0.12 mm was collected from the crystallization vial and mounted on a glass fiber. The crystallographic data (collected up to θ=27.5°) are listed in Table 4.

TABLE 4

Crystal Data and Structure Refinement for Form J

| Identification code | Form J (Pentahydrate) |
|---|---|
| Empirical formula | $C_{29}H_{28}F_3N_6O^+$ • $Cl^-$ • 5 $H_2O$ |
| Fw | 659.10 |
| T [K] | 296(2) |
| λ [Å] | 0.71073 |
| Crystal system | Monoclinic |
| Space group | P 2$_1$/c |
| Unit cell dimensions | |
| a [Å] | 16.7220(4) |
| b [Å] | 7.5920(2) |
| c [Å] | 29.920(8) |
| β [°] | 121.543(9) |
| V [Å$^3$] | 3237.2(9) |
| Z | 4 |
| D$_c$ [g/cm$^3$] | 1.352 |
| μ [mm$^{-1}$] | 0.186 |
| F(000) | 1384 |
| Crystal size [mm] | 0.45 × 0.25 × 0.12 |
| θ range for data collection [°] | 2.8 → 27.5 |
| Reflections collected | 24343 |
| Independent reflections | 7410 [R$_{int}$ = 0.0450] |

TABLE 4-continued

Crystal Data and Structure Refinement for Form J

| Identification code | Form J (Pentahydrate) |
|---|---|
| Completeness to θ = 27.5° [%] | 99.6 |
| Max. and min. transmission | 0.9781 and 0.9211 |
| Data/restraints/parameters | 7410/0/542 |
| Goodness-of-fit on F$^2$ | 1.030 |
| Final R indices [I > 2σ(I)] | R1 = 0.0630, wR2 = 0.1502 |
| R indices (all data) | R1 = 0.1064, wR2 = 0.1758 |

The asymmetric unit comprises the cation, the chloride anion and five water molecules (pentahydrate). The water molecules are connected via hydrogen bonding (H-Bonds) with the anion, the cation and neighboring water molecules.

The important consequence of the present H-Bonds arrangement is the fact that in this crystal both charged atoms (i.e. the protonated nitrogen from the API and the chloride anion) are bridged/separated by several molecules of water.

FIG. 43 shows a characteristic X-Ray Powder Diffraction (XRPD) pattern for Form J of ponatinib hydrochloride. The XRPD pattern of Form J shown in FIG. 43 shows at least one or more of the peaks having a relative intensity of 20% or greater in degrees two theta (2θ): 6.1; 7.0; 13.3; 16.4; 20.7; 22.2; 23.9; 25.5; and 29.1. In certain embodiments, Form J is characterized by a XRPD pattern comprising one or more of the following peaks two theta (2θ): 7.0; 22.2; and 25.5. In certain embodiments, the XRPD pattern of Form J shows two peaks, three peaks, four peaks or five peaks.

Characteristics of Form K (HCl8):

Form K was discovered in the context of a single crystal analysis. The single crystals were grown in the slow evaporation experiment conducted with TFE/H2O mixture 50:50. One block-like single crystal of approximate size 0.40× 0.30×0.25 mm was analyzed. Although the crystal was large, it diffracted quite poorly, which is an indication of partial disorder in the structure. Therefore the measurement was recorded only up to θ=25°. The crystallographic parameters are listed in Table 5.

TABLE 5

Crystal data and structure refinement for Form K

| Identification code | Form K ( Trifluorethanol solvate hydrate) |
|---|---|
| Empirical formula | $C_{29}H_{28}F_3N_6O^+$ • $Cl^-$ • $C_2H_3F_3O$ • 0.75 $H_2O$ |
| Fw | 682.58 |
| T [K] | 296(2) |
| λ [Å] | 0.71073 |
| Crystal system | Triclinic |
| Space group | P-1 |
| Unit cell dimensions | |
| a [Å] | 9.726(2) |
| b [Å] | 12.270(3) |
| c [Å] | 14.476(4) |
| α [°] | 91.694(7) |
| β [°] | 98.963(8) |
| γ [°] | 99.390(9) |
| V [Å$^3$] | 1680.9(7) |
| Z | 2 |
| D$_c$ [g/cm$^3$] | 1.349 |
| μ [mm$^{-1}$] | 0.187 |
| F(000) | 707 |
| Crystal size [mm$^3$] | 0.40 × 0.30 × 0.25 |
| θ range for data collection [°] | 2.1 → 25 |
| Reflections collected | 8812 |
| Independent reflections | 5866 [R$_{int}$ = 0.0247] |
| Completeness to θ = 25° [%] | 99.0 |

TABLE 5-continued

Crystal data and structure refinement for Form K

| Identification code | Form K ( Trifluorethanol solvate hydrate) |
|---|---|
| Max. and min. transmission | 0.9548 and 0.9290 |
| Data/restraints/parameters | 5866/0/440 |
| Goodness-of-fit on $F^2$ | 1.035 |
| Final R indices [I > 2σ(I)] | R1 = 0.0762, wR2 = 0.2160 |
| R indices (all data) | R1 = 0.0931, wR2 = 0.2366 |

The structure of the mixed TFE solvated/hydrated form comprises the cation, the chloride anion and two neutral entities: the trifluoroethanol and the water molecules. In this structure, although water molecules are involved in the H-bonding they do not separate the charged atoms (contrary to the pentahydrated and trihydrated forms. The TFE and water molecules acted only as donors in the hydrogen bonding network. In particular for the water molecules, only one of the hydrogen atoms acts as donor, which could be responsible for the disorder of the water molecules and the fact that the ratio of the water molecules compared to the API molecules is not stoichiometric.

FIG. 44 shows a characteristic X-Ray Powder Diffraction (XRPD) pattern for Form K of ponatinib hydrochloride. The XRPD pattern of Form K shown in FIG. 44 shows at least one or more of the peaks having a relative intensity of 20% or greater in degrees two theta (2θ): 6.1; 7.4; 13.5; 17.4; 18.5; 20.7; 23.9; and 28.3. In certain embodiments, Form K is characterized by a XRPD pattern comprising one or more of the following peaks two theta (2θ): 7.4 and 23.9. In certain embodiments, the XRPD pattern of Form K shows two peaks, three peaks, four peaks or five peaks.

Characteristics of Amorphous Form of Ponatinib Hydrochloride:

FIG. 45 shows XRPD patterns of Form A of ponatinib hydrochloride (bottom pattern) and amorphous ponatinib hydrochloride (top pattern) (solvent:2,2,2-trifluroethanol). It is readily apparent that Form A has a distinct set of peaks at particular angles two theta whereas the amorphous ponatinib hydrochloride does not have any defined peaks.

In addition, amorphous ponatinib hydrochloride has a unique melting temperature as compared to Form A of amorphous ponatinib hydrochloride. FIG. 46 shows a characteristic Differential Scanning Calorimetry (DSC) thermogram of amorphous ponatinib hydrochloride. An intense endothermic event with a peak of 259.4° C. was observed, corresponding to the melting point of the amorphous form. This melting point is distinct from that observed with Form A of ponatinib hydrochloride, which demonstrated a melting point of 264.1° C.

Unique and distinct physical properties of amorphous ponatinib hydrochloride and Form A of ponatinib hydrochloride do not seem to be attributed to purity of the respective materials. In the case of amorphous ponatinib hydrochloride, the material was determined by HPLC to have a purity of 99.7877% (area percent) (see FIGS. 47A-47C), whereas the purity of Form A of ponatinib hydrochloride was determined to be 99.8% (area percent).

Example 1

Discovery of Polymorphic Forms

Initial efforts to discover polymorphic forms of ponatinib hydrochloride were divided into two phases. Phase 1 included starting-material characterization, feasibility testing and solubility studies to provide data for the solvent selection for Phase 2. Phase 2 included 192 polymorph screening experiments at milliliter (ml) scale. These initial efforts led to the discovery of eight polymorphic forms, Form A, Form B, Form C, Form D, Form E, Form F, Form G and Form H.

Phase 1: Starting Material Characterization

Approximately 24 grams of the compound ponatinib hydrochloride was provided as a light yellow solid. This starting material was characterized by XRPD, digital imaging, DSC, TGMS and HPLC. The starting material, 3-(imidazo[1,2-b]pyridazin-3-ylethynyl)-4-methyl-N-{4-[(4-methylpiperazin-1-yl)methyl]-3-(trifluoromethyl) phenyl}benzamide mono hydrochloride, is provided as a crystalline material (designated HCl) and its chemical purity was assessed by HPLC as 99.8%. TGA and TGMS analyses showed 0.7% of mass loss (residual ethanol) in the temperature interval 25° C.-240° C. prior to the thermal decomposition process. DSC analysis showed an endothermic event with $T_{peak}$=264.8° C., probably related to melting and/or decomposition of the compound, 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride.

Phase 1: Solubility Study

Quantitativesolubilitytestingwasperformedonponatinib-hydrochloridestartingmaterial, employing a set of 20 solvents. Slurries were prepared with an equilibration time of 24 hours after which the slurries were filtrated. The solubility was determined from the saturated solutions by HPLC. The residual solids were characterized by XRPD. The results are summarized in Table 6.

TABLE 6

Solubility Study of 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride

| Experiment | Solvent name | Solubility (mg/ml) | XRPD Form[1] |
|---|---|---|---|
| QSA1 | Diethylene glycol diethylether | 0.36 | HCl1 |
| QSA2 | Diethyl ether | UR, <0.22[2] | HCl1 |
| QSA3 | Dimethyl Sulfoxide | 71.65 | HCl1 |
| QSA4 | Isobutyl isobutymte | UR, <0.22[2] | HCl1 |
| QSA5 | Dimethylacetamide N,N- | 35.64 | HCl1 |
| QSA6 | Pentyl ether | UR, <0.22[2] | HCl1 |
| QSA7 | Cyclohexanone | 0.64 | HCl1 |
| QSA8 | Xylene, p- | UR, <0.22[2] | HCl1 |
| QSA9 | Isobutanol | 0.91 | HCl1 |
| QSA10 | Butyl acetate | UR, <0.22[2] | HCl1 |
| QSA11 | Heptane, n- | UR, <0.22[2] | HCl1 |
| QSA12 | Water | 1.67 | HCl2 |
| QSA13 | Trifluoroethanol 2,2,2- | OR[3] | Am[4] |
| QSA14 | Hexafluorobenzene | UR, <0.22[2] | HCl1 |
| QSA15 | Isopropanol | 0.64 | HCl1 |
| QSA16 | Isopropyl acetate | UR, <0.22[2] | HCl1 |
| QSA17 | Dichloroethane 1,2- | 0.27 | HCl1 |
| QSA18 | Acetonitrile | 0.44 | HCl1 |
| QSA19 | Tetrahydrofumn | 0.42 | HCl1 |
| QSA20 | Methanol | 29.66 | HCl1 |
| QSA21 | Water | 1.85 | HCl2b |
| QSA23 | Heptane, n- | UR, <0.22[2] | HCl1 |
| QSA24 | Heptane, n- | UR, <0.22[2] | HCl1 |
| QSA25 | Acetonitrile | 0.38 | HCl1 |
| QSA26 | Acetonitrile | 0.39 | HCl1 |
| QSA27 | Dimethyl sulfoxide | 86.44 | HCl1 |
| QSA28 | Dimethyl sulfoxide | 85.18 | HCl1 |
| QSA29 | Diethyl ether | UR, <0.22[2] | HCl1 |
| QSA30 | Water | 1.66 | HCl2b |
| QSA31 | Dimethyl sulfoxide | 93.14 | HCl1 |

TABLE 6-continued

Solubility Study of 3-(imidazo[1,2-b]pyridazin-3-
ylethynyl)-4-methyl-N-{4-[(4-methylpiperazin-1-
yl)methyl]-3-(trifluoromethyl)phenyl}benzamide mono hydrochloride

| Experiment | Solvent name | Solubility (mg/ml) | XRPD Form[1] |
|---|---|---|---|
| QSA32 | 2-Methyltetrahydrofuran | UR, <0.22[2] | HCl1 |
| QSA33 | Ethanol | 4.58 | HCl1 |

All tests were conducted at room temperature with stirring.
[1]The solid form obtained from the slurry was assessed based on the XRPD analysis.
[2]Under Range, lower then detection limit, the concentration is lower than 0.22 mg/ml
[3]Over Range, the material was dissolved, the concentration is higher then 200 mg/ml.
[4]Amorphous In 19 of the experiments shown in Table 6, the materials analyzed following the solubility assessments in 19 different solvents appeared to be the same form as the starting material designated form HCl. In the experiment QSA13 performed in 2,2,2-trifluoroethanol, the material dissolved completely at the selected concentration and the sample obtained after evaporation of the solvent resulted in amorphous material. The solids from two slurries in water (QSA12 and QSA21) resulted in two different forms, Form HCl2 and Form HCl2b, respectively. After a few days stored at ambient conditions, the form HCl2 converted to Form HCl2b and it could therefore not be further characterized. Upon further characterization, the Form HCl2b was determined to be a hydrated form (ratio API/water 1:1.4).

Phase 1: Feasibility Study

Feasibility tests were performed to attempt to obtain amorphous starting material that could be employed in some crystallization techniques of the Phase 2 portion of the study. Two techniques were employed i.e. grinding and freeze-drying. The results are presented below.

Grinding. Two grinding experiments were performed with two different durations at a frequency of 30 Hz. After 60 minutes of grinding, the crystalline starting material converted to amorphous. After 120 min, the resulting material remained amorphous with a chemical purity of 99.6%.

Freeze-drying. Eight freeze-drying experiments were performed with 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride. These experiments are summarized in Table 7.

The solubility of compound ponatinib hydrochloride in tetrahydrofuran, 2-methyltetrahydrofuran and dichloromethane was too low to apply the freeze drying procedure in good conditions. With solvents such as methanol, 2,2,2-trifluoroethanol (TFE) and TFE/water mixtures, amorphous material was obtained. In the samples obtained from neat TFE or with high TFE content in the solvent mixtures, 11% of residual solvent was detected in the dried powders (according to the TGMS results). The samples obtained from methanol and TFE/water 50:50 contained less residual solvent only 0.9% and 1.5%, respectively. The amount of residual solvent in the amorphous material produced from TFE/water 50:50 could be reduced to below 1% after extra drying for 24 hours. For both amorphous samples obtained from methanol and TFE/water 50:50, the chemical purity was assessed to be 99.8% by HPLC. Because creeping was observed in the freeze-drying experiment with methanol, the procedure using TFE/water 50:50 was selected to be used to produce the amorphous ponatinib hydrochloride to be used in the cooling-evaporation crystallizations and vapor diffusion onto solids experiments of Phase 2.

Phase 2: Polymorph Discovery

The polymorph screening experiments for ponatinib hydrochloride were carried out at milliliter (ml) scale using 192 different conditions in which six different crystallization procedures were applied: (1) cooling-evaporation; (2θ) anti-solvent addition; (3) grinding; (4) slurry; (5) vapor diffusion into solutions; and (6) vapor diffusion onto solids. After the screening experiments were completed, the materials were collected and analyzed by XRPD and digital imaging.

Cooling-Evaporative Crystallization Experiments. The 36 cooling-evaporative experiments shown at Table 8 at ml scale were performed in 1.8 ml vials, employing 36 different solvents and solvent mixtures and 1 concentration. In each vial, 25 mg of amorphous ponatinib hydrochloride was weighed. Then the screening solvent was added to reach a concentration of circa 60 mg/ml. The vials, also containing a magnetic stirring bar, were closed and placed in an Avantium Crystal 6 to undergo a temperature profile, (as described in Table 9 below). The mixtures were cooled to 5° C. and held at that temperature for 48 hours before placing the vials under vacuum. The solvents were evaporated for several days at 200 mbar or 10 mbar and analyzed by XRPD and digital imaging.

TABLE 7

Freeze-drying feasibility study of 3-(imidazo[1,2-b]pyridazin-3-ylethynyl)-4-methyl-N-{4-
[(4-methylpiperazin-1-yl)methyl]-3-(trifluoromethyl)phenyl}benzamide mono hydrochloride

| Experiment | Solvent | Form (XRPD) | Solvent content (%)[1] | Purity (%)[2] |
|---|---|---|---|---|
| GEN2 | Dimethyl sulfoxide | — (not dry) | — | — |
| GEN3 | Methanol | Am powdery | 0.9 | 99.8 |
| GEN4 | 2,2,2-Trifluoroethanol/Water 90/10 | Am powdery | 10.8 | — |
| GEN5 | 2,2,2-Trifluoroethanol/Water 50/50 | Am powdery | 1.5 | 99.8 |
| GEN6 | 2,2,2-Trifluoroethanol | Am powdery | 11.0 | — |
| GEN7 | Tetrahydrofuran | — | — | — |
| GEN8 | 2-Methyltetrahydrofuran | — | — | — |
| GEN9 | Dichloromethane | — | — | — |

[1]Based on the TGMS results.
[2]Chemical purity determined by HPLC.

TABLE 8

Experimental conditions for the 36 ml experiments using the cooling-evaporation method

| Experiment | Solvent | Weight (mg) | Volume (µl) |
|---|---|---|---|
| PSM1 | Methyl butyl ether, tert- | 24.8 | 400 |
| PSM2 | Methyl acetate | 24.0 | 400 |
| PSM3 | Chloroform | 25.1 | 400 |
| PSM4 | Methanol | 24.1 | 400 |
| PSM5 | Tetrahydrofuran | 21.9 | 400 |
| PSM6 | Hexane, n- | 21.8 | 400 |
| PSM7 | Ethanol | 25.2 | 400 |
| PSM8 | Cyclohexane | 23.3 | 400 |
| PSM9 | Acetonitrile | 21.8 | 400 |
| PSM10 | Ethylene glycol dimethyl ether | 23.1 | 400 |
| PSM11 | Isopropyl acetate | 20.8 | 400 |
| PSM12 | Heptane, n- | 25.0 | 400 |
| PSM13 | Water | 23.3 | 400 |
| PSM14 | Methylcyclohexane | 25.2 | 400 |
| PSM15 | Dioxane, 1,4- | 27.2 | 400 |
| PSM16 | Isobutanol | 21.9 | 400 |
| PSM17 | Toluene | 23.3 | 400 |
| PSM18 | Butyl acetate | 23.1 | 400 |
| PSM19 | Hexanone, 2- | 24.4 | 400 |
| PSM20 | Chlorobenzene | 21.5 | 400 |
| PSM21 | Ethoxyethanol, 2- | 22.9 | 400 |
| PSM22 | Xylene, m- | 22.6 | 400 |
| PSM23 | Cumene | 23.4 | 400 |
| PSM24 | Anisole | 22.0 | 400 |
| PSM25 | Methanol/Chloroform (50/50) | 23.9 | 400 |
| PSM26 | Methanol/Ethyl formate (50/50) | 24.8 | 400 |
| PSM27 | Methanol/Acetonitrile (50/50) | 23.2 | 400 |
| PSM28 | Acetonitrile/Chloroform (50/50) | 23.2 | 400 |
| PSM29 | Cyclohexane/Tetrahydrofuran (50/50) | 22.9 | 400 |
| PSM30 | Cyclohexane/Chloroform (50/50) | 23.8 | 400 |
| PSM31 | Cyclohexane/Dioxane, 1,4- (50/50) | 24.9 | 400 |
| PSM32 | Cyclohexane/N-methyl-2-pyrrolidone (50/50) | 22.1 | 400 |
| PSM33 | Heptane, n-/Cyclohexane (50/50) | 23.9 | 400 |
| PSM34 | Tetrahydrofuran/N-methyl-2-pyrrolidone (50/50) | 24.9 | 400 |
| PSM35 | Tetrahydronaphthalene, 1,2,3,4-/Cyclohexane (50/50) | 22.9 | 400 |
| PSM36 | Tetrahydronaphthalene, 1,2,3,4-/Cumene (50/50) | 22.6 | 400 |

TABLE 9

Temperature profile employed for the 36 cooling-evaporative experiments

| Experiments | Heating rate | $T_{initial}$ | Hold | Cooling rate | $T_{final}$ | Hold |
|---|---|---|---|---|---|---|
| PSM1-36 | 10 | 60 | 60 | 1 | 5 | 48 |

Crash-crystallization with anti-solvent addition Experiments. For the crash-crystallization experiments, 36 different crystallization conditions were applied, using 1 solvent and 24 different anti-solvents (see Table 9). The anti-solvent addition experiments have been performed forwards. A stock solution was prepared, the concentration of ponatinib hydrochloride being that attained at saturation at ambient temperature after equilibration for 24 hours before filtering into 8 ml vials. To each of these vials a different anti-solvent was added, using a solvent to anti-solvent ratio of 1:0.25. Because no precipitation occurred, this ratio was increased to 1:4 with a waiting time of 60 minutes between each addition. As no precipitation occurred yet, the solvents were completely evaporated under vacuum at room temperature. After evaporation, the experiments resulted to have no yield.

TABLE 9 crash-crystallization experiments

| Experiment | Solvent | Anti-Solvent | Ratio S:AS (1:x) |
|---|---|---|---|
| AS1 | Ethyl formate | Methyl butyl ether, tert- | 4 |
| AS2 | Ethyl formate | Chloroform | 4 |
| AS3 | Ethyl formate | Diisopropyl ether | 4 |
| AS4 | Ethyl formate | Cyclohexane | 4 |
| AS5 | Ethyl formate | Trimethylpentane, 2,2,4- | 4 |
| AS6 | Ethyl formate | Heptane, n- | 4 |
| AS7 | Ethyl formate | Octane, n- | 4 |
| AS8 | Ethyl formate | Nonane, n- | 4 |
| AS9 | Ethyl formate | Diethoxymethane | 4 |
| AS10 | Ethyl formate | Dimethyl-4-heptanone,2,6- | 4 |
| AS11 | Ethyl formate | Methyltetrahydrofuran, 2- | 4 |
| AS12 | Ethyl formate | Cumene | 4 |
| AS13 | Ethyl formate | Methylcyclohexane | 4 |
| AS14 | Ethyl formate | Acetonitrile | 4 |
| AS15 | Ethyl formate | Fluorobenzene | 4 |
| AS16 | Ethyl formate | Diethyl carbonate | 4 |
| AS17 | Ethyl formate | Dimethyl-3-butanone,2,2- | 4 |
| AS18 | Ethyl formate | Dichloroethane, 1,2- | 4 |
| AS19 | Ethyl formate | Xylene, p- | 4 |
| AS20 | Ethyl formate | Isoamyl acetate | 4 |
| AS21 | Ethyl formate | Toluene | 4 |
| AS22 | Ethyl formate | Cyclohexanone | 4 |
| AS23 | Ethyl formate | Chlorobenzene | 4 |
| AS24 | Ethyl formate | Anisole | 4 |
| AS25 | Dimethyl Sulfoxide | Water | 4 |
| AS26 | Dimethyl Sulfoxide | Tetrahydrofuran | 4 |
| AS27 | Dimethyl Sulfoxide | Methyltetrahydrofuran, 2- | 4 |
| AS28 | Dimethyl Sulfoxide | Acetonitrile | 4 |
| AS29 | Dimethylacetamide N,N- | Water | 4 |
| AS30 | Dimethylacetamide N,N- | Tetrahydrofuran | 4 |
| AS31 | Dimethylacetamide N,N- | Methyltetrahydrofuran, 2- | 4 |
| AS32 | Dimethylacetamide N,N- | Acetonitrile | 4 |
| AS33 | Methanol | Water | 4 |
| AS34 | Methanol | Tetrahydrofuran | 4 |
| AS35 | Methanol | Methyltetrahydrofuran, 2- | 4 |
| AS36 | Methanol | Acetonitrile | 4 |

Grinding Experiments. The drop-grinding technique uses a small amount of solvent added to the material 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride, which is grinded in a stainless steel grinder jar with 2 stainless steel grinding balls. In this manner, the effect of 24 different solvents (see Table 10) was investigated. Typically 30 mg of starting material was weighed in the grinding container and 10 µl of solvent was added to the container. The grinding experiments were performed at 30 Hz during 120 min. Each wet material was subsequently analyzed by XRPD and digital imaging.

TABLE 10

Experimental Conditions for Grinding Experiments

| Experiment | Solvent | Weight (mg) | Volume (µl) |
|---|---|---|---|
| GRP1 | Hexafluorobenzene | 30.6 | 10 |
| GRP2 | Cyclohexane | 31.4 | 10 |
| GRP3 | Acetonitrile | 28.8 | 10 |
| GRP4 | Ethylene glycol dimethyl ether | 28.6 | 10 |
| GRP5 | Diethoxymethane | 29.9 | 10 |
| GRP6 | Heptane, n- | 31.0 | 10 |
| GRP7 | Trimethylpentane, 2,2,4- | 31.0 | 10 |
| GRP8 | Water | 30.0 | 10 |
| GRP9 | Nitromethane | 30.0 | 10 |
| GRP10 | Dioxane, 1,4- | 29.8 | 10 |
| GRP11 | Trifluorotoluene, alpha, alpha, alpha- | 30.5 | 10 |

TABLE 10-continued

Experimental Conditions for Grinding Experiments

| Experiment | Solvent | Weight (mg) | Volume (μl) |
|---|---|---|---|
| GRP12 | Toluene | 30.4 | 10 |
| GRP13 | Nitropropane, 2- | 30.3 | 10 |
| GRP14 | Nitropropane, 1- | 30.4 | 10 |
| GRP15 | Xylene, p- | 30.6 | 10 |
| GRP16 | Fluorooctane,1- | 30.6 | 10 |
| GRP17 | Isoamyl acetate | 30.3 | 10 |
| GRP18 | Xylene o- | 29.0 | 10 |
| GRP19 | Nonane, n- | 29.8 | 10 |
| GRP20 | Cyclohexanone | 29.8 | 10 |
| GRP21 | Diethyleneglycol-dimethylether | 29.7 | 10 |
| GRP22 | Butylbenzene, sec- | 29.1 | 10 |
| GRP23 | Decane | 28.9 | 10 |
| GRP24 | Limonene, (R)-(+)- | 28.6 | 10 |

Slurry Experiments. A total of 48 slurry experiments were performed with the compound ponatinib hydrochloride and 24 solvents at 1000 and 30° C., for 2 weeks. Table 11 summarizes the experimental conditions. The experiments were carried out by stirring a suspension of the material in a solvent at a controlled temperature. At the end of the slurry time, the vials were centrifuged and solids and mother liquids separated. The solids were further dried under full vacuum at room temperature and analyzed by XRPD and digital imaging.

TABLE 11

Experimental Conditions for the Slurry Experiments

| Experiment | Solvent | Weight (mg) | Volume (ul) | Temperature (° C.) |
|---|---|---|---|---|
| SLP1 | Methyl butyl ether, tert- | 26.4 | 250 | 10 |
| SLP2 | Methyl acetate | 28.9 | 250 | 10 |
| SLP3 | Chloroform | 25.0 | 250 | 10 |
| SLP4 | Methanol | 23.0 | 250 | 10 |
| SLP5 | Tetrahydrofuran | 25.9 | 250 | 10 |
| SLP6 | Hexane, n- | 23.8 | 250 | 10 |
| SLP7 | Ethanol | 24.1 | 250 | 10 |
| SLP8 | Cyclohexane | 27.0 | 250 | 10 |
| SLP9 | Acetonitrile | 28.5 | 250 | 10 |
| SLP10 | Dimethoxyethane, 1,2- | 26.6 | 200 | 10 |
| SLP11 | Isopropyl acetate | 24.1 | 250 | 10 |
| SLP12 | Heptane, n- | 25.3 | 250 | 10 |
| SLP13 | Water | 22.6 | 250 | 10 |
| SLP14 | Methylcyclohexane | 24.6 | 250 | 10 |

TABLE 11-continued

Experimental Conditions for the Slurry Experiments

| Experiment | Solvent | Weight (mg) | Volume (ul) | Temperature (° C.) |
|---|---|---|---|---|
| SLP15 | Dioxane, 1,4- | 26.7 | 250 | 10 |
| SLP16 | Isobutanol | 25.1 | 250 | 10 |
| SLP17 | Toluene | 24.0 | 250 | 10 |
| SLP18 | Butyl acetate | 26.7 | 250 | 10 |
| SLP19 | Hexanone 2- | 25.0 | 250 | 10 |
| SLP20 | Chlorobenzene | 26.0 | 250 | 10 |
| SLP21 | Ethoxyethanol, 2- | 26.0 | 250 | 10 |
| SLP22 | Xylene, m- | 25.8 | 250 | 10 |
| SLP23 | Cumene | 24.5 | 250 | 10 |
| SLP24 | Anisole | 26.7 | 250 | 10 |
| SLP25 | Methyl butyl ether, tert- | 23.7 | 250 | 30 |
| SLP26 | Methyl acetate | 28.2 | 250 | 30 |
| SLP27 | Chloroform | 26.6 | 250 | 30 |
| SLP28 | Methanol | 25.5 | 250 | 30 |
| SLP29 | Tetrahydrofuran | 25.2 | 250 | 30 |
| SLP30 | Hexane, n- | 27.1 | 250 | 30 |
| SLP31 | Ethanol | 28.6 | 250 | 30 |
| SLP32 | Cyclohexane | 25.9 | 250 | 30 |
| SLP33 | Acetonitrile | 28.4 | 250 | 30 |
| SLP34 | Dimethoxyethane, 1,2- | 23.2 | 200 | 30 |
| SLP35 | Isopropyl acetate | 26.2 | 250 | 30 |
| SLP36 | Heptane, n- | 24.4 | 250 | 30 |
| SLP37 | Water | 25.8 | 250 | 30 |
| SLP38 | Methylcyclohexane | 28.4 | 250 | 30 |
| SLP39 | Dioxane, 1,4- | 26.7 | 250 | 30 |
| SLP40 | Isobutanol | 25.1 | 250 | 30 |
| SLP41 | Toluene | 24.3 | 250 | 30 |
| SLP42 | Butyl acetate | 26.4 | 250 | 30 |
| SLP43 | Hexanone, 2- | 26.1 | 250 | 30 |
| SLP44 | Chlorobenzene | 25.2 | 250 | 30 |
| SLP45 | Ethoxyethanol, 2- | 25.4 | 250 | 30 |
| SLP46 | Xylene, m- | 24.9 | 250 | 30 |
| SLP47 | Cumene | 24.5 | 250 | 30 |
| SLP48 | Anisole | 25.3 | 250 | 30 |

Vapor Diffusion Into Solutions. For the vapour diffusion experiments, saturated solutions of ponatinib hydrochloride were exposed to solvent vapours at room temperature for two weeks. A volume of saturated solution was transferred to an 8 ml vial which was left open and placed in a closed 40 ml vial with 2 ml of anti-solvent (see Table 12). After two weeks, the samples were checked for solid formation. The samples were dried under vacuum (200 mbar or 10 mbar) and resulted to have no yield. Based on the results, additional experiments were performed with 12 different crystallization conditions as described in the table, experiments ID VDL25-VDL36.

TABLE 12

Experimental Conditions for the Vapor Diffusion Into Solutions

| Experiment | Solvent of solution | Volume solution (ul) | Anti-Solvent |
|---|---|---|---|
| VDL1 | Ethyl formate | 875 | Pentane |
| VDL2 | Ethyl formate | 875 | Dichloromethane |
| VDL3 | Ethyl formate | 875 | Methyl butyl ether, tert- |
| VDL4 | Ethyl formate | 875 | Chloroform |
| VDL5 | Ethyl formate | 875 | Diisopropyl ether |
| VDL6 | Ethyl formate | 875 | Cyclohexane |
| VDL7 | Ethyl formate | 875 | Trimethylpentane, 2,2,4- |
| VDL8 | Ethyl formate | 875 | Heptane, n- |
| VDL9 | Ethyl formate | 875 | Octane, n- |
| VDL10 | Ethyl formate | 875 | Diethoxymethane |
| VDL11 | Ethyl formate | 875 | Methyltetrahydrofuran, 2- |
| VDL12 | Ethyl formate | 875 | Methylcyclohexane |
| VDL13 | Ethyl formate | 875 | Acetonitrile |
| VDL14 | Ethyl formate | 875 | Fluorobenzene |
| VDL15 | Ethyl formate | 875 | Diethyl carbonate |
| VDL16 | Ethyl formate | 875 | Dimethyl-3-butanone, 2,2- |

TABLE 12-continued

Experimental Conditions for the Vapor Diffusion Into Solutions

| Experiment | Solvent of solution | Volume solution (ul) | Anti-Solvent |
|---|---|---|---|
| VDL17 | Ethyl formate | 875 | Dimethyl-3-pentanone, 2,4- |
| VDL18 | Ethyl formate | 875 | Dichloroethane, 1,2- |
| VDL19 | Ethyl formate | 875 | Xylene, p- |
| VDL20 | Ethyl formate | 875 | Isoamyl acetate |
| VDL21 | Ethyl formate | 875 | Toluene |
| VDL22 | Ethyl formate | 875 | Ethylbenzene |
| VDL23 | Ethyl formate | 875 | Amylalcohol, tert- |
| VDL24 | Ethyl formate | 875 | Chlorobenzene |
| VDL25 | Dimethyl Sulfoxide | 500 | Water |
| VDL26 | Dimethyl Sulfoxide | 500 | Tetrahydrofuran |
| VDL27 | Dimethyl Sulfoxide | 500 | Methyltetrahydrofuran, 2- |
| VDL28 | Dimethyl Sulfoxide | 500 | Acetonitrile |
| VDL29 | Dimethylacetamide N,N- | 1000 | Water |
| VDL30 | Dimethylacetamide N,N- | 1000 | Tetrahydrofuran |
| VDL31 | Dimethylacetamide N,N- | 1000 | Methyltetrahydrofuran, 2- |
| VDL32 | Dimethylacetamide N,N- | 1000 | Acetonitrile |
| VDL33 | Methanol | 1000 | Water |
| VDL34 | Methanol | 1000 | Tetrahydrofuran |
| VDL35 | Methanol | 1000 | Methyltetrahydrofuran, 2- |
| VDL36 | Methanol | 1000 | Acetonitrile |

Vapor Diffusion Onto Solids. For the vapour diffusion experiments, amorphous ponatinib hydrochloride was exposed to solvent vapours at room temperature for two weeks. The 8 ml vials with the amorphous API were left open and placed in a closed 40 ml vial with 2 ml of anti-solvent (see Table 13). After two weeks, the solids were analyzed by XRPD and digital imaging. If the solids were liquefied by the vapours, the samples were dried under vacuum (200 mbar or 10 mbar) before they were analyzed by XRPD and digital imaging.

TABLE 13

Experimental Conditions for the Vapor Diffusion Onto Solids

| Experiment | Anti solvent | Weight (mg) |
|---|---|---|
| VDS1 | Methyl formate | 21.4 |
| VDS2 | Pentane | 23.0 |
| VDS3 | Dichloromethane | 26.4 |
| VDS4 | Methyl butyl ether, tert- | 22.7 |
| VDS5 | Chloroform | 24.3 |
| VDS6 | Methanol | 25.2 |
| VDS7 | Tetrahydrofuran | 26.1 |
| VDS8 | Diisopropyl ether | 23.1 |
| VDS9 | Trifluoroethanol, 2,2,2- | 24.5 |
| VDS10 | Hexafluorobenzene | 23.1 |
| VDS11 | Cyclohexane | 22.4 |
| VDS12 | Acetonitrile | 22.4 |
| VDS13 | Dichloroethane, 1,2- | 23.6 |
| VDS14 | Thiophene | 22.1 |
| VDS15 | Ethylene glycol dimethyl ether | 22.7 |
| VDS16 | Diethoxymethane | 20.5 |
| VDS17 | Heptane, n- | 24.9 |
| VDS18 | Trimethylpentane, 2,2,4- | 27.3 |
| VDS19 | Water | 21.7 |
| VDS20 | Methylcyclohexane | 27.5 |
| VDS21 | Nitromethane | 23.6 |
| VDS22 | Dioxane, 1,4- | 23.4 |
| VDS23 | Trifluorotoluene, alpha, alpha, alpha- | 22.4 |
| VDS24 | Dimethyl-3-butanone, 2,2- | 22.4 |
| VDS25 | Toluene | 22.6 |
| VDS26 | Nitropropane, 2- | 23.5 |
| VDS27 | Octane, n- | 26.7 |
| VDS28 | Butyl acetate | 22.9 |
| VDS29 | Dimethylcyclohexane, 1,2-(cis\trans-mixture) | 24.1 |
| VDS30 | Cyclopentanone | 24.4 |
| VDS31 | Nitropropane, 1- | 24.3 |
| VDS32 | Chlorobenzene | 22.9 |
| VDS33 | Xylene, p- | 24.0 |
| VDS34 | Fluorooctane,1- | 24.3 |
| VDS35 | Isoamyl acetate | 24.9 |
| VDS36 | Xylene, o- | 23.7 |

In the crystallization experiments during these initial efforts, XRPD analysis of the dry (and if applicable wet) samples obtained revealed the presence of seven additional polymorphic forms in addition to amorphous materials and the starting material, Form A. The seven forms are designated HCl2, HCl2b, HCl3-class, HCl5, HCL5b, HCl6-class and the mixture HCl1+HCl4.

The occurrence of the different forms obtained in Phase 2 of these initial efforts is presented in FIG. 2. XRPD patterns and digital images representative of each form obtained in these Phase 2 experiments were obtained. The characterization of the forms obtained in Phase 1 of these initial efforts is summarized in Table 14.

TABLE 14

Characterization of Certain Polymorphic Forms of ponatinib hydrochloride

| Polymorphic form | Occurrence[a] | Crystallization solvent/mode[b] | Form nature[c] | Endotherms (° C.)[d] | Purity (%)[e] |
|---|---|---|---|---|---|
| Form A: HCl1[g] | (129, 50.8%) | Various/PSM, GRP, SLP | Anhydrate | 264.1 | 99.8 |
| Form B: HCl2 | (4, 1.5%) | Water/PSM, SLP | Nd[f] | Nd | Nd |

TABLE 14-continued

Characterization of Certain Polymorphic Forms of ponatinib hydrochloride

| Polymorphic form | Occurrence[a] | Crystallization solvent/mode[b] | Form nature[c] | Endotherms (° C.)[d] | Purity (%)[e] |
|---|---|---|---|---|---|
| Form C: HCl2b | (6, 2.4) | Water/GRP | Hydrate (1:1.4) | 122.9, 158.2, 256.2 | 99.8 |
| Form D: HCl3-Class | (9, 3.5%) | Toluene/PSM, GRP | Nd | Nd | Nd |
| Form F: HCl5 | (1, 0.4%) | Butyl acetate/VDS | Nd | Nd | Nd |
| Form G: HCl5b | (1, 0.4%) | Butyl acetate/VDS + drying | Nd | Nd | Nd |
| Form H: HCl6-Class | (5, 2.0%) | Methanol/VDS | Nd | Nd | Nd |
| Form E: HCl1 + HCl4 | (1, 0.4%) | Hexafluorobenzene/GRP | Nd | Nd | Nd |

[a]Occ: the total occurrence included 216 experiments carried out in Phase 2 for which 39 samples were analyzed additionally wet or the mother liquor was evaporated and analyzed giving a total of 254 materials characterized. For example, "(3, 1.2%)" correspond to 3 occurrences of the form out of 254 measurements, giving a percentage of 1.2%. For 62 out of the 254 measurements (9%), the product yield or the scattering intensity of some products was too low to identify the solid form, or the materials were wet.
[b]Crystallization modes: cooling-evaporative (PSM), crash crystallization with anti-solvent addition (AS), grinding (GRP), slurry (SLP), vapour diffusion onto solid (VDS) and vapour diffusion into solution (VDL). Freeze-drying (FD) was used to produce amorphous material (see Phase 1 experiments). QSA (quantitative solubility experiment), see Phase 1 experiments.
[c]Solvation state assessed from the TGMS results.
[d]Endotherms assessed from the DSC results.
[e]Chemical purity assessed from HPLC results.
[f]Not determined in this experiment.
[g]Structure determined by single crystal analysis.

The polymorphic forms identified in these Phase 1 and Phase 2 experiments and shown in FIG. 2 were assigned primarily on XRPD analysis. In the course of this analysis, it was observed that some patterns had similarities in the general fingerprint of the XRPD pattern but showed some small differences like peaks shifting or smaller additional peaks. These types of patterns were clustered as a class of patterns (e.g. HCl3-Class). Based on the XRPD, it was concluded that the similarity between the XRPD patterns within a class is explained by the fact that these solid forms are isomorphic hydrates/solvates (similar crystal packing but slightly different unit cell parameters caused by the incorporation of the different solvents and water in the crystal structure).

The classes of isomorphic solvates were designated by a number (HCl3-Class) or a number-letter combination (for example HCl2 and HCl2b). The class of isomorphic solvates/hydrates designated by a letter-number combination indicates that few sub-classes were observed for this class in the experiment (example HCl2 and HCl2b). When more than three sub-classes could be identified within the class, all XRPD patterns corresponding to a class of isomorphic solvates/hydrates were regrouped under one number (example HCl3-Class).

The isomorphic solvates within a certain class or between classes designated with the same number showed a higher degree of similarity of their XRPD patterns than in the case of the classes of isomorphic solvates designated with different numbers. For these different classes of isomorphic hydrates/solvates, the larger differences in the XRPD patterns reflect that the crystal structure packing is significantly different.

In some XRPD patterns, one or two additional peaks were observed compared to the identified forms. Since these peaks could not be assigned clearly to the known forms, they were indicated as "plus peaks".

Example 2

Further Discovery of Polymorphic Forms

Follow on efforts were undertaken to analyze single crystals of 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride. Such efforts led to the discovery of five different pseudo polymorphs with two of these additional polymorphic forms being previously undiscovered. These two newly discovered polymorphic forms are designated herein as HCl7 (also referred to herein as "Form J") and HCl 8 (also referred to herein as "Form K"). In these later experiments, three different crystallization techniques were used to grow single crystals of suitable size for analysis: (1) slow evaporation of crystallization solvent; (2θ) diffusion of anti-solvent into a solution of 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride; and (3) temperature controlled crystallization. In total, 54 crystallization experiments were performed in these later experiments to attempt to grow single crystals of the hydrated form of ponatinib hydrochloride salt for structure determination.

With regard to temperature controlled crystallization, 24 experiments were prepared with mixtures of alcohols and water (see Table 15). For each experiment, 10 mg of ponatinib hydrochloride was used. The mixtures of API and solvents were heated fast up to 80° C. and slowly

TABLE 15

Experimental Conditions of the Temperature Controlled Crystallization Experimentals

| Exp | Alcohol [µl] | Water [µl] | Water/Alcohol | Outcome |
|---|---|---|---|---|
| 1 | MeOH (100) | 900 | 9/1 | White powder (trihydrate) |
| 2 | MeOH (200) | 800 | 8/2 | White powder (trihydrate) |
| 3 | MeOH (300) | 700 | 7/3 | White powder (trihydrate) |

TABLE 15-continued

Experimental Conditions of the Temperature Controlled Crystallization Experimentals

| Exp | Alcohol [µl] | Water [µl] | Water/Alcohol | Outcome |
|---|---|---|---|---|
| 4 | MeOH (400) | 600 | 6/4 | White powder (trihydrate) |
| 5 | MeOH (500) | 500 | 5/5 | White powder/yellow oil |
| 6 | MeOH (600) | 400 | 4/6 | White powder/yellow oil |
| 7 | MeOH (700) | 300 | 3/7 | White powder/yellow oil |
| 8 | MeOH (800) | 200 | 2/8 | Oil/very small yellow crystals |
| 9 | MeOH (900) | 100 | 1/9 | Oil/very small yellow crystals |
| 10 | EtOH (100) | 900 | 9/1 | White powder (trihydrate) |
| 11 | EtOH (200) | 800 | 8/2 | White powder (trihydrate) |
| 12 | EtOH (300) | 700 | 7/3 | White powder (trihydrate) |
| 13 | EtOH (400) | 600 | 6/4 | White powder (trihydrate) |
| 14 | EtOH (500) | 500 | 5/5 | White powder/yellow oil |
| 15 | EtOH (600) | 400 | 4/6 | White powder/yellow oil |
| 16 | EtOH (700) | 300 | 3/7 | White powder/yellow oil |
| 17 | EtOH (800) | 200 | 2/8 | Oil/very small yellow crystals |
| 18 | EtOH (900) | 100 | 1/9 | Small yellow crystals |
| 19 | TFE (100) | 900 | 9/1 | White powder/yellow oil |
| 20 | TFE (200) | 800 | 8/2 | White powder/yellow oil |
| 21 | TFE (300) | 700 | 7/3 | Yellow oil |
| 22 | TFE (400) | 600 | 6/4 | Yellow oil |
| 23 | TFE (500) | 500 | 5/5 | Oil/very small yellow crystals |
| 24 | TFE (600) | 400 | 4/6 | Oil/very small yellow crystals |

With regard to vapor diffusion into solution, 25 experiments were performed. For each experiment, 10 mg of ponatinib hydrochloride was dissolved in 1 ml of mixture of TFE/Water (10:90) or MeOH/Water (30:70). Each solution was placed in a 6 ml vial, which was inserted in a 20 ml vial containing 3 ml of anti-solvent. The vials were kept at room temperature for 2-4 weeks. The details are reported in Table 16.

TABLE 16

Experimental Conditions of the Vapor Diffusion Experiments

| Exp | Solvent | Anti-solvent | Outcome |
|---|---|---|---|
| 25 | TFE/H$_2$O | Ethyl Acetate | No crystals |
| 26 | TFE/H$_2$O | n-Heptane | No crystals |
| 27 | TFE/H$_2$O | 2-Butanol | No crystals |
| 28 | TFE/H$_2$O | MEK | No crystals |
| 29 | TFE/H$_2$O | o-Xylene | White powder |
| 30 | TFE/H$_2$O | THF | No crystals |
| 31 | TFE/H$_2$O | Toluene | Oil |
| 32 | TFE/H$_2$O | Cyclohexane | Oil |
| 33 | TFE/H$_2$O | 1,4-Dioxan | No crystals |
| 34 | TFE/H$_2$O | 2-MeTHF | Oil |
| 35 | TFE/H$_2$O | Cyclohexanone | Oil |
| 36 | TFE/H$_2$O | Acetonitryle | No crystals |
| 37 | MeOH/H$_2$O | Propionitryle | Oil |
| 38 | MeOH/H$_2$O | Toluene | Light yellow crystals |
| 39 | MeOH/H$_2$O | 1,4-Dioxan | No crystals |
| 40 | MeOH/H$_2$O | Diethylether | Oil |
| 41 | MeOH/H$_2$O | n-Heptane | Oil |
| 42 | MeOH/H$_2$O | o-Xylene | Light yellow crystals |
| 43 | MeOH/H$_2$O | THF | No crystals |
| 44 | MeOH/H$_2$O | Acetone | No crystals |
| 45 | MeOH/H$_2$O | Cyclohexane | Oil |
| 46 | MeOH/H$_2$O | Butyl Acetate | Light yellow needle crystals |
| 47 | MeOH/H$_2$O | i-Propyl Acetate | Light yellow needle crystals |
| 48 | MeOH/H$_2$O | 2-Pentanol | Cream plate crystals |
| 54 | Ethanol | Ethylacetate | Yellow crystals |

With regard to slow evaporation of solvents, 10 mg of ponatinib hydrochloride was placed in an 8 ml vial and 2 ml of solvent (mixture of solvents) was added. In those cases in which the solids did not dissolve, the vial was heated to 90° C. Subsequently, the mixture was left to cool slowly to room temperature (see Table 17). For the last entry in Table 17, Exp. 53, the material had not completely dissolved after having been held several hours at 90° C.

TABLE 17

Experimental conditions of the slow evaporation experiments

| Exp | Solvents (ratio) | Temperature [° C.] | Outcome |
|---|---|---|---|
| 49 | TFE/H$_2$O (50:50) | RT | Yellow crystals |
| 50 | EtOH/H$_2$O (70:30) | 60 | Yellow oil/small crystals |
| 51 | MeOH/H$_2$O (70:30) | 60 | Yellow oil/small crystals |
| 52 | i-PrOH/H$_2$O (70:30) | 60 | Yellow oil/small crystals |
| 53 | H$_2$O | 90 | White powder |

Each of the polymorphic forms disclosed herein are made from specific crystallization/solvent modes using ponatinib HCl as the starting material. While the synthesis of ponatinib HCl has been described previously (e.g., WO 2007/075869 and WO 2011/053938), the following synthesis of ponatinib HCl is provided at Example 6.

Example 3

Stress Test of Ponatinib Hydrochloride Form A

Form A is a crystalline, anhydrous solid that has been reproducibly obtained from a range of solvents. Form HCl-1 is intrinsically chemically stable, which directly correlates to the thermodynamic stability of the HCl 1 form. Form HCl-1 is stable to thermal, pressure, and humidity stress as well as exposure to some solvent vapors, and is thermodynamically stable. Numerous studies have been conducted to confirm its stability in both the formulated (tablets) and unformulated (drug substance) state. The results of such studies are provided in Table 18 below:

TABLE 18

Stress Studies on Ponatinib Hydrochloride Form A

| Sample | Stress Type | Stress Conditions | Analytical | Results |
|---|---|---|---|---|
| Drug Substance | Thermal | 70° C. for up to 72 hours | TGMS, HPLC and XRPD | No change in form approximately 0.1% mass loss due to ethanol evaporation No apparent degradation |
| | | 220° C. for 5 minutes | TGMS, HPLC and XRPD | No change in form approximately 1% mass loss due to ethanol evaporation No apparent degradation |
| | Humidity | DVS cycling (0-95-0% RH followed by 0-45% RH) | DVS, XRPD, and TGMS | No change in form No change in DVS isotherm Slight reduction in ethanol content by TGMS |
| | | Exposure to humidity (0%, 22%, 40%, 75% and 97% RH) for 6 days | XRPD, TG and DSC | No change in form |
| | Solvent vapors | Ethanol vapors at ambient temperature for 2 weeks | XRPD digital photographs | Form HCl-1 remained and unchanged in samples of 100% Form HCl-1 and 50:50 mixture of HCl-1/amorphous ponatinib HCl |
| | Pressure | Tablet press (drug substance only): 4 ton (50 kN/cm$^2$) and 8 ton (100 kN/cm$^2$) | XRPD and digital photographs | No changes observed in ponatinib HCl for the pressed drug-only tablets |

Form HCl-1 is stable to thermal, pressure, and humidity stress as well as exposure to some solvent vapors, and is the most thermodynamically stable solid form isolated to date.

Experiments were carried out to test the physical stability of the crystalline Form HCl1 as follows:

The crystalline Form HCl1 and a physical mixture of HCl1 and amorphous material 50:50 were exposed to ethanol vapour for two weeks (see vapour diffusion experiments). Tablets were prepared by subjecting the crystalline Form HCl1 to a pressure of 50 and 100 kN/cm$^2$ (or 4 and 8 ton/cm$^2$) for 10 sec. Form A was stored in capsules for up to 17 months at ambient conditions. These samples were analyzed by high resolution XRPD.

The results obtained are summarized in Table 19 and the XRPD measurements and digital images were obtained. They showed that within the stress conditions applied, the polymorphic Form HCl1 remained unchanged, confirming its good physical stability.

Example 4

Stability of Certain Polymorphic Forms

Samples of the 8 solid forms of HCl salt were chosen to study their physical stability. Two samples representative of each relevant polymorphic forms of the HCl salt obtained were selected. Each sample was re-analyzed by XRPD. The physical stability of the forms after being stored at ambient conditions for 8 months. The results are summarized below:

HCl1, HCl2b, HCl3-Class, HCl5b and HCl6-Class are physically stable under the investigated conditions;

HCl2 converted to HCl2b (this conversion already occurred after storage of the sample under ambient conditions for 1 day);

HCl5 converted to HCl5b (this conversion already occurred following drying for 3 days under full vacuum);

The mixture HCl1+HCl4 converted to HCl1 after 8 months at ambient conditions.

TABLE 19

Results of follow-up work on Form A

| Experiment | Stress condition | XRPD (Form) |
|---|---|---|
| VDS37 | Vapour diffusion (starting material HCl1), 2 ml Ethanol | HCl1 |
| VDS38 | Vapour diffusion (starting material HCl1 and Am), 2 ml Ethanol | HCl1 |
| GEN12.1 | 10 sec, 50 kN | HCl1 |
| GEN12.2 | 10 sec, 50 kN, crushed tablet | HCl1 |
| GEN12.3 | 10 ses, 100 kN | HCl1 |
| GEN12.4 | 10 ses, 100 kN, crushed tablet | HCl1 |
| Capsule 2 mg sample 1 | Ambient conditions for 17 months | HCl1 |
| Capsule 2 mg sample 2 | Ambient conditions for 17 months | HCl1 |
| Capsule 2 mg sample 3 | Ambient conditions for 17 months | HCl1 |

TABLE 20

Physical stability of forms of HCl salt

| Starting form[a] | Polymorphic form obtained[b] | Crystallization solvent/mode[c] | Form nature[d] | Form after storage under ambient conditions for 8 months |
|---|---|---|---|---|
| SM | HCl1 | — | Anhydrate | HCl1 |
| HCl1 or Am | HCl2 | Water/AS, PSM, SLP | Nd[e] | HCl2b[f] |
| HCl1 or Am | HCl2b | Water/AS, GRP, QSA | Hydrate (1:1.4) | HCl2b |
| HCl1 or Am | HCl3-Class | aromatics/PSM, GRP, VDS | Nd | HCl3-Class |
| Am | HCl5 | Butyl acetate/VDS | Nd | HCl5b[f] |
| Am | HCl5b | Butyl acetate/VDS + drying | Nd | HCl5b |
| Am | HCl6-Class | Methanol/VDS, VDL | Nd | HCl6-Class |
| HCl1 | HCl1 + HCl4 | Hexafluorobenzene/GRP | Nd | HCl1 |

[a]Starting material (SM): Form HCl1 or amorphous material (Am) obtained by freeze-drying.
[b]As classified by XRPD after completion of the crystallization experiment.
[c]Crystallization modes: cooling-evaporative (PSM), crash crystallization with anti-solvent addition (AS), grinding (GRP), slurry (SLP), vapour diffusion onto solid (VDS) and vapour diffusion into solution (VDL). QSA (quantitative solubility experiment).
[d]Solvation state assessed from the TGMS results.
[e]Nd = not determined.
[f]HCl2 and HCl5 converted to HCl2b and HCl5b after respectively storage at room temperature for a 1 day or drying under vacuum for 3 days.

Example 5

Preparation of Form A

Form A of ponatinib HCl is formed as a crystalline material by addition of a solution of HCl (1.0 equivalents) in ethanol to an ethanolic solution of the ponatinib free base. The drug substance, ponatinib HCl, is crystallized in the last step of the drug substance synthetic process by addition of seed crystals which results in a very consistent and characteristic particle size and range for the drug substance. Ethanol content in the last 10 multi-kilogram scale batches of ponatinib HCl in the HCl-1 form ranged from 0.8-1.2%.

No evidence of ethanol or water was found in the HCl-1 form; hence the Form A is an anhydrate. In addition, the crystal packing of the HCl-1 form does not contain voids capable of accommodating ethanol or other small organic molecules. Additional studies to investigate the ethanol content and the removal of ethanol from ponatinib HCl during drying have indicated that the ethanol appears to be associated with the surface of the crystals in Form A of ponatinib HCl.

Form HCl-1 is characterized by the consistent presence of residual ethanol in all batches of drug substance at a level of approximately 1% by weight. Crystallographic studies and other studies have shown that residual ethanol is present (trapped) on the surface of the crystals, and is not part of the crystalline unit cell, and that HCl-1 is not an ethanol solvate or channel solvate. Ethanol levels in the last ten multi-kilogram scale drug substance batches have ranged from 0.8 to 1.2%.

II. Polymorphic Forms of Ponatinib Free Base

The preparation of ponatinib free base starting material (AP23534) is shown and discussed below in the synthesis section of the disclosure (see Scheme 1). Preparation of amorphous free base is discussed in the section of the disclosure entitled "*Feasibility Study on Ponatinib Free Base Compound*" set out herein below.

Through XRPD analysis, a total of eleven polymorphic forms of ponatinib were discovered, including anhydrate, and hydrate, solvate and isomorphic hydrate/solvate forms, beginning from ponatinib free base starting material. The eleven new polymorphic forms are referred to herein as: Form A, Form B (or B-Class forms), Form C, Form D, Form E (or E-Class), Form F, Form G, Form H (or H-Class forms), Form I, Form J and Form K.

The anhydrate Form A (melting point ~200° C.) was the predominant crystalline form found in the screening. Form B includes four isomorphic solvates, namely a 1:1 dioxane solvate, a 1:1 perfluorobenzene solvate, a 1:0.4 2-methyl-THF solvate, and a 1:1 cyclohexanone solvate. Form E includes chloroform and dichloromethane isomorphic solvates. Form D is a solvated form (e.g. DMA). Form F is a monohydrated form. Form H includes two isomorphic solvates, a 1:0.6 1-propanol solvate and a 1:0.93 2-methoxyethanol solvate.

The assignment of the forms obtained in the Phase 3 and Phase 4 experiments was primarily based on the XRPD analysis. From this, it could be observed that some patterns had similarities in the general fingerprint of the XRPD pattern but showed some small differences such as peaks shifting and/or small additional peaks. These types of patterns were clustered as a class of patterns (e.g. B-Class). Based on the XRPD, similarity between the XRPD patterns within a class can indicate that these solid forms are isomorphic hydrates/solvates (similar crystal packing but slightly different unit cell parameters caused by the incorporation of the different solvents and water in the crystal structure). The classes of isomorphic solvates were designated by a letter (B-Class).

In some XRPD patterns, one or more additional peaks were observed compared to various identified forms. Since these peaks could not always be assigned clearly to the known forms, they were indicated as "plus peaks" where appropriate, (e.g. "Form F plus peaks").

The polymorph screen for ponatinib comprised six types of crystallization methods, carried out on milliliter scale. The methods included: crash-crystallization with anti-solvent addition; grinding; slurry experiments; vapor diffusion into solution; cooling-evaporative crystallization; and vapor diffusion onto solids. These methods were discussed above for preparation of the various ponatinib hydrochloride polymorphs. Any differences in the methods when applied to the ponatinib free base polymorphs will be discussed below.

The crystal structures of Form A and the two Form B solvates were determined by single crystal X-ray data analysis. These studies showed the conformation adopted by Form A in the crystal structure and the solvent inclusion in the two Form B solvates.

In general, these various crystalline forms of ponatinib disclosed herein have physical properties (such as high stability, etc.) that are advantageous for the commercial preparation of solid dosage forms as compared to amorphous ponatinib. The distinction between crystalline ponatinib and amorphous ponatinib can be readily seen with the same type of physical chemical data (e.g., DSC, XRPD, thermal analysis) that is used to distinguish the individual crystalline forms of ponatinib disclosed herein.

FIGS. 48 and 49 provide tabular summaries are provided for ten of the eleven solid forms of ponatinib that include polymorphs and pseudo-polymorphs identified as Forms A through J disclosed herein. (Form K will be discussed separated herein below and is not part of this tabular summary). FIGS. 48 and 49 collectively provide origin, occurrence, and various characteristics of the ponatinib polymorphs.

With reference to FIG. 48, "LC" refers to a low crystalline ponatinib (e.g. Form C) used as the starting material for various other polymorphs. "A" refers to Form A, the most abundant crystalline form of ponatinib, which can be used to prepare other forms via the various crystallization modes mentioned above. The footnotes appearing in the table of FIG. 48 are as follows:
 (a) As classified by XRPD after completion of the crystallization experiments;
 (b) Crystallization modes: cooling-evaporative (PSM), crash crystallization with anti-solvent addition (AS), grinding (GRP), slurry (SLP), vapour diffusion onto solid (VDS) and vapour diffusion into solution (VDL). Freeze-drying (FD) was used to produce low crystalline material (see Phase 3 experiments). QSA: Quantitative Solubility Experiments (Phase 3);
 (c) Occ: the total occurrence included 192 experiments carried out in Phase 4 for which 61 samples were analyzed additionally wet or the mother liquor was evaporated and analyzed giving a total of 253 materials characterized. For example, "(6, 2.4%)" correspond to 6 occurrences of the form out of 253 measurements, giving a percentage of 2.4%. For 4 out of the 253 measurements (1.6%), the product yield or the scattering intensity of some products was too low to identify the solid form, or the materials were wet;
 (d) PO: preferred orientation effect; and
 (e) Starting material: Form A or low crystalline (LC) material obtained by freeze-drying.

With reference to the foregoing methodologies used in assessing the ponatinib hydrochloride polymorphs, the polymorphs of 3-(imidazo[1,2-b]pyridazin-3-ylethynyl)-4-methyl-N-{4-[(4-methyl piperazin-1-yl)methyl]-3-(trifluoromethyl)phenyl}benzamide free base are discussed below. Characteristics of Ponatinib Form A The anhydrate Form A (same crystalline form as the starting material) was the predominant crystalline form discovered in screening. The chemical structure of ponatinib Form A has been unambiguously established by single crystal X-ray crystallography. The observed solid form of ponatinib is the anhydrous crystalline solid Form A.

FIG. 50 represents the molecular structure and numbering scheme of Form A ponatinib free base compound (anhydrate) obtained from single-crystal X-ray diffraction. Based on this structure analysis, it was determined that Form A is an anhydrated form.

The crystallographic data for the anhydrate Form A (collected up to θ=26°) are listed in Table 21.

TABLE 21

Crystal Data and Structure Refinement for Ponatinib Form A

| Identification code | S10010A_AS37 |
|---|---|
| Empirical formula | $C_{29}H_{27}F_3N_6O$ |
| Formula weight | 532.57 |
| T[K] | 298(2) |
| λ [Å] | 0.71073 |
| Crystal system | Triclinic |
| Space group | P-1 |
| Unit cell dimensions | |
| a [Å] | 9.182(2) |
| b [Å] | 10.187(2) |
| c [Å] | 14.871(5) |
| α [°] | 95.746(6) |
| β [°] | 99.546(7) |
| γ [°] | 92.391(5) |
| V [Å$^3$] | 1362.4(6) |
| Z | 2 |
| $D_c$[g/cm$^3$] | 1.298 |
| μ [mm$^{-1}$] | 0.096 |
| F(000) | 556 |
| Crystal size [mm$^3$] | 0.43 × 0.25 × 0.20 |
| θ range for data collection [°] | 2.3 → 26 |
| Reflections collected | 8369 |
| Independent reflections | 5340 [$R_{int}$ = 0.0253] |
| Completeness to θ = 26° [%] | 99.6 |
| Max. and min. transmission | 0.9810 and 0.9598 |
| Data/restraints/parameters | 5340/0/357 |
| Goodness-of-fit on F$^2$ | 1.023 |
| Final R indices [I > 2σ(I)] | R1 = 0.0583, wR2 = 0.1371 |
| R indices (all data) | R1 = 0.0932, wR2 = 0.1612 |
| Extinction coefficient | 0.044(5) |

FIG. 51 presents a comparison of the experimental XRPD pattern with the calculated pattern (with FWHM=0.1°) based on the crystal structure determined for Form A. The close similarity of the two XRPD patterns indicates that the crystal structure of Form A is representative for the bulk material.

In the XRPD patterns shown in FIG. 51, at least one or all of the following peaks in degrees two theta (2θ) is shown for crystalline Form A: 6.2; 8.8; 9.9; 11.2; 12.3; 12.9; 13.5; 13.8; 14.2; 14.4; 16.0; 16.4; 17.2; 17.6; 18.0; 18.2; 19.3; 19.5; 19.8; 20.6; 21.5; 21.9; 22.2; 22.6; 23.1; 24.0; 24.4; 25.1; 25.6; 25.9; 26.8; 27.4; 27.8; 29.1; and 29.8. In certain embodiments, Form A is characterized by a XRPD pattern comprising one or more of the following peaks two theta (2θ): 6.2; 12.3; 13.8; 14.4; 16.0; 16.4; 17.2; 17.6; 18.2; 19.5; 19.8; 20.6; 21.5; 22.2; 24.0; 25.9; 26.8; 27.4; and 27.8. In the XRPD patterns shown in FIG. 51, at least one or all of the following peaks in degrees two theta (2θ) is shown for Form A: 12.3; 13.8; 14.4; 17.6; 19.8; 20.6; 21.5; 22.6; and 24.0. In certain embodiments, Form A is characterized by a XRPD pattern comprising one or more of the following peaks two theta (2θ): 12.3; 13.8; 17.6; 19.8; 20.6; 21.5; 22.6; and 24.0. In certain embodiments, the XRPD pattern of Form A shows two peaks, three peaks, four peaks or five peaks selected from those above. In certain embodiments, the crystalline Form A of ponatinib free base is characterized by an XRPD pattern substantially similar to the upper XRPD pattern (obtained) in FIG. 51. In certain embodiments, the crystalline Form A comprises an XRPD pattern with characteristic peaks expressed in degrees two-theta as shown in either the lower (simulated) or upper (obtained) pattern in FIG. 51.

With reference to FIG. 52, the melting point of ponatinib in the anhydrate Form A was determined by differential scanning calorimetry (DSC). Two samples of ponatinib, AP24534 Lot 1285.206A (treated with 1-PrOH) and AP24524 Lot 1-PrOH Not Treated, were analyzed in a pin-holed crucible in the temperature range of 30° C. to 350° C. at a heating rate of 10° C. per minute using dry $N_2$ gas purge. An endothermic event with a peak of 199.6° C. was observed, corresponding to the melting point of ponatinib Form A.

Characteristics of Ponatinib Form B (B-Class) Polymorphs

Characteristics of Ponatinib/1,4-Dioxane 1:1 Solvated Form B

Single-crystal X-ray diffraction analysis was employed to determine the crystal structure of the 1:1 1,4-dioxane solvated Form B. FIG. 53 represents the molecular structure and numbering scheme of the 1:1 1,4-dioxane solvated Form B obtained from single-crystal X-ray diffraction.

The crystallographic data for the 1:1 1,4-dioxane solvated Form B (collected up to e=27.4°) are listed in Table 22.

TABLE 22

Crystal Data and Structure Refinement for Ponatinib/1,4-dioxane 1:1 solvated Form B

| Identification code | S10010A_PSM32 |
| --- | --- |
| Empirical formula | $C_{29}H_{27}F_3N_6O \cdot C_4H_8O_2$ |
| Formula weight | 620.67 |
| T [K] | 298(2) |
| λ [Å] | 0.71073 |
| Crystal system | Triclinic |
| Space group | P-1 |
| Unit cell dimensions | |
| a [Å] | 8.311(2) |
| b [Å] | 12.691(4) |
| c [Å] | 15.779(6) |
| α [°] | 81.015(8) |
| β [°] | 88.388(8) |
| γ [°] | 82.209(7) |
| V [Å³] | 1628.7(9) |
| Z | 2 |
| $D_c$ [g/cm³] | 1.266 |
| A [mm⁻¹] | 0.095 |
| F(000) | 652 |
| Crystal size [mm³] | 0.40 × 0.36 × 0.10 |
| θ range for data collection [°] | 3 → 27.4 |
| Reflections collected | 11721 |
| Independent reflections | 7312 [$R_{int}$ = 0.0330] |
| Completeness to θ = 27.4° [%] | 99.0% |
| Max. and min. transmission | 0.9906 and 0.9631 |
| Data/restraints/parameters | 7312/6/411 |
| Goodness-of-fit on $F^2$ | 1.032 |
| Final R indices [I > 2σ(I)] | R1 = 0.0945, wR2 = 0.2337 |
| R indices (all data) | R1 = 0.1580, wR2 = 0.2815 |
| Extinction coefficient | 0.023(5) |

FIG. 54 presents the calculated pattern based on the crystal structure determined for Ponatinib/1,4-dioxane 1:1 solvated Form B.

In the XRPD pattern shown in FIG. 54, at least one or all of the following peaks in degrees two theta (2θ) is shown for Ponatinib/1,4-dioxane 1:1 solvated Form B: 5.6; 7.2; 9.8; 10.8; 12.1; 12.5; 12.8; 14.5; 15.3; 15.8; 17.0; 17.3; 17.5; 18.5; 19.0; 19.5; 20.0; 20.3; 21.1; 21.6; 22.4; 22.8; 23.5; 24.1; 24.5; 25.3; 26.0; 26.4; 27.0; 27.5; 28.4; 30.8; and 32.0. In certain embodiments, Ponatinib/1,4-dioxane 1:1 solvated Form B is characterized by a XRPD pattern comprising one or more of the following peaks two theta (2θ): 5.6; 10.8; 12.1; 14.5; 15.3; 15.8; 17.0; 17.3; 18.5; 19.0; 20.0; 20.3; 21.6; 22.4; 24.5; and 26.0. In the XRPD pattern shown in FIG. 54, at least one or all of the following peaks in degrees two theta (2θ) is shown for Ponatinib/1,4-dioxane 1:1 solvated Form B: 5.6; 12.1; 14.5; 15.3; 15.8; 17.3; 18.5; 19.0; 20.3; 21.6; and 26.0. In certain embodiments, Ponatinib/1,4-dioxane 1:1 solvated Form B is characterized by a XRPD pattern comprising one or more of the following peaks two theta (2θ): 5.6; 14.5; 15.3; 15.8; 19.0; 20.3; and 26.0. In certain embodiments, the XRPD pattern of Ponatinib/1,4-dioxane 1:1 solvated Form B shows two peaks, three peaks, four peaks or five peaks selected from those given above. In certain embodiments, the Ponatinib/1,4-dioxane 1:1 solvated Form B is characterized by an XRPD pattern substantially similar to the XRPD pattern in FIG. 54. In certain embodiments, the Ponatinib/1,4-dioxane 1:1 solvated Form B is crystalline.

Characteristics of Ponatinib/Perfluorobenzene 1:1 Solvated Form B

Single-crystal X-ray diffraction analysis was employed to determine the crystal structure of the 1:1 perfluorobenzene solvated Form B. FIG. 55 represents the molecular structure and numbering scheme of the 11:1 perfluorobenzene solvated Form B obtained from single-crystal X-ray diffraction. The similarities between the unit cells and the crystal packing of the 1,4-dioxane solvate and fluorobenzene solvate confirmed that the Form B-class materials are isomorphic solvates.

The crystallographic data for the 1:1 perfluorobenzene solvated Form B (collected up to θ=27.6°) are listed in Table 23.

TABLE 23

Crystal Data and Structure Refinement for Ponatinib/perfluorobenzene 1:1 solvated Form.

| Identification code | S10010A_VDL6 |
| --- | --- |
| Empirical formula | $C_{29}H_{27}F_3N_6O \cdot C_6H_5F$ |
| Fw | 628.67 |
| T [K] | 298(2) |
| λ [Å] | 0.71073 [Å] |
| Crystal system | Triclinic |
| Space group | P-1 |
| Unit cell dimensions | |
| a [Å] | 8.182(3) |
| b [Å] | 12.863(4) |
| c [Å] | 15.877(6) |
| α [°] | 80.412(13) |
| β [°] | 88.093(14) |
| γ [°] | 81.688(11) |
| V [Å³] | 1630.3(10) |
| Z | 2 |
| $D_c$ [g/cm³] | 1.281 |
| μ [mm⁻¹] | 0.096 |
| F(000) | 656 |
| Crystal size [mm³] | 0.45 × 0.25 × 0.20 |
| θ range for data collection [°] | 3 → 27.6 |
| Reflections collected | 10370 |
| Independent reflections | 7321 [$R_{int}$ = 0.0315] |
| Completeness to θ = 27.6° [%] | 96.9 |
| Max. and min. transmission | 0.9811 and 0.9583 |
| Data / restraints / parameters | 7321 / 0 / 381 |
| Goodness-of-fit on $F^2$ | 1.052 |
| Final R indices [I > 2σ(I)] | R1 = 0.0885, wR2 = 0.2377 |
| R indices (all data) | R1 = 0.1181, wR2 = 0.2691 |
| Extinction coefficient | 0.127(16) |

FIG. 56 shows a comparison of the experimental XRPD pattern with the calculated pattern (with FWHM=0.1) based on the crystal structure determined for Form B1:1 perfluorobenzene solvate. The close similarity of the two XRPD patterns indicates that the crystal structure of Form B1:1 perfluorobenzene is representative for the bulk material.

In the XRPD patterns shown in FIG. 56, at least one or all of the following peaks in degrees two theta (2θ) is shown for Form B1:1 ponatinib/perfluorobenzene solvate: 7.0; 8.2; 9.8;

11.0; 11.5; 12.4; 12.8; 124.0; 14.4; 15.3; 16.0; 16.6; 17.2; 18.2; 19.0; 19.5; 20.0; 20.1; 21.1; 22.0; 22.5; 22.7; 23.5; 24.0; 24.5; 25.1; 26.0; 27.0; 27.8; 28.2; 31.8; and 35.4. In certain embodiments, Form B1:1 ponatinib/perfluorobenzene solvate is characterized by a XRPD pattern comprising one or more of the following peaks two theta (2θ): 5.6; 11.0; 12.4; 12.8; 14.4; 15.3; 16.0; 16.6; 17.2; 18.2; 19.0; 20.1; 22.0; 22.5; 22.7; 23.5; 24.5; 26.0; and 28.2. In the XRPD pattern shown in FIG. 56, at least one or all of the following peaks in degrees two theta (2θ) is shown for Form B 1:1 ponatinib/perfluorobenzene solvate: 5.6; 12.4; 15.3; 16.0; 19.0; 20.1; 22.0; 22.5; 22.7; and 26.0. In certain embodiments, Form B1:1 ponatinib/perfluorobenzene solvate is characterized by a XRPD pattern comprising one or more of the following peaks two theta (2θ): 5.6; 12.4; 15.3; 22.0; and 26.0. In certain embodiments, the XRPD pattern of Form B 1:1 ponatinib/perfluorobenzene solvate shows two peaks, three peaks, four peaks or five peaks. In certain embodiments, the Form B1:1 ponatinib/perfluorobenzene solvate is characterized by an XRPD pattern substantially similar to the upper XRPD pattern in FIG. 56. In certain embodiments, the Form B1:1 ponatinib/perfluorobenzene solvate is characterized by an XRPD pattern substantially similar to the lower XRPD pattern in FIG. 56. In certain embodiments, the crystalline Form B comprises an x-ray powder diffraction pattern with characteristic peaks expressed in degrees two-theta as shown in either the upper or lower pattern in FIG. 56.

Characteristics of Ponatinib/Cyclohexanone 1:1 Solvated Form B and Ponatinib/2-methylTHF 1:0.4 Solvated Form B.

FIG. 57 shows a comparison of XRPD patterns of two other B-Class forms to the XRPD pattern obtained for Form A. The top pattern was obtained for GEN8.1, which is a 1:0.4 ponatinib/2-methylTHF solvate (B-Class, freeze drying, solvent=2-methylTHF). The middle pattern was obtained for QSA7.1, which is a 1:1 ponatinib/cyclohexanone solvate (B-Class, solvent=cyclohexanone). The bottom pattern is that obtained for anhydrate Form A.

In the upper XRPD pattern shown in FIG. 57, at least one or all of the following peaks in degrees two theta (2θ) is shown for Form B 1:0.4 ponatinib/2-methylTHF solvate: 5.6; 9.5; 10.5; 11.2; 12.0; 12.5; 13.5; 14.0; 15.0; 15.5; 16.2; 16.8; 17.0; 18.1; 18.8; 20.1; 21.2; 22.1; 26.0; 26.1; 27.5; and 28.2. In certain embodiments, Form B 1:0.4 ponatinib/2-methylTHF solvate is characterized by a XRPD pattern comprising one or more of the following peaks two theta (2θ): 5.6; 12.0; 14.0; 15.0; 15.5; 16.8; 18.1; 20.1; and 26.0. In the upper XRPD pattern shown in FIG. 57, at least one or all of the following peaks in degrees two theta (2θ) is shown for Form B 1:0.4 ponatinib/2-methylTHF solvate: 5.6; 12.0; 14.0; 20.1; 22.1 and 26.0. In certain embodiments, Form B 1:0.4 ponatinib/2-methylTHF solvate is characterized by a XRPD pattern comprising one or more of the following peaks two theta (2θ): 5.6; 14.0; 20.1; and 26.0. In certain embodiments, the XRPD pattern of Form B 1:0.4 ponatinib/2-methylTHF solvate shows two peaks, three peaks, four peaks or five peaks selected from those given above. In certain embodiments, the Form B 1:0.4 ponatinib/2-methylTHF solvate is characterized by an XRPD pattern substantially similar to the upper XRPD pattern in FIG. 57. In certain embodiments, the crystalline Form B comprises an x-ray powder diffraction pattern with characteristic peaks expressed in degrees two-theta as shown in the upper pattern in FIG. 57.

In the middle XRPD pattern shown in FIG. 57, at least one or all of the following peaks in degrees two theta (2θ) is shown for Form B 1:1 ponatinib/cyclohexanone solvate: 5.6; 9.5; 11.0; 12.0; 12.9; 14.0; 15.2; 16.2; 16.8; 17.0; 18.1; 18.8; 19.5; 20.1; 21.8; 22.3; 23.0; 24.5; 26.1; 27.5; 28.0; and 28.2. In certain embodiments, Form B 1:1 ponatinib/cyclohexanone solvate is characterized by a XRPD pattern comprising one or more of the following peaks two theta (2θ): 5.6; 11.0; 12.0; 12.9; 14.0; 15.2; 16.8; 18.1; 18.8; 20.1; 21.8; 22.3; 24.5; and 26.1. In the middle XRPD pattern shown in FIG. 57, at least one or all of the following peaks in degrees two theta (2θ) is shown for Form B 1:1 ponatinib/cyclohexanone solvate: 5.6; 14.0; 15.2; 16.8; 20.1; 21.8; 22.3; and 26.1. In certain embodiments, Form B 1:1 ponatinib/cyclohexanone solvate is characterized by a XRPD pattern comprising one or more of the following peaks two theta (2θ): 5.6; 14.0; 15.2; 16.8; 20.1; 22.3; and 26.1. In certain embodiments, the XRPD pattern of Form B 1:1 ponatinib/cyclohexanone solvate shows two peaks, three peaks, four peaks or five peaks selected from those given above. In certain embodiments, the Form B 1:1 ponatinib/cyclohexanone solvate is characterized by an XRPD pattern substantially similar to the middle XRPD pattern in FIG. 57. In certain embodiments, the crystalline Form B comprises an x-ray powder diffraction pattern with characteristic peaks expressed in degrees two-theta as shown in the middle pattern in FIG. 57.

FIG. 58 is the DSC curve obtained for the B-Class 1:1 ponatinib/cyclohexanone solvate (QSA7.1), showing endothermic events at $T_{peak}=110.1°$ C. and $T_{peak}=198.6°$ C.

FIG. 59 is the plot showing TGA and SDTA thermograms of B-Class 1:1 ponatinib/cyclohexanone solvate (QSA7.1).

TGMS data for the B-Class 1:1 ponatinib/cyclohexanone solvate (QSA7.1) showed mass losses of 14.8% (cyclohexanone and water) and 0.2% (cyclohexanone) occurring within the temperature intervals of 50-160° C. and 160-210° C., respectively. The ponatinib/cyclohexanone ratio was assessed from the TGMS data to be about 1.0/0.96.

Experiments to determine the purity of the B-Class 1:1 ponatinib/cyclohexanone solvate (QSA7.1) were performed using HPLC. From HPLC it was determined that the purity of the B-Class 1:1 ponatinib/cyclohexanone solvate (QSA7.1) is 99.7460% (area percent).

FIG. 60 is the DSC curve obtained for the B-Class 1:0.4 ponatinib/2-methylTHF solvate (GEN8.1), showing endothermic events at $T_{peak}=67.1°$ C. and $T_{peak}=197.5°$ C.

FIG. 61 is the plot showing TGA and SDTA thermograms of B-Class 1:0.4 ponatinib/2-methylTHF solvate (GEN8.1).

TGMS data for the B-Class 1:0.4 ponatinib/2-methylTHF solvate (GEN8.1) showed mass losses of 3.1% (2-methylTHF), 1.9% and 1.0% (2-methylTHF) occurring within the temperature intervals of 40-90° C., 90-165° C. and 165-215° C., respectively. The ponatinib/2-methylTHF ratio was assessed from the TGMS data to be about 1.0/0.4.

Experiments to determine the purity of the B-Class 1:0.4 ponatinib/2-methylTHF solvate (GEN8.1) were performed using HPLC. From HPLC it was determined that the purity of the B-Class 1:0.4 ponatinib/2-methylTHF solvate (GEN8.1) is 99.5939% (area percent).

Characteristics of Ponatinib Form C (Low Crystalline) Polymorph

The low crystalline Form C can be obtained in the slurry experiments from crystalline Form A in methanol as the solvent. Form C was found to contain solvated methanol with the ratio of Ponatinib/methanol of about 1:0.2.

FIG. 62 is the DSC curve obtained for low crystalline Form C (GEN3.1) showing an endothermic event at $T_{peak}=95.9°$ C., an exothermic event at $T_{peak}=135.3°$ C., and an endothermic event at $T_{peak}=198.1°$ C.

FIG. 63 is the plot showing TGA and SDTA thermograms of low crystalline Form C (GEN3.1).

TGMS data for Form C (GEN3.1) showed a mass loss of 1.3% (methanol) occurring within the temperature interval of 40-150° C. The ponatinib/methanol ratio was assessed from the TGMS data to be about 1.0/0.2.

Form C was analyzed by X-ray powder diffraction (XRPD). FIG. 64 shows XRPD patterns of a XRPD overlay of starting material crystalline Form A (the bottom pattern) and low crystalline Form C (the upper pattern).

In the upper XRPD pattern shown in FIG. 64, at least one or all of the following peaks in degrees two theta (2θ) is shown for Form C: 3.2; 11.1; 11.7; 12.8; 13.3; 13.5; 14.2; 17.1; 18.2; 20.8; 22.3; and 26.5. In certain embodiments, Form C is characterized by a XRPD pattern comprising one or more of the following peaks two theta (2θ): 3.2; 12.8; 14.2; 17.1; 18.2; 20.8; 22.3 and 26.5. In the XRPD pattern shown in FIG. 64, at least one or all of the following peaks in degrees two theta (2θ) is shown for Form C: 3.2; 12.8; 14.2; and 18.2. In certain embodiments, the XRPD pattern of Form C shows two peaks, three peaks, four peaks or five peaks selected from those given above. In certain embodiments, the Form C is characterized by an XRPD pattern substantially similar to the upper XRPD pattern in FIG. 64. In certain embodiments, the crystalline Form C comprises an x-ray powder diffraction pattern with characteristic peaks expressed in degrees two-theta as shown in FIG. 64.

Experiments to determine the purity of Form C (GEN3.1) were performed using HPLC. From HPLC it was determined that the purity of Form C of ponatinib is 99.5725% (area percent).

Characteristics of Ponatinib Form D Polymorph

Form D may be obtained from crystalline Form A by crash-crystallization in N,N-dimethylacetamide (DMA) by anti-solvent addition. Produced in this manner, Form D was found to be a DMA solvate with the ratio of Ponatinib/DMA of about 1:1.

FIG. 65 is the DSC curve obtained for Form D (GEN5.1R1) showing endothermic events at $T_{peak}$=103.3° C., $T_{peak}$=125.6° C., and $T_{peak}$=198.4° C.

FIG. 66 is the plot showing TGA and SDTA thermograms of low crystalline Form D (GEN5.1R1).

TGMS data for Form D (GEN5.1R1) showed a mass loss of 13.8% (N,N-dimethylaceamide) occurring within the temperature interval of 40-140° C. The ponatinib/DMA ratio was assessed from the TGMS data to be about 1.0/0.98.

Form D was analyzed by X-ray powder diffraction (XRPD). FIG. 67 shows XRPD patterns of a XRPD overlay (from bottom to top) of starting material crystalline Form A; Form D (GEN5.1R1); and a remeasurment after 3-days (GEN5.1R4), whereby the sample analyzed likely contains B-Class forms along with Form D.

In the middle XRPD pattern shown in FIG. 67, at least one or all of the following peaks in degrees two theta (2θ) is shown for Form D: 6.2; 8.0; 10.8; 11.5; 12.4; 13.5; 13.8; 14.5; 15.6; 16.5; 17.6; 18.5; 19.3; 19.8; 20.1; 20.8; 21.6; 22.1; 23.8; 26.0; 27.1; and 29.6. In certain embodiments, Form D is characterized by a XRPD pattern comprising one or more of the following peaks two theta (2θ): 6.2; 10.8; 12.4; 13.8; 14.5; 15.6; 16.5; 18.5; 20.2; 20.8; 21.6; 26.0; and 27.1. In the middle XRPD pattern shown in FIG. 67, at least one or all of the following peaks in degrees two theta (2θ) is shown for Form D: 6.2; 12.4; 14.5; 15.6; 16.5; 18.5; 20.2; 20.8; 21.6; 26.0; and 27.1. In certain embodiments, Form D is characterized by a XRPD pattern comprising one or more of the following peaks two theta (2θ): 6.2; 15.6; 16.5; 18.5; 20.2; 21.6; 26.0; and 27.1. In certain embodiments, the XRPD pattern of Form D shows two peaks, three peaks, four peaks or five peaks selected from those given above. In certain embodiments, Form D of ponatinib is characterized by an XRPD pattern substantially similar to the middle XRPD pattern in FIG. 67. In certain embodiments, the crystalline Form D comprises an x-ray powder diffraction pattern with characteristic peaks expressed in degrees two-theta as shown in FIG. 67.

Experiments to determine the purity of Form D were performed using HPLC. From HPLC it was determined that the purity of Form D of ponatinib is 99.5056% (area percent).

Characteristics of Ponatinib Form E (E-Class) Polymorphs

The E-Class solvents are prepared from either crystalline Form A or low crystalline Form C in slurry and solubility experiments, using solvents such as tetrahydrofuran (THF), chloroform and dichloromethane (DCM), or by vapor diffusion onto solids.

Based on thermal analyses, one sample representative of Form E was assigned as a ponatinib/tetrahydrofuran (THF) 1:1 solvated form. Another sample representative of Form E appears to be a chloroform solvate, but this material was not characterized further other than by XRPD.

FIG. 68 is the DSC curve obtained for E-Class ponatinib/THF 1:1 solvate (GEN7.1) showing endothermic events at $T_{peak}$=95.9° C. and $T_{peak}$=198.1° C.

FIG. 69 is the plot showing TGA and SDTA thermograms of E-Class ponatinib/THF 1:1 solvate (GEN7.1).

TGMS data for E-Class ponatinib/THF 1:1 solvate (GEN7.1) showed a mass loss of 11.7% (THF) occurring within the temperature interval of 40-130° C. The ponatinib/THF ratio was assessed from the TGMS data to be about 1.0/0.98.

The two above mentioned Class-E polymorphs were analyzed by X-ray powder diffraction (XRPD). FIG. 70 shows XRPD patterns of a XRPD overlay (from bottom to top) of starting material crystalline Form A; E-Class ponatinib/THF 1:1 solvate (GEN7.1); and E-Class ponatinib/chloroform solvate (SLP3.1).

In the upper XRPD pattern shown in FIG. 70, at least one or all of the following peaks in degrees two theta (2θ) is shown for E-Class ponatinib/THF 1:1 solvate (GEN7.1): 6.2; 7.0; 10.0; 13.0; 15.1; 16.4; 17.2; 18.5; 20.4; 20.5; 22.5; 24.4; 25.6; and 27.0. In certain embodiments, E-Class ponatinib/THF 1:1 solvate (GEN7.1) is characterized by a XRPD pattern comprising one or more of the following peaks two theta (2θ): 6.2; 7.0; 10.0; 15.1; 16.4; 17.2; 18.5; 20.4; 20.5 24.4; and 27.0. In the upper XRPD pattern shown in FIG. 70, at least one or all of the following peaks in degrees two theta (2θ) is shown for E-Class ponatinib/THF 1:1 solvate (GEN7.1): 6.2; 15.1; 16.4; 17.2; 18.5; 20.4; 24.4; and 27.0. In certain embodiments, E-Class ponatinib/THF 1:1 solvate (GEN7.1) is characterized by a XRPD pattern comprising one or more of the following peaks two theta (2θ): 6.2; 15.1; 16.4; 20.4; and 20.5. In certain embodiments, the XRPD pattern of E-Class ponatinib/THF 1:1 solvate (GEN7.1) shows two peaks, three peaks, four peaks or five peaks selected from those given above. In certain embodiments, E-Class ponatinib/THF 1:1 solvate is characterized by an XRPD pattern substantially similar to the upper XRPD pattern in FIG. 70. In certain embodiments, the crystalline Form E comprises an x-ray powder diffraction pattern with characteristic peaks expressed in degrees two-theta as shown in the upper pattern in FIG. 70.

In the middle XRPD pattern shown in FIG. 70, at least one or all of the following peaks in degrees two theta (2θ) is shown for E-Class ponatinib/chloroform solvate (SLP3.1):

6.2; 7.0; 8.7; 9.8; 12.1; 12.5; 13.0; 15.2; 16.4; 17.2; 18.5; 20.0; 21.0; 23.0; 24.4; 25.0; and 26.2. In certain embodiments, E-Class ponatinib/chloroform solvate (SLP3.1) is characterized by a XRPD pattern comprising one or more of the following peaks two theta (2θ): 6.2; 7.0; 13.0; 15.2; 16.4; 17.2; 18.5; 20.0; 21.0; 24.4; 25.0; and 26.2. In certain embodiments, the XRPD pattern of E-Class ponatinib/chloroform solvate (SLP3.1) shows two peaks, three peaks, four peaks or five peaks selected from those given above. In certain embodiments, E-Class ponatinib/chloroform solvate is characterized by an XRPD pattern substantially similar to the middle XRPD pattern in FIG. 70. In certain embodiments, the crystalline Form E comprises an x-ray powder diffraction pattern with characteristic peaks expressed in degrees two-theta as shown in the middle pattern in FIG. 70.

Experiments to determine the purity of E-Class ponatinib/THF 1:1 solvate (GEN7.1) were performed using HPLC. From HPLC it was determined that the purity of E-Class ponatinib/THF 1:1 solvate (GEN7.1) of ponatinib is 99.5120% (area percent).

Characteristics of Ponatinib Form F Polymorph

Form F was formed from Form A in specific experimental conditions such as in the presence of polar solvents. Analysis of Form F by TGMS showed that Form F loses 3.3% of water in the first temperature range of 25-140° C. From these results it could be concluded that the first endotherm event observed corresponded to a dehydration process and that Form F was a hydrated form, e.g. a 1:1 hydrate with water.

From the screening experiments, selected samples of pure Form F (6 samples) and mixtures of Forms A and F (6 samples) were re-analyzed by XRPD after storage at ambient temperature for 4-months. The results are shown in Table 24 below.

TABLE 24

Samples of pure Form F and mixtures of Forms A + F re-analyzed by XRPD after 4-month storage.

| Obtained form[a] | Cryst. Mode[b] (number of samples remeasured)[c] | Solvent (S), anti-solvent (AS) | Form(s) after re-analysis[d] |
|---|---|---|---|
| Form F | AS (1 wet harvested) | (S) 2-Methoxyethanol, (AS) water | A |
| | AS (1) | (S) Acetone, (AS) water | A + F |
| | AS (2) | (S) Methanol, 4-hydroxy-4-methyl-2-pentanone, (AS) Water | F |
| | SLP (1) | | |
| | VDL (1) | 1,2-Dimethoxyethane (S) Methanol, (AS) Water | |
| A + F | PSM (1) AS (1) SLP (2), VDS (1, 1 wet harvested) | Water, (S) 2-Methoxyethanol, (AS) water Water | A + F |

[a]As classified by XRPD after completion of the crystallization experiments.
[b]Crystallization modes: cooling-evaporative (PSM), crash crystallization with anti-solvent addition (AS), slurry (SLP), vapour diffusion onto solid (VDS) and vapour diffusion into solution (VDL).
[c]From the screen, some experiments were selected to be remeasured by XRPD after storage for 4 months at ambient temperature.
[d]As classified by XRPD after storage of the samples for 4 months at ambient conditions.

The results in Table 24 show that in most of the cases the polymorphic forms remained unchanged. The results obtained in the crash crystallization with anti-solvent experiment (2-methoxyethanol/water) showed that when the sample was harvested wet, the Form F material obtained converted to Form A after 4 months. Also in the anti-solvent addition experiment with acetone/water, Form F converted to a mixture of Forms A and F after 4 months.

FIG. 71 shows the TGA and SDTA plots obtained for Form F (AS16.2). Form F (AS16.2) showed a first endotherm followed by are crystallization in the temperature range of 130-140° C. The melting point of Form F (AS16.2) was observed at about 189° C.

As mentioned, TGMS data for Form F (AS16.2) showed a mass loss of 3.3% (water) occurring within the temperature interval of 25-140° C. The ponatinib/water ratio was assessed from the TGMS data to be about 1.0/1.01 for Form F.

Form F (SLP10.1) was analyzed by X-ray powder diffraction (XRPD). In FIG. 83, a number of XRDP patterns are shown in stacked arrangement and wherein the pattern for Form F (SLP10.1) is the fifth pattern from the top. This sample, (SLP10.1), was obtained in the slurry experiments using 1,2-dimethoxyethane as the solvent.

In the XRPD pattern shown as the pattern fifth from the top in FIG. 83, at least one or all of the following peaks in degrees two theta (2θ) is shown for ponatinib Form F: 7.2; 13.2; 14.1; 15.9; 18.1; 20.4; 21.1; 22.0; 23.5; 24.2; 25.5; and 26.8. In certain embodiments, Form F is characterized by a XRPD pattern comprising one or more of the following peaks two theta (2θ): 7.2; 13.2; 14.1; 15.9; 18.1; 20.4; 23.5; 25.5 and 26.8. In the XRPD pattern shown as the pattern fifth from the top in FIG. 83, at least one or all of the following peaks in degrees two theta (2θ) is shown for Form F: 7.2; 14.1; 18.1; 20.4; 25.5; and 26.8. In certain embodiments, the XRPD pattern of Form F shows two peaks, three peaks, four peaks or five peaks selected from those given above. In certain embodiments, ponatinib Form F is characterized by an XRPD pattern substantially similar to the XRPD pattern fifth from the top in FIG. 83. In certain embodiments, the crystalline Form F comprises an x-ray powder diffraction pattern with characteristic peaks expressed in degrees two-theta as shown in the pattern fifth from the top in FIG. 83.

Characteristics of Ponatinib Form H (H-Class) Polymorphs

Characteristics of Ponatinib/1-Propanol 1:1 Solvated Form H

Solid recovered from a dissolution experiment with 1-propanol was determined to be a 1-propanol solvate of Form H.

The DSC curve obtained for H-Class ponatinib/1-propanol solvate (SAS35) showed endothermic events appearing at $T_{peak}$ of about 93° C. and $T_{peak}$ of about 192° C.

The TGMS data for H-Class ponatinib/1-propanol solvate (SAS35) showed a mass loss of 9.2% (1-propanol) occurring within the temperature interval of 25-120° C. The ponatinib/1-propanol ratio was assessed from the TGMS data to be about 1.0/0.9 for H-Class ponatinib/1-propanol solvate (SAS35). Another sample, (SAS30) showed a mass loss corresponding to a 1:0.6 solvate, but this sample was later determined to have partially converted back to crystalline anhydrate Form A, thus reducing the overall solvent loss observed for the bulk sample.

H-Class solvate (SAS35) was analyzed by X-ray powder diffraction (XRPD) wherein at least one or all of the following peaks in degrees two theta (2θ) appeared: 6.1; 6.8; 10.0; 12.0; 13.2; 13.5; 16.0; 16.5; 16.0; 16.5; 18.0; 19.0; 19.5; 20.4; 21.0; 22.5; 25.0; 25.5; 26.2; 27.0; and 27.5. In certain embodiments, Form H is characterized by a XRPD pattern comprising one or more of the following peaks two theta (2θ): 12.0; 13.2; 13.5; 18.0; 25.0 and 25.5. In certain embodiments, the XRPD pattern of Form H shows two peaks, three peaks, four peaks or five peaks selected from those given above.

Characteristics of Ponatinib/2-Methoxyethanol 1:1 Solvated Form H

Ponatinib free base can form isomorphic solvates of Form H in other alcohols. A 2-methoxyethanol solvate was obtained by a vapor diffusion into liquid procedure, beginning with Form A as the starting material and using 2-methoxyethanol as solvent. The purity of this form was assessed to be 98.0%. TGMS confirmed it to be the 1:0.93 ponatinib/2-methoxyethanol solvate, which desolvated at about 96° C. After desolvation, a melting point of about 198.8° C. was observed in the DSC, which corresponds closely to the melting point of Form A.

The DVS experiment showed a loss of weight during desorption of about 3.6%, which was not regained during sorption to 45% RH. XRPD analysis at the end of the DVS experiments indicated no physical change. While possible that partial desolation occurred, the process did not cause the crystal structure to collapse (as indicated by the TG-MS about 12% weight loss is observed during the desolvation).

Form H, however, converted to Form A during 10 months of storage under ambient conditions, and also after one week in a humidity chamber at accelerated stress conditions (40° C., 75% RH).

FIG. 72 is the DSC curve obtained for Form H (VLD1, dried solid from stock) showing endothermic events at $T_{peak}$=96.1° C. (desolvation event) and $T_{peak}$=198.8° C. The endothermal event at 198.8° C. is suspected to be the melting event of Form A.

FIG. 73 is a characteristic overlay of TGA and SDTA thermograms of Form H (VLD1, dried solid from stock).

The DVS experiment for Form H (VLD1, dried solid from stock) showed a loss of weight of about 11.7% (2-methoxyethanol) in the temperature range of 25-120° C. From these results, the first endotherm event observed corresponded to a desolvation process and that Form H (VLD1, dried solid from stock) was a 1:0.93 ponatinib/2-methoxyethanol solvate.

FIG. 74 presents a series of XRPD patterns obtained for various samples of Form H of ponatinib, along with the XRPD of Form A. In FIG. 74: Plot 1 is Form H (VLD2 experiment, after 2-weeks and drying); Plot 2 is Form H (VLD1 experiment, after 2-weeks and drying); Plot 3 is Form H (VLD1 experiment, dried solid from stock after DVS); Plot 4 is Form H (VLD1, dried solid from stock); Plot 5 is Form H (VLD19); and the bottom plot is the XRPD for Form A. The XRPD patterns shown as Plots 1-5 are substantially similar.

In the XRPD pattern shown as Plot 5 in FIG. 74, at least one or all of the following peaks in degrees two theta (2θ) is shown for ponatinib Form H: 6.2; 6.5; 10.1; 12.0; 13.2; 15.0; 15.5; 16.0; 16.5; 18.0; 19.1; 19.6; 20.5; 21.1; 23.0; 23.7; and 25.5. In certain embodiments, Form H is characterized by a XRPD pattern comprising one or more of the following peaks two theta (2θ): 6.2; 12.0; 13.2; 16.0; 18.0; 19.1; 19.6; 20.5; 21.1; 23.0; and 25.5. In the XRPD pattern shown shown as Plot 5 in FIG. 74, at least one or all of the following peaks in degrees two theta (2θ) is shown for Form H: 6.2; 12.0; 18.0; and 25.5. In certain embodiments, the XRPD pattern of Form H shows two peaks, three peaks, four peaks or five peaks selected from those above. In certain embodiments, ponatinib Form H is characterized by an XRPD pattern substantially similar to any one of patterns 1-5 in FIG. 74. In certain embodiments, the crystalline Form H comprises an x-ray powder diffraction pattern with characteristic peaks expressed in degrees two-theta as shown in any one of the patterns 1-5 in FIG. 74.

Experiments to determine the purity of Form H (VLD1 dried solid from stock) were performed using HPLC. From HPLC it was determined that the purity of Form H of ponatinib (VLD1 dried solid from stock) is 98.0464% (area percent).

FIG. 75 is a characteristic FT-IR spectrum obtained from Form H of ponatinib (VLD1 dried from stock) (Plot 1) in overlay with the FT-IR spectrum obtained for Form A (Plot 2). Percent transmittance (%) is shown on the vertical axis and wavenumber (cm$^{-1}$) is shown on the horizontal axis.

FIG. 76 is a characteristic FT-IR spectrum obtained from Form H of ponatinib (VLD1 dried from stock) (Plot 1) in overlay with the FT-IR spectrum obtained for Form A (Plot 2:), for the region of wavelength 1750-600 nm. Percent transmittance (%) is shown on the vertical axis and wavenumber (cm$^{-1}$) is shown on the horizontal axis. This overlay identifies several characteristic peaks for Form H, and also several characteristic peaks for Form A. In this regard, some of the characteristic peaks for Form A in FIG. 76 (Plot 2) include: 1605; 1415; 1295; 1250; 1150; 1145; 1110; 1100; 895; 855; and 790 cm$^{-1}$.

Characteristics of Ponatinib Form I Low Crystalline Polymorph

The low crystalline Form I was obtained by a freeze-drying technique in dichloromethane (DCM).

Based on thermal analyses, Form I (GEN9.1) contains a slight level of solvated DCM, corresponding to a ponatinib/DCM ratio of about 1:0.03.

FIG. 77 is the DSC curve obtained for Form I (GEN9.1) showing an exothermic event at $T_{peak}$=100.1° C. and an endothermic event at $T_{peak}$=196.7° C.

FIG. 78 is the plot showing TGA and SDTA thermograms of Form I (GEN9.1).

TGMS data for Form I (GEN9.1) showed a mass loss of 0.5% (DCM) occurring within the temperature interval of 40-175° C. (slightly solvated). The ponatinib/DCM ratio was assessed from the TGMS data to be about 1.0/0.03.

The Form I (GEN9.1) was analyzed by X-ray powder diffraction (XRPD). FIG. 77 shows XRPD overlay (from bottom to top) of starting material crystalline Form A and Form I (GEN9.1).

In the upper XRPD pattern shown in FIG. 79, at least one or all of the following peaks in degrees two theta (2θ) is shown for Form I (GEN9.1): 6.5; 8.2; 9.8; 14.3; 15.5; 17.5; 21.2; 23.1; and 26.5. In certain embodiments, Form I (GEN9.1) is characterized by a XRPD pattern comprising one or more of the following peaks two theta (2θ): 6.5; 8.2; 9.8; 14.3; 15.5; 17.5; 21.2; and 26.5. In the upper XRPD pattern of FIG. 79, at least one or all of the following peaks in degrees two theta (2θ) is shown for Form I (GEN9.1): 6.5; 8.2; 15.5; 17.5; 21.2; and 26.5. In certain embodiments, Form I (GEN9.1) is characterized by a XRPD pattern comprising one or more of the following peaks two theta (2θ): 8.2; and 15.5. In certain embodiments, the XRPD pattern of Form I (GEN9.1) shows two peaks, three peaks, four peaks or five peaks selected from those given above. In certain embodiments, ponatinib Form I is characterized by an XRPD pattern substantially similar to the top pattern in FIG. 79. In certain embodiments, the crystalline Form I comprises an x-ray powder diffraction pattern with characteristic peaks expressed in degrees two-theta as shown in the upper pattern in FIG. 79.

Experiments to determine the purity of Form I (GEN9.1) were performed using HPLC. From HPLC it was determined that the purity of Form I (GEN9.1) of ponatinib is 99.5802% (area percent).

Characteristics of Ponatinib Form J Polymorph

Form J was obtained by a vapor diffusion onto solids method. The purity was assessed to 96.5%. The TGMS analysis (weight loss of 11.4% thiophene during the interval 25-130° C.) confirmed that Form J "low crystalline" is a 1:0.82 ponatinib/thiophine solvate, which desolvates at 83.7° C. After desolvation, a melting point event occurs at about 197.3° C., which may be the melting of Form A.

The DVS experiment showed a weight loss during desorption of about 1.3%. The weight appears not to be regained during the sorption phase, at least up to 45% relative humidity (RH), (mass uptake about 0.33%). The XRPD analysis at the end of the DVS experiments indicated that the material converted to Form A.

Low crystalline Form J also converted to Form A after 10 months of storage under ambient conditions, and after 1-week under stress conditions, (40° C., 75% RH).

Two samples of ponatinib Form J (designated VDS2 and VDS10 of screen S10010A) were analyzed by X-ray powder diffraction (XRPD). FIG. 78 shows XRPD overlay patterns (from top to bottom): Plot 6 is the XRPD pattern for Form A (VDS2, after stability study); Plot 7 is the XRPD pattern for Form J (VDS2); Plot 8 is the XRPD pattern of Form J (VDS10 of screen S10010A); and Plot 9 is another XRPD pattern of ponatinib Form A.

In the XRPD Plots 7 and 8 shown in FIG. 80, at least one or all of the following peaks in degrees two theta (2θ) is shown for Form J of ponatinib: 5.8; 7.0; 12.1; 15.1; 16.8; 18.1; 18.6; 19.1; 19.5; 20.1; 21.1; 21.8; 22.8; 25.0; 25.7; and 27.0. In certain embodiments, Form J of ponatinib is characterized by a XRPD pattern comprising one or more of the following peaks two theta (2θ): 5.8; 7.0; 12.1; 15.1; 16.8; 18.1; 19.1; 19.5; 20.1; 21.1; 21.8; 22.8; 25.0; 25.7; and 27.0. In the upper XRPD pattern of FIG. 80, at least one or all of the following peaks in degrees two theta (2θ) is shown for Form J of ponatinib: 5.8; 7.0; 12.1; 15.1; 16.8; 18.6; 19.1; 19.5; 21.8; 22.8; 25.0; 25.7; and 27.0. In certain embodiments, Form J of ponatinib is characterized by a XRPD pattern comprising one or more of the following peaks two theta (2θ): 5.8; 7.0; 12.1; 15.1; 18.6; 19.5; 21.8; 25.0; 25.7; and 27.0. In certain embodiments, the XRPD pattern of Form J of ponatinib shows two peaks, three peaks, four peaks or five peaks selected from those given above. In certain embodiments, Form J of ponatinib is characterized by an XRPD pattern substantially similar to either one of Plots 7 and 8 in FIG. 80. In certain embodiments, the crystalline Form J comprises an x-ray powder diffraction pattern with characteristic peaks expressed in degrees two-theta as shown in either one of Plots 7 and 8 in FIG. 80.

Experiments to determine the purity of Form J (VDS2) were performed using HPLC. From HPLC it was determined that the purity of Form J (VDS2) of ponatinib is 96.4509% (area percent).

FIG. 81 is a characteristic FT-IR spectrum obtained from Form J (VDS2) of ponatinib (Plot 1) in overlay with the FT-IR spectrum obtained for Form A (Plot 2). Percent transmittance (%) is shown on the vertical axis and wavenumber ($cm^{-1}$) is shown on the horizontal axis.

FIG. 82 is a characteristic FT-IR spectrum obtained from Form J (VDS2) of ponatinib (Plot 1) in overlay with the FT-IR spectrum obtained for Form A (Plot 2), for the region of wavelength 1750-600 nm. Percent transmittance (%) is shown on the vertical axis and wavenumber ($cm^{-1}$) is shown on the horizontal axis.

Characteristics of Ponatinib Form K Polymorph

Solid Form K was found in sample SAS58 (MSZW experiment): 25 mg/mL in 1-propanol/acetonitrile 30/70.

The TGMS thermogram showed negligible mass loss (<0.04% in the temperature interval 25-175° C.) prior to melting. From the SDTA signal, the melting point of Form K is 184° C.

The DSC curve obtained for ponatinib Form K showed an endothermic event appearing at $T_{peak}$ of about 184° C.

Ponatinib Form K was analyzed by X-ray powder diffraction (XRPD) wherein at least one or all of the following peaks in degrees two theta (2θ) appeared: 10.0; 11.0; 13.4; 14.6; 15.2; 16.0; 17.0; 17.5; 18.0; 19.6; 20.9; 22.1; 22.8; 24.1; 24.8; 26.5; 27.1; 28.5; and 30.5. In certain embodiments, Form K is characterized by a XRPD pattern comprising one or more of the following peaks two theta (2θ): 10.0; 11.0; 13.4; 14.6; 15.2; 16.0; 19.6; 20.9; 22.1; 22.8; 24.1; 24.8; and 26.5. In certain embodiments, Form K is characterized by a XRPD pattern comprising one or more of the following peaks two theta (2θ): 10.0; 11.0; 13.4; 14.6; 15.2; 19.6; 22.1; 22.8; and 24.1. In certain embodiments, the XRPD pattern of Form K shows two peaks, three peaks, four peaks or five peaks selected from those above.

Overlay of XRPD Patterns for Selected Ponatinib Polymorphs

FIG. 83 is an overlay of the XRPD results obtained for selected ponatinib free base polymorphs. From bottom to top, the XRPD patterns shown were obtained for: Form A (SM); B-Class (QSAS7.1); Form C, low crystalline (GEN3.1); Form D (GEN5.1); E-Class (SLP3.1); Form F (SLP10.1); Form G (AS19.1), discussed herein below; Form H (VDL19.1); Form I, low crystalline (GEN9.1); and Form J, low crystalline (VDS10.1).

Characteristics of Ponatinib Form G Polymorph

FIG. 83 depicts ponatinib Form G, which was obtained by a crash-crystallization/anti-solvent process wherein the solvent used was 3-methyl-1-butanol and the anti-solvent used was cyclohexane. Ponatinib Form G was analyzed by X-ray powder diffraction (XRPD) wherein at least one or all of the following peaks in degrees two theta (2θ) appeared: 5.0; 6.5; 9.5; 12.0; 12.5; 14.0; 15.0; 16.5; 17.2; 18.4; 20.0; 21.0; 22.8; 23.5; 24.6; and 29.5. In certain embodiments, Form G is characterized by a XRPD pattern comprising one or more of the following peaks two theta (2θ): 5.0; 6.5; 9.5; 14.0; 15.0; 16.5; 17.2; 18.4; 20.0; and 22.8. In certain embodiments, Form G is characterized by a XRPD pattern comprising one or more of the following peaks two theta (2θ): 5.0; 6.5; 9.5; 14.0; 17.2; 18.4; 20.0; and 22.8. In certain embodiments, the XRPD pattern of Form G shows two peaks, three peaks, four peaks or five peaks selected from those given above. In certain embodiments, Form G of ponatinib is characterized by an XRPD pattern substantially similar to the pattern forth from the top of overlaid patterns in FIG. 83. In certain embodiments, the crystalline Form G comprises an x-ray powder diffraction pattern with characteristic peaks expressed in degrees two-theta as shown in the pattern forth from the top in FIG. 83.

Example 6

Discovery of Polymorphic Forms of Ponatinib

Initial efforts to discover polymorphic forms of ponatinib were divided into two phases. Phase 3 involved starting-material characterization, feasibility testing and solubility study to provide data for the solvents selection for phase 4. Phase 4 involved 192 polymorph screening experiments at milliliter (ml) scale. These initial efforts led to the discovery of eleven polymorphic forms of ponatinib free base, Form A, Form B, Form C, Form D, Form E, Form F, Form G, Form H, Form I, Form J, and Form K.
Phase 1: Starting Material Characterization The compound ponatinib free base was obtained by the synthesis discussed herein below, which is characterized by an amide coupling reaction of an amine subunit and a methyl ester subunit. Approximately 20 grams of the free base (combined from two batches, designated as F09-05575 and F09-05576) were obtained as a light yellow solid. This starting material was characterized by XRPD, digital imaging, DSC, TGMS and HPLC.

FIG. 84 shows the XRPD patterns of the free base starting material, with the two patterns representing the two batches (F09-05575: lower pattern; and F09-05576: upper pattern) mentioned above.

FIG. 85 is the DSC curve for ponatinib free base starting material batch F09-05575, showing endothermic events at $T_{peak}=182.6°$ C. and $T_{peak}=199.0°$ C. (major). The major endotherm corresponds to the melting event, which may be accompanied by a desolvation process (as observed in the TGA/SDTA trace for this batch).

FIG. 86 is the DSC curve for ponatinib free base starting material batch F09-05576, showing an endothermic event at $T_{peak}=199.6°$ C. The endotherm corresponds to the melting event, which may be accompanied by a desolvation process (as observed in the TGA/SDTA trace for this batch).

FIG. 87 is the plot showing TGA and SDTA thermograms of ponatinib free base starting material batch F09-05575.

FIG. 88 is the plot showing TGA and SDTA thermograms of ponatinib free base starting material batch F09-05576.

TGA and TGMS analyses showed mass loss in one single step for the batch F09-05575, (0.9% in the temperature interval of 25-210° C.) whereas a two-step mass loss was observed in batch F09-05576 (0.3% mass loss in the temperature interval of 25-120° C. and 0.9% in the interval 120-210° C.). The mass losses observed in both batches correspond to 2-methyltetrahydrofuran (as confirmed by the m/z ratio's observed in the MS data). The presence of this solvent in residual quantities could originate from the last synthesis steps of ponatinib free base compound.

Experiments to determine the purity of ponatinib free base compound were performed using HPLC. From HPLC it was determined that the purity of batch F09-05575 is 99.5166% (area percent), and the purity of batch F09-05576 is 99.6869% (area percent).

In various embodiments, alternative methods of preparing Form A gave samples of varying crystallinity.
Alternative Ponatinib Form a Free Base Preparation Methods
Preparation 1

A M010578 sample from 180 g run ABL411057 (2-Me-THF, 1.1 equiv. of aniline, 1.6 equiv. of KOtBu) was crystallized from neat 1-propanol, followed by a trituration of the 1-PrOH moist product in neat acetonitrile to give Form A in 99.39 a % purity.

Preparation 2

Two samples from 180 g run ABL411060 (2-Me-THF, 26° C. IT, 1.1 equiv. of aniline, 1.6 equiv. of KOtBu) were obtained from a solution of M010578 in 1-PrOH obtained after solvent swap from 2-Me-THF to 1-PrOH. The 1-PrOH solution was split 9:1.

779.5 g (9 parts) of the above solution of M010578 in 1-PrOH were allowed to crystallize at ambient temperature overnight. After filtration, the moist filter cake was triturated in 160 g of acetonitrile at 40° C., filtered and dried (50° C., 3 mbar) to obtain 211.6 g of ponatinib free base Form A (99.87 a %).

260 g of acetonitrile were added to 86.6 g (1 part) of the above solution of M010578 in 1-PrOH. The suspension was filtered after 1 h, the filter cake washed with ACN/1-PrOH (3:1 v/v), and dried to obtain 25.6 g free base (99.27 a %). Crystallization and isolation from 1-propanol followed by a trituration in acetonitrile gave product of higher HPLC purity than isolation by precipitation from a mixture of ACN/1-PrOH.

Phase 1: Solubility Study

Quantitative solubility testing was performed on ponatinib free base starting material, employing a set of 20 solvents. Slurries were prepared with an equilibration time of 24 hours after which the slurries were filtered. The solubility was determined from the saturated solutions by HPLC. The residual solids were characterized by XRPD. The results are summarized in Table 25 below.

TABLE 25

Solubility Study of 3-(imidazo[1,2-b]pyridazin-3-ylethynyl)-4-methyl-N-{4-[(4-methylpiperazin-1-yl)methyl]-3-(trifluoromethyl)phenyl}benzamide

| Experiment | Solvent name | Solubility (mg/ml) | XRPD Form[1] |
|---|---|---|---|
| QSA1 | Diethylene glycol diethylether | 32.35 | A |
| QSA2 | Diethyl Ether | 0.95 | A |
| QSA3 | Dimethyl Sulfoxide | 124.45 | A |
| QSA4 | Isobutyl isobutyrate | 2.5 | A |
| QSA5 | Dimethylacetamide N,N- | OR[3] | A |
| QSA6 | Pentyl ether | UR, <0.21[2] | A |
| QSA7 | Cyclohexanone | 30.78 | B-Class |
| QSA8 | Xylene, p- | 0.8 | A |
| QSA9 | Isobutanol | 20.95 | A |
| QSA10 | Butyl acetate | 8.04 | A |
| QSA11 | Heptane, n- | UR, <0.21[2] | A |
| QSA12 | Water | UR, <0.21[2] | A |
| QSA13 | Trifluoroethanol 2,2,2- | OR[3] | A |
| QSA14 | Hexafluorobenzene | 0.21 | A |
| QSA15 | isopropanol | 11.23 | A |
| QSA16 | Isopropyl acetate | 5.8 | A |
| QSA17 | Dichloroethane 1,2- | 10.8 | A |
| QSA18 | Acetonitrile | 1.53 | A |
| QSA19 | Tetrahydrofuran | 146.17 | A |
| QSA20 | Methanol | 42.95 | A |
| QSA21 | Water | UR, <0.21[2] | A |
| QSA22 | Water | UR, <0.21[2] | A |
| QSA23 | Heptane, n- | UR, <0.21[2] | A |
| QSA24 | Heptane, n- | UR, <0.21[2] | A |
| QSA27 | Dimethyl sulfoxide | 139.72 | A |
| QSA28 | Dimethyl sulfoxide | 138.56 | A |
| QSA29 | Acetonitrile | 1.15 | A |
| QSA30 | Acetonitrile | 1.38 | A |
| QSA31 | 2-Methyltetrahydrofuran | 35.5 | A |
| QSA32 | Ethanol | 25.2 | A |

[1]The solid form obtained from the slurry was assessed based on the XRPD analysis.
[2]Under Range, lower than detection limit, the concentration is lower than 0.21 mg/mL.
[3]Over Range, the material was dissolved, the concentration is higher than 200 mg/mL.

The materials obtained from in 19 out of 22 different solubility assessments were the same polymorph as the starting material free base, designated Form A. The solid from the slurry with cyclohexanone shows a different XRPD, which was designated the B-Class of forms. Form B was further characterized as four solvates, as discussed herein above.

Feasibility Study on Ponatinib Free Base Compound

Feasibility tests were performed to attempt to obtain amorphous free base material that could be employed in some crystallization techniques of Phase 4. Two techniques were employed, i.e., grinding and freeze-drying. The results are presented below.

Grinding. As summarized in Table 26 below, two grinding experiments were performed with two different durations at a frequency of 30 Hz. After 60 or 120 minutes of grinding, the material remained crystalline, (Form A).

TABLE 26

Grinding Feasibility Sudy of Ponatinib Free Base.

| Experiment | Time (min) | Form (XRPD) |
|---|---|---|
| GEN1.1 | 60 | A |
| GEN1.2 | 120 | A |

Freeze-drying. Eight freeze-drying experiments were performed with ponatinib free base compound. These experiments are summarized in Table 27 below.

TABLE 27

Freeze-drying feasibility study of 3-(imidazo[1,2-b]pyridazin-3-ylethynyl)-4-methyl-N-{4-[(4-methylpiperazin-1-yl)methyl]-3-(trifluoromethyl)phenyl}benzamide mono hydrochloride

| Experiment | Solvent | Form (XRPD) | Solvent content (%)[1] | Purity (%)[2] |
|---|---|---|---|---|
| GEN2 | Dimethyl sulfoxide | — (not dry) | — | — |
| GEN3 | Methanol | C low crystalline | 1.3 | 99.6 |
| GEN4 | 2,2,2-Trifluoroethanol/ Water 90/10 | Am gel | — | — |
| GEN5 | N,N-Dimethylacetamide/ Water 90/10 | D | 13.8 | 99.5 |
| GEN6 | 2,2,2-Trifluoroethanol | Am gel | — | — |
| GEN7 | Tetrahydrofuran | E-Class | 11.7 | 99.5 |
| GEN8 | 2-Methyltetrahydrofuran | B-Class | 6.0 | 99.6 |
| GEN9 | Dichloromethane | I low crystalline | 0.5 | 99.6 |

[1]Based on the TGMS results;
[2]Chemical purity determined by HPLC.

With solvents such as 2,2,2-trifluoroethanol (TFE) and TFE/water mixtures, amorphous material was obtained. In the experiments carried out in 2-methyltetrahydrofuran, DMA/water 90:10 and THF, three new crystalline forms were observed and were designated B-Class, D and E-Class. The B-Class and E-Class of forms were also observed in the screen Phase 4, for which the results suggested that they are isomorphic structures. In the remaining experiments performed in methanol and dichloromethane, two low crystalline materials were produced (Form C low crystalline and Form I low crystalline, respectively).

The new crystalline forms were further analyzed by DSC, TGMS and HPLC to determine their characteristics. Form D and Form E were identified as solvates (1:1 API/DMA and 1:1 API/THF, respectively).

The low crystalline materials obtained from methanol (C low crystalline) and dichloromethane (I low crystalline) had a limited amount of residual solvent (1.3% in the temperature interval 40° C.-150° C. and 0.5% in the interval 40° C.-175° C., respectively).

Since the freeze-drying procedure in methanol was not optimal to produce low crystalline material, the procedure in dichloromethane was selected to produce this material to be used in the cooling/evaporative crystallizations and vapour diffusion onto solids experiments of Phase 4.

Based on the results of the feasibility studies and the solubility behaviour of ponatinib free base, the solvents for the Phase 4 experiments were selected.

Solvent Assessment

In order to to select the screening solvents and to determine the concentration range to be used in the screen, quantitative solubility testing was performed on the free base starting material batch F09-05575. This screen employed a set of 20 solvents. For each solvent, a standard 1.8 ml screw cap vial was charged with 40 mg of the starting material, 200 μl of the solvent and a magnetic stirring bar. The vials were then closed and equilibrated at 25° C. for 24 h while stirring. The resulting mixtures (slurries) were filtered (0.5 micron) and the isolated mother liquors diluted to two dilutions selected according to the calibration curve. Quantities of the API in the diluted solutions were determined via HPLC analysis (DAD). The calibration curve was obtained from two independently prepared stock solutions of the free base compound in 2,2,2-trifluoroethanol.

Subsequently to the solubility determination, the residual solvent was evaporated from each vial (slurry) under vacuum at ambient temperature. All of the resulting residues were analyzed by X-ray powder diffraction to assay for new crystalline forms.

Feasibility Study

The experimental conditions of the feasibility study on the free base compound are summarized in Table 28 below. Following the experiments, HPLC analysis was performed to determine the purity and thermal analysis to determine the thermal behaviour of the forms.

TABLE 28

Condition Applied for the Feasibility Study on Ponatinib Free Base Compound.

| Experiment | Solvent | Form (XRPD) | Solvent content (%)[1] | Purity (%)[2] |
|---|---|---|---|---|
| GEN2 | Dimethyl sulfoxide | — (not dry) | — | — |
| GEN3 | Methanol | C low crystalline | 1.3 | 99.6 |
| GEN4 | 2,2,2-Trifluoroethanol / Water (90/10) | Am gel | — | — |
| GEN5 | N,N-Dimethylacetamide / Water (90/10) | D | 13.8 | 99.5 |
| GEN6 | 2,2,2-Trifluoroethanol | Am gel | — | — |
| GEN7 | Tetrahydrofuran | E-class | 11.7 | 99.5 |
| GEN8 | 2-Methyltetrahydrofuran | B-class | 6.0 | 99.6 |
| GEN9 | Dichloromethane | I low crystalline | 0.5 | 99.6 |

[1]Solvent content assessed by TGA;
[2]Purity assessed by HPLC

Polymorph Screening Experimental Design and Protocols

The polymorph screening experiments for the ponatinib free base compound were carried out at milliliter (ml) scale using 192 different conditions in which the following six different crystallization procedures were applied: cooling-evaporation, anti-solvent addition, grinding, slurry, vapor diffusion into solutions and vapor diffusion onto solids.

Cooling-Evaporative Crystallization Experiments

The 24 cooling-evaporative experiments at ml scale were performed in 8 ml vials, employing 24 different solvents and 1 concentration. In each vial, 25 mg of ponatinib free base was liquid dosed (with dichloromethane). The samples were freeze dried to obtain powdery low crystalline material. Then, the screening solvent was added to reach a concentration of circa 60 mg/ml, (see Table 29 below). The vials were closed and a temperature profile was obtained as described in Table 30 below. The mixtures were cooled to 5° C. and held at that temperature for 48 h before placing the vials under vacuum. The solvents were evaporated for several days at 200 mbar or 10 mbar and analyzed by XRPD and digital imaging.

TABLE 29

Experimental Conditions for the 24 mL Experiments using the Cooling-Evaporation Method.

| Experiment | Solvent | Weight (mg) | Volume (μl) |
|---|---|---|---|
| PSM25 | Chloroform | 21.8 | 380 |
| PSM26 | Methyl butyl ether, tert- | 21.9 | 380 |
| PSM27 | Methanol | 22.8 | 380 |
| PSM28 | Cyclohexane | 22.7 | 380 |
| PSM29 | Acetonitrile | 22.0 | 380 |
| PSM30 | Heptane, n- | 22.3 | 380 |
| PSM31 | Methanol / Chloroform (50/50) | 22.7 | 380 |
| PSM32 | Dioxane, 1,4- | 22.2 | 380 |
| PSM33 | Butyl acetate | 21.0 | 380 |
| PSM34 | Chlorobenzene | 21.4 | 380 |
| PSM35 | Xylene, m- | 21.2 | 380 |
| PSM36 | Ethanol | 20.4 | 380 |
| PSM37 | Water | 32.8 | 500 |
| PSM38 | Methanol / Acetonitrile (50/50) | 27.4 | 450 |
| PSM39 | Acetonitrile / Chloroform (50/50) | 25.8 | 450 |
| PSM40 | Cyclohexane / Tetrahydrofuran (50/50) | 22.9 | 400 |
| PSM41 | Methyl butyl ether, tert- / Xylene, m- (50/50) | 22.7 | 400 |
| PSM42 | Cyclohexane / Dioxane, 1,4- (50/50) | 23.1 | 400 |
| PSM43 | Cyclohexane / N-methyl-2-pyrrolidone (50/50) | 22.7 | 400 |
| PSM44 | Heptane, n- / Cyclohexane (50/50) | 22.8 | 400 |
| PSM45 | Tetrahydrofuran / N-methyl-2-pyrrolidone (50/50) | 21.4 | 350 |
| PSM46 | Tetrahydronaphthalene, 1,2,3,4- / Methylcyclohexane (50/50) | 21.3 | 350 |
| PSM47 | Butyl acetate / N-methyl-2-pyrrolidone (50/50) | 20.8 | 350 |
| PSM48 | Tetrahydronaphthalene, 1,2,3,4- / Cumene (50/50) | 19.9 | 350 |

TABLE 30

Temperature Profile used for the (24) Cooling-Evaporative Experiments.

| Experiments | Heating rate | $T_{initial}$ | Hold | Cooling rate | $T_{final}$ | Hold |
|---|---|---|---|---|---|---|
| PSM1-24 | 10 | 60 | 60 | 1 | 5 | 48 |

Crash-Crystallization with Anti-Solvent Addition

For the crash-crystallization experiments, 48 different crystallization conditions were applied, using 23 different solvents and 18 different anti-solvents (see Table 31 below). For each solvent, a stock solution was prepared, the concentration of ponatinib free base in each case being that attained at saturation at ambient temperature after equilibration for 17 hours before filtering into a set of 8 ml vials. To each of these vials, a different anti-solvent was added, using a solvent to anti-solvent ratio of 1:0.25. In those cases where no precipitation occurred, this ratio was increased to 1:4 with a waiting time of 60 minutes between the additions. Solids precipitated in the waiting time between the anti-solvent additions were separated by centrifugation. If no solids were obtained, the solvents were completely evaporated under vacuum at room temperature. If solids were obtained, they were analysed by XRPD and digital imaging.

TABLE 31

Experimental Design of the Crash-Crystallization Experiments with Anti-Solvent Addition.

| Experiment | Solvent | Anti-Solvent | Ratio S:AS (1:x) |
|---|---|---|---|
| AS1 | Acetone | Cyclohexane | 4 |
| AS2 | Ethyl formate | Methyl butyl ether, tert- | 4 |
| AS3 | Ethyl formate | Chloroform | 4 |
| AS4 | Ethyl formate | Diethoxymethane | 4 |
| AS5 | Acetone | Water | 1 |
| AS6 | Tetrahydrofuran | Cyclohexane | 1 |
| AS7 | Ethyl formate | Isoamyl acetate | 4 |
| AS8 | Ethylene glycol dimethyl ether | Chloroform | 4 |
| AS9 | Butanone, 2- | Cyclohexane | 4 |
| AS10 | Dioxane, 1,4- | Chloroform | 4 |
| AS11 | Ethyl formate | Anisole | 4 |
| AS12 | Methyltetrahydrofuran, 2- | Cyclohexane | 0.25 |
| AS13 | Ethylene glycol dimethyl ether | Diisopropyl ether | 1 |
| AS14 | Tetrahydrofuran | Toluene | 1 |
| AS15 | Dioxane, 1,4- | Diisopropyl ether | 4 |
| AS16 | Methanol | Water | 1 |
| AS17 | Dioxane, 1,4- | Cyclohexane | 1 |
| AS18 | Ethylene glycol dimethyl ether | Cyclohexane | 1 |
| AS19 | Methyl-1-Butanol, 3- | Cyclohexane | 4 |
| AS20 | Methyltetrahydrofuran, 2- | Methylcyclohexane | 1 |
| AS21 | Methyl-2-butanone, 3- | Trimethylpentane, 2,2,4- | 1 |
| AS22 | Amylalcohol, tert- | Trimethylpentane, 2,2,4- | 1 |
| AS23 | Dioxane, 1,4- | Methylcyclohexane | 1 |
| AS24 | Ethylene glycol dimethyl ether | Heptane, n- | 1 |
| AS25 | Ethyl formate | Xylene, p- | 1 |
| AS26 | Dioxane, 1,4- | Heptane, n- | 1 |
| AS27 | Ethyl acetate | Cyclohexane | 4 |
| AS28 | Cyclohexanone | Cyclohexane | 4 |
| AS29 | Diethyleneglycol-dimethylether | Water | 0.25 |
| AS30 | Cyclohexanone | Water | 4 |
| AS31 | Ethoxyethanol, 2- | Water | 0.25 |
| AS32 | Hydroxy-4-methyl-2-pentanone, 4- | Water | 1 |
| AS33 | Methoxyethanol, 2- | Water | 1 |
| AS34 | Dimethylformamide, N,N- | Water | 0.25 |
| AS35 | Dimethylacetamide, N,N- | Heptane, n- | 4 |
| AS36 | Isoamyl acetate | Diethoxymethane | 4 |
| AS37 | Propionitrile | Trimethylpentane, 2,2,4- | 4 |
| AS38 | Amylalcohol, tert- | Cumene | 4 |
| AS39 | Ethylene glycol dimethyl ether | Anisole | 4 |
| AS40 | Butyl acetate | Heptane, n- | 4 |
| AS41 | Amylalcohol, tert- | Methylcyclohexane | 4 |
| AS42 | Butyronitrile | Chlorobenzene | 4 |
| AS43 | Butyl acetate | Xylene, p- | 4 |
| AS44 | Cyclohexanone | Diethyl carbonate | 4 |
| AS45 | Butyl acetate | Dimethyl-4-heptanone, 2,6- | 4 |
| AS46 | Dimethylformamide, N,N- | Xylene, p- | 4 |
| AS47 | Cyclohexanone | Nonane, n- | 4 |
| AS48 | Ethoxyethanol, 2- | Dimethyl-4-heptanone, 2,6- | 4 |

Grinding Experiments

The drop-grinding technique uses a small amount of solvent added to the ponatinib free base material which is ground in a stainless steel grinder jar with 2 stainless steel grinding balls. In this manner, the effect of 24 different solvents (see Table 32 below) was investigated. Typically, 30 mg of starting material was ground and analyzed.

TABLE 32

Experimental Conditions for the Grinding Experiments

| Experiment | Solvent | Weight (mg) | Volume (ul) |
|---|---|---|---|
| GRP1 | Hexafluorobenzene | 28.6 | 10 |
| GRP2 | Cyclohexane | 31.0 | 10 |
| GRP3 | Acetonitrile | 30.2 | 10 |
| GRP4 | Ethylene glycol dimethyl ether | 30.5 | 10 |
| GRP5 | Diethoxymethane | 29.7 | 10 |
| GRP6 | Heptane, n- | 30.4 | 10 |
| GRP7 | Trimethylpentane, 2,2,4- | 30.1 | 10 |
| GRP8 | Water | 29.7 | 10 |
| GRP9 | Nitromethane | 29.9 | 10 |
| GRP10 | Dioxane, 1,4- | 30.9 | 10 |
| GRP11 | Trifluorotoluene, alpha, alpha, alpha- | 29.5 | 10 |
| GRP12 | Toluene | 29.7 | 10 |
| GRP13 | Nitropropane, 2- | 29.9 | 10 |
| GRP14 | Nitropropane, 1- | 29.5 | 10 |
| GRP15 | Xylene, p- | 30.7 | 10 |
| GRP16 | Fluorooctane,1- | 29.6 | 10 |
| GRP17 | Isoamyl acetate | 24.1 | 10 |
| GRP18 | Xylene o- | 30.2 | 10 |
| GRP19 | Nonane,n- | 29.5 | 10 |
| GRP20 | Cyclohexanone | 30.6 | 10 |
| GRP21 | Diethyleneglycol-dimethylether | 29.9 | 10 |
| GRP22 | Butylbenzene, sec- | 29.7 | 10 |
| GRP23 | Decane | 30.1 | 10 |
| GRP24 | Limonene, (R)-(+)- | 29.4 | 10 |

Slurry Experiments

A total of 48 slurry experiments were performed with ponatinib free base, 24 solvents at each of 10° C. and 30° C., for 2 weeks. Table 33 below summarizes the experimental conditions. The experiments are carried out by stirring a suspension of the material in a solvent at a controlled temperature. At the end of the slurry time, the vials were centrifuged and solids and mother liquids separated. The solids were further dried under full vacuum at room temperature and analyzed by XRPD and digital imaging.

TABLE 33

Experimental Conditions for the Slurry Experiments

| Experiment | Solvent | Weight (mg) | Volume (ul) | Temperature (° C.) |
|---|---|---|---|---|
| SLP1 | Methyl butyl ether, tert- | 24.3 | 250 | 10 |
| SLP2 | Methyl acetate | 26.3 | 250 | 10 |
| SLP3 | Chloroform | 55.7 | 250 | 10 |
| SLP4 | Methanol | 23.4 | 250 | 10 |
| SLP5 | Tetrahydrofuran | 27.1 | 250 | 10 |
| SLP6 | Hexane, n- | 24.4 | 250 | 10 |
| SLP7 | Ethanol | 26.9 | 250 | 10 |
| SLP8 | Cyclohexane | 25.1 | 250 | 10 |
| SLP9 | Acetonitrile | 24.8 | 250 | 10 |
| SLP10 | Dimethoxyethane, 1,2- | 24.4 | 200 | 10 |
| SLP11 | Isopropyl acetate | 23.9 | 250 | 10 |
| SLP12 | Heptane, n- | 25.7 | 250 | 10 |
| SLP13 | Water | 28.1 | 250 | 10 |
| SLP14 | Methylcyclohexane | 27.8 | 250 | 10 |
| SLP15 | Dioxane, 1,4- | 25.5 | 250 | 10 |
| SLP16 | Isobutanol | 24.2 | 250 | 10 |
| SLP17 | Toluene | 27.4 | 250 | 10 |
| SLP18 | Butyl acetate | 27.0 | 250 | 10 |
| SLP19 | Hexanone 2- | 24.6 | 250 | 10 |
| SLP20 | Chlorobenzene | 27.8 | 250 | 10 |
| SLP21 | Ethoxyethanol, 2- | 25.6 | 250 | 10 |
| SLP22 | Xylene, m- | 24.4 | 250 | 10 |
| SLP23 | Cumene | 25.0 | 250 | 10 |
| SLP24 | Anisole | 25.1 | 250 | 10 |
| SLP25 | Methyl butyl ether, tert- | 25.8 | 250 | 30 |
| SLP26 | Methyl acetate | 25.1 | 250 | 30 |
| SLP27 | Chloroform | 84.8 | 250 | 30 |
| SLP28 | Methanol | 25.0 | 250 | 30 |
| SLP29 | Tetrahydrofuran | 23.6 | 250 | 30 |
| SLP30 | Hexane, n- | 20.4 | 250 | 30 |
| SLP31 | Ethanol | 23.9 | 250 | 30 |
| SLP32 | Cyclohexane | 28.3 | 250 | 30 |
| SLP33 | Acetonitrile | 24.1 | 250 | 30 |
| SLP34 | Dimethoxyethane, 1,2- | 25.2 | 200 | 30 |
| SLP35 | Isopropyl acetate | 23.9 | 250 | 30 |
| SLP36 | Heptane, n- | 24.1 | 250 | 30 |
| SLP37 | Water | 24.0 | 250 | 30 |
| SLP38 | Methylcyclohexane | 25.3 | 250 | 30 |
| SLP39 | Dioxane, 1,4- | 24.6 | 250 | 30 |
| SLP40 | Isobutanol | 26.7 | 250 | 30 |
| SLP41 | Toluene | 26.3 | 250 | 30 |
| SLP42 | Butyl acetate | 24.1 | 250 | 30 |
| SLP43 | Hexanone 2- | 26.4 | 250 | 30 |
| SLP44 | Chlorobenzene | 25.3 | 250 | 30 |
| SLP45 | Ethoxyethanol, 2- | 26.6 | 250 | 30 |
| SLP46 | Xylene, m- | 24.7 | 250 | 30 |
| SLP47 | Cumene | 23.8 | 250 | 30 |
| SLP48 | Anisole | 24.1 | 250 | 30 |

Vapor Diffusion into Solutions

For the vapor diffusion experiments, saturated solutions of ponatinib free base were exposed to solvent vapors at room temperature for two weeks. A volume of saturated solution was transferred to an 8 ml vial which was left open and placed in a closed 40 ml vial with 2 ml of anti-solvent (see Table 34 below). After two weeks, the samples were checked on solid formation. If solids were present the liquid was separated from the solid. The samples were dried under vacuum (200 mbar or 10 mbar) before they were analyzed by XRPD and digital imaging.

TABLE 34

Experimental Conditions for the Vapor-Diffusion into Solutions

| Experiment | Solvent of solution | Volume solution (ul) | Anti-Solvent |
|---|---|---|---|
| VDL1 | Dichloromethane | 900 | Cyclohexane |
| VDL2 | Ethyl formate | 1000 | Chloroform |
| VDL3 | Acetone | 1000 | Water |
| VDL4 | Tetrahydrofuran | 450 | Cyclohexane |
| VDL5 | Ethyl formate | 1000 | Isoamyl acetate |
| VDL6 | Tetrahydrofuran | 450 | Fluorobenzene |
| VDL7 | Methyltetrahydrofuran, 2- | 500 | Cyclohexane |
| VDL8 | Ethyl acetate | 1000 | Trimethylpentane, 2,2,4- |
| VDL9 | Ethylene glycol dimethyl ether | 500 | Diisopropyl ether |
| VDL10 | Dioxane, 1,4- | 1000 | Diisopropyl ether |
| VDL11 | Methanol | 500 | Water |
| VDL12 | Dioxane, 1,4- | 1000 | Cyclohexane |
| VDL13 | Methyltetrahydrofuran, 2- | 500 | Methylcyclohexane |
| VDL14 | Methyl-2-butanone, 3- | 1000 | Trimethylpentane, 2,2,4- |
| VDL15 | Amylalcohol tert- | 1000 | Trimethylpentane, 2,2,4- |
| VDL16 | Dioxane, 1,4- | 1000 | Water |
| VDL17 | Dioxane, 1,4- | 1000 | Octane, n- |

TABLE 34-continued

Experimental Conditions for the Vapor-Diffusion into Solutions

| Experiment | Solvent of solution | Volume solution (ul) | Anti-Solvent |
|---|---|---|---|
| VDL18 | Ethoxyethanol, 2- | 500 | Water |
| VDL19 | Methoxyethanol, 2- | 500 | Water |
| VDL20 | Isoamyl acetate | 1000 | Heptane, n- |
| VDL21 | Propionitrile | 1000 | Chlorobenzene |
| VDL22 | Isoamyl acetate | 1000 | Trimethylpentane, 2,2,4- |
| VDL23 | Butyronitrile | 1000 | Chlorobenzene |
| VDL24 | Butyl acetate | 1000 | Xylene, p- |

Vapor-Diffusion onto Solids

For the vapor diffusion experiments, amorphous ponatinib free base was exposed to solvent vapors at room temperature for two weeks. The API was liquid dosed into 8 ml vials and then freeze dried. The 8 ml vials with the amorphous material were left open and placed in a closed 40 ml vial with 2 ml of anti solvent (see Table 35 below). After two weeks, the solids were analyzed by XRPD and digital imaging. If the solids were liquefied by the vapors, the samples were dried under vacuum (200 mbar or 10 mbar) before they were analyzed by XRPD and digital imaging.

TABLE 35

Experimental Conditions for the Vapor-Diffusion onto Solids

| Experiment | Anti solvent | Weight (mg) |
|---|---|---|
| VDS1 | Chloroform | 19.3 |
| VDS2 | Methanol | 18.8 |
| VDS3 | Tetrahydrofuran | 24.3 |
| VDS4 | Diisopropyl ether | 22.7 |
| VDS5 | Trifluoroethanol, 2,2,2- | 22.3 |
| VDS6 | Hexafluorobenzene | 23.7 |
| VDS7 | Cyclohexane | 22.6 |
| VDS8 | Acetonitrile | 27.1 |
| VDS9 | Dichloroethane, 1,2- | 24.0 |
| VDS10 | Thiophene | 23.2 |
| VDS11 | Dimethylcarbonate | 24.4 |
| VDS12 | Heptane, n- | 25.3 |
| VDS13 | Trimethylpentane, 2,2,4- | 24.5 |
| VDS14 | Water | 26.1 |
| VDS15 | Dioxane, 1,4- | 24.6 |
| VDS16 | Trifluorotoluene, alpha, alpha, alpha- | 23.1 |
| VDS17 | Dimethyl-3-butanone, 2,2- | 23.7 |
| VDS18 | Octane, n- | 25.2 |
| VDS19 | Dimethylcyclohexane, 1,2- (cis\trans-mixture) | 26.1 |
| VDS20 | Cyclopentanone | 24.7 |
| VDS21 | Chlorobenzene | 26.4 |
| VDS22 | Xylene, p- | 25.6 |
| VDS23 | Fluorooctane,1- | 28.1 |
| VDS24 | Isoamyl acetate | 25.2 |

Physical Stability and Scale-Up of Selected Ponatinib Polymorphs

The purpose of this study was to reproduce and further characterize solid forms of ponatinib that were identified in the studies discussed herein above. From this study, it was determined that Forms D (isomorphic solvates) and Form F (monohydrate) are physically stable for a period of at least 10 months at ambient conditions. Forms from the B-Class and E-Class, as well as Form G, H, I (low crystalline) and J (low crystalline), converted to Form A over a period of 10 months at ambient conditions.

Scale-up of Form H and J (low crystalline) were successful. Scale-up attempt of Form G resulted in Form A. The scale-up project was carried out in three phases as follows:

Phase 1: investigation of the physical stability by XRPD of the various forms obtained in the previous studies after storage at ambient conditions for 8-10 months;

Phase 2: scale-up of selected solid forms of ponatinib free base to 50-120 mg for further characterization; and Phase 3: Determination of solvation state, thermal characteristics and physical stability of the material from phase 2.

Phase 1 Results

Form D (isomorphic solvate) and Form F (monohydrate) are stable for the duration of the study. The isomorphic solvates of Form B-Class and Form E-Class all converted to Form A. Forms G, H, I (low crystalline), and J (low crystalline) all converted to Form A. FIG. 89 presents a tabular summary of the physical stability of several of the ponatinib solid forms.

Phase 2: Scale Up of Selected Ponatinib Free Base Forms

Forms G, H and J (low crystalline) were selected for scale-up trials. Experimental conditions for the scale-ups were taken from the polymorph screen disclosed herein. Forms H and J (low crystalline) were successfully scaled-up. FIG. 90 presents a tabular summary of the results from the scale-up experiments for selected free base forms.

Phase 3: Characterization of the Forms Obtained in the Scale-Up

The solid forms that were scaled up in the previous phase and of which the form was confirmed by XRPD were further characterized by: DSC, TGMS, FTIR, HPLC and DVS. Form A resulting from the attempts to scale-up Form G was not further characterized. In addition the physical stability to accelerated ageing conditions (one week at 40° C. and 75% RH) was investigated. FIG. 91 presents a tabular summary of various characterizations of ponatinib free base forms successfully reproduced at the 120 mg scale.

Pharmaceutical Compositions and Treatment of Physiological Conditions Therewith

The present disclosure provides pharmaceutical compositions that comprise a therapeutically effective amount of a crystalline form of ponatinib hydrochloride disclosed herein and at least one pharmaceutically acceptable carrier, vehicle or excipient. A unit dosage form of a pharmaceutical composition comprises in certain embodiments a single crystal form of ponatinib hydrochloride as the API. Alternatively, a unit dosage form of a pharmaceutical composition comprises more than one crystal form of ponatinib hydrochloride. In certain embodiments, more than about 50%, more than about 70%, more than about 80%, or more than about 90%, of a single crystalline form present in the composition is of one of the selected forms. In any of the foregoing embodiments, one or all of the crystal forms is substantially pure. For example, a pharmaceutical composition comprises in certain embodiments substantially pure Form A of ponatinib hydrochloride and at least one pharmaceutically acceptable carrier, vehicle or excipient. Alternatively, a pharmaceutical composition comprises Form A and Form J of ponatinib hydrochloride and at least one pharmaceutically acceptable carrier, vehicle or excipient. Other variations of this theme will be readily apparent to those of skill in the art given the benefit of this disclosure.

The at least one pharmaceutically acceptable carrier, diluent, vehicle or excipient can readily be selected by one of ordinary skill in the art and will be determined by the desired mode of administration. Illustrative examples of suitable modes of administration include oral, nasal, parenteral, topical, transdermal, and rectal. The pharmaceutical compositions disclosed herein may take any pharmaceutical form recognizable to the skilled artisan as being suitable.

Suitable pharmaceutical forms include solid, semisolid, liquid, or lyophilized formulations, such as tablets, powders, capsules, suppositories, suspensions, liposomes, and aerosols.

Various solid forms of ponatinib, and various solid forms of ponatinib hydrochloride, may be administered singly or in any combination at a therapeutically effective amount to a subject in need of treatment. Similarly, any of the solid forms of ponatinib and ponatinib hydrochloride disclosed herein may be formulated singly or in any combination into a pharmaceutical composition that can be subsequently used to treat various disease states in humans or other animals. For example, pharmaceutical compositions comprising any single one or combination of polymorphs of ponatinib and/or ponatinib hydrochloride may be used for treating CML or Ph+ALL in a subject in need thereof, by the administration of a therapeutically effective amount of the pharmaceutical composition to the subject in need thereof.

III. Synthesis of Ponatinib and Ponatinib Hydrochloride

Ponatinib free base and Ponatinib HCl are the products of the convergent four step synthesis depicted in Scheme 1. Step 1 involves the synthesis of the "methyl ester" intermediate AP25047 from starting materials AP24595, AP28141, and AP25570. Step 2 involves the synthesis of the "aniline" intermediate, AP24592, from starting material AP29089. Step 3 is the base catalyzed coupling of AP25047 and AP24592 to generate ponatinib free base, also designated as AP24534, which is isolated as the free base. Step 4 is the formation and crystallization of the mono-hydrochloride salt of ponatinib in ethanol.

A representative route of synthesis of ponatinib HCl is designated as Process C.

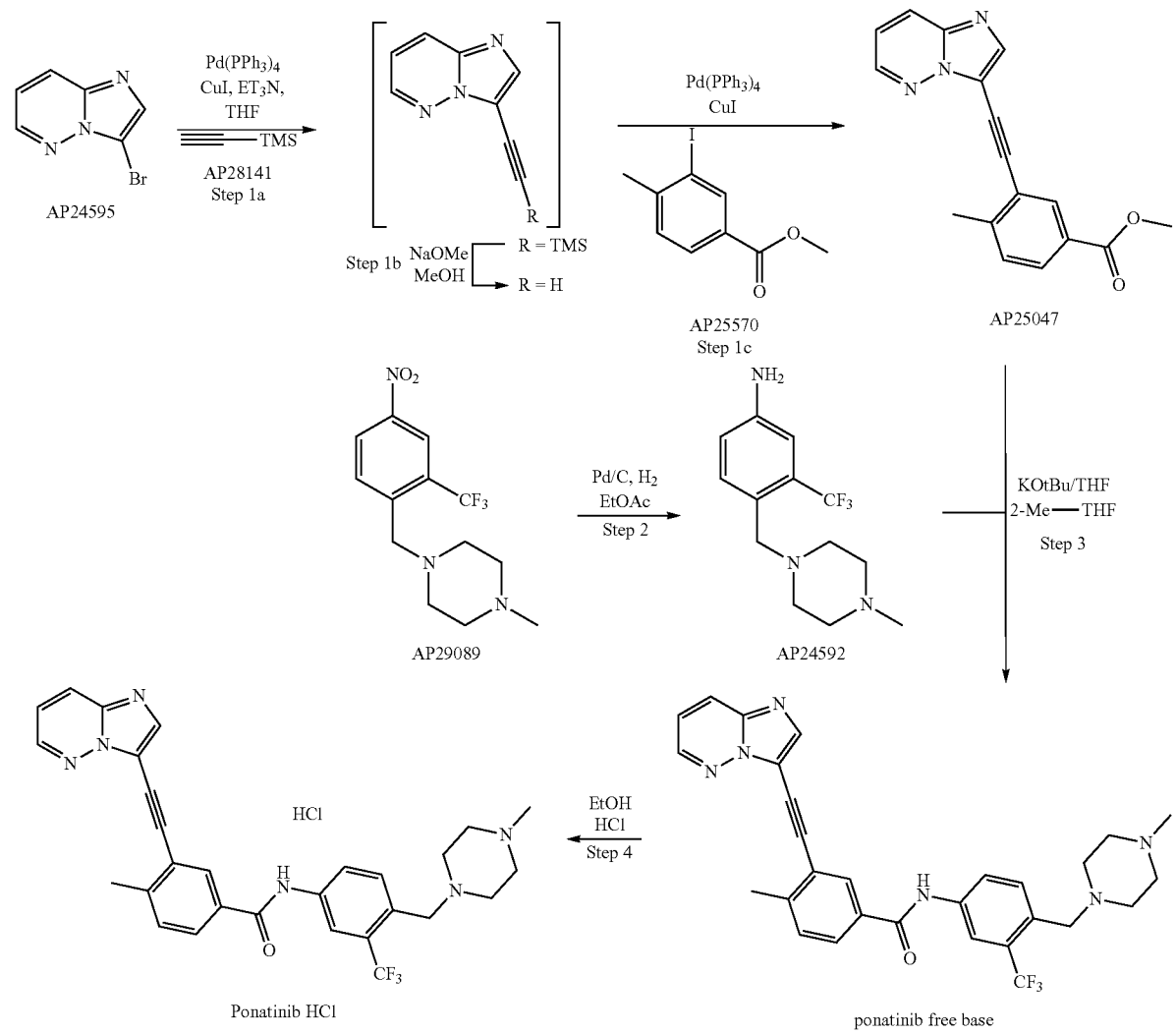

Scheme 1: Process C

Step 1: Synthesis of AP25047 ("Methyl Ester") Intermediate Summary and Synthetic Scheme Step 1 of the ponatinib HCl process is the synthesis of the methyl ester intermediate AP25047 in a three reaction sequence (designated 1a, 1b, and 1c), carried out without intermediate isolation ("telescoped"), from starting materials AP24595, AP25570, and AP28141, as depicted in Scheme 1. The array of two aromatic ring systems connected by a single alkyne linker is constructed through two tandem, palladium/copper-catalyzed Sonogashira couplings and an in situ desilylation reaction under basic conditions. The crude AP25047 product is then subjected to a series of processing steps designed to remove residual inorganic catalysts and process by-products. These operations include the crystallization of AP25047 as the HCl salt from a non-polar solvent, toluene (Unit Operation 1.3), an aqueous work-up and silica gel plug filtration (Unit Operation 1.4), and crystallization from a polar solvent, 2-propanol (Unit Operation 1.5). The two crystallizations provide orthogonal purifications for rejection of related substance impurities with differing polarities. The crystallization and solvent wash of the HCl salt from toluene is controlled by an in-process analytical test for a specific process impurity. The final crystallization of the AP25047 intermediate from 2-propanol has been subjected to multi-variate DoE studies to define the design space for robust rejection of other impurities arising from the telescoped reactions. A series of eight in-process tests in Step 1 provide quantitative, analytical control for reaction completions, impurity rejection, and effective removal of residual solvents.

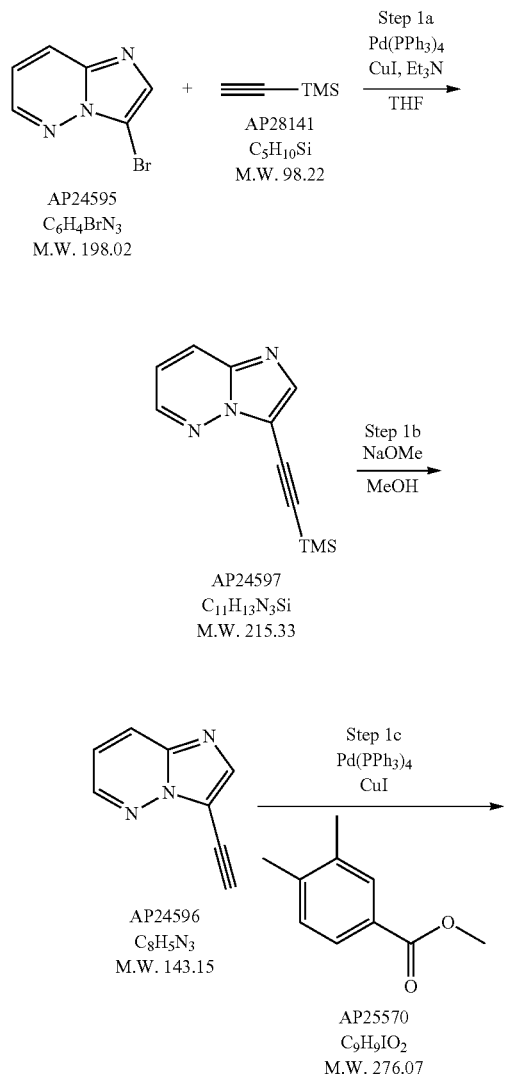

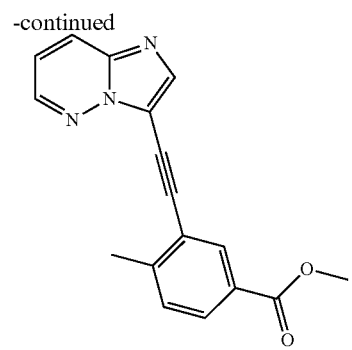

AP25047
$C_{17}H_{13}N_3O_2$
M.W. 291.30

Unit Operation 1.1: $1^{st}$ Sonogashira Reaction

AP24595, palladium tetrakis triphenylphosphine (Pd(PPh$_3$)$_4$), copper (1) iodide (CuI), triethylamine, and tetrahydrofuran (THF) are charged to the reactor. The mixture is stirred and degassed with nitrogen and then pre-degassed AP28141 is charged. The resulting mixture is brought to 45-55° C. and held for not less than 3 hours. The reaction completion is determined by IPC-1 (HPLC). If the IPC-1 criterion is met, the mixture is concentrated to a target volume and cooled.

Unit Operation 1.2: Deprotection/$2^{nd}$ Sonogashira Reaction

AP25570, additional palladium tetrakis triphenylphosphine (Pd(PPh$_3$)$_4$), copper (1) iodide (CuI), and tetrahydrofuran (THF) are charged to the reactor. The mixture is concentrated and the water content is determined by IPC-2 (KF). If the IPC-2 criterion is met, the mixture is warmed to 45-60° C. and 25% sodium methoxide solution in methanol is slowly added. The reaction mixture is stirred and held for 30-60 minutes at 45-55° C. The reaction progress is determined by IPC-3 (HPLC). The reaction mixture may be held at a lower temperature during the IPC analysis. If the IPC-3 criterion is met, the process is continued to Unit Operation 1.3.

Unit Operation 1.3: Isolation of AP25047-HCl

While stirring, the cool reaction mixture is quenched by addition of hydrogen chloride gas. A precipitate forms, and residual hydrogen chloride is removed from the suspension by a nitrogen purge. Tetrahydrofuran (THF) is replaced with toluene by an azeotropic distillation under reduced pressure. The resulting warm slurry is filtered in an agitated filter dryer and the filter cake is triturated and washed with warm toluene. The content of process impurity AP29116 is determined by IPC-4 (H PLC). If the IPC-4 criterion is met, the wet filter cake is dried with agitation under a flow of nitrogen and reduced pressure at 35-45° C. (jacket temperature). The drying is monitored by IPC-5 (LOD, gravimetric). If the IPC-5 criterion is met, the crude AP25047 HCl is discharged and packaged in FEP bags in a plastic container. The isolated AP25047 HCl can be held for up to 7 days prior to forward processing.

Unit Operation 1.4: Work-Up

The crude AP25047 HCl solid is charged to a reactor with dichloromethane (DCM) and washed with aqueous ammonia. The aqueous phase is back extracted with DCM for yield recovery purposes and the combined organic phase is washed a second time with aqueous ammonia. The organic layer is then washed with aqueous hydrochloric acid until the aqueous phase reaches a pH of 1-2, as indicated by IPC-6 (pH strips). If the IPC-6 criterion is met, the organic phase is treated with aqueous sodium bicarbonate until the aqueous wash reaches a pH of NLT 7, as indicated by IPC-7 (pH strips). The organic phase is briefly concentrated followed by the addition of fresh dichloromethane. The organic solution is passed through a silica gel pad, which is then rinsed with additional fresh dichloromethane for increased product recovery.

Unit Operation 1.5: Crystallization of AP25047

The dichloromethane solution is concentrated under reduced pressure, and the dichloromethane is replaced with 2-propanol by azeotropic distillation under reduced pressure to the targeted final volume range. The resulting suspension is then cooled and further aged with agitation.

Unit Operation 1.6: Isolation/Drying

The precipitated product is isolated in an agitated filter dryer under a flow of nitrogen, and the filter cake is rinsed with 2-propanol. The wet filter cake is dried with agitation under a flow of nitrogen and reduced pressure at 45-55° C. (jacket temperature). The drying is monitored by IPC-8 (LOD, gravimetric). If the IPC-8 criterion is met, the product is sampled and packaged into polyethylene bags and placed within a heat sealed mylar coated aluminum foil bag, within an HDPE shipping container (Expected yield range, 65-89%).

Step 2: Synthesis of AP24592 ("Aniline") Intermediate

Summary and Synthetic Scheme

Step 2 of the ponatinib HCl process is the synthesis of the aniline intermediate, AP24592, by catalytic hydrogenation of the nitro-aromatic starting material AP29089, as depicted below. The reaction is carried out in ethyl acetate, a solvent in which the starting material and product are highly soluble. The catalyst for this reaction is palladium on carbon, and hydrogen is introduced as a gas directly into the reaction mixture. At the completion of the reaction, a solvent exchange from ethyl acetate to n-heptane via distillation prompts the spontaneous crystallization of AP24592, resulting in material with high purity. This crystallization has been shown to have a significant purification effect, as most of the process impurities remain solubilized in n-heptane.

The three in-process controls in Step 2 are an HPLC of the reaction mixture to confirm consumption of starting material, a GC measurement of ethyl acetate following the azeotropic solvent exchange to n-heptane, and a gravimetric determination of solvent loss on drying.

Scheme 3:
Step 1 - Step 2: Synthesis of AP24592

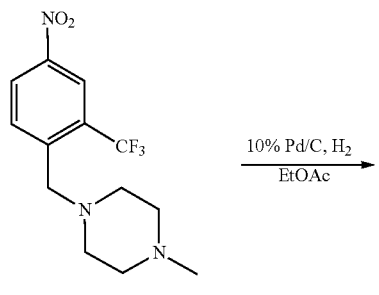

AP29089
$C_{13}H_{16}F_3N_3O_2$
M.W. 303.28

10% Pd/C, $H_2$
EtOAc
→

-continued

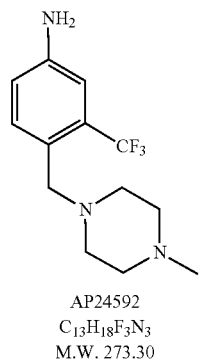

AP24592
$C_{13}H_{18}F_3N_3$
M.W. 273.30

Unit Operation 2.1: Dissolution and Hydrogen Purging

AP29089, 10% palladium on carbon, and ethyl acetate are charged to a reactor, and the suspension is stirred under hydrogen pressure.

Unit Operation 2.2: Hydrogenation

The reactor is pressurized with hydrogen until a stable pressure range is achieved and the mixture is then stirred under hydrogen atmosphere for at least 4 additional hours. The reactor is depressurized and a sample taken to assess reaction completion (IPC-1). If the IPC-1 criterion is met, the process is continued to Unit Operation 2.3

Unit Operation 2.3: Concentration/Crystallization

The reaction mixture is passed through a filter cartridge to remove the catalyst, and the cartridge is washed with additional ethyl acetate. The combined filtrate and wash solution is concentrated under vacuum to remove a target volume of ethyl acetate. n-Heptane is charged, and the distillation is continued under vacuum to a target volume. The ethyl acetate content is determined by IPC-2 (GC). If the IPC-2 criterion is met, the process is continued to Unit Operation 2.4.

Unit Operation 2.4: Isolation/Drying

The solid product is dried under vacuum at a target temperature range. The end of drying is determined by IPC-3 (LOD, gravimetric). AP24592 is obtained as a white to yellow solid in a range of 80-97% (based on AP29089 input).

Step 3: Synthesis of Ponatinib Free Base

Summary and Synthetic Scheme

Step 3 is the synthesis of the free base of ponatinib by the base-catalyzed reaction of AP25047 and AP24592, presented in Scheme 4. The reaction is carried out in the presence of a strong base, potassium tert-butoxide, under essentially water-free conditions to minimize the undesired hydrolysis of the methyl ester of AP25047 to the corresponding unreactive carboxylic acid. The presence of this by-product results in not only loss of yield, but in complications in downstream processing during the reaction workup. Drying of the reaction mixture by a series of azeotropic distillations, controlled by an in-process test for water, ensures a robust reaction and nearly quantitative consumption of starting materials. The parameters of the reaction conditions and crystallization, in which process impurities are robustly rejected, are well understood on the basis of DoE studies.

Scheme 4: Step 3-Synthesis of AP24534 Free Base

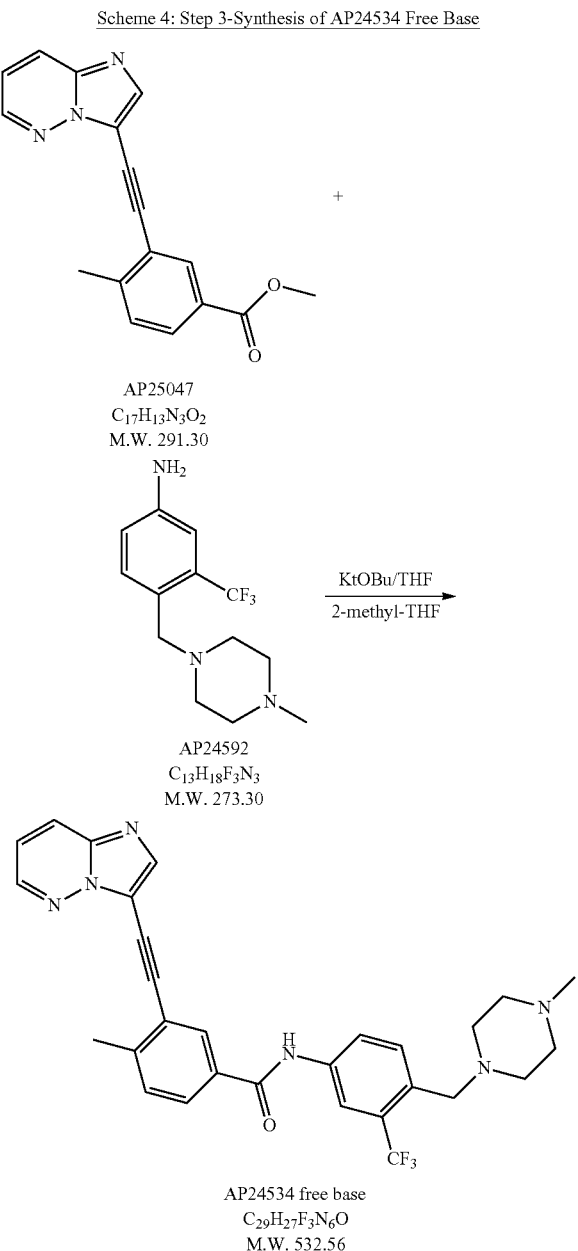

Unit Operation 3.1: Drying Reaction Mixture

AP25047, AP24592, and 2-methyl tetrahydrofuran (2-Me-THF) are charged to a reactor. The mixture is concentrated at reduced pressure to a target volume. Additional 2-methyl tetrahydrofuran is added and the distillation repeated. Following another charge of 2-methyl tetrahydrofuran and a distillation cycle, the water content of the mixture is determined in IPC-1(KF). If the IPC-1 criterion is met, the process is continued to Unit Operation 3.2.

Unit Operation 3.2: Reaction

The suspension is maintained with stirring at a target temperature of 13-23° C. range while potassium tert-butoxide (KOtBu) is charged. After a period of not less than 3 hours, the reaction progress is determined by HPLC (IPC-2). If the IPC criterion is met, the process is continued to Unit Operation 3.3.

Unit Operation 3.3: Quench and Extractions

The reaction mixture is diluted with 2-methyltetrahydrofuran (2-Me-THF), and quenched by the addition of aqueous sodium chloride solution. The organic layer is separated and the aqueous layer is extracted twice with 2-methyl tetrahydrofuran. The combined organic layers are sequentially washed with aqueous sodium chloride and water. The organic layer is then aged at 15-30° C.

Unit Operation 3.4: Concentration/Solvent Exchange

After aging (see Unit Operation 3.3), the mixture is passed through a cartridge filter and concentrated under vacuum to a target volume. 1-Propanol is charged and allowed to stir at elevated temperature to furnish a solution, which is distilled under vacuum to a target volume and then cooled slowly to a temperature range of 20-30° C.

Unit Operation 3.5: Crystallization

The product solution in 1-propanol is aged with stirring at a temperature of 20-30° C. until the presence of solids is visually observed. Acetonitrile is charged to the suspension with stirring and the resulting suspension is aged for an additional 60-120 minutes at 20-30° C. with agitation prior to isolation in the next Unit Operation.

Unit Operation 3.6: Isolation/Drying

The slurry generated in Unit Operation 3.5 is isolated under vacuum in a filter/dryer. The solids are washed twice with a mixture of 1-propanol and acetonitrile. The solids are then dried under vacuum and monitored by IPC-3 (LOD, gravimetric). If the IPC criterion is met, the product is discharged as an off-white to yellow solid and packaged in double polyethylene bags for storage at ambient temperatures.

Step 4: Synthesis of Ponatinib HCl

Summary and Synthetic Scheme

Step 4 of the ponatinib HCl process is the formation of the mono-hydrochloride salt through combination of equimolar quantities of ponatinib free base with hydrochloric acid in ethanol and induction of crystallization through seeding. The parameters of this process have been examined in DoE studies for effects on the generation of the desired solid form and particle size distribution of this process. The synthetic scheme for Step 4 is presented in Scheme 5.

Scheme 5: Step 4 - Synthesis of Ponatinib HCl

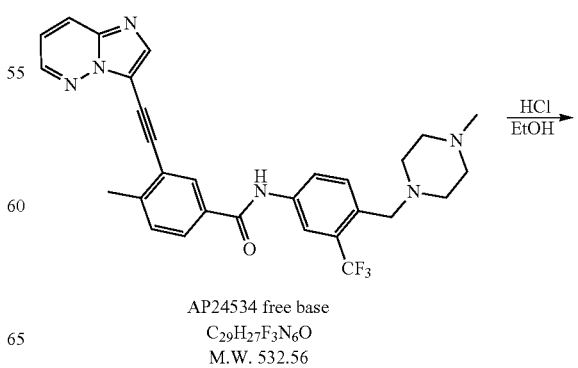

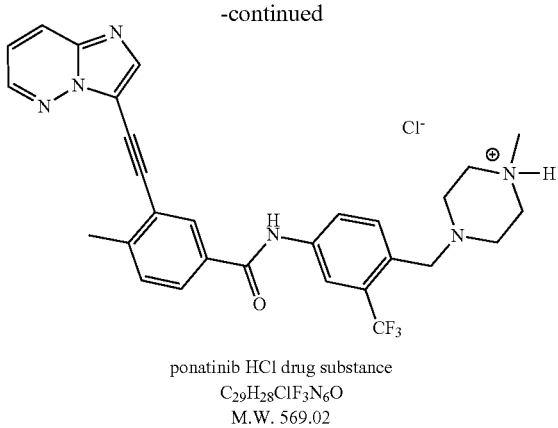

ponatinib HCl drug substance
$C_{29}H_{28}ClF_3N_6O$
M.W. 569.02

Unit Operation 4.1: Dissolution

AP24534 free base and absolute ethanol (EtOH) are charged to a reactor and stirred at 60-75° C. to generate a solution. Dissolution is verified by visual observation.

Unit Operation 4.2: Clarification

The solution is passed through a filter, which is then washed with ethanol at 60-78° C.

Unit Operation 4.3: Acidification/Seeding

The product solution is concentrated under vacuum to a target volume. With stirring, an initial portion (approximately 25%) of a solution of 1N hydrogen chloride in ethanol is then charged to the reactor. The solution is treated with qualified seed crystals of AP24534 HCl at a temperature of 60-70° C. to initiate crystallization. The process is continued to Unit Operation 4.4.

Unit Operation 4.4: Crystallization

Once the presence of solids in the reactor is verified by visual observation, the remainder (approximately 75%) of the 1N hydrogen chloride solution in ethanol is slowly added to the stirred mixture. The mixture is aged for at least 10 minutes and IPC-1 is performed to determine the pH of the solution. If the IPC criterion is met, the mixture is cooled to a temperature of 5-15° C. and aged with stirring.

Unit Operation 4.5: Isolation/Drying

The solid product is isolated by filtration and washed with ethanol at a temperature of 5-15° C. Excess ethanol is removed from the solid product by slow agitation and nitrogen flow at ambient temperature. The solid is then dried under vacuum at 60-70° C. The drying is monitored by IPC-2 (LOD, gravimetric). If the IPC-2 criterion is met, ponatinib HCl is discharged as an off-white to yellow solid and packaged in double polyethylene bags for storage in plastic drums at 20-30° C.

It is to be understood that the foregoing description is exemplary and explanatory in nature, and is intended to illustrate the presently disclosed general inventive concept and its preferred embodiments. Through routine experimentation, those of skill in the art given the benefit of the instant disclosure may recognize apparent modifications and variations without departing from the spirit and scope of the present disclosure. Thus, the present disclosure is not limited by the above description, but rather by the following claims and their equivalents.

What is claimed is:

1. A process for preparing crystalline Form A of 3-(imidazo[1,2-b]pyridazin-3-ylethynyl)-4-methyl-N-{4-[(4-methylpiperazin-1-yl)methyl]-3-(trifluoromethyl) phenyl}benzamide hydrochloride, the process comprising:
   (a) dissolving 3-(imidazo[1,2-b]pyridazin-3-ylethynyl)-4-methyl-N-{4-[(4-methylpiperazin-1-yl)methyl]-3-(trifluoromethyl)phenyl}benzamide in ethanol to generate a solution;
   (b) acidifying the solution with hydrochloric acid;
   (c) seeding the solution;
   (d) leaving the solution to crystallize; and
   (e) isolating crystalline Form A of 3-(imidazo[1,2-b]pyridazin-3-ylethynyl)-4-methyl-N-{4-[(4-methylpiperazin-1-yl)methyl]-3-(trifluoromethyl) phenyl}benzamide hydrochloride.

2. The process of claim 1, wherein (b) acidifying the solution with hydrochloric acid comprises adding a hydrogen chloride solution in ethanol to the ethanol solution of (a).

3. Crystalline Form A of ponatinib hydrochloride obtained by the process of claim 2.

* * * * *